(12) United States Patent
Berinstein et al.

(10) Patent No.: US 8,207,314 B2
(45) Date of Patent: Jun. 26, 2012

(54) TUMOR ANTIGENS FOR PREVENTION AND/OR TREATMENT OF CANCER

(75) Inventors: Neil Berinstein, Toronto (CA); Scott Gallichan, Campbellville (CA); Corey Lovitt, Bolton (CA); Mark Parrington, Bradford (CA); Laszlo Radvanyi, Houston, TX (US); Devender Singh-Sandhu, Thornhill (CA)

(73) Assignee: Sanofi Pasteur Limited, Toronto (CA)

( * ) Notice: Subject to any disclaimer, the term of this patent is extended or adjusted under 35 U.S.C. 154(b) by 1019 days.

(21) Appl. No.: 10/557,066

(22) PCT Filed: Apr. 15, 2004

(86) PCT No.: PCT/US2004/015202
§ 371 (c)(1),
(2), (4) Date: Jul. 30, 2007

(87) PCT Pub. No.: WO2004/104039
PCT Pub. Date: Dec. 2, 2004

(65) Prior Publication Data
US 2010/0278848 A1    Nov. 4, 2010

Related U.S. Application Data

(60) Provisional application No. 60/471,119, filed on May 16, 2003, provisional application No. 60/471,193, filed on May 16, 2003.

(51) Int. Cl.
*C07H 21/02* (2006.01)
*C07H 21/04* (2006.01)
*A61K 48/00* (2006.01)

(52) U.S. Cl. .............. 536/23.1; 536/23.2; 536/23.5; 514/44 R

(58) Field of Classification Search .................. None
See application file for complete search history.

(56) References Cited

U.S. PATENT DOCUMENTS

| | | | |
|---|---|---|---|
| 5,093,258 A | 3/1992 | Cohen et al. | |
| 5,141,742 A | 8/1992 | Buraun et al. | |
| 5,262,177 A | 11/1993 | Brown et al. | |
| 5,505,941 A | 4/1996 | Paoletti et al. | |
| 5,833,975 A | 11/1998 | Paoletti et al. | |
| 5,942,235 A | 8/1999 | Paoletti et al. | |
| 5,972,597 A | 10/1999 | Paoletti et al. | |
| 6,774,226 B1 | 8/2004 | Jager et al. | |
| 6,780,586 B1 | 8/2004 | Gish et al. | |
| 6,911,529 B1 | 6/2005 | Jager et al. | |
| 6,969,518 B2 | 11/2005 | Houghton et al. | |
| 6,969,609 B1 | 11/2005 | Schlom et al. | |
| 7,211,432 B2 | 5/2007 | Schlom et | |
| 7,217,421 B1 | 5/2007 | McArthur et al. | |
| 7,851,213 B2 | 12/2010 | Berinstein et al. | |
| 8,017,590 B1 | 9/2011 | Berinstein et al. | |
| 8,021,664 B2 | 9/2011 | Berinstein et al. | |
| 2001/0018058 A1 | 8/2001 | Reed et al. | |
| 2002/0034749 A1 | 3/2002 | Billing-Medel et al. | |
| 2002/0068691 A1* | 6/2002 | Salceda et al. | 514/1 |
| 2003/0031681 A1* | 2/2003 | McCart et al. | 424/186.1 |
| 2003/0124128 A1 | 7/2003 | Lillie et al. | |
| 2004/0152144 A1 | 8/2004 | Sun et al. | |
| 2004/0223949 A1 | 11/2004 | Astsaturov et al. | |
| 2005/0063093 A1 | 3/2005 | Hong et al. | |
| 2005/0112099 A1 | 5/2005 | Berinstein et al. | |
| 2005/0186180 A1 | 8/2005 | Schlom et al. | |
| 2005/0214848 A1 | 9/2005 | Billing-Medel et al. | |
| 2006/0154291 A1 | 7/2006 | Billing-Medel et al. | |
| 2007/0128655 A1 | 6/2007 | Obata | |
| 2008/0010759 A1 | 1/2008 | Scherl | |

FOREIGN PATENT DOCUMENTS

WO WO 02/059377 A2 * 8/2002
WO WO 03/004989 A2 * 1/2003

OTHER PUBLICATIONS

Chang et al (Apoptosis 7:13-21, 2002).*
Bosher, et al. The developmentally regulated transcription factor AP-2 is involved in c-erbB-2 overexpression in human mammary carcinoma. Proc. Natl. Acad, Sci. USA 92: 744-747 (Jan. 1995).
Chang, et al. Structure and function of GC79/TRPS1, a novel androgen-repressible apoptosis gene. Apoptosis. 7: 13-21 (2002).
Accession No. AX829127 (Dec 12, 2003).
Accession No. AF183810 (Jan. 10, 2000).
Accession No. AAF23614 (Jan. 10, 2000).
Momeni, et al. Mutations in a new gene, encoding a zinc-finger protein, cause tricho-rhino-phalangeal syndrome type I. Nat Genet 24, 71-4 (2000).
Malik, et al, Deletion of the GATA domain of TRPS1 causes an absence of facial hair and provides new insights into the bone disorder in inherited tricho-rhino-phalangeal syndromes. Mol Cell Bid 22. 8592-600 (2002).
Ludecke, H.J. et al. Genotypic and phenotypic spectrum in tricho-rhino-phalangeal syndrome types I and III. Am J Hum Genet 68, 81-91 (2001).
Kaiser, E.J. et al. Novel missense mutations in the TRPS1 transcription factor define the nuclear localocalization signal. Eur J Hum Genet 12, 121-6 (2004). Ginesteir, C. et al. Distinct and complementary information provided by use of tissue anal DNA microarrays in the study of breast tumor markers. Am J Pathol 161, 1223-33 (2002).
Kobayashi, H. et al. Missense mutation of TRPS1 in a family of tricho-rhino-phalangeal syndrome type III. Am J Med Genet 107, 26-9 (2002).
Gentile, et al. A novel mutation in exon 7 in a family with mild tricho-rhino-phalangeal syndrome type Clin Genet 63, 166-7 (2003).
Hatamura, I. et al. A nonsense mutation in TRPS1 in a Japanese family with tricho-rhino-phalangeal syndrome type I. Clin Genet 59, 366-7 (2001).

(Continued)

*Primary Examiner* — Peter J Reddig
(74) *Attorney, Agent, or Firm* — Patrick J Halloran; Reza Yacoob

(57) ABSTRACT

The present invention relates to a nucleic acid encoding a polypeptide and the use of the nucleic acid or polypeptide in preventing and/or treating cancer. In particular, the invention relates to improved vectors for the insertion and expression of foreign genes encoding tumor antigens for use in immunotherapeutic treatment of cancer.

21 Claims, 26 Drawing Sheets

OTHER PUBLICATIONS

Chang, et al. Differentially expressed genes in androgen-dependent and -independent prostate carcinomas. Cancer Res 57, 4075-81 (1997).

Kunath, et al. Expression of Trps1 during mouse embryonic development. Mech Dev 119 Suppl 1, S117-20 (2002).

Malik, et al. Transcriptional repression and developmental functions of the atypical vertebrate GATA protein TRPS1. Embo J 20, 1715-25 (2001).

Chang, et al. Characterization of a zinc-finger protein and its association with apoptosis in prostate cancer cells. J Natl Cancer Inst 92, 1414-21 (2000).

Kaiser, et al. The RING finger protein RNF4, a co-regulator of transcription, interacts with the TRPS1 transcription factor. J Biol Chem 278, 38780-5 (2003).

Tremblay, et al. Novel roles for GATA transcription factors in the regulation of steroidogenesis. J Steroid Biochem Mol Biol 85, 291-8 (2003).

Savinainen, et al. Expression and copy number analysis TRPS1, EIF3S3 and MYC genes in breast and prostate cancer. Br. J. Cancer 90, 1041-1046 (2004).

Williams, et al. Analysis of differential protein expression in normal and neoplastic human breast epithelial cell lines, Electrophoresis, 19: 333-343 (1998).

Derisi, et al. Use of a cDNA microarray to gene expression patterns human cancer. Nature Genetics 14: 457-460 (1996).

Welford, et al. Detection of differentially expressed genes in primary tumor tissues using representational differences analysis coupled to microarray hybridization. Nucleic Acids Research 26(12): 3059-3065 (1998).

Khan, et al. Expression profiling in cancer using cDNA microarrays. Electrophoresis 20: 223-229 (1999).

Radvanyi, et al. The gene associated with trichorhinophalangeal syndrome in humans is overexpressed in breast cancer. PNAS 102(31): 11005-11010 (2005).

Jager, et al. Identification of a naturally processed NY-ESO-1 peptide recognized by CD8+ T cells in the context of HLA-B51. Cancer Immunity, vol. 2, p. 12 (2002).

Jager, et al. Identification of a Tissue-specific Putative Transcription Factor in Breast Tissue by Serological Screening of a Cancer Library, Cancer Research, 61. 2055-2061 (2001).

Sharma, et al. Class I Major Histocompatibility Complex Anchor Substitutions Alter the Conformation of T Cell Receptor Contacts. J. Biol. Chem. 276(24): 21443-21449 (2001).

Jager, et al. Identification of tumor-restricted antigens . . . Cancer Immunity. 2: 5 (Jun. 28, 2002).

Tartaglia, et al. NYVAC: A Highly Attenuated Strain of Vaccine Virus. Virology. 188: 217-232 (1992).

Tartaglia, et al. Protection of Cats against Feline Leukemia Virus by Vaccination with Canarypox Virus Recombinant, ALVAC-FL. J. Virol. 67(4): 2370-2375 (Apr. 1993).

Tartaglia, et al. Therapeutic vaccines against melanoma and colorectal cancer. Vaccine. 19(2): 2571-2575 (2001).

Bakker, et al. Analogues of CTL epitopes with improved MHC class-I binding capacity elicit anti-melanoma CTL recognizing the wild-type epitope. Int. J. Cancer 70, 302-309 (1997).

Boon, et al. Tumor Antigens Recognized by T Lymphocytes. Ann. Rev. Immunol 2:337-365 (1994).

Hodge, et al. Admixture of Recombinant Vaccinia Virus Containing the Gene for the Costimulatory Molecule B7 and a Recombinant Vaccinia Virus Containing a Tumor-associated Antigen Gene Results in Enhanced Specific T-Cell Responses and Antitumor Immunity. Cancer Res. 55: 3598-3603 (1995).

Hodge, et al. Diversified prime and boost protocols using recombinant vaccinia virus and recombinant non-replicating avian pox virus to enhance T-cell immunity and antitumor responses. Vaccine, 15(6/7): 759-768 (1997).

Hodge, et al. A Triad of Costimulatory Molecules Synergize to Amplify T-Cell Activation. Cancer Res. 59: 5800-5807 (1999).

Irvine, et al. Recombinant Virus Vaccination Against "Self" Antigens Using Anchor-Fixed Immunogens. Cancer Res. 59: 2536-2540 (1999).

Kawashima, et al. The Multi-epitope Approach for Immunotherapy for Cancer: Identification of Several CTL Epitopes from Various Tumor-Associated Antigens Expressed on Solid Epithelial Tumors. Human Immunol. 59:1-14 (1998).

Marshall, et al. Phase I study in advanced cancer patients of a diversified prime-and-boost vaccination protocol using recombinant vaccinia virus and recombinant nonreplicating avipox virus to elicit anti-carcinoembryonic antigen immune responses. J. Clin, Oncol. 18, 3964-3973 (2000).

Mateo, et al. An HLA-A2 Polyepitope Vaccine for Melanoma Immunotherapy. J. Immunol. 163(7): 4058-4063 (1999).

Oertli, et al. Rapid Induction of Specific Cytotoxic T Lymphocytes Against Melanoma-Associated Antigens by a Recombinant Vaccinia Virus Vector Expressing Multiple Immunodominant Epitopes and Costimulatory Molecules In Vivo. Human Gene Therapy, 13(4): 569-575 (Mar. 2002).

Pardoll, D.M. Cancer vaccines; a road map for the next decade. Current Opinion in Immunology. 8: 619-621 (1998).

Parker, et al. Sequence motifs important for peptide binding to the human MHC class I molecule, HLA-A2. J. Immunol. 149: 3580-3587 (1992).

Rosenberg, S.A. Progress in human tumour immunology and immunotherapy. Nature 411, 380-384 (2001).

Spagnoli, et al. Cytotoxic T-cell induction in Metastatic Melanoma Patients Undergoing Recombinant Vaccinia Virus-Based Immuno-Gene Therapy. Recent Results in Cancer Research, 160: 195-201 (2002).

Xiang, et al. An Autologous Oral DNA Vaccine Protects Against Murine Melanoma. Proc. Natl. Acad. Sci. USA. 97 (10): 5492-5497 (2000).

Van Den Eynde, et al. Tumor Antigens Recognized by T Lymphocytes. Int. J. Clin. Lab. Res. 27: 81-86 (1997).

Van Den Eynde. et al. New tumor antigens recognized by T cells. Curr. Opin. Immunol. 9, 674-681 (1995).

Tsao, et al. Hypopigmentation Associated with an Adenovirus-Mediated gp100/MART-1-Transduced Dendritic Cell Vaccine for Metastatic Melanoma. Arch. Dermatol. 138: 799-802 (2002).

* cited by examiner

FIGURE 1A

```
AAC2-1  ATGGGTTCCCCCGCCGCCCCGGAGGGAGCGCTGGGCTACGTCCGCGAGTTCACTCGCCACTCCT
AAC2-2  ATGGGTTCCCCCGCCGCCCCGGAGGGAGCGCTGGGCTACGTCCGCGAGTTCACTCGCCACTCCT

AAC2-1  CCGACGTGCTGGGCAACCTCAACGAGCTGCGCCTGCGCGGGATCCTCACTGACGTCACGCTGCT
AAC2-2  CCGACGTGCTGGGCAACCTCAACGAGCTGCGCCTGCGCGGGATCCTCACTGACGTCACGCTGCT

AAC2-1  GGTTGGCGGGCAACCCCTCAGAGCACACAAGGCAGTTCTCATCGCCTGCAGTGGCTTCTTCTAT
AAC2-2  GGTTGGCGGGCAACCCCTCAGAGCACACAAGGCAGTTCTCATCGCCTGCAGTGGCTTCTTCTAT

AAC2-1  TCAATTTTCCGGGGCCGTGCGGGAGTCGGGGTGGACGTGCTCTCTCTGCCCGGGGGTCCCGAAG
AAC2-2  TCAATTTTCCGGGGCCGTGCGGGAGTCGGGGTGGACGTGCTCTCTCTGCCCGGGGGTCCCGAAG

AAC2-1  CGAGAGGCTTCGCCCCTCTATTGGACTTCATGTACACTTCGCGCCTGCGCCTCTCTCCAGCCAC
AAC2-2  CGAGAGGCTTCGCCCCTCTATTGGACTTCATGTACACTTCGCGCCTGCGCCTCTCTCCAGCCAC

AAC2-1  TGCACCAGCAGTCCTAGCGGCCGCCACCTATTTGCAGATGGAGCACGTGGTCCAGGCATGCCAC
AAC2-2  TGCACCAGCAGTCCTAGCGGCCGCCACCTATTTGCAGATGGAGCACGTGGTCCAGGCATGCCAC

AAC2-1  CGCTTCATCCAGGCCAGCTATGAACCTCTGGGCATCTCCCTGCGCCCCCTGGAAGCAGAACCCC
AAC2-2  CGCTTCATCCAGGCCAGCTATGAACCTCTGGGCATCTCCCTGCGCCCCCTGGAAGCAGAACCCC

AAC2-1  CAACACCCCCAACGGCCCCTCCACCAGGTAGTCCCAGGCGCTCCGAAGGACACCCAGACCCACC
AAC2-2  CAACACCCCCAACGGCCCCTCCACCAGGTAGTCCCAGGCGCTCCGAAGGACACCCAGACCCACC

AAC2-1  TACTGAATCTCGAAGCTGCAGTCAAGGCCCCCCCAGTCCAGCCAGCCCTGACCCCAAGGCCTGC
AAC2-2  TACTGAATCTCGAAGCTGCAGTCAAGGCCCCCCCAGTCCAGCCAGCCCTGACCCCAAGGCCTGC

AAC2-1  AACTGGAAAAAGTACAAGTACATCGTGCTAAACTCTCAGGCCTCCCAAGCAGGGAGCCTGGTCG
AAC2-2  AACTGGAAAAAGTACAAGTACATCGTGCTAAACTCTCAGGCCTCCCAAGCAGGGAGCCTGGTCG

AAC2-1  GGGAGAGAAGTTCTGGTCAACCTTGCGCCCAAGCCAGGCTCCCCAGTGGAGACGAGGCCTCCAG
AAC2-2  GGGAGAGAAGTTCTGGTCAACCTTGCCCCCAAGCCAGGCTCCCCAGTGGAGACGAGGCCTCCAG

AAC2-1  CAGCAGCAGCAGCAGCAGCAGCAGCAGCAGTGAAGAAGGACCCATTCCTGGTCCCCAGAGCAGG
AAC2-2  CAGCAGCAGCAGCAGCAGCAGCAGC***AGTGAAGAAGGACCCATTCCTGGTCCCCAGAGCAGG

AAC2-1  CTCTCTCCAACTGCTGCCACTGTGCAGTTCAAATGTGGGGCTCCAGCCAGTACCCCCTACCTCC
AAC2-2  CTCTCTCCAACTGCTGCCACTGTGCAGTTCAAATGTGGGGCTCCAGCCAGTACCCCCTACCTCC

AAC2-1  TCACATCCCAGGCTCAAGACACCTCTGGATCACCCTCTGAACGGGCTCGTCCACTACCGGGAAG
AAC2-2  TCACATCCCAGGCTCAAGACACCTCTGGATCACCCTCTGAACGGGCTCGTCCACTACCGGGAAG

AAC2-1  TGAATTTTTCAGCTGCCAGAACTGTGAGGCTGTGGCAGGGTGCTCATCGGGGCTGGACTCCTT
AAC2-2  TGAATTTTTCAGCTGCCAGAACTGTGAGGCTGTGGCAGGGTGCTCATCGGGG*CTGGACTCCTT

AAC2-1  GGTTCCTGGGGACGAAGACAAACCCTATAAGTGTCAGCTGTGCCGGTCTTCGTTCCGCTACAAG
AAC2-2  GGTTCCTGGGGACGAAGACAAACCCTATAAGTGTCAGCTGTGCCGGTCTTCGTTCCGCTACAAG

AAC2-1  GGCAACCTTGCCAGTCACCGTACAGTGCACACAGGGGAAAAGCCTTACCACTGCTCAATCTGCG
AAC2-2  GGCAACCTTGCCAGTCATCGTACAGTGCACACAGGGGAAAAGCCTTACCACTGCTCAATCTGCG
```

FIGURE 1B

```
AAC2-1    GAGCCCGTTTTAACCGGCCAGCAAACCTGAAAACGCACAGCCGCATCCATTCGGGAGAGAAGCC
AAC2-2    GAGCCCGTTTTAACCGGCCAGCAAACCTGAAAACGCACAGCCGCATCCATTCGGGAGAGAAGCC

AAC2-1    GTATAAGTGTGAGACGTGCGGCTCGCGCTTTGTACAGGTGGCACATCTGCGGGCGCACGTGCTG
AAC2-2    GTATAAGTGTGAGACGTGCGGCTCGCGCTTTGTACAGGTGGCACATCTGCGGGCGCACGTGCTG

AAC2-1    ATCCACACCGGGGAGAAGCCCTACCCTTGCCCTACCTGCGGAACCCGCTTCCGCCACCTGCAGA
AAC2-2    ATCCACACCGGGGAGAAGCCCTACCCTTGCCCTACCTGCGGAACCCGCTTCCGCCACCTGCAGA

AAC2-1    CCCTCAAGAGCCACGTTCGCATCCACACCGGAGAGAAGCCTTACCACTGCGACCCCTGTGGCCT
AAC2-2    CCCTCAAGAGCCACGTTCGCATCCACACCGGAGAGAAGCCTTACCACTGCGACCCCTGTGGCCT

AAC2-1    GCATTTCCGGCACAAGAGTCAACTGCGGCTGCATCTGCGCCAGAAACACGGAGCTGCTACCAAC
AAC2-2    GCATTTCCGGCACAAGAGTCAACTGCGGCTGCATCTGCGCCAGAAACACGGAGCTGCTACCAAC

AAC2-1    ACCAAAGTGCACTACCACATTCTCGGGGGGCCCTAG (SEQ ID NO.: 597)
AAC2-2    ACCAAAGTGCACTACCACATTCTCGGGGGGCCCTAG (SEQ ID NO.: 4)
```

FIGURE 1C

```
AAC2-1    MGSPAAPEGALGYVREFTRHSSDVLGNLNELRLRGILTDVTLLVGGQPLRAHKAVLIACSGFFYSIFRG
AAC2-2    MGSPAAPEGALGYVREFTRHSSDVLGNLNELKLRGILTDVTLLVGGQPLRAHKAVLIACSGFFYSIFRG

AAC2-1    RAGVGVDVLSLPGGPEARGFAPLLDFMYTSRLRLSPATAPAVLAAATYLQMEHVVQACERFIQASYEPL
AAC2-2    RAGVGVDVLSLPGGPEARGFAPLLDFMYTSRLRLSPATAPAVLAAATYLQMEHVVQACERFIQASYEPL

AAC2-1    LPGGPEARGFAPLLDFMYTSRLRLSPATAPAVLAAATYLQMEHVVQACERFIQASYEPLGISLRPLEAE
AAC2-2    LPGGPEARGFAPLLDFMYTSRLRLSPATAPAVLAAATYLQMEHVVQACERFIQASYEPLGISLRPLEAE

AAC2-1    PPTPPTAPPPGSPRRSEGHPDPPTESPSCSQGPPSPASFDPKACNWKFYKYIVLNSQASQAGSLVGERS
AAC2-2    PPTPPTAPPPGSPPRSEGHPDPPTESRSCSQGPPSPASFDPKACNWKKYKYIVLNSQASQAGSLVGEPS

AAC2-1    SGQPCPQARLPSGDEASSSSSSSSSSSEEGPIPGPQSRLSPTAATVQFKCGAPASTPYLLTSQAQDTS
AAC2-2    SGQPCPQARLPSGDEASSSSSSSSSSS*EEGPIPGPQSRLSPTAATVQFKCGAPASTPYLLTSQAQDTS

AAC2-1    GSPSERARPLPGVNFSAARTVRLNQSAHRGLDSLVPGDEDKPYKCQLCRSSFRYKGNLASHRTVHTGEK
AAC2-2    GSPSERARPLPGSEFFSCCNCEAVAGCSSGLDSLVPGDEDKPYKCQLCRSSFRYRGNLASHRTVHTGEK

AAC2-1    PYHCSICGARFNRPANLKTHSRIHSGEKPYKCETCGSRFVQVAHLRAHVLIHTGEKPYPCPTCGTRFRH
AAC2-2    PYHCSICGARFNRPANLKTHSRIHSGEKPYKCETCGSRFVQVAHLRAHVLIHTGEKPYPCPTCGTRFRH

AAC2-1    LQTLKSHVRIHTGEKPYHCDPCGLHFRHKSQLPLHLPQKHGAATNTKVHYHILGGP  (SEQ ID NO.: 2)
AAC2-2    LQTLKSHVRIHTGEKPYHCDPCGLHFRHKSQLRLHLPQKHGAATNTKVHYHILGGP  (SEQ ID NO.: 5)
```

FIGURE 7
BFA4 cDNA Sequence

```
ATGGTCCGGAAAAAGAACCCCCCTCTGAGAAACGTTGCAAGTGAAGGCGAGGGCCAGATCCTGGAGCCTATAGGTACAGAAAGCA
AGGTATCTGGAAAGAACAAAGAATTCTCTGCAGATCAGATGTCAGAAAATACGGATCAGAGTGATGCTGCAGAACTAAATCATAAG
GAGGAACATAGCTTGCATGTTCAAGATCCATCTTCTAGCAGTAAGAAGGACTTGAAAAGCGCAGTTCTGAGTGAGAAGGCTGGCTT
CAATTATGAAAGCCCCAGTAAGGGAGGAAACTTTCCCTCCTTTCCGCATGATGAGGTGACAGACAGAAATATCTTGGCTTTCTCAT
TTCCAGCTGCTGGGGGAGTCTGTGAGCCCTTGAAGTCTCCGCAAAGAGCAGAGGCAGATGACCCTCAAGATATGGCCTGCACCCCC
TCAGGGACTCACTGGAGACAAAGGAAGATCAGAAGATGTCACCAAAGGCTACAGAGGAAACAGGGCAAGCACAGAGTGGTCAAGC
CAATTGTCAAGGTTTGAGCCCAGTTTCAGTGGCCTCAAAAAGCCCACAAGTGCCTTCAGATGGGGGTGTAAGACTGAATAAATCCA
AAACTGACTTACTGGTGAATGACAACCCAGACCCGGCACCTCTGTCTCCGAGACTTCAGGACTTTAAATGCAATATCTCTGGATAT
GGTTACTACGGCAACGACCCCACAGATCTGATTAAGCACTTCCGAAAGTATCACTTAGGACTGCATAACCGCACCAGGCAAGATGC
TGAGCTGGACAGCAAAATCTTGGCCCTTCATAACATGGTGCAGTTCAGCCATTCCAAAGACTTCCAGAAGGTCAACCGTTCTGTCT
TTTCTGGTGTGCTGCAGGACATCAATTCTTCAAGGCCTGTTTTACTAAATGGGACCTATGATGTGCAGGTGACTTCAGGTGGAACA
TCATTGGCATTGGACGGAAAACACCAGATTGCCAAGGGAACACCAAGTATTTCCGCTGTAAATTCTGCAATTTCACTTATATGGG
CAACTCATCCACCGAATTAGAACAACATTTTCTTCAGACTCACCCAAACAAAATAAAAGCTTCTCTCCCCTCCTCTGAGGTTGCAA
AACCTTCAGAGAAAAACTCTAACAAGTCCATCCCTGCACTTCAATCCAGTGATTCTGGAGACTTGGGAAAATGGCAGGACAAGATA
ACAGTCAAAGCAGGAGATGACACTCCTGTTGGGTACTCAGTGCCCATAAAGCCCCTCGATTCCTCTAGACAAAATGGTACAGAGGC
CACCCAGTTACTACTGGTGTAAATTTTGTAGTTTCAGCTGTGAGTCATCTAGCTCACTTAAACTGCTAGAACATTATGGCAAGCAGC
ACGGAGCAGTGCAGTCAGGCGGCCTTAATCCAGAGTTAAATGATAAGCTTTCCAGGGGCTCTGTCATTAATCAGAATGATCTAGCC
AAAAGTTCAGAAGGAGAGACAATGACCAAGACAGACAAGAGCTCGAGTGGGGCTAAAAAGAAGGACTTCTCCAGCAAGGAGCCGA
GGATAATATGGTAACGAGCTATAATTGTCAGTTCTGTGACTTCCGATATTCCAAAAGCCATGGCCCTGATGTAATTGTAGTGGGGC
CACTTCTCCGTCATTATCAACAGCTCCATAACATTCACAAGTGTACCATTAAACACTGTCCATTCTGTCCCAGAGGACTTTGCAGC
CCAGAAAAGCACCTTGGAGAAATTACTTATCCGTTTGCTTGTAGAAAAAGTAATTGTTCCCACTGTGCACTCTTGCTTCTGCACTT
GTCTCCTGGGGCGGCTGGAAGCTCGCGAGTCAAACATCAGTGCCATCAGTGTTCATTCACCACCCTGACGTAGATGTACTCCTCT
TTCACTATGAAAGTGTGCATGAGTCCCAAGCATCGGATGTCAAACAAGAAGCAAATCACCTGCAAGGATCGGATGGGCAGCAGTCT
GTCAAGGAAAGCAAAGAACACTCATGTACCAAATGTGATTTTATTACCCAAGTGGAAGAAGAGATTTCCCGACACTACAGGAGAGC
ACACAGCTGCTACAAATGCCGTCAGTGCAGTTTTACAGCTGCCGATACTCAGTCACTACTGGAGCACTTCAACACTGTTCACTGCC
AGGAACAGGACATCACTACAGCCAACGGCGAAGAGGCACGGTCATGCCATATCCACCATCAAAGAGGAGCCCAAAATTGACTTCAGG
GTCTACAATCTGCTAACTCCAGACTCTAAAATGGGAGAGCCAGTTTCTGAGAGTGTGGTGAAGAGAGAGAAGCTGGAAGAGAAGGA
CGGGCTCAAAGAGAAAGTTTGGACCGAGAGTTCCAGTGATGACCTTCGCAATGTGACTTGGAGAGGGGCAGACATCCTGCGGGCGA
GTCCGTCATACACCCAAGCAAGCCTGGGGCTGCTGACGCCTGTGTCTGGCACCCAAGAGCAGACAAAGACTCTAAGGGATAGTCCC
AATGTGGAGGCCGCCCATCTGGCGCGACCTATTTATGGCTTGGCTGTGGAAACCAAGGGATTCCTGCAGGGGGCGCCAGCTGGCGG
AGAGAAGTCTGGGGCCCTCCCCCAGCAGTATCCTGCATCGGGAGAAAACAAGTCCAAGGATGAATCCCAGTCCCTGTTACGGAGGC
GTAGAGGCTCCGGTGTTTTTTGTGCCAATTGCCTGACCACAAAGACCTCTCTCTGGCGAAAGAATGCAAATGGCGGATATGTATGC
AACGCGTGTGGCCTCTACCAGAAGCTTCACTCGACTCCCAGCCTTTAAACATCATTAAACAAAACAACGGTGAGCAGATTATTAG
GAGGAGAACAAGAAAGCGCCTTAACCCAGAGGCACTTCAGGCTGAGCAGCTCAACAAACAGCAGAGGGGCAGCAATGAGGAGCAAG
TCAATGGAAGCCCGTTAGAGAGGAGGTCAGAAGATCATCTAACTGAAAGTCACCAGAGAGAAATTCCACTCCCCAGCCTAAGTAAA
TACGAAGCCCAGGGTTCATTGACTAAAAGCCATTCTGCTCAGCAGCCAGTCCTGGTCAGCCAAACTCTGGATATTCACAAAAGGCAT
GCAACCTTTGCACATTCAGATAAAAAGTCCTCAGGAAAGTACTGGAGATCCAGGAAATAGTTCATCCGTATCTGAAGGGAAAGGAA
GTTCTGAGAGAGGCAGTCCTATAGAAAAGTACATGAGACCTGCGAAACACCCAAATTATTCACCACCAGGCAGCCCTATTGAAAAG
TACCAGTACCCACTTTTTGGACTTCCCTTTGTACATAATGACTTCCAGAGTGAAGCTGATTGGCTGCGGTTCTGGAGTAAATATAA
GCTCTCCGTTCCTGGGAATCCGCACTACTTGAGTCACGTGCCCTGGCCTACCAAATCCTTGCCAAAACTATGTGCCTTATCCCACCT
TCAATCTGCCTCCTCATTTTTCAGCTGTTGGATCAGACAATGACATTCCTCTAGATTTGGCGATCAAGCATTCCAGACCTGGGCCA
ACTGCAAACGGTGCCTCCAAGGAGAAAACGAAGGCACCACCAAATGTAAAAAATGAAGGTCCCTTGAATGTAGTAAAAACAGAGAA
AGTTGATAGAAGTACTCAAGATGAACTTTCAACAAAATGTGTGCACTGTGGCATTGTCTTTCTGGATGAAGTGATGTATGCTTTGC
ATATGAGTTGCCATGGTGACAGTGGACCTTTCCAGTGCAGCATATGCCAGCATCTTTGCACGGACAAATATGACTTCACAACACAT
ATCCAGAGGGGCCTGCATAGGAACAATGCACAAGTGGAAAAAAATGGAAAACCTAAAGAGTAA
```
(SEQ ID NO.: 28)

FIGURE 8

BFA4 Amino Acid Sequence

MVRKKNPPLRNVASEGEGQILEPIGTESKVSGKNKEFSADQMSENTDQSDAAELNHKEEHSLHVQDPSSS
SKKDLKSAVLSEKAGFNYESFSKGGNFPSFPHDEVTDRNMLAFSFPAAGGVCEPLKSPQRAEADDPQDMA
CTPSGDSLETKEDQKMSPKATEETGQAQSGQANCQGLSPVSVASKNPQVPSDGGVRLNKSKTDLLVNDNP
DPAPLSPELQDFKCNICGYGYYGNDPTDLIKHFRKYHLGLHNRTRQDAELDSKILALHNMVQFSHSKDFQ
KVNRSVFSGVLQDINSSRPVLLNGTYDVQVTSGGTFIGIGRKTPDCQGNTKYFRCKFCNFTYMGNSSTEL
EQHFLQTHPNKIKASLPSSEVAKPSEKNSNKSIPALQSSDSGDLGKWQDKITVKAGDDTPVGYSVPIKPL
DSSRQNGTEATSYYWCKFCSFSCESSSSLKLLEHYGKQHGAVQSGGLNPELNDKLSRGSVINQNDLAKSS
EGETMTKTDKSSSGAKKKDFSSKGAEDNMVTSYNCQFCDFRYSKSHGPDVIVVGPLLRHYQQLHNIHKCT
IKHCPFCPRGLCSPEKHLGEITYPFACRKSNCSHCALLLLHLSPGAAGSSRVKHQCHQCSFTTPDVDVLL
FHYESVHESQASDVKQEANHLQGSDGQQSVKESKEHSCTKCDFITQVEEEISRHYRRAHSCYKCRQCSFT
AADTQSLLEHFNTVHCQEQDITTANGEEDGHAISTIKEEPKIDFRVYNLLTPDSKMGEPVSESVVRREKL
EEKDGLKEKVWTESSSDDLRNVTWRGADILRGSPSYTQASLGLLTFVSGTQEQTKTLRDSPNVEAAHLAR
PIYGLAVETKGFLQGAPAGGEKSGALPQQYPASGENKSKDESQSLLRRRGSGVFCANCLTTKTSLWRKN
ANGGYVCNACGLYQKLHSTPRPLNIIKQNNGEQIIRRRTRKRLNPEALQAEQLNKQQRGSNEEQVNGSPL
ERRSEDHLTESHQREIPLPSLSKYEAQGSLTKSHSAQQPVLVSQTLDIHKRMQPLHIQIKSPQESTGDPG
NSSSVSEGKGSSERGSPIEKYMRPAKHPNYSPPGSPIEKYQYPLFGLPFVHNDFQSEADWLRFWSKYKLS
VPGNPHYLSHVPGLPNPCQNYVPYPTFNLPPHFSAVGSDNDIPLDLAIKHSRPGPTANGASKEKTRAPPN
VKNEGPLNVVKTEKVDRSTQDELSTKCVHCGIVPLDEVMYALHMSCHGDSGPFQCSICQHLCTDKYDFTT
HIQRGLHRNNAQVEKNGKPKE (SEQ ID NO.: 29)

FIGURE 9

A. BCY1 cDNA Sequence

TGCAAGATTAAGGCCTTGAGGGCCAAGACCAACACCTACATCAAGACACCGGTGAGGGGCGAGGAACCAGTGTTCAT
GGTGACAGGGCGACGGGAGGACGTGGCCACAGCCCGGCGGGAAATCATCTCAGCAGCGGAGCACTTCTCCATGATCC
GTGCCTCCCGCAACAAGTCAGGCGCCGCCTTTGGTGTGGCTCCTGCTCTGCCCGGCCAGGTGACCATCCGTGTGCGG
GTGCCCTACCGCGTGGTGGGGCTGGTGGTGGGCCCCAAAGGGCAACCATCAAGCGCATCCAGCAGCAAACCAACAC
ATACATTATCACACCAAGCCGTGACCGCGACCCCGTGTTCGAGATCACGGGTGCCCCAGGCAACGTGGAGCGTGCGC
GCGAGGAGATCGAGACGCACATCGCGGTGCGCACTGGCAAGATCCTCGAGTACAACAATGAAAACGACTTCCTGGCG
GGGAGCCCCGACGCAGCAATCGATAGCCGCTACTCCGACGCCTGGCGGGTGCACCAGCCCGGCTGCAAGCCCCTCTC
CACCTTCCGGCAGAACAGCCTGGGCTGCATCGGCGAGTGCGGAGTGGACTCTGGCTTTGAGGCCCCACGCCTGGGTG
AGCAGGGCGGGGACTTTGGCTACGGCGGGTACCTCTTTCCGGGCTATGGCGTGGGCAAGCAGGATGTGTACTACGGC
GTGGCCGAGACTAGCCCCCCGCTGTGGGCGGGCCAGGAGAACGCCACGCCCACCTCCGTGCTCTTCTCCTCYCCTC
CTCCTCCTCCTCCTCTTCCGCCAAGGCCCGCGCTGGGCCCCGGGCGCACACCGCTCCCCTGCCACTTCCGCGGGAC
CCGAGCTGGCCGGACTCCCGAGGCGCCCCCGGGAGAGCCGCTCCGGGCTTCTCTAAACTTGGTGGGGGCGGCCTG
CGGAGCCCCGCAGCCGGCGGCGGGATTGCATGGTCTGCTTTGAGAGCGAAGTGACTGCCGCCCTTGTGCCCTGCGG
ACACAACCTGTTCTGCATGGAGTGTGCAGTACGCATCTGCGAGAGGACGGACCCAGAGTGTCCCGTCTGCCACATCA
CAGCCCACGCAAGCCATCCGAATATTCTCCTAAGCCCCGTGCCCCATGCCTCCGGGGCCCACTCCACTGGGCCCACCC
TGGACCTGTTTTCCACTAAAGCCTTTTGGAAAGCGGTGATTTGAGGGGCAAGGTGCTTAGAGATACTCGCTCGCTGG
GGAAGGGGGGAGGGAGGCAGTGGTGGCTGGAGGGTGCGCCACTTTCAGAGCCTCTGGTCACCCTGTCCTGGAAAGAT
TGGGAGGGGGCCAGACTGAAAATTTTACTAGAGTTACAACTCTGATACCTCAACACACCCTTAAATCTGGAAGCAGC
TAAGAGAAACTTTTGTTTTGCCAGAGGTGGCCACTAAGGCATTCTGACGCCCTCTGCCCACCTCCCCGCTGTGTGT
CACTCCACCCCTTCTTCCGAGGAGGGGGTGGGTAAAAGGGAGAGGGAGAATTACCACCTGTATCTAGAGGTGCTCTT
TGCAATCCCTAAGCCCTCTGGTCCTGACCTCCGACCTCCCAGCTCTGTCTTGTTCCTTGTCTTTGTCTTTCTTCCCT
TCCCCCTGCCCCTGCCCCTACCAGCCCAGCTTGGGGACACCATCCTTCTGGGGAGAAGTAGGGGGAGGAATATTTG
GATGGTCCCTCCATTCCTCTTCAGGCATCTGGAGGCCCTCTCCCCCACTCCTCCAAAGAAACATCTCAAATTATTGA
TGGAATGTATCCCCATTCTCAGTGAAAATGTGAGGAGGGGACTAATACTGGGGTAAAGGGTCAAACCCCCACCTTCA
TCACTATGGGCATTATATTTAGGGAGTAGTTCTTGGGCTGGATTTTCTGGTTGTGGAAGTGGGGGCGCCAGAGTAGT
GTGTCTGCTATTTAAAGGAGCAGGAAAGGGCGTGAGGCAGGAGAGACTGGTGGAGGGAAGAGCTGCTCCTCCCA
TGCAGTGCCCGACTCCCTGCACCCCTCTCAACCTGACCTGAACCTTTATTGAATCCTTATTAGCTTGAATCCTTATT
AGCTTGAATCCTCCATGCAAATCATGGAGTCTGTGTCCCACCTGATGTGGTTGAGGAGAAGCCAGGTCTTCAAAGAG
GGGTCAGCCTGGGGCAAAGCAGGACTGGGGGAGGTGGGCAGCAGGGCCTATTCTGAGAATCACATATTGTTACAGG
CCTTGCACCCCCTTTGCTGCTTCCCTCCTGCTCATTTGGGGCTGCCACCAGCTCTCCACCCTCCTGGTTCCGCTGGC
CGGGCCAAGAGAGGATGGAGGGATGGGAGTCCCAGGAGATCCTTGTAAATAGTGGGGTGGGACTGTTCTGAGTGATC
ACCCGAGCACTTAAAGCTCCAGAGTCCCATTCTTCCTGGATGGAGCAGGTGGAGGTGCAGAGGGGATTCCTCCTCT
CCTTCCTCCTGTCGAGAATTAACACCTCTCCACAGCCTCCAGAACACCAGCCAGGAGGGGTGGGGAAGGA
GGTCACAGCCAAGAAAACTGCCCTGTCGACGACTTCCCTCCTTCCCGCCTATGTGAGCCATCCTGAGATGTCTGTACA
ATAGAAACCAAACCAAATGGGCACCCTCGGTTGCCGGGGGCAGGTGGGGAGGGGGGTGGGAAGAAGGGATGTCTGT
CTGTCGTCCCCCTCCCCCTCTCCACTCTTTACCCACAAAGGCAGAAGACTGTTACACTAGGGGCTCAGCAAATTCA
ATCCCACCCTTACCAATTGAGCCAAACCTAGAAACAAACACAAAACACGAATAGTGAGAGACAAAATAGAGGAGAGA
AAGAGAGCATGAGAGGGAGCGAGACAGGCGACCAACACAGAGGAGAGAAAACAAAAATAGCAAAAAAAAAAAAAA
AA (SEQ ID NO.: 30)

B. BCY1 Amino Acid Sequence (SEQ ID NO.: 31)

```
MAELRLKGSS  NTTECVPVPT  SEHVAEIVGR  QGCKIKALRA  KTNTYIKTPV
RGEEPVFMVT  GRREDVATAR  REIISAAEHF  SMIRASRNKS  GAAFGVAPAL
PGQVTIRVRV  PYRVVGLVVG  PKGATIKRIQ  QQTNTYIITP  SRDRDPVFEI
TGAPGNVERA  REEIETHIAV  RTGKILEYNN  ENDFLAGSPD  AAIDSRYSDA
WRVHQPGCKP  LSTFRQNSLG  CIGECGVDSG  FEAPRLGEQG  GDFGYGGYLF
PGYGVGKQDV  YYGVAETSPP  LWAGQENATP  TSVLFSSASS  SSSSSAKARA
GPPGAHRSPA  TSAGPELAGL  PRRPPGEPLQ  GFSKLGGGGL  RSPGGGRDCM
VCFESEVTAA  LVPCGHNLFC  MECAVRICER  TDPECPVCHI  TAAQAIRIFS
```

FIGURE 11

```
ATGACAAAGAGGAAGAAGACCATCAACCTTAATATACAAGACGCCCAGAAGAGGACTGCTCTACACTGGGCCTGTGT
CAATGGCCATGAGGAAGTAGTAACATTTCTGGTAGACAGAAAGTGCCAGCTTGACGTCCTTGATGGCGAACACAGGA
CACCTCTGATGAAGGCTCTACAATGCCATCAGGAGGCTTGTGCAAATATTCTGATAGATTCTGGTGCCGATATAAAT
CTCGTAGATGTGTATGGCAACATGGCTCTCCATTATGCTGTTTATAGTGAGATTTTGTCAGTGGTGGCAAAACTGCT
GTCCCATGGTGCAGTCATCGAAGTGCACAACAAGGCTAGCCTCACACCACTTTTACTATCCATAACGAAAAGAAGTG
AGCAAATTGTGGAATTTTTGCTGATAAAAAATGCAAATGCGAATGCAGTTAATAAGTATAAATGCACAGCCCTCATG
CTTGCTGTATGTCATGGATCATCAGAGATAGTTGGCATGCTTCTTCAGCAAAATGTTGACGTCTTTGCTGCAGATAT
ATGTGGAGTAACTGCAGAACATTATGCTGTTACTTGTGGATTTCATCACATTCATGAACAAATTATGGAATATATAC
GAAAATTATCTAAAAATCATCAAAATACCAATCCAGAAGGAACATCTGCAGGAACACCTGATGAGGCTGCACCCTTG
GCGGAAAGAACACCTGACACAGCTGAAAGCTTGGTGGAAAAAACACCTGATGAGGCTGCACCCTTGGTGGAAAGAAC
ACCTGACACGGCTGAAAGCTTGGTGGAAAAAACACCTGATGAGGCTGCATCCTTGGTGGAGGGAACATCTGACAAAA
TTCAATGTTTGGAGAAAGCGACATCTGGAAAGTTCGAACAGTCAGCAGAAGAAACACCTAGGGAAATTACGAGTCCT
GCAAAAGAAACATCTGAGAAATTTACGTGGCCAGCAAAAGGAAGACCTAGGAAGATCGCATGGGAGAAAAAGAAGA
CACACCTAGGGAAATTATGAGTCCCGCAAAAGAAACATCTGAGAAATTTACGTGGGCAGCAAAAGGAAGACCTAGGA
AGATCGCATGGGAGAAAAAGAAACACCTGTAAAGACTGGATGCGTGGCAAGAGTAACATCTAATAAAAACTAAAGTT
TTGGAAAAAGGAAGATCTAAGATGATTGCATGTCCTACAAAAGAATCATCTACAAAAGCAAGTGCCAATGATCAGAG
GTTCCCATCAGAATCCAAACAAGAGGAAGATGAAGAATATTCTTGTGATTCTCGGAGTCTCTTTGAGAGTTCTGCAA
AGATTCAAGTGTGTATACCTGAGTCTATATATCAAAAAGTAATGGAGATAAATAGAGAAGTAGAAGAGCCTCCTAAG
AAGCCATCTGCCTTCAAGCCTGCCATTGAAATGCAAAACTCTGTTCCAAATAAAGCCTTTGAATTGAAGAATGAACA
AACATTGAGAGCAGATCCGATGTTCCCACCAGAATCCAAACAAAAGGACTATGAAGAAAATTCTTGGGATTCTGAGA
GTCTCTGTGAGACTGTTTCACAGAAGGATGTGTGTTTACCCAAGGCTACACATCAAAAAGAAATAGATAAAATAAAT
GGAAAATTAGAAGAGTCTCCTAATAAAGATGGTCTTCTGAAGGCTACCTGCGGAATGAAAGTTTCTATTCCAACTAA
AGCCTTAGAATTGAAGGACATGCAAACTTTCAAAGCGGAGCCTCCGGGAAGCCATCTGCCTTCGAGCCTGCCACTG
AAATGCAAAAGTCTGTCCCAAATAAAGCCTTGGAATTGAAAAATGAACAAACATGGAGAGCAGATGAGATACTCCCA
TCAGAATCCAAACAAAAGGACTATGAAGAAAATTCTTGGGATACTGAGAGTCTCTGTGAGACTGTTTCACAGAAGGA
TGTGTGTTTACCCAAGGCTGCGCATCAAAAAGAAATAGATAAAATAAATGGAAAATTAGAAGGGTCTCCTGTTAAAG
ATGGTCTTCTGAAGGCTAACTGCGGAATGAAAGTTTCTATTCCAACTAAAGCCTTAGAATTGATGGACATGCAAACT
TTCAAAGCAGAGCCTCCCGAGAAGCCATCTGCCTTCGAGCCTGCCATTGAAATGCAAAAGTCTGTTCCAAATAAAGC
CTTGGAATTGAAGAATGAACAAACATTGAGAGCAGATCCCATCAGAATCCAAACAAAAGGACTATGAAG
AAAGTTCTTGGGATTCTGAGAGTCTCTGTGAGACTGTTTCACAGAAGGATGTGTGTTTACCCAAGGCTACACATCAA
AAAGAAATAGATAAAATAAATGGAAAATTAGAAGAGTCTCCTGATAATGATGGTTTTCTGAAGGCTCCCTGCAGAAT
GAAAGTTTCTATTCCAACTAAAGCCTTAGAATTGATGGACATGCAAACTTTCAAAGCAGAGCCTCCCGAGAAGCCAT
CTGCCTTCGAGCCTGCCATTGAAATGCAAAAGTCTGTTCCAAATAAAGCCTTGGAATTGAAGAATGAACAAACATTG
AGAGCAGATCAGATGTTCCCTTCAGAATCAAAACAAAAGAAGGTTGAAGAAAATTCTTGGGATTCTGAGAGTCTCCG
TGAGACTGTTTCACAGAAGGATGTGTGTGTAGAAGGCTACACATCAAAAAGAAATGGATAAAATAAGTGGAAAAT
TAGAAGATTCAACTAGCCTATCAAAAATCTTGGATACAGTTCATTCTTGTGAAAGAGCAAGGGAACTTCAAAAAGAT
CACTGTGAACAACGTACAGGAAAAATGGAACAAATGAAAAAGAAGTTTTGTGTACTGAAAAAGAAACTGTCAGAAGC
AAAAGAAATAAATCACAGTTAGAGAACCAAAAAGTTAAATGGGAACAAGAGCTCTGCAGTGTGAGATTGACTTTAA
ACCAAGAAGAAGAGAAGAGAAGAAATGCCGATATATTAAATGAAAAAATTAGGGAAGAATTAGGAAGAATCGAAGAG
CAGCATAGGAAAGAGTTAGAAGTGAAACAACAACTTGAACAGGCTCTCAGAATACAAGATATAGAATTGAAGAGTGT
AGAAAGTAATTTGAATCAGGTTTCTCACACTCATGAAAATGAAAATTATCTCTTACATGAAAATTGCATGTTGAAAA
AGGGAAATTGCCATGCTAAAACTGGAAATAGCCACACTGAAACACCAATACCAGGAAAAGGAAAATAAATACTTTGAG
GACATTAAGATTTTAAAAGAAAAGAATGCTGAACTTCAGATGACCCTAAAACTGAAAGAGGAATCATTAACTAAAAG
GGCATCTCAATATAGTGGGCAGCTTAAAGTTCTGATAGCTGAGAACACAATGCTCACTTCTAAATTGAAGGAAAAAC
AAGACAAAGAAATACTAGAGGCAGAAATTGAATCACACCATCCTAGACTGGCTTCTGCTGTACAAGACCATGATCAA
ATTGTGACATCAAGAAAAAGTCAAGAACCTGCTTTCCACATTGCAGGAGATGCTTGTTTGCAAAGAAAAATGAATGT
TGATGTGAGTAGTACGATATATAACAATGAGGTGCTCCATCAACCACTTTCTGAAGCTCAAAGGAAATCCAAAAGCC
TAAAAATTAATCTCAATTATGCAGGAGATGCTCTAAGAGAAAATACATTGGTTTCAGAACATGCACAAAGAGACCAA
CGTGAAACAGTGTCAAATGAAGGAAGCTGAACACATGTATCAAAACGAACAAGATAATGTGAACAAACACACTGA
ACAGCAGGAGTCTCTAGATCAGAAATTATTTCAACTACAAAGCAAAAATATGTGGCTTCAACAGCAATTAGTTCATG
CACATAAGAAAGCTGACAACAAAAGCAAGATAACAATTGATATTCATTTCTTGAGAGGAAAATGCAACATCATCTC
CTAAAAGAGAAAAATGAGGAGATATTTAATTACAATAAGCATTTAAAAAACCGTATATATCAATATGAAAAAGAGAA
AGCAGAAACAGAAAACTCATGA (SEQ ID NO.: 32)
```

FIGURE 12

MTKRKKTINLNIQDAQKRTALHWACVNGHEEVVTFLVDRKCQLDVLDGEHRTPLMKALQCHQEACANILIDSGADIN
LVDVYGNMALHYAVYSEILSVVAKLLSHGAVIEVHNKASLTPLLLSITKRSEQIVEFLLIKNANANAVNKYKCTALM
LAVCHGSSEIVGMLLQQNVDVFAADICGVTAEHYAVTCGFHHIHEQIMEYIRKLSKNHQNTNPEGTSAGTPDEAAPL
AERTPDTAESLVEKTPDEAAPLVERTPDTAESLVEKTPDEAASLVEGTSDKIQCLEKATSGKFEQSAEETPREITSP
AKETSEKFTWPAKGRPRKIAWEKKEDTPREIMSPAKETSEKFTWAAKGRPRKIAWEKKETPVKTGCVARVTSNKTKV
LEKGRSKMIACPTKESSTKASANDQRFPSESKQEEDEEYSCDSRSLFESSAKIQVCIPESIYQKVMEINREVEEPPK
KPSAFKPAIEMQNSVPNKAFELKNEQTLRADPMFPPESKQKDYEENSWDSESLCETVSQKDVCLPKATHQKEIDKIN
GKLEESPNKDGLLKATCGMKVSIPTKALELKDMQTFKAEPPGKPSAFEPATEMQKSVPNKALELKNEQTWRADEILF
SESKQKDYEENSWDTESLCETVSQKDVCLPKAAHQKEIDKINGKLEGSPVKDGLLKANCGMKVSIPTKALELMDMQT
FKAEPPEKPSAFEPAIEMQKSVPNKALELKNEQTLRADEILPSESKQKDYEESSWDSESLCETVSQKDVCLPKATHQ
KEIDKINGKLEESPDNDGPLKAPCRMKVSIPTKALELMDMQTFKAEPPERPSAFEPAIEMQKSVFNKALELKNEQTL
RADQMFPSESKQKKVEENSWDSESLRETVSQKDVCVPKATHQKEMDKISGKLEDSTSLSKILDTVHSCERARELQKD
HCEQRTGKMEQMKKKFCVLKKKLSEAKEIKSQLENQKVKWEQELCSVRLTLNQEEEKRRNADILNEKIREELGRIEE
QHRKELEVKQQLEQALRIQDIELKSVESNLNQVSHTHENENYLLHENCMLKKETAMLKLEIATLKHQYQEKENKYFE
DIKILKERNAELQMTLKLKEESLTKRASQYSGQLKVLIAENTMLTSKLKEKQDKEILEAEIESHHPRLASAVQDHDQ
IVTSRKSQEPAFHIAGDACLQRKMNVDVSSTIYNNEVLHQPLSEAQRKSKSLKINLNYAGDALRENTLVSEHAQRDQ
RETQCQMKEAEHMYQNEQDNVNKHTEQQESLDQKLFQLQSKNMWLQQQLVHAHKKADNKSKITIDIHFLERKMQHHL
LKEKNEEIFNYNNHLKNRIYQYEKEKAETENS (SEQ ID NO.: 33)

FIGURE 14

A. BCZ4 cDNA

ATGGACATTGAAGCATATCTTGAAAGAATTGGCTATAAGAAGTCTAGGAACAAATTGGACTTGGAAACATTAACTGA
CATTCTTCAACACCAGATCCGAGCTGTTCCCTTTGAGAACCTTAACATCCATTGTGGGGATGCCATGGACTTAGGCT
TAGAGGCCATTTTTGATCAAGTTGTGAGAAGAAATCGGGGTGGATGGTGTCTCCAGGTCAATCATCTTCTGTACTGG
GCTCTGACCACTATTGGTTTTGAGACCACGATGTTGGGAGGGTATGTTTACAGCACTCCAGCCAAAAAATACAGCAC
TGGCATGATTCACCTTCTCCTGCAGGTGACCATTGATGGCAGGAACTACATTGTCGATGCTGGGTTTGGACGCTCAT
ACCAGATGTGGCAGCCTCTGGAGTTAATTTCTGGGAAGGATCAGCCTCAGGTGCCTTGTGTCTTCCGTTTGACGGAA
GAGAATGGATTCTGGTATCTAGACCAAATCAGAAGGGAACAGTACATTCCAAATGAAGAATTTCTTCATTCTGATCT
CCTAGAAGACAGCAAATACCGAAAAATCTACTCCTTTACTCTTAAGCCTCGAACAATTGAAGATTTTGAGTCTATGA
ATACATACCTGCAGACATCTCCATCATCTGTGTTTACTAGTAAATCATTTTGTTCCTTGCAGACCCCAGATGGGGTT
CACTGTTTGGTGGGCTTCACCCTCACCCATAGGAGATTCAATTATAAGGACAATACAGATCTAATAGAGTTCAAGAC
TCTGAGTGAGGAAGAAATAGAAAAAGTGCTGAAAAATATATTTAATATTTCCTTGCAGAGAAAGCTTGTGCCCAAAC
ATGGTGATAGATTTTTTACTATTTAG (SEQ ID NO.: 34)

B. BCZ4 Amino Acid Sequence

MDIEAYLERIGYKKSRNKLDLETLTDILQHQIRAVPFENLNIHCGDAMDLGLEAIFDQVVRRNRGGWCLQVNHLLYW
ALTTIGFETTMLGGYVYSTPAKKYSTGMIHLLLQVTIDGRNYIVDAGFGRSYQMWQPLELISGKDQPQVPCVFRLTE
ENGFWYLDQIRREQYIPNEEFLHSDLLEDSKYRKIYSFTLKPRTIEDFESMNTYLQTSPSSVFTSKSFCSLQTPDGV
HCLVGFTLTHRRFNYKDNTDLIEFKTLSEEEIEKVLKNIFNISLQRKLVPKHGDRFFTI (SEQ ID NO.: 35)

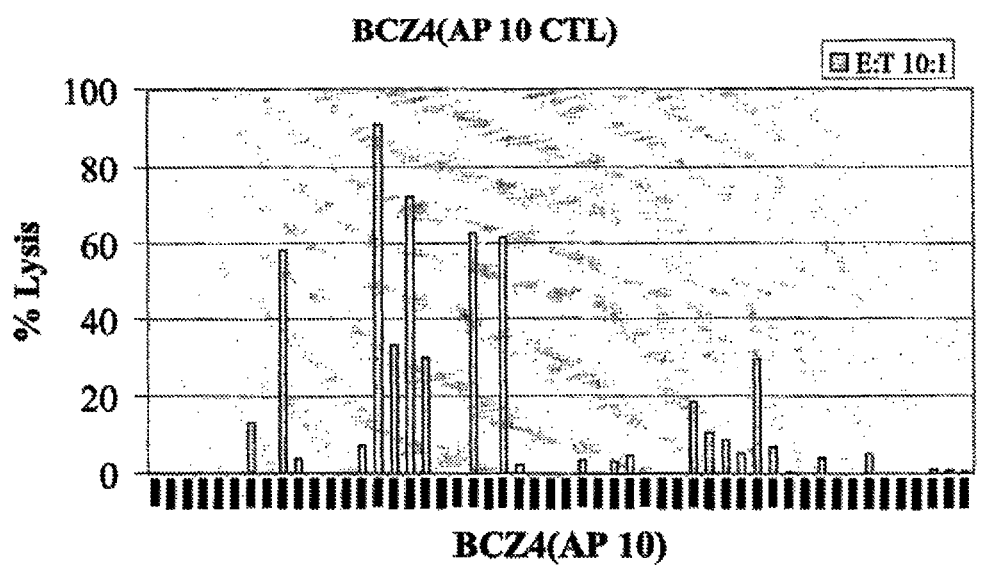

FIGURE 16

A. BFY3 cDNA

```
ATGCTTTGGAAATTGACGGATAATATCAAGTACGAGGACTGCGAGGACCGTCACGACGGCACCA
GCAACGGGACGGCACGGTTGCCCCAGCTGGGCACTGTAGGTCAATCTCCCTACACGAGCGCCCC
GCCGCTGTCCCACACCCCCAATGCCGACTTCCAGCCCCCATACTTCCCCCCACCCTACCAGCCT
ATCTACCCCCAGTCGCAAGATCCTTACTCCCACGTCAACGACCCCTACAGCCTGAACCCCCTGC
ACGCCCAGCCGCAGCCGCAGCACCCAGGCTGGCCCGGCCAGAGGCAGAGCCAGGAGTCTGGGCT
CCTGCACACGCACCGGGGGCTGCCTCACCAGCTGTCGGGCCTGGATCCTCGCAGGGACTACAGG
CGGCACGAGGACCTCCTGCACGGCCCACACGCGCTCAGCTCAGGACTCGGAGACCTCTCGATCC
ACTCCTTACCTCACGCCATCGAGGAGGTCCCGCATGTAGAAGACCCGGGTATTAACATCCCAGA
TCAAACTGTAATTAAGAAAGGCCCCGTGTCCCTGTCCAAGTCCAACAGCAATGCCGTCTCCGCC
ATCCCTATTAACAAGGACAACCTCTTCGGCGGCGTGGTGAACCCCAACGAAGTCTTCTGTTCAG
TTCCGGGTCGCCTCTCGCTCCTCAGCTCCACCTCGAAGTACAAGGTCACGGTGGCGGAAGTGCA
GCGGCGGCTCTCACCACCCGAGTGTCTCAACGCGTCGCTGCTGGGCGGAGTGCTCCGGAGGGCG
AAGTCTAAAAATGGAGCAAGATCTTTAAGAGAAAAACTGGACAAAATAGGATTAAATCTGCCTG
CAGGGAGACGTAAAGCTGCCAACGTTACCCTGCTCACATCACTAGTAGAGGGAGAAGCTGTCCA
CCTAGCCAGGGACTTTGGGTACGTGTGCGAAACCGAATTTCCTGCCAAAGCAGTAGCTGAATTT
CTCAACCGACAACATTCCGATCCCAATGAGCAAGTGACAAGAAAAAACATGCTCCTGGCTACAA
AACAGATATGCAAAGAGTTCACCGACCTGCTGGCTCAGGACCGATCTCCCCTGGGGAACTCACG
GCCCAACCCCATCCTGGAGCCCGGCATCCAGAGCTGCTTGACCCACTTCAACCTCATCTCCCAC
GGCTTCGGCAGCCCCGCGGTGTGTGCCGCGGTCACGGCCCTGCAGAACTATCTCACCGAGGCCC
TCAAGGCCATGGACAAAATGTACCTCAGCAACAACCCCAACAGCCACACGGACAACAACGCCAA
AAGCAGTGACAAGAGGAGAAGCACAGAAAGTGA (SEQ ID NO.: 36)
```

B. BFY3 Amino Acid

```
MLWKLTDNIK  YEDCEDRHDG  TSNGTARLPQ  LGTVGQSPYT  SAPPLSHTPN
ADFQPPYFPP  PYQPIYPQSQ  DPYSHVNDPY  SLNPLHAQPQ  PQHPGWPGQR
QSQESGLLHT  HRGLPHQLSG  LDPRRDYRRH  EDLLHGPHAL  SSGLGDLSIH
SLPHATEEVP  HVEDPGINIP  DQTVIKKGPV  SLSKSNSNAV  SAIPINKDNL
FGGVVNPNEV  FCSVPGRLSL  LSSTSKYKVT  VAEVQRRLSP  PECLNASLLG
GVLRRAKSKN  GGRSLREKLD  KIGLNLPAGR  RKAANVTLLT  SLVEGEAVHL
ARDFGYVCET  EFPAKAVAEF  LNRQHSDPNE  QVTRKNMLLA  TKQICKEFTD
LLAQDRSPLG  NSRPNPILEP  GIQSCLTHFN  LISHGFGSPA  VCAAVTALQN
YLTEALKAMD  KMYLSNNPNS  HTDNNAKSSD  KEEKHRK (SEQ ID NO.: 37)
```

TUMOR ANTIGENS FOR PREVENTION AND/OR TREATMENT OF CANCER

RELATED APPLICATIONS

This application claims priority to Ser. Nos. 60/471,119 filed May 16, 2003 and 60/471,193 filed May 16, 2003.

SEQUENCE LISTING

The instant application contains a Sequence Listing which has been submitted as an ASCII text file in the instant application via EFS-Web on Jan. 19, 2012 and is hereby incorporated by reference in its entirety. The ASCII copy was created on Jan. 20, 2012, is named 10557066SEQ-2.txt and is 157 kilobytes in size.

FIELD OF THE INVENTION

The present invention relates to a nucleic acid encoding a polypeptide and the use of the nucleic acid or polypeptide in preventing and/or treating cancer. In particular, the invention relates to improved vectors for the insertion and expression of foreign genes encoding tumor antigens for use in immunotherapeutic treatment of cancer.

BACKGROUND OF THE INVENTION

There has been tremendous increase in last few years in the development of cancer vaccines with Tumour-associated antigens (TAAs) due to the great advances in identification of molecules based on the expression profiling on primary tumours and, normal cells with the help of several techniques such as high density microarray, SEREX, immunohistochemistry (IHC), RT-PCR, in-situ hybridization (ISH) and laser capture microscopy (Rosenberg, Immunity, 1999; Sgroi et al, 1999, Schena et al, 1995, Offring a et al, 2000). The TAAs are antigens expressed or over-expressed by tumour cells and could be specific to one or several tumours for example CEA antigen is expressed in colorectal, breast and lung cancers. Sgroi et al (1999) identified several genes differentially expressed in invasive and metastatic carcinoma cells with combined use of laser capture microdissection and cDNA microarrays. Several delivery systems like DNA or viruses could be used for therapeutic vaccination against human cancers (Bonnet et al, 2000) and can elicit immune responses and also break immune tolerance against TAAs. Tumour cells can be rendered more immunogenic by inserting transgenes encoding T cell co-stimulatory molecules such as B7.1 or cytokines such as IFN-γ, IL2, or GM-CSF, among others. Co-expression of a TAA and a cytokine or a co-stimulatory molecule has also been shown to be useful in developing effective therapeutic vaccines (Hodge et al, 95, Bronte et al, 1995, Chamberlain et al, 1996).

There is a need in the art for reagents and methodologies useful in stimulating an immune response to prevent or treat cancers. The present invention provides such reagents and methodologies which overcome many of the difficulties encountered by others in attempting to treat cancer.

SUMMARY OF THE INVENTION

The present invention provides an immunogenic target for administration to a patient to prevent and/or treat cancer. In particular, the immunogenic target is a tumor antigen ("TA") and/or an angiogenesis-associated antigen ("AA"). In one embodiment, the immunogenic target is encoded by SEQ ID NO.: 34 or SEQ ID NO.: 36 or has the amino acid sequence of SEQ ID NO.: 35 or SEQ ID NO.: 37. In certain embodiments, the TA and/or AA are administered to a patient as a nucleic acid contained within a plasmid or other delivery vector, such as a recombinant virus. The TA and/or AA may also be administered in combination with an immune stimulator, such as a co-stimulatory molecule or adjuvant.

BRIEF DESCRIPTION OF THE DRAWINGS

FIG. 1. A, B. Nucleotide sequences of AAC2-1 and AAC2-2. C. Alignment of predicted amino acid sequence of AAC2-1 and AAC2-2. Missing nucleotides or amino acids are indicated by a "*". Differences between sequences are underlined.

FIG. 7. BFA4 cDNA sequence.

FIG. 8. BFA4 amino acid sequence.

FIG. 9. BCY1 nucleotide (A) and amino acid (B) sequences.

FIG. 11. BFA5 cDNA sequence.

FIG. 12. BFA5 amino acid sequence.

FIG. 14. BCZ4 cDNA (A) and amino acid (B) sequences.

FIG. 16. BFY3 cDNA (A) and amino acid (B) sequences.

DETAILED DESCRIPTION

Figure 2:
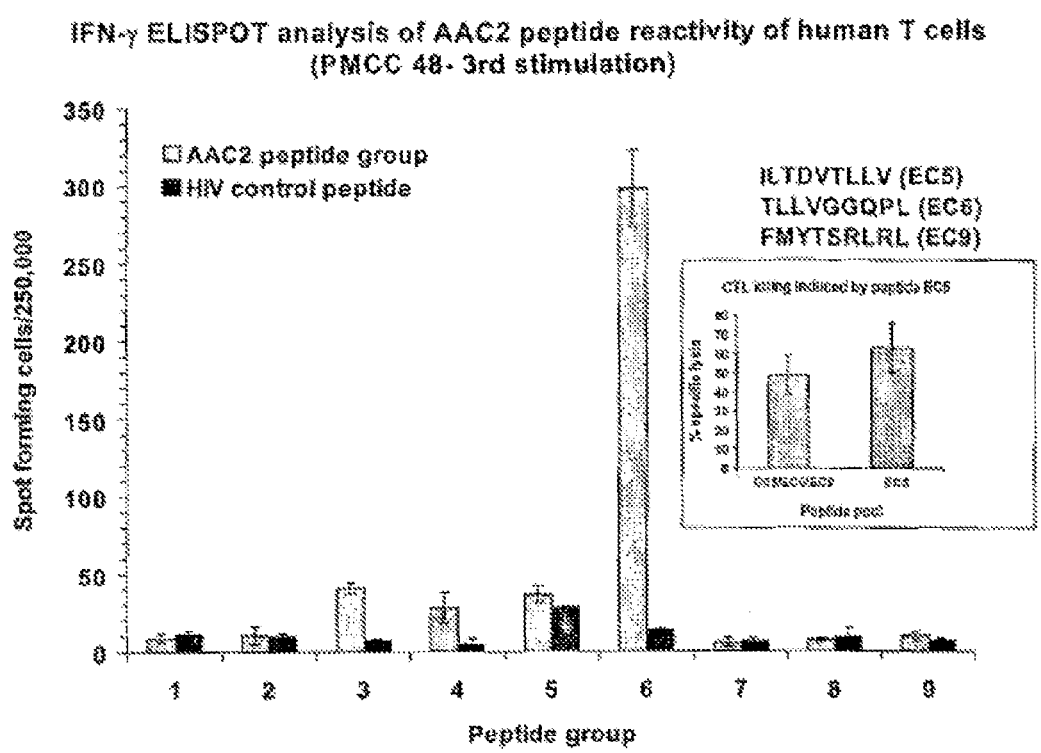
FIG. 2. A Human lymphocytes differentiate into effector cells secreting IFN-γ in response to peptides derived from the AAC2-2 protein. T cells were stimulated with the groups of peptides shown in Table III (groups 1-9). After three rounds of stimulation, the lymphocytes were analyzed for peptide-specific IFN-γ production by ELISPOT. The graph in the inset shows that activated cells stimulated by peptide Group #6 (EC5 (SEQ ID NO: 68), EC6 (SEQ ID NO: 69), and EC9 (SEQ ID NO: 70)) are capable of antigen-specific CTL activity killing peptide loaded T2 target cells. Peptide EC5 elicits dominant activity in inducing both CTL activity and IFN-γ secretion.

The present invention provides reagents and methodologies useful for treating and/or preventing cancer. All references cited within this application are incorporated by reference.

In one embodiment, the present invention relates to the induction or enhancement of an immune response against one or more tumor antigens ("TA") to prevent and/or treat cancer. In certain embodiments, one or more TAs may be combined. In preferred embodiments, the immune response results from expression of a TA in a host cell following administration of a nucleic acid vector encoding the tumor antigen or the tumor antigen itself in the form of a peptide or polypeptide, for example.

As used herein, an "antigen" is a molecule such as a polypeptide or a portion thereof that produces an immune response in a host to whom the antigen has been administered. The immune response may include the production of antibodies that bind to at least one epitope of the antigen and/or the generation of a cellular immune response against cells expressing an epitope of the antigen. The response may be an enhancement of a current immune response by, for example, causing increased antibody production, production of antibodies with increased affinity for the antigen, or an increased or more effective cellular response (i.e., increased T cells or T cells with higher anti-tumor activity). An antigen that produces an immune response may alternatively be referred to as being immunogenic or as an immunogen. In describing the present invention, a TA may be referred to as an "immunogenic target".

TA includes both tumor-associated antigens (TAAs) and tumor-specific antigens (TSAs), where a cancerous cell is the source of the antigen. A TAA is an antigen that is expressed on the surface of a tumor cell in higher amounts than is observed on normal cells or an antigen that is expressed on normal cells during fetal development. A TSA is an antigen that is unique to tumor cells and is not expressed on normal cells. TA further includes TAAs or TSAs, antigenic fragments thereof, and modified versions that retain their antigenicity.

TAs are typically classified into five categories according to their expression pattern, function, or genetic origin: cancer-testis (CT) antigens (i.e., MAGE, NY-ESO-1); melanocyte differentiation antigens (i.e., Melan A/MART-1, tyrosinase, gp100); mutational antigens (i.e., MUM-1, p53, CDK-4); overexpressed 'self' antigens (i.e., HER-2/neu, p53); and, viral antigens (i.e., HPV, EBV). For the purposes of practicing the present invention, a suitable TA is any TA that induces or enhances an anti-tumor immune response in a host in whom the TA is expressed. Suitable TAs include, for example, gp100 (Cox et al., *Science*, 264:716-719 (1994)), MART-1/Melan A (Kawakami et al., *J. Exp. Med.*, 180:347-352 (1994)), gp75 (TRP-1) (Wang et al., *J. Exp. Med.*, 186: 1131-1140 (1996)), tyrosinase (Wolfel et al., *Eur. J. Immunol.*, 24:759-764 (1994); WO 200175117; WO 200175016; WO 200175007), NY-ESO-1 (WO 98/14464; WO 99/18206), melanoma proteoglycan (Hellstrom et al., *J. Immunol.*, 130:1467-1472 (1983)), MAGE family antigens (i.e., MAGE-1, 2, 3, 4, 6, 12, 51; Van der Bruggen et al., *Science*, 254:1643-1647 (1991); U.S. Pat. No. 6,235,525; CN 1319611), BAGE family antigens (Boel et al., *Immunity*, 2:167-175 (1995)), GAGE family antigens (i.e., GAGE-1,2; Van den Eynde et al., *J. Exp. Med.*, 182:689-698 (1995); U.S. Pat. No. 6,013,765), RAGE family antigens (i.e., RAGE-1; Gaugler et al., *Immunogenetics*, 44:323-330 (1996); U.S. Pat. No. 5,939,526), N-acetylglucosaminyltransferase-V (Guilloux et al., *J. Exp. Med.*, 183:1173-1183 (1996)), p15 (Robbins et al., *J. Immunol.* 154:5944-5950 (1995)), β-catenin (Robbins et al., *J. Exp. Med.*, 183:1185-1192 (1996)), MUM-1 (Coulie et al., *Proc. Natl. Acad. Sci.* USA, 92:7976-7980 (1995)), cyclin dependent kinase-4 (CDK4) (Wolfel et al., *Science*, 269:1281-1284 (1995)), p21-ras (Fossum et al., *Int. J. Cancer*, 56:40-45 (1994)), BCR-abl (Bocchia et al., *Blood*, 85:2680-2684 (1995)), p53 (Theobald et al., *Proc. Natl. Acad. Sci.* USA, 92:11993-11997 (1995)), p185 HER2/neu (erb-B1; Fisk et al., *J. Exp. Med.*, 181:2109-2117 (1995)), epidermal growth factor receptor (EGFR) (Harris et al., *Breast Cancer Res. Treat*, 29:1-2 (1994)), carcinoembryonic antigens (CEA) (Kwong et al., *J. Natl. Cancer Inst.*, 85:982-990 (1995) U.S. Pat. Nos. 5,756,103; 5,274,087; 5,571,710; 6,071,716; 5,698,530; 6,045,802; EP 263933; EP 346710; and, EP 784483); carcinoma-associated mutated mucins (i.e., MUC-1 gene products; Jerome et al., *J. Immunol.*, 151:1654-1662 (1993)); EBNA gene products of EBV (i.e., EBNA-1; Rickinson et al., *Cancer Surveys*, 13:53-80 (1992)); E7, E6 proteins of human papillomavirus (Ressing et al., *J. Immunol*, 154:5934-5943 (1995)); prostate specific antigen (PSA; Xue et al., *The Prostate*, 30:73-78 (1997)); prostate specific membrane antigen (PSMA; Israeli, et al., *Cancer Res.*, 54:1807-1811 (1994)); idiotypic epitopes or antigens, for example, immunoglobulin idiotypes or T cell receptor idiotypes (Chen et al., *J. Immunol.*, 153:4775-4787 (1994)); KSA (U.S. Pat. No. 5,348,887), kinesin 2 (Dietz, et al. Biochem Biophys Res Commun 2000 Sep. 7; 275(3):731-8), HIP-55, TGFβ-1 anti-apoptotic factor (Toomey, et al. Br J Biomed Sci 2001; 58(3): 177-83), tumor protein D52 (Bryne J. A., et al., Genomics, 35:523-532 (1996)), HIFT, NY-BR-1 (WO 01/47959), NY-BR-62, NY-BR-75, NY-BR-85, NY-BR-87, NY-BR-96 (Scanlan, M. Serologic and Bioinformatic Approaches to the Identification of Human Tumor Antigens, in *Cancer Vaccines* 2000, Cancer Research Institute, New York, N.Y.), BFA4 (SEQ ID NOS.: 28 and 29), BCY1 (SEQ ID NOS.: 30 and 31), BFA5 (SEQ ID NOS.: 32 and 33), BCZ4 (SEQ ID NOS.: 34 and 35), and BFY3 (SEQ ID NOS. 36 and 37), including "wild-type" (i.e., normally encoded by the genome, naturally-occurring), modified, and mutated versions as well as other fragments and derivatives thereof. Any of these TAs may be utilized alone or in combination with one another in a co-immunization protocol.

In certain cases, it may be beneficial to co-immunize patients with both TA and other antigens, such as angiogenesis-associated antigens ("AA"). An AA is an immunogenic molecule (i.e., peptide, polypeptide) associated with cells involved in the induction and/or continued development of blood vessels. For example, an AA may be expressed on an endothelial cell ("EC"), which is a primary structural component of blood vessels. For treatment of cancer, it is preferred that that the AA be found within or near blood vessels that supply a tumor. Immunization of a patient against an AA preferably results in an anti-AA immune response whereby angiogenic processes that occur near or within tumors are prevented and/or inhibited.

Exemplary AAs include, for example, vascular endothelial growth factor (i.e., VEGF; Bernardini, et al. *J. Urol.*, 2001, 166(4): 1275-9; Starnes, et al. *J. Thorac. Cardiovasc. Surg.,* 2001, 122(3): 518-23; Dias, et al. *Blood,* 2002, 99: 2179-2184), the VEGF receptor (i.e., VEGF-R, flk-1/KDR; Starnes, et al. *J. Thorac. Cardiovasc. Surg.,* 2001, 122(3): 518-23), EPH receptors (i.e., EPHA2; Gerety, et al. 1999, *Cell,* 4: 403-414), epidermal growth factor receptor (i.e., EGFR; Ciardeillo, et al. Clin. Cancer Res., 2001, 7(10): 2958-70), basic fibroblast growth factor (i.e., bFGF; Davidson, et al. Clin. Exp. Metastasis 2000, 18(6): 501-7; Poon, et al. Am J. Surg., 2001, 182(3):298-304), platelet-derived cell growth factor (i.e., PDGF-B), platelet-derived endothelial cell growth factor (PD-ECGF; Hong, et al. J. Mol. Med., 2001, 8(2):141-8), transforming growth factors (i.e., TGF-α; Hong, et al. J. Mol. Med., 2001, 8(2):141-8), endoglin (Balza, et al. *Int. J. Cancer,* 2001, 94: 579-585), Id proteins (Benezra, R. Trends Cardiovasc. Med., 2001, 11(6):237-41), proteases such as uPA, uPAR, and matrix metalloproteinases (MMP-2, MMP-9; Djonov, et al. J. Pathol., 2001, 195(2):147-55), nitric oxide synthase (Am. J. Ophthalmol., 2001, 132(4):551-6), aminopeptidase (Rouslhati, E. Nature Cancer, 2: 84-90, 2002), thrombospondins (i.e., TSP-1, TSP-2; Alvarez, et al. Gynecol. Oncol., 2001, 82(2):273-8; Seki, et al. Int. J. Oncol., 2001, 19(2):305-10), k-ras (Zhang, et al. Cancer Res., 2001, 61(16):6050-4), Wnt (Zhang, et al. *Cancer Res.,* 2001, 61(16):6050-4), cyclin-dependent kinases (CDKs; Drug Resist. Updat. 2000, 3(2):83-88), microtubules (Timar, et al. 2001. *Path. Oncol. Res.,* 7(2): 85-94), heat shock proteins (i.e., HSP90 (Timar, supra)), heparin-binding factors (i.e., heparinase; Gohji, et al. Int. J. Cancer, 2001, 95(5):295-301), synthases (i.e., ATP synthase, thymidilate synthase), collagen receptors, integrins (i.e., αυ3, αυβ5, α1β1, α2β1, α5β1), the surface proteolglycan NG2, AAC2-1 (SEQ ID NO.:1), or AAC2-2 (SEQ ID NO.:2), among others, including "wild-type" (i.e., normally encoded by the genome, naturally-occurring), modified, mutated versions as well as other fragments and derivatives thereof. Any of these targets may be suitable in practicing the present invention, either alone or in combination with one another or with other agents.

In certain embodiments, a nucleic acid molecule encoding an immunogenic target is utilized. The nucleic acid molecule may comprise or consist of a nucleotide sequence encoding one or more immunogenic targets, or fragments or derivatives thereof, such as that contained in a DNA insert in an ATCC Deposit. The term "nucleic acid sequence" or "nucleic acid molecule" refers to a DNA or RNA sequence. The term encompasses molecules formed from any of the known base analogs of DNA and RNA such as, but not limited- to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5' methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, among others.

An isolated nucleic acid molecule is one that: (1) is separated from at least about 50 percent of proteins, lipids, carbohydrates, or other materials with which it is naturally found when total nucleic acid is isolated from the source cells; (2) is not linked to all or a portion of a polynucleotide to which the nucleic acid molecule is linked in nature; (3) is operably linked to a polynucleotide which it is not linked to in nature; and/or, (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use. As used herein, the term "naturally occurring" or "native" or "naturally found" when used in connection with biological materials such as nucleic acid molecules, polypeptides, host cells, and the like, refers to materials which are found in nature without manipulation by man. Similarly, "non-naturally occurring" or "non-native" as used herein refers to a material that is not found in nature or that has been structurally modified or synthesized by man.

The identity of two or more nucleic acid or polypeptide molecules is determined by comparing the sequences. As known in the art, "identity" means the degree of sequence relatedness between nucleic acid molecules or polypeptides as determined by the match between the units making up the molecules (i.e., nucleotides or amino acid residues). Identity measures the percent of identical matches between the smaller of two or more sequences with gap alignments (if any) addressed by a particular mathematical model or computer program (i.e., an algorithm). Identity between nucleic acid sequences may also be determined by the ability of the related sequence to hybridize to the nucleic acid sequence or isolated nucleic acid molecule. In defining such sequences, the term "highly stringent conditions" and "moderately stringent conditions" refer to procedures that permit hybridization of nucleic acid strands whose sequences are complementary, and to exclude hybridization of significantly mismatched nucleic acids. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. (see, for example, Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited)). The term "moderately stringent conditions" refers to conditions under which a DNA duplex with a greater degree of base pair mismatching than could occur under "highly stringent conditions" is able to form. Exemplary moderately stringent conditions are 0.015 M sodium chloride, 0.0015 M sodium citrate at 50-65° C. or 0.015 M sodium chloride, 0.0015 M sodium citrate, and 20% formamide at 37-50° C. By way of example, moderately stringent conditions of 50° C. in 0.015 M sodium ion will allow about a 21% mismatch. During hybridization, other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions.

Hybridization experiments are usually carried out at pH 6.8-7.4; however, at typical ionic strength conditions, the rate of hybridization is nearly independent of pH.

In certain embodiments of the present invention, vectors are used to transfer a nucleic acid sequence encoding a polypeptide to a cell. A vector is any molecule used to transfer a nucleic acid sequence to a host cell. In certain cases, an expression vector is utilized. An expression vector is a nucleic acid molecule that is suitable for transformation of a host cell and contains nucleic acid sequences that direct and/or control the expression of the transferred nucleic acid sequences. Expression includes, but is not limited to, processes such as transcription, translation, and splicing, if introns are present. Expression vectors typically comprise one or more flanking sequences operably linked to a heterologous nucleic acid sequence encoding a polypeptide. Flanking sequences may be homologous (i.e., from the same species and/or strain as the host cell), heterologous (i.e., from a species other than the host cell species or strain), hybrid (i.e., a combination of flanking sequences from more than one source), or synthetic, for example.

A flanking sequence is preferably capable of effecting the replication, transcription and/or translation of the coding sequence and is operably linked to a coding sequence. As used herein, the term operably linked refers to a linkage of polynucleotide elements in a functional relationship. For instance, a promoter or enhancer is operably linked to a coding sequence if it affects the transcription of the coding sequence. However, a flanking sequence need not necessarily be contiguous with the coding sequence, so long as it functions correctly. Thus, for example, intervening untranslated yet transcribed sequences can be present between a promoter sequence and the coding sequence and the promoter sequence may still be considered operably linked to the coding sequence. Similarly, an enhancer sequence may be located upstream or downstream from the coding sequence and affect transcription of the sequence.

In certain embodiments, it is preferred that the flanking sequence is a trascriptional regulatory region that drives high-level gene expression in the target cell. The transcriptional regulatory region may comprise, for example, a promoter, enhancer, silencer, repressor element, or combinations thereof. The transcriptional regulatory region may be either constitutive, tissue-specific, cell-type specific (i.e., the region is drives higher levels of transcription in a one type of tissue or cell as compared to another), or regulatable (i.e., responsive to interaction with a compound). The source of a transcriptional regulatory region may be any prokaryotic or eukaryotic organism, any vertebrate or invertebrate organism, or any plant, provided that the flanking sequence functions in a cell by causing transcription of a nucleic acid within that cell. A wide variety of transcriptional regulatory regions may be utilized in practicing the present invention.

Suitable transcriptional regulatory regions include, for example, the CMV promoter (i.e., the CMV-immediate early promoter); promoters from eukaryotic genes (i.e., the estrogen-inducible chicken ovalbumin gene, the interferon genes, the gluco-corticoid-inducible tyrosine aminotransferase gene, and the thymidine kinase gene); and the major early and late adenovirus gene promoters; the SV40 early promoter region (Bernoist and Chambon, 1981, *Nature* 290:304-10); the promoter contained in the 3' long terminal repeat (LTR) of Rous sarcoma virus (RSV) (Yamamoto, et al., 1980, *Cell* 22:787-97); the herpes simplex virus thymidine kinase (HSV-TK) promoter (Wagner et al., 1981, *Proc. Natl. Acad. Sci. U.S.A.* 78:1444-45); the regulatory sequences of the metallothionine gene (Brinster et al., 1982, Nature 296:39-42); prokaryotic expression vectors such as the beta-lactamase promoter (VIIIa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Tissue- and/or cell-type specific transcriptional control regions include, for example, the elastase I gene control region which is active in pancreatic acinar cells (Swift et al., 1984, Cell 38:639-46; Ornitz et al., 1986, Cold Spring Harbor Symp. Quant. Biol. 50:399-409 (1986); MacDonald, 1987, *Hepalology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region in testicular, breast, lymphoid and mast cells (Leder et al., 1986, Cell 45:485-95); the albumin gene control region, in liver (Pinkert et al., 1987, *Genes and Devel.* 1:268-76); the alpha-feto-protein gene control region in liver (Krumlauf et al., 1985, *Mol. Cell. Biol.*, 5:1639-48; Hammer et al., 1987, *Science* 235:53-58); the alpha 1-antitrypsin gene control region in liver (Kelsey et al., 1987, *Genes and Devel.* 1:161-71); the beta-globin gene control region in myeloid cells (Mogram et al., 1985, Nature 315:338-40; Kollias et al., 1986, *Cell* 46:89-94); the myelin basic protein gene control region in oligodendrocyte cells in the brain (Readhead et al., 1987, Cell 48:703-12); the myosin light chain-2 gene control region in skeletal muscle (Sani, 1985, *Nature* 314:283-86); the gonadotropic releasing hormone gene control region in the hypothalamus (Mason et al., 1986, *Science* 234:1372-78), and the tyrosinase promoter in melanoma cells (Hart, I. Semin Oncol 1996 February; 23(1):154-8; Siders, et al. *Cancer Gene Ther* 1998 Sep-Oct; 5(5):281-91), among others. Inducible promoters that are activated in the presence of a certain compound or condition such as light, heat, radiation, tetracycline, or heat shock proteins, for example, may also be utilized (see, for example, WO 00/10612). Other suitable promoters are known in the art.

As described above, enhancers may also be suitable flanking sequences. Enhancers are cis-acting elements of DNA, usually about 10-300 bp in length, that act on the promoter to increase transcription. Enhancers are typically orientation- and position-independent, having been identified both 5' and 3' to controlled coding sequences. Several enhancer sequences available from mammalian genes are known (i.e., globin, elastase, albumin, alpha-feto-protein and insulin). Similarly, the SV40 enhancer, the cytomegalovirus early promoter enhancer, the polyoma enhancer, and adenovirus enhancers are useful with eukaryotic promoter sequences. While an enhancer may be spliced into the vector at a position 5' or 3' to nucleic acid coding sequence, it is typically located at a site 5' from the promoter. Other suitable enhancers are known in the art, and would be applicable to the present invention.

While preparing reagents of the present invention, cells may need to be transfected or transformed. Transfection refers to the uptake of foreign or exogenous DNA by a cell, and a cell has been transfected when the exogenous DNA has been introduced inside the cell membrane. A number of transfection techniques are well known in the art (i.e., Graham et al., 1973, Virology 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197). Such techniques can be used to introduce one or more exogenous DNA moieties into suitable host cells.

In certain embodiments, it is preferred that transfection of a cell results in transformation of that cell. A cell is transformed when there is a change in a characteristic of the cell, being transformed when it has been modified to contain a new nucleic acid. Following transfection, the transfected nucleic acid may recombine with that of the cell by physically integrating into a chromosome of the cell, may be maintained transiently as an episomal element without being replicated, or may replicate independently as a plasmid. A cell is stably transformed when the nucleic acid is replicated with the division of the cell.

The present invention further provides isolated immunogenic targets in polypeptide form. A polypeptide is considered isolated where it: (1) has been separated from at least about 50 percent of polynucleotides, lipids, carbohydrates, or other materials with which it is naturally found when isolated from the source cell; (2) is not linked (by covalent or noncovalent interaction) to all or a portion of a polypeptide to which the "isolated polypeptide" is linked in nature; (3) is operably linked (by covalent or noncovalent interaction) to a polypeptide with which it is not linked in nature; or, (4) does not occur in nature. Preferably, the isolated polypeptide is substantially free from any other contaminating polypeptides or other contaminants that are found in its natural environment that would interfere with its therapeutic, diagnostic, prophylactic or research use.

Immunogenic target polypeptides may be mature polypeptides, as defined herein, and may or may not have an amino terminal methionine residue, depending on the method by which they are prepared. Further contemplated are related polypeptides such as, for example, fragments, variants (i.e., allelic, splice), orthologs, homologues, and derivatives, for example, that possess at least one characteristic or activity (i.e., activity, antigenicity) of the immunogenic target. Also related are peptides, which refers to a series of contiguous amino acid residues having a sequence corresponding to at least a portion of the polypeptide from which its sequence is derived. In preferred embodiments, the peptide comprises about 5-10 amino acids, 10-15 amino acids, 15-20 amino acids, 20-30 amino acids, or 30-50 amino acids. In a more preferred embodiment, a peptide comprises 9-12 amino acids, suitable for presentation upon Class I MHC molecules, for example.

A fragment of a nucleic acid or polypeptide comprises a truncation of the sequence (i.e., nucleic acid or polypeptide) at the amino terminus (with or without a leader sequence) and/or the carboxy terminus. Fragments may also include variants (i.e., allelic, splice), orthologs, homologues, and other variants having one or more amino acid additions or substitutions or internal deletions as compared to the parental sequence. In preferred embodiments, truncations and/or deletions comprise about 10 amino acids, 20 amino acids, 30 amino acids, 40 amino acids, 50 amino acids, or more. The polypeptide fragments so produced will comprise about 10 amino acids, 25 amino acids, 30 amino acids, 40 amino acids, 50 amino acids, 60 amino acids, 70 amino acids, or more. Such polypeptide fragments may optionally comprise an amino terminal methionine residue. It will be appreciated that such fragments can be used, for example, to generate antibodies or cellular immune responses to immunogenic target polypeptides.

A variant is a sequence having one or more sequence substitutions, deletions, and/or additions as compared to the subject sequence. Variants may be naturally occurring or artificially constructed. Such variants may be prepared from the corresponding nucleic-acid molecules. In preferred embodiments, the variants have from 1 to 3, or from 1 to 5, or from 1 to 10, or from 1 to 15, or from 1 to 20, or from 1 to 25, or from 1 to 30, or from 1 to 40, or from 1 to 50, or more than 50 amino acid substitutions, insertions, additions and/or deletions.

An allelic variant is one of several possible naturally-occurring alternate forms of a gene occupying a given locus on a chromosome of an organism or a population of organisms. A splice variant is a polypeptide generated from one of several RNA transcript resulting from splicing of a primary transcript. An ortholog is a similar nucleic acid or polypeptide sequence from another species. For example, the mouse and human versions of an immunogenic target polypeptide may be considered orthologs of each other. A derivative of a sequence is one that is derived from a parental sequence those sequences having substitutions, additions, deletions, or chemically modified variants. Variants may also include fusion proteins, which refers to the fusion of one or more first sequences (such as a peptide) at the amino or carboxy terminus of at least one other sequence (such as a heterologous peptide).

"Similarity" is a concept related to identity, except that similarity refers, to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Substitutions may be conservative, or non-conservative, or any combination thereof. Conservative amino acid modifications to the sequence of a polypeptide (and the corresponding modifications to the encoding nucleotides) may produce polypeptides having functional and chemical characteristics similar to those of a parental polypeptide. For example, a "conservative amino acid substitution" may involve a substitution of a native amino acid residue with a non-native residue such that there is little or no effect on the size, polarity, charge, hydrophobicity, or hydrophilicity of the amino acid residue at that position and, in particular, does not result in decreased immunogenicity. Suitable conservative amino acid substitutions are shown in Table I.

TABLE I

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptide using well-known techniques. For identifying suitable areas of the molecule that may be changed without destroying biological activity (i.e., MHC binding, immunogenicity), one skilled in the art may target areas not believed to be important for that activity. For example, when similar polypeptides with similar activities from the same species or from other species are known, one skilled in the art may compare the amino acid sequence of a polypeptide to such similar polypeptides. By performing such analyses, one can identify residues and portions of the molecules that are conserved among similar polypeptides. It will be appreciated that changes in areas of the molecule that are not conserved relative to such similar polypeptides would be less likely to adversely affect the biological activity and/or structure of a polypeptide. Similarly, the residues required for binding to MHC are known, and may be modified to improve binding. However, modifications resulting in decreased binding to MHC will not be appropriate in most situations. One skilled in the art would also know that, even in relatively conserved regions, one may substitute chemically similar amino acids for the naturally occurring residues while retaining activity. Therefore, even areas that may be important for biological activity or for structure may be subject to conservative amino acid substitutions without destroying the biological activity or without adversely affecting the polypeptide structure.

Other preferred polypeptide variants include glycosylation variants wherein the number and/or type of glycosylation sites have been altered compared to the subject amino acid sequence. In one embodiment, polypeptide variants comprise a greater or a lesser number of N-linked glycosylation sites than the subject amino acid sequence. An N-linked glycosylation site is characterized by the sequence Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. To affect O-linked glycosylation of a polypeptide, one would modify serine and/or threonine residues.

Additional preferred variants include cysteine variants, wherein one or more cysteine residues are deleted or substituted with another amino acid (e.g., serine) as compared to the subject amino acid sequence set. Cysteine variants are useful when polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, the isolated polypeptides of the current invention include fusion polypeptide segments that assist in purification of the polypeptides. Fusions can be made either at the amino terminus or at the carboxy terminus of the subject polypeptide variant thereof. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein. Suitable fusion segments include, among others, metal binding domains (e.g., a poly-histidine segment), immunoglobulin binding domains (i.e., Protein A, Protein G, T cell, B cell, Fc receptor, or complement protein antibody-binding domains), sugar binding domains (e.g., a maltose binding domain), and/or a "tag" domain (i.e., at least a portion of α-galactosidase, a strep tag peptide, a T7 tag peptide, a FLAG peptide, or other domains that can be purified using compounds that bind to the domain, such as monoclonal antibodies). This tag is typically fused to the polypeptide upon expression of the polypeptide, and can serve as a means for affinity purification of the sequence of interest polypeptide from the host cell. Affinity purification can be accomplished, for example, by column chromatography using antibodies against the tag as an affinity matrix. Optionally, the tag can subsequently be removed from the purified sequence of interest polypeptide by various means such as using certain peptidases for cleavage. As described below, fusions may also be made between a TA and a co-stimulatory components such as the chemokines CXC10 (IP-10), CCL7 (MCP-3), or CCL5 (RANTES), for example.

A fusion motif may enhance transport of an immunogenic target to an MHC processing compartment, such as the endoplasmic reticulum. These sequences, referred to as traduction or transcytosis sequences, include sequences derived from HIV tat (see Kim et al. 1997 J. Immunol. 159:1666), *Drosophila* antennapedia (see Schutze-Redelmeier et al. 1996 J. Immunol. 157:650), or human period-1 protein (hPER1; in particular, SRRHHCRSKAKRSRHH (SEQ ID NO.: 42)).

In addition, the polypeptide or variant thereof may be fused to a homologous polypeptide to form a homodimer or to a heterologous polypeptide to form a heterodimer. Heterologous peptides and polypeptides include, but are not limited to: an epitope to allow for the detection and/or isolation of a fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide or variant thereof.

In certain embodiments, it may be advantageous to combine a nucleic acid sequence encoding an immunogenic target, polypeptide, or derivative thereof with one or more co-stimulatory component(s) such as cell surface proteins, cytokines or chemokines in a composition of the present invention. The co-stimulatory component may be included in the composition as a polypeptide or as a nucleic acid encoding the polypeptide, for example. Suitable co-stimulatory molecules include, for instance, polypeptides that bind members of the CD28 family (i.e., CD28, ICOS; Hutloff, et al. *Nature* 1999, 397: 263-265; Peach, et al. *J Exp Med* 1994, 180: 2049-2058) such as the CD28 binding polypeptides B7.1 (CD80; Schwartz, 1992; Chen et al, 1992; Ellis, et al. *J. Immunol.*, 156(8): 2700-9) and B7.2 (CD86; Ellis, et al. *J. Immunol.*, 156(8): 2700-9); polypeptides which bind members of the integrin family (i.e., LFA-1 (CD11a/CD18); Sedwick, et al. *J Immunol* 1999, 162: 1367-1375; Wülfing, et al. *Science* 1998, 282: 2266-2269; Lub, et al. *Immunol Today* 1995, 16: 479-483) including members of the ICAM family (i.e., ICAM-1, -2 or -3); polypeptides which bind CD2 family members (i.e., CD2, signalling lymphocyte activation molecule (CDw150 or "SLAM"; Aversa, et al. *J Immunol* 1997, 158: 4036-4044)) such as CD58 (LFA-3; CD2 ligand; Davis, et al. *Immunol Today* 1996, 17: 177-187) or SLAM ligands (Sayos, et al. *Nature* 1998, 395: 462-469); polypeptides which bind heat stable antigen (HSA or CD24; Zhou, et al. *Eur J Immunol* 1997, 27: 2524-2528); polypeptides which bind to members of the TNF receptor (TNFR) family (i.e., 4-1BB (CD137; Vinay, et al. *Semin Immunol* 1998, 10: 481-489), OX40 (CD134; Weinberg, et al. *Semin Immunol* 1998, 10: 471-480; Higgins, et al. *J Immunol* 1999, 162: 486-493), and CD27 (Lens, et al. *Semin Immunol* 1998, 10: 491-499)) such as 4-1BBL (4-1BB ligand; Vinay, et al. *Semin Immunol* 1998, 10: 481-48; DeBenedette, et al. *J Immunol* 1997, 158: 551-559), TNFR associated factor-1 (TRAF-1; 4-1BB ligand; Saoulli, et al. *J Exp Med* 1998, 187: 1849-1862, Arch, et al. *Mol Cell Biol* 1998, 18: 558-565), TRAF-2 (4-1BB and OX40 ligand; Saoulli, et al. *J Exp Med* 1998, 187: 1849-1862; Oshima, et al. *Int Immunol* 1998, 10: 517-526, Kawamata, et al. *J Biol Chem* 1998, 273: 5808-5814), TRAF-3 (4-1BB and OX40 ligand; Arch, et al. *Mol Cell Biol* 1998, 18: 558-565; Jang, et al. *Biochem Biophys Res Commun* 1998, 242: 613-620; Kawamata S, et al. *J Biol Chem* 1998, 273: 5808-5814), OX40L (OX40 ligand; Gramaglia, et al. *J Immunol* 1998, 161: 6510-6517), TRAF-5 (OX40 ligand; Arch, et al. *Mol Cell Biol* 1998, 18: 558-565; Kawamata, et al. *J Biol Chem* 1998, 273: 5808-5814), and CD70 (CD27, ligand; Couderc, et al. *Cancer Gene Ther.,* 5(3): 163-75). CD154 (CD40 ligand or "CD40L"; Gurunathan, et al. *J. Immunol.,* 1998, 161: 4563-4571; Sine, et al. *Hum. Gene Ther.,* 2001, 12: 1091-1102) may also be suitable.

One or more cytokines may also be suitable co-stimulatory components or "adjuvants", either as polypeptides or being encoded by nucleic acids contained within the compositions of the present invention (Parmiani, et al. Immunol Lett 2000 Sep. 15; 74(1): 41-4; Berzofsky, et al. Nature Immunol. 1: 209-219). Suitable cytokines include, for example, interleukin-2 (IL-2) (Rosenberg, et al. *Nature Med.* 4: 321-327 (1998)), IL-4, IL-7, IL-12 (reviewed by Pardoll, 1992; Harries, et al. J. Gene Med. 2000 Jul-Aug; 2(4):243-9; Rao, et al. *J. Immunol.* 156: 3357-3365 (1996)), IL-15 (Xin, et al. *Vaccine,* 17:858-866, 1999), IL-16 (Cruikshank, et al. J. Leuk Biol. 67(6): 757-66, 2000), IL-18 (*J. Cancer Res. Clin. Oncol.* 2001. 127(12): 718-726), GM-CSF (CSF (Disis, et al. *Blood,* 88: 202-210 (1996)), tumor necrosis factor-alpha (TNF-α), or interferons such as IFN-α or INF-γ. Other cytokines may also be suitable for practicing the present invention, as is known in the art.

Chemokines may also be utilized. For example, fusion proteins comprising CXCL10 (IP-10) and CCL7 (MCP-3) fused to a tumor self-antigen have been shown to induce anti-tumor immunity (Biragyn, et al. *Nature Biotech.* 1999, 17: 253-258). The chemokines CCL3 (MIP-1α) and CCL5 (RANTES) (Boyer, et al. *Vaccine,* 1999, 17 (Supp. 2): S53-S64) may also be of use in practicing the present invention. Other suitable chemokines are known in the art.

It is also known in the art that suppressive or negative regulatory immune mechanisms may be blocked, resulting in enhanced immune responses. For instance, treatment with anti-CTLA-4 (Shrikant, et al. *Immunity,* 1996, 14: 145-155; Sutmuller, et al. *J. Exp. Med.,* 2001, 194: 823-832), anti-CD25 (Sutmuller, supra), anti-CD4 (Matsui, et al. *J. Immunol.,* 1999, 163: 184-193), the fusion protein IL13Ra2-Fc (Terabe, et al. *Nature Immunol.,* 2000, 1: 515-520), and combinations thereof (i.e., anti-CTLA-4 and anti-CD25, Sutmuller, supra) have been shown to upregulate anti-tumor immune responses and would be suitable in practicing the present invention.

Any of these components may be used alone or in combination with other agents. For instance, it has been shown that a combination of CD80, ICAM-1 and LFA-3 ("TRICOM") may potentiate anti-cancer immune responses (Hodge, et al. *Cancer Res.* 59: 5800-5807 (1999). Other effective combinations include, for example, IL-12+GM-CSF (Ahlers, et al. *J. Immunol.,* 158: 3947-3958 (1997); Iwasaki, et al. *J. Immunol.* 158: 4591-4601 (1997)), IL-12+GM-CSF+TNF-α (Ahlers, et al. *Int. Immunol.* 13: 897-908 (2001)), CD80+IL-12 (Fruend, et al. *Int. J. Cancer,* 85: 508-517 (2000); Rao, et al. supra), and CD86+GM-CSF+IL-12 (Iwasaki, supra). One of skill in the art would be aware of additional combinations useful in carrying out the present, invention. In addition, the skilled artisan would be aware of additional reagents or methods that may be used to modulate such mechanisms. These reagents and methods, as well as others known by those of skill in the art, may be utilized in practicing the present invention.

Additional strategies for improving the efficiency of nucleic acid-based immunization may also be used including, for example, the use of self-replicating viral replicons (Caley, et al. 1999. *Vaccine,* 17: 3124-2135; Dubensky, et al. 2000. Mol. Med. 6: 723-732; Leitner, et al. 2000. *Cancer Res.* 60: 51-55), codon optimization (Liu, et al. 2000. *Mol. Ther.,* 1: 497-500; Dubensky, supra; Huang, et al. 2001. *J. Virol.* 75: 4947-4951), in vivo electroporation (Widera, et al. 2000. *J. Immunol.* 164: 4635-3640), incorporation of CpG stimulatory motifs (Gurunathan, et al. *Ann. Rev. Immunol.,* 2000, 18: 927-974; Leitner, supra; Cho, et al. J. Immunol. 168(10): 4907-13), sequences for targeting of the endocytic or ubiquitin-processing pathways (Thomson, et al. 1998. *J. Virol.* 72: 2246-2252; Velders, et al. 2001. *J. Immunol.* 166: 5366-5373), Marek's disease virus type 1 VP22 sequences (J. Virol. 76(6):2676-82, 2002), prime-boost regimens (Gurunathan, supra; Sullivan, et al. 2000. *Nature,* 408: 605-609; Hanke, et al. 1998. Vaccine, 16: 439-445; Amara, et al. 2001. *Science,* 292: 69-74), and the use of mucosal delivery vectors such as *Salmonella* (Darji, et al. 1997. *Cell,* 91: 765-775; Woo, et al. 2001. Vaccine, 19: 2945-2954). Other methods are known in the art, some of which are described below.

Chemotherapeutic agents, radiation, anti-angiogenic compounds, or other agents may also be utilized in treating and/or preventing cancer using immunogenic targets (Sebti, et al. *Oncogene* 2000 Dec. 27; 19(56):6566-73). For example, in treating metastatic breast cancer, useful chemotherapeutic agents include cyclophosphamide, doxorubicin, paclitaxel, docetaxel, navelbine, capecitabine, and mitomycin C, among others. Combination chemotherapeutic regimens have also proven effective including cyclophosphamide+methotrexate+5-fluorouracil; cyclophosphamide+doxorubicin+5-fluorouracil; or, cyclophosphamide+doxorubicin, for example. Other compounds such as prednisone, a taxane, navelbine, mitomycin C, or vinblastine have been utilized for various reasons. A majority of breast cancer patients have estrogen-receptor positive (ER+) tumors and in these patients, endocrine therapy (i.e., tamoxifen) is preferred over chemotherapy. For such patients, tamoxifen or, as a second line therapy, progestins (medroxyprogesterone acetate or megestrol acetate) are preferred. Aromatase inhibitors (i.e., aminoglutethimide and analogs thereof such as letrozole) decrease the availability of estrogen needed to maintain tumor growth and may be used as second or third line endocrine therapy in certain patients.

Other cancers may require different chemotherapeutic regimens. For example, metastatic colorectal cancer is typically treated with Camptosar (irinotecan or CPT-11), 5-fluorouracil or leucovorin, alone or in combination with one another. Proteinase and integrin inhibitors such as the MMP inhibitors marimastate (British Biotech), COL-3 (Collagenex), Neovastat (Aeterna), AG3340 (Agouron), BMS-275291 (Bristol Myers Squibb), CGS 27023A (Novartis) or the integrin inhibitors Vitaxin (Medimmune), or MED1522 (Merck KgaA) may also be suitable for use. As such, immunological targeting of immunogenic targets associated with colorectal cancer could be performed in combination with a treatment using those chemotherapeutic agents. Similarly, chemotherapeutic agents used to treat other types of cancers are well-known in the art and may be combined with the immunogenic targets described herein.

Many anti-angiogenic agents are known in the art and would be suitable for co-administration with the immunogenic target vaccines (see, for example, Timar, et al. 2001. Pathology Oncol. Res., 7(2): 85-94). Such agents include, for example, physiological agents such as growth factors (i.e., ANG-2, NK1, 2, 4 (HGF), transforming growth factor beta (TGF-β)), cytokines (i.e., interferons such as IFN-α, -β, -γ, platelet factor 4 (PF-4), PR-39), proteases (i.e., cleaved AT-III, collagen XVIII fragment (Endostatin)), HmwKallikrein-d5 plasmin fragment (Angiostatin), prothrombin-F1-2, TSP-1), protease inhibitors (i.e., tissue inhibitor of metalloproteases such as TIMP-1, -2, or -3; maspin; plasminogen activator-inhibitors such as PAI-1; pigment epithelium derived factor (PEDF)), Tumstatin (available through ILEX, Inc.), antibody products (i.e., the collagen-binding antibodies HUIV26, HUI77, XL313; anti-VEGF; anti-integrin (i.e., Vitaxin, (Lxsys))), and glycosidases (i.e., heparinase-I, -III). "Chemical" or modified physiological agents known or believed to have anti-angiogenic potential include, for example, vinblastine, taxol, ketoconazole, thalidomide, dolestatin, combrestatin A, rapamycin (Guba, et al. 2002, Nature Med., 8: 128-135), CEP-7055 (available from Cephalon, Inc.), flavone acetic acid, Bay 12-9566 (Bayer Corp.), AG3340 (Agouron, Inc.), CGS. 27023A (Novartis), tetracylcine derivatives (i.e., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protamine), cationic peptide-VEGF, Suramin (polysulphonated napthyl urea), compounds that interfere with the function or production of VEGF (i.e., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide, 2-methoxyestradiol, aminosterols (i.e., squalamine), glutathione analogues (i.e., N-acteyl-L-cysteine), combretastatin A-4 (Oxigene), Eph receptor blocking agents (Nature, 414:933-938, 2001), Rh-Angiostatin, Rh-Endostatin (WO 01/93897), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phanylalanin-N-methylamides (i.e., Batimistat, Marimastat), AG3340, and minocycline. Many other suitable agents are known in the art and would suffice in practicing the present invention.

The present invention may also be utilized in combination with "non-traditional" methods of treating cancer. For example, it has recently been demonstrated that administration of certain anaerobic bacteria may assist in slowing tumor growth. In one study, Clostridium novyi was modified to eliminate a toxin gene carried on a phage episome and administered to mice with colorectal tumors (Dang, et al. P.N.A.S. USA, 98(26): 15155-15160, 2001). In combination with chemotherapy, the treatment was shown to cause tumor necrosis in the animals. The reagents and methodologies described in this application may be combined with such treatment methodologies.

Nucleic acids encoding immunogenic targets may be administered to patients by any of several available techniques. Various viral vectors that have been successfully utilized for introducing a nucleic acid to a host include retrovirus, adenovirus, adeno-associated Virus (AAV), herpes virus, and poxvirus, among others. It is understood in the art that many such viral vectors are available in the art. The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.).

Preferred retroviral vectors are derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include Ψ2, PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, *Hum. Gene Ther.*, 5 (3): 343-79; Culver, K., et al., *Cold Spring Harb. Symp; Quant. Biol.*, 59: 685-90); Oldfield, E., 1993, *Hum. Gene Ther.*, 4 (1): 39-69). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the nucleic acid of the vector occurs.

Adenoviral vectors have proven especially useful for gene transfer into eukaryotic cells (Rosenfeld, M., et al., 1991, *Science*, 252 (5004): 431-4; Crystal, R., et al., 1994, *Nat. Genet.*, 8 (1): 42-51), the study eukaryotic gene expression (Levrero, M., et al., 1991, *Gene*, 101 (2): 195-202), vaccine development (Graham, F. and Prevec, L., 1992, *Biotechnology*, 20: 363-90), and in animal models (Stratford-Perricaudet, L., et al., 1992, *Bone Marrow Transplant.*, 9 (Suppl. 1): 151-2; Rich, D., et al., 1993, *Hum. Gene Ther.*, 4 (4): 461-76). Experimental routes for administrating recombinant Ad to different tissues in vivo have included intratracheal instillation (Rosenfeld, M., et al., 1992, Cell, 68 (1): 143-55) injection into muscle (Quantin, B., et al., 1992, *Proc. Natl. Acad. Sci. U.S.A.*, 89 (7): 2581-4), peripheral intravenous injection (Herz, J., and Gerard, R., 1993, *Proc. Natl. Acad. Sci. U.S.A.*, 90 (7): 2812-6) and stereotactic inoculation to brain (Le Gal La Salle, G., et al., 1993, *Science*, 259 (5097): 988-90), among others.

Adeno-associated virus (AAV) demonstrates high-level infectivity, broad host range and specificity in integrating into the host cell genome (Hermonat, P., et al., 1984, *Proc. Natl. Acad. Sci. U.S.A.*, 81 (20): 6466-70). And Herpes Simplex Virus type-1 (HSV-1) is yet another attractive vector system, especially for use in the nervous system because of its neurotropic property (Geller, A., et al., 1991, *Trends Neurosci.*, 14 (10): 428-32; Glorioso, et al., 1995, *Mol. Biotechnol.*, 4 (1): 87-99; Glorioso, et al., 1995, *Annu. Rev. Microbiol.*, 49: 675-710).

Poxvirus is another useful expression vector (Smith, et al. 1983, *Gene*, 25 (1): 21-8; Moss, et al, 1992, *Biotechnology*, 20: 345-62; Moss, et al, 1992, *Curr. Top. Microbiol. Immunol.*, 158: 25-38; Moss, et al. 1991. Science, 252: 1662-1667). Poxviruses shown to be useful include vaccinia, NYVAC, avipox, fowlpox, canarypox, ALVAC, and ALVAC(2), among others.

NYVAC (vP866) was derived from the Copenhagen vaccine strain of vaccinia virus by deleting six nonessential regions of the genome encoding known or potential virulence factors (see, for example, U.S. Pat. Nos. 5,364,773 and 5,494,807). The deletion loci were also engineered as recipient loci for the insertion of foreign genes. The deleted regions are: thymidine kinase gene (TK; J2R); hemorrhagic region (u; B13R+B14R); A type inclusion body region (ATI; A26L); hemagglutinin gene (HA; A56R); host range gene region (C7L-K1L); and, large subunit, ribonucleotide reductase (I4L). NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265,189). NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

ALVAC-based recombinant viruses (i.e., ALVAC-1 and ALVAC-2) are also suitable for use in practicing the present invention (see, for example, U.S. Pat. No. 5,756,103). ALVAC(2) is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC(1) and ALVAC(2) have been demonstrated to be useful in expressing foreign DNA sequences, such as TAs (Tartaglia et al., 1993 a,b; U.S. Pat. No. 5,833,975). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is TROVAC. TROVAC refers to an attenuated fowlpox that was a plaque-cloned isolate derived from the FP-1 vaccine strain of fowlpoxvirus which is licensed for vaccination of 1 day old chicks. TROVAC was likewise deposited under the terms of the Budapest Treaty with the ATCC, accession number 2553.

"Non-viral" plasmid vectors may also be suitable in practicing the present invention. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFastBacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA Cloning® kit, PCR2.1®®plasmid derivatives, Invitrogen, Carlsbad, Calif.). Bacterial vectors may also be used with the current invention. These vectors include, for example, *Shigella, Salmonella, Vibrio cholerae, Laclobacillus, Bacille calmette guérin* (BCG), and *Streptococcus* (see for example, WO 88/6626; WO 90/0594; WO 91/13157; WO 92/1796; and WO 92/21376). Many other non-viral plasmid expression vectors and systems are known in the art and could be used with the current invention.

Suitable nucleic acid delivery techniques include DNA-ligand complexes, adenovirus-ligand-DNA complexes, direct injection of DNA, $CaPO_4$ precipitation, gene gun techniques, electroporation, and colloidal dispersion systems, among others. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.*, 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

An immunogenic target may also be administered in combination with one or more adjuvants to boost the immune response. Exemplary adjuvants are shown in Table II below:

TABLE II

Types of Immunologic Adjuvants

| Type of Adjuvant | General Examples | Specific Examples/References |
|---|---|---|
| Gel-type | Aluminum hydroxide/phosphate ("alum adjuvants") | (Aggerbeck and Heron, 1995) |
| | Calcium phosphate | (Relyveld, 1986) |

TABLE II-continued

Types of Immunologic Adjuvants

| Type of Adjuvant | General Examples | Specific Examples/References |
|---|---|---|
| Microbial | Muramyl dipeptide (MDP) | (Chedid et al., 1986) |
| | Bacterial exotoxins | Cholera toxin (CT), *E. coli* labile toxin (LT)(Freytag and Clements, 1999) |
| | Endotoxin-based adjuvants | Monophosphoryl lipid A (MPL) (Ulrich and Myers, 1995) |
| | Other bacterial | CpG oligonucleotides (Corral and Petray, 2000), BCG sequences (Krieg, et al. Nature, 374: 576), tetanus toxoid (Rice, et al. J. Immunol., 2001, 167: 1558-1565) |
| Particulate | Biodegradable Polymer microspheres | (Gupta et al., 1998) |
| | Immunostimulatory complexes (ISCOMs) | (Morein and Bengtsson, 1999) |
| | Liposomes | (Wassef et al., 1994) |
| Oil-emulsion and surfactant-based adjuvants | Freund's incomplete adjuvant | (Jensen et al., 1998) |
| | Microfluidized emulsions | MF59 (Ott et al., 1995) SAF (Allison and Byars, 1992) (Allison, 1999) |
| | Saponins | QS-21 (Kensil, 1996) |
| Synthetic | Muramyl peptide derivatives | Murabutide (Lederer, 1986) Threony-MDP (Allison, 1997) |
| | Nonionic block copolymers | L121 (Allison, 1999) |
| | Polyphosphazene (PCPP) | (Payne et al., 1995) |
| | Synthetic polynucleotides | Poly A: U, Poly I: C (Johnson, 1994) |
| | Thalidomide derivatives | CC-4047/ACTIMID (J. Immunol., 168(10): 4914-9) |

The immunogenic targets of the present invention may also be used to generate antibodies for use in screening assays or for immunotherapy. Other uses would be apparent to one of skill in the art. The term "antibody" includes antibody fragments, as are known in the art, including Fab, $Fab_2$, single chain antibodies (Fv for example), humanized antibodies, chimeric antibodies, human antibodies, produced by several methods as are known in the art. Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et. al. *Using Antibodies: A Laboratory Manual, Portable Protocol No.* 1, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). The antibodies or derivatives therefrom may also be conjugated to therapeutic moieties such as cytotoxic drugs or toxins, or active fragments thereof such as diphtheria A chain, exotoxin A chain, ricin A chain, abrin A chain, curcin, crotin, phenomycin, enomycin, among others. Cytotoxic agents may also include radiochemicals. Antibodies and their derivatives may be incorporated into compositions of the invention for use in vitro or in vivo.

Nucleic acids, proteins, or derivatives thereof representing an immunogenic target may be used in assays to determine the presence of a disease state in a patient, to predict prognosis, or to determine the effectiveness of a chemotherapeutic or other treatment regimen. Expression profiles, performed as is known in the art, may be used to determine the relative level of expression of the immunogenic target. The level of expression may then be correlated with base levels to determine whether a particular disease is present within the patient, the patient's prognosis, or whether a particular treatment regimen is effective. For example, if the patient is being treated with a particular chemotherapeutic regimen, a decreased level of expression of an immunogenic target in the patient's tissues (i.e., in peripheral blood) may indicate the regimen is decreasing the cancer load in that host. Similarly, if the level of expression is increasing, another therapeutic modality may need to be utilized. In one embodiment, nucleic acid probes corresponding to a nucleic acid encoding an immunogenic target may be attached to a biochip, as is known in the art, for the detection and quantification of expression in the host.

It is also possible to use nucleic acids, proteins, derivatives therefrom, or antibodies thereto as reagents in drug screening assays. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokarnik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

Administration of a composition of the present invention to a host may be accomplished using any of a variety of techniques known to those of skill in the art. The composition(s) may be processed in accordance with conventional methods of pharmacy to produce medicinal agents for administration to patients, including humans and other mammals (i.e., a "pharmaceutical composition"). The pharmaceutical composition is preferably made in the form of a dosage unit containing a given amount of DNA, viral vector particles, polypeptide or peptide, for example. A suitable daily dose for a human or other mammal may vary widely depending on the condition of the patient and other factors, but, once again, can be determined using routine methods.

The pharmaceutical composition may be administered orally, parentally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable for accomplishing or enhancing the delivery of a nucleic acid, polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a nucleic acid or polypeptide used to induce or enhance an effective immune response. It is preferred that compositions of the present invention provide for the induction or enhancement of an anti-tumor immune response in a host which protects the host from the development of a tumor and/or allows the host to eliminate an existing tumor from the body.

For oral administration, the pharmaceutical composition may be of any of several forms including, for example, a capsule, a tablet, a suspension, or liquid, among others. Liquids may be administered by injection as a composition with suitable carriers including saline, dextrose, or water. The term parenteral as used herein includes subcutaneous, intravenous, intramuscular, intrasternal, infusion, or intraperitoneal administration. Suppositories for rectal administration of the drug can be prepared by mixing the drug with a suitable non-irritating excipient such as cocoa butter and polyethylene glycols that are solid at ordinary temperatures but liquid at the rectal temperature.

The dosage regimen for immunizing a host or otherwise treating a disorder or a disease with a composition of this invention is based on a variety of factors, including the type of disease, the age, weight, sex, medical condition of the patient, the severity of the condition, the route of administration, and the particular compound employed. For example, a poxviral vector may be administered as a composition comprising $1 \times 10^6$ infectious particles per dose. Thus, the dosage regimen may vary widely, but can be determined routinely using standard methods.

A prime-boost regimen may also be utilized (see, for example, WO 01/30382 A1) in which the targeted immunogen is initially administered in a priming, step in one form followed by a boosting step in which the targeted immunogen is administered in another form. The form of the targeted immunogen in the priming and boosting steps are different. For instance, if the priming step utilized a nucleic acid, the boost may be administered as a peptide. Similarly, where a priming step utilized one type of recombinant virus (i.e., ALVAC), the boost step may utilize another type of virus (i.e., NYVAC). This prime-boost method of administration has been shown to induce strong immunological responses.

While the compositions of the invention can be administered as the sole active pharmaceutical agent, they can also be used in combination with one or more other compositions or agents (i.e., other immunogenic targets, co-stimulatory molecules, adjuvants). When administered as a combination, the individual components can be formulated as separate compositions administered at the same time or different times, or the components can be combined as a single composition.

Injectable preparations, such as sterile injectable aqueous or oleaginous suspensions, may be formulated according to known methods using suitable dispersing or wetting agents and suspending agents. The injectable preparation may also be a sterile injectable solution or suspension in a non-toxic parenterally acceptable diluent or solvent. Suitable vehicles and solvents that may be employed are water, Ringer's solution, and isotonic sodium chloride solution, among others. For instance, a viral vector such as a poxvirus may be prepared in 0.4% NaCl. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

For topical administration, a suitable topical dose of a composition may be administered one to four, and preferably two or three times daily. The dose may also be administered with intervening days during which no does is applied. Suitable compositions may comprise from 0.001% to 10% w/w, for example, from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin (e.g., liniments, lotions, ointments, creams, or pastes) and drops suitable for administration to the eye, ear, or nose.

The pharmaceutical compositions may also be prepared in a solid form (including granules, powders or suppositories). The pharmaceutical compositions may be subjected to conventional pharmaceutical operations such as sterilization and/or may contain conventional adjuvants, such as preservatives, stabilizers, wetting agents, emulsifiers, buffers etc. Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting sweetening, flavoring, and perfuming agents.

Pharmaceutical compositions comprising a nucleic acid or polypeptide of the present invention may take any of several forms and may be administered by any of several routes. In preferred embodiments, the compositions are administered via a parenteral route (intradermal, intramuscular or subcutaneous) to induce an immune response in the host. Alternatively, the composition may be administered directly into a lymph node (intranodal) or tumor mass (i.e., intratumoral administration). For example, the dose could be administered subcutaneously at days 0, 7, and 14. Suitable methods for immunization using compositions comprising TAs are known in the art, as shown for p53 (Hollstein et al., 1991), p21-ras (Almoguera et al., 1988), HER-2 (Fendly et al., 1990), the melanoma-associated antigens (MAGE-1; MAGE-2) (van der Bruggen et al., 1991), p97 (Hu et al., 1988), melanoma-associated antigen E (WO 99/30737) and carcinoembryonic antigen (CEA) (Kantor et al., 1993; Fishbein et al., 1992; Kaufman et al., 1991), among others.

Preferred embodiments of administratable compositions include, for example, nucleic acids or polypeptides in liquid preparations such as suspensions, syrups, or elixirs. Preferred injectable preparations include, for example, nucleic acids or polypeptides suitable for parental, subcutaneous, intradermal, intramuscular or intravenous administration such as sterile suspensions or emulsions. For example, a recombinant poxvirus may be in admixture with a suitable carrier, diluent, or excipient such as sterile water, physiological saline, glucose or the like. The composition may also be provided in lyophilized form for reconstituting, for instance, in isotonic aqueous, saline buffer. In addition, the compositions can be co-administered or sequentially administered with other antineoplastic, anti-tumor or anti-cancer agents and/or with agents which reduce or alleviate ill effects of antineoplastic, anti-tumor or anti-cancer agents.

A kit comprising a composition of the present invention is also provided. The kit can include a separate container containing a suitable carrier, diluent or excipient. The kit can also include an additional anti-cancer, anti-tumor or antineoplastic agent and/or an agent that reduces or alleviates ill effects of antineoplastic, anti-tumor or anti-cancer agents for co- or sequential-administration. Additionally, the kit can include instructions for mixing or combining ingredients and/or administration.

A better understanding of the present invention and of its many advantages will be had from the following examples, given by way of illustration.

EXAMPLES

Example 1

AAC2 Tumor Associated Antigen

A version of the AAC2 coding sequence (AAC2-1) was provided by a collaborator and found to have high sequence similarity to a murine bcl-6-associated zinc finger protein ("BAZF"). Based on this sequence information, PCR primers were designed as shown below:

```
(forward primer;                SEQ ID NO.: 6)
CACCATGGGT TCCCCCGCCG CCCCGGA (reverse primer;                SEQ ID NO.: 7)
CTAGGGCCCC CCGAGAATGT GGTAGTGCAC TTT
```

RNA was isolated from confluent HUVEC (BioWhittacker; Cat. No. CC2517, Lot No. 1F0141) cultures using Trizol™ as indicated by the manufacturer (Life Technologies, Inc., Cat. No. 15596). High fidelity RT-PCR was then performed using the forward and reverse primers (24 cycles at 94 degrees, 2 min.; 94 degrees, 30 sec; 56.8 degrees, 30 sec; 68 degrees, 1 min 40 sec; cycle 25 is 68 degrees, 7 min) resulting in the isolation of a 1,447 base pair cDNA. The cDNA was cloned into the pEF6-TOPO eukaryotic expression plasmid and termed "pEF6-hAAC2-2". The cDNA pEF6-hAAC2-2 was sequenced using four primers and aligned to the sequence of AAC2-1 and murine BAZF (FIG. 1). As shown therein, AAC2-2 is missing the serine residue (S) found at position 245 in AAC2-1. Secondly, a stretch of 17 amino acids at positions 298 to 316 (SEFFSCQNCEAV-AGCSS) of AAC2-2 showed only 11.8% sequence identity with amino acids 298-316 of AAC2-1 (FIG. 1). Interestingly, the stretch of 17 amino acids between positions 298 and 316 is 100% identical with murine BAZF suggesting that this may be critical for transcription factor function along with the long stretch of serines (zinc finger). AAC2-2 was then cloned into the pcDNA3.1-zeo eukaryotic expression plasmid ("pcDNA3.1-hAAC2-2").

Example 2

Human T-cell Reactivity Against AA C-2 Peptides

Using the AAC2-2 amino acid sequence, a library of 9-mer peptides predicted to bind to HLA-A-0201 was constructed (Table III; "N" indicates the sequence is not found within the mouse homolog, while "Y" indicates the sequence is found within the mouse homolog). Twenty-three of the peptides were dissolved in DMSO at 10 mg/ml (Table IV) and used in human PBMC cultures to test for their ability to elicit CD8 and CD4αβ T-cell responses in vitro.

TABLE III

Predicted HLA-A-0201-binding nonamer peptides of human AAC2-2

| Designation | Sequence | Position in Protein | SEQ ID NO. |
|---|---|---|---|
| CLP-2954 | RLSPTAATV | AAC2(256-264) | 44 |
| CLP-2955 | SIFRGRAGV | AAC2(65-73) | 45 |
| CLP-2956 | DVLGNLNEL | AAC2(23-31) | 46 |
| CLP-2957 | GVGVDVLSL | AAC2(72-80) | 47 |
| CLP-2958 | LLTSQAQDT | AAC2(277-285) | 48 |
| CLP-2959 | VLNSQASQA | AAC2(201-209) | 49 |
| CLP-2960 | VQFKCGAPA | AAC2(264-272) | 50 |
| CLP-2961 | GQPCPQARL | AAC2(219-227) | 51 |
| CLP-2962 | GAHRGLDSL | AAC2(312-320) | 52 |
| CLP-2963 | GAPASTPYL | AAC2(269-277) | 53 |
| CLP-2964 | VVQACHRFI | AAC2(123-131) | 54 |
| CLP-2965 | PLGISLRPL | AAC2(137-145) | 55 |
| CLP-2966 | PLRAHKAVL | AAC2(48-56) | 56 |
| CLP-2967 | FVQVAHLRA | AAC2(394-402) | 57 |
| CLP-2968 | APLLDFMYT | AAC2(90-98) | 58 |
| CLP-2969 | RAGVGVDVL | AAC2(70-78) | 59 |
| CLP-2970 | CETCGSRFV | AAC2(387-395) | 60 |
| CLP-2971 | ATAPAVLAA | AAC2(106-114) | 61 |
| CLP-2972 | SRFVQVAHL | AAC2(392-400) | 62 |
| CLP-2973 | CNWKKYKYI | AAC2(192-200) | 63 |
| CLP-2974 | SPAAPEGAL | AAC2(3-11) | 64 |
| EC-1 | ALGYVREFT | AAC2(10-18) | 65 |

TABLE III-continued

Predicted HLA-A-0201-binding nonamer peptides of human AAC2-2

| Designation | Sequence | Position in Protein | SEQ ID NO. |
|---|---|---|---|
| EC-3 | RLRGILTDV | AAC2(32-40) | 66 |
| EC-4 | GILTDVTLL | AAC2(35-43) | 67 |
| EC-5 | ILTDVTLLV | AAC2(36-44) | 68 |
| EC-6 | TLLVGGQPL | AAC2(41-49) | 69 |
| EC-9 | FMYTSRLRL | AAC2(95-103) | 70 |
| EC-10 | RLSPATAPA | AAC2(102-110) | 71 |
| EC-11 | AVLAAATYL | AAC2(110-118) | 72 |
| EC-12 | ATYLQMEHV | AAC2(115-123) | 73 |
| EC-13 | LQMEHVVQA | AAC2(118-126) | 74 |
| EC-21 | QVAHLRAHV | AAC2(390-398) | 75 |
| EC-22 | HLQTLKSHV | AAC2(418-426) | 76 |
| EC-24 | VVQACHRFI | AAC2(123-131) | 77 |

Using GM-CSF and IL-4, dendritic cells (DC) were generated from peripheral blood monocytes of blood donors expressing HLA-A-0201. DC were pulsed with the different pools of 9-mer AAC2-2 peptides shown in Table IV.

TABLE IV

AAC2-2 Peptide Groups

| Group # | Peptide No. | Sequences | Positions in Protein |
|---|---|---|---|
| 1 | CLP 2954 | RLSPTAATV (SEQ ID NO,: 44) | AAC2(256-264) |
|   | CLP 2956 | DVLGNLNEL (SEQ ID NO,: 45) | AAC2(23-31) |
|   | CLP 2957 | GVGVDVLSL (SEQ ID NO,: 46) | AAC2(72-80) |
| 2 | CLP 2959 | VLNSQASQA (SEQ ID NO,: 49) | AAC2(201-209) |
|   | CLP 2960 | VQFKCGAPA (SEQ ID NO,: 50) | AAC2(264-272) |
|   | CLP 2963 | GAPASTPYL (SEQ ID NO,: 53) | AAC2(269-277) |
| 3 | CLP 2964 | VVQACHRFI (SEQ ID NO,: 54) | AAC2(123-131) |
|   | CLP 2968 | APLLDFMYT (SEQ ID NO,: 58) | AAC2(90-98) |
| 4 | CLP 2971 | ATAPAVLAA (SEQ ID NO,: 61) | AAC2(106-114) |
|   | CLP 2973 | CNWKKYKYI (SEQ ID NO,: 63) | AAC2(192-200) |
| 5 | EC 1 | ALGYVREFT (SEQ ID NO,: 65) | AAC2(10-18) |
|   | EC 3 | RLRGILTDV (SEQ ID NO,: 66) | AAC2(32-40) |
|   | EC 3 | GILTDVTLL (SEQ ID NO,: 67) | AAC2(35-43) |
| 6 | EC 5 | ILTDVTLLV (SEQ ID NO,: 68) | AAC2(36-44) |
|   | EC 6 | TLLVGGQPL (SEQ ID NO,: 69) | AAC2(41-49) |
|   | EC 9 | FMYTSRLRL (SEQ ID NO,: 70) | AAC2(95-103) |
| 7 | EC 10 | RLSPATAPA (SEQ ID NO,: 71) | AAC2(102-110) |
|   | EC 11 | AVLAAATYL (SEQ ID NO,: 72) | AAC2(110-118) |
|   | EC 12 | ATYLQMEHV (SEQ ID NO,: 73) | AAC2(115-123) |
| 8 | EC 13 | LQMEHVVQA (SEQ ID NO,: 74) | AAC2(118-126) |
|   | EC 21 | QVAHLRAHV (SEQ ID NO,: 75) | AAC2(390-398) |
| 9 | EC 22 | HLQTLKSHV (SEQ ID NO,: 76) | AAC2(418-426) |
|   | EC 24 | VVQACHRFI (SEQ ID NO,: 77) | AAC2(123-131) |

These DC were used to stimulate autologous T-cell-enriched PBMC preparations. The T cells were re-stimulated with autologous PBMC and then re-stimulated with CD40-ligand-activated autologous B cells. After the third and fourth round of stimulation with each peptide pool, ELISPOT analysis for IFN-γ production indicated that the T cells responded most strongly to one of the pools of AAC2-2 peptides (peptide group 6; FIG. 2). Peptide group 6 includes the following peptides: ILTDVTLLV (aa 36-44), TLLVGGQPL (aa 41-49), and FMYTSRLRL (aa 95-103). Flow cytometric analysis (FACS) showed that the lymphocytes from this peptide-specific line consisted of >50% CD8 T cells with a memory (CD45RO+) phenotype. Very few cells (<2%) were stained with anti-CD56 antibodies, indicating that the observed IFN-γ production was not due to NK cell activity.

Analysis of CTL activity from this peptide pool-specific T-cell line also demonstrated that the activated T cells were capable of killing peptide-loaded TAP-deficient T2 cells in an HLA-A-0201-restricted fashion. This analysis also revealed that ILTDVTLLV was a dominant peptide that stimulated the majority of the peptide-specific CTL activity. Thus, it was determined that AAC2-2 peptides are immunogenic in the human immune system.

Example 3

Immunogenicity of AAC2-2 In Vivo

Figure 3:
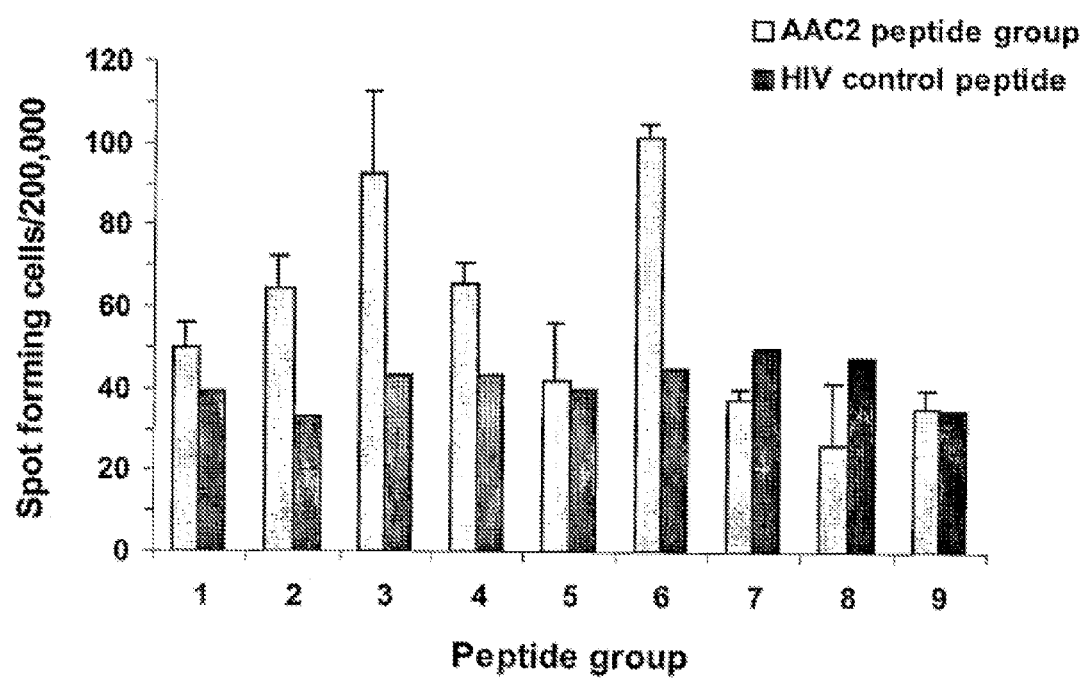
FIG. 3. Murine T cells from HLA-A2-Kb transgenic mice recognize and secrete IFN-γ in response to DNA immunization with a human AAC2-2-encoding DNA plasmid. Spleen cells from pEF6-hAAC2-2-immunized mice were re-stimulated with the different groups of peptides. After six days, the cells were harvested and tested for IFN-γ secretion in response to each respective peptide group or a control HLA-A2-binding 9-mer HIV peptide. ELISPOT plates were incubated over-night and developed. Each group responded with high levels of IFN-γ production (over 250 spots) in response to PMA and ionomycin used as a positive control. One of the highly reactive peptides groups (group 6) is also recognized by human lymphocytes from the HLA-A-0201+ donors tested so far.

Using DNA immunization into HLA-A2-Kb transgenic mice, it was found that the AAC2-2 protein is processed into immunogenic peptides and can elicit an HLA-A-0201-restricted T-cell response in vivo. Mice were immunized on day 1 by injection with pEF6-hAAC2-2 and boosted with the same plasmid at day 21. Lymphocytes were harvested from immunized mice 21 days after boosting and re-stimulated in vitro with the different groups of AAC2-2 peptides shown in Table IV. Peptide-specific effector T-cell function towards these peptides was found using IFN-γ ELISPOT analysis (FIG. 3). It was found that the same pool of peptides (group 6) previously shown to be strongly immunogenic in human PBMC cultures also elicited significant reactivity by T cells after DNA vaccination (FIG. 3). Thus, the AAC2 gene product administered as a DNA-based vaccine is immunogenic in vivo and elicits a strong cell-mediated immune response characterized by the activation of CTL activity.

Example 4

Therapeutic AAC2-2 Vaccine

Figure 4:
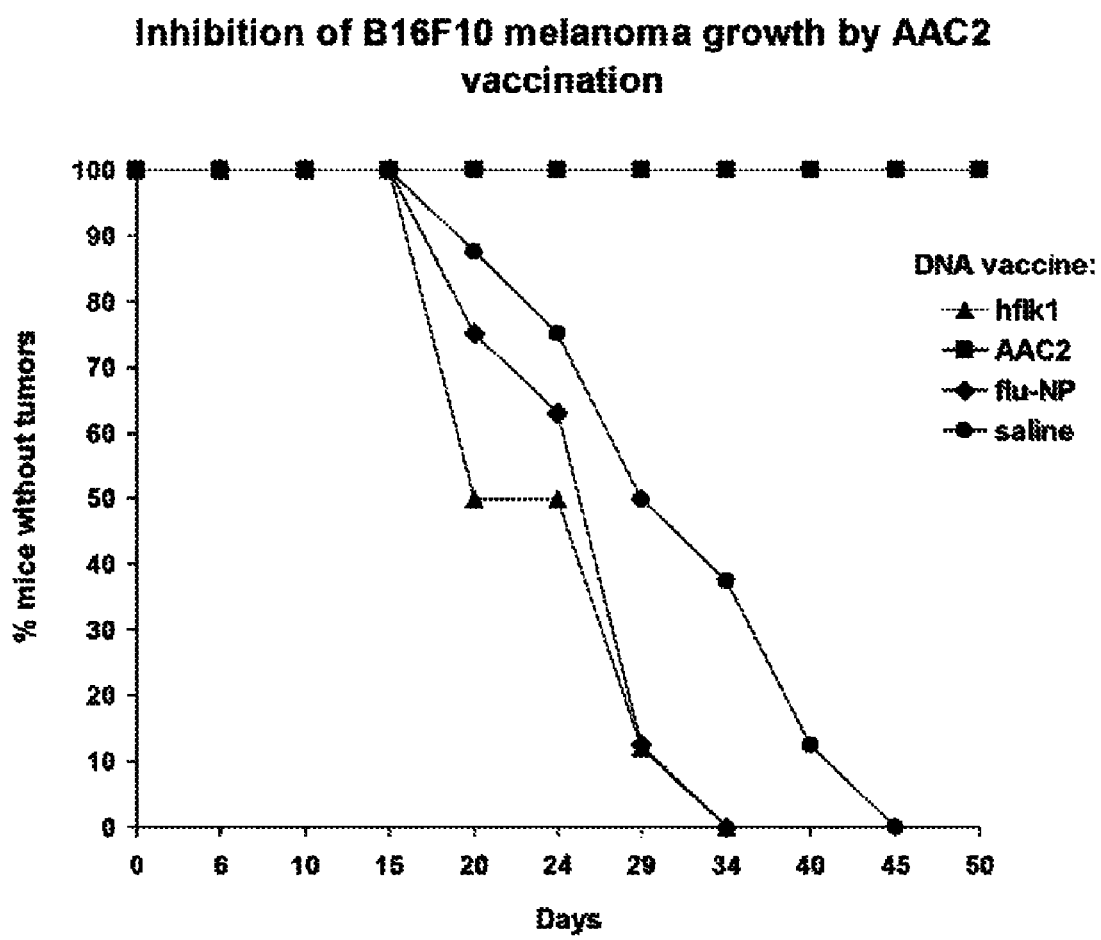
FIG. 4. DNA vaccination with a gene encoding human AAC2-2 completely abrogates: the growth of implanted B16F10 melanoma cells. This effect is not due to a non-specific immune response as shown by the inability of plasmid encoding flu-NP protein and the human flk1 (VEGFR-2) to prevent tumor growth.
Figure 5:
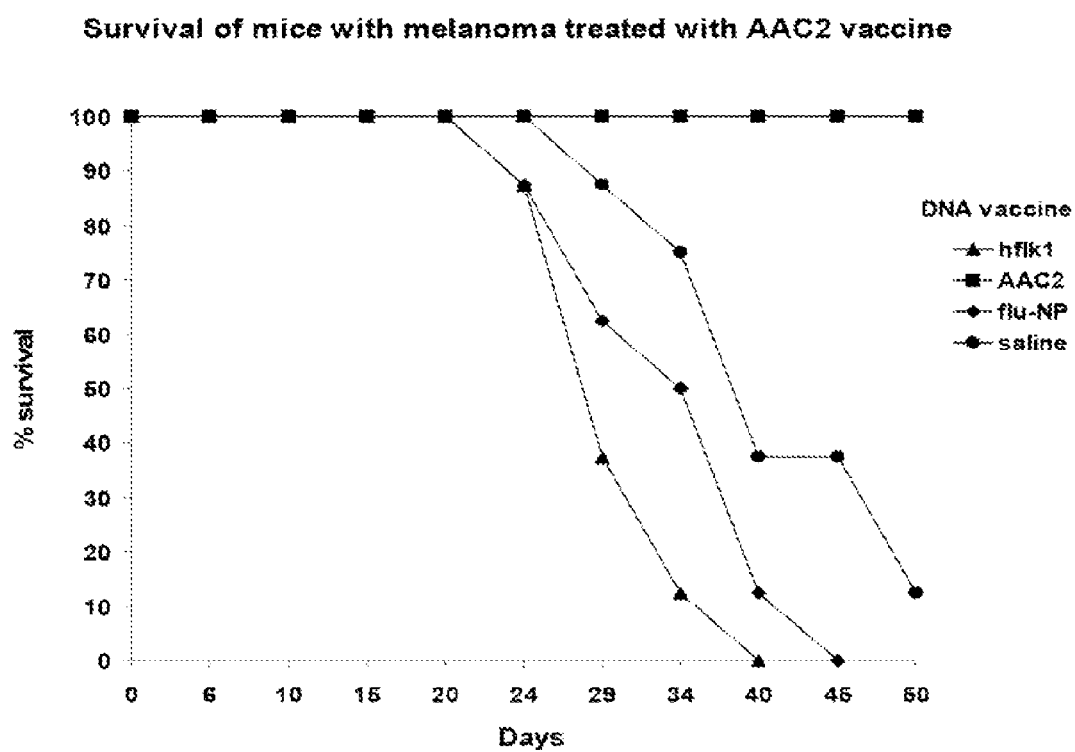
FIG. 5. Survival of mice after implantation of B16F10 melanoma cells into C57BL/6 mice showing the ability of DNA vaccination with a human AAC2-2 vector to completely protect against the effects of tumor growth. This protective effect is antigen-specific and can not be elicited through vaccination with other genes.

Therapeutic vaccination against the AAC2-2 gene product using the pEF6-hAAC2-2 DNA vaccine was found to completely block the growth of a solid tumor. Groups of eight C57BL/6 mice were subcutaneously challenged with $10^4$ B16F10 melanoma cells, a vigorous and relatively non-immunogenic tumor cell line. The mice were then immunized at weekly intervals starting at 6 days after tumor challenge. Control mice (eight per group) treated either with a plasmid encoding the flu-NP protein or saline alone all developed large tumors. In contrast, all the mice (8/8) immunized with pEF6-hAAC2-2 had no detectable tumor over a 50-day period (FIG. 4). All mice remained tumor-free through 80 days (data not shown). FIG. 5 plots the survival of mice treated with the different DNA vectors shown after melanoma implantation showing again the complete effectiveness of AAC2-2 vaccination in protecting mice against melanoma growth. No adverse health effects have been observed as a result of immunization with the human AAC2-2 gene-encoding vector (immunized mice were as active as control mice and showed no weight loss).

As shown in FIGS. 4 and 5, vaccination with a plasmid encoding the human VEGFR-2 (pBLAST-hflk1) did not protect tumor-challenged mice. In fact, the tumors grew even more rapidly in these mice. Analysis of sera from mice vaccinated with the pBLAST-hflk1 plasmid by ELISA found that IgG against the VEGFR-2 protein is induced in significant titres (data not shown). These results suggest that an antibody-based immune response directed against VEGFR-2 may not be not effective in preventing angiogenesis and solid tumor growth.

Figure 6:
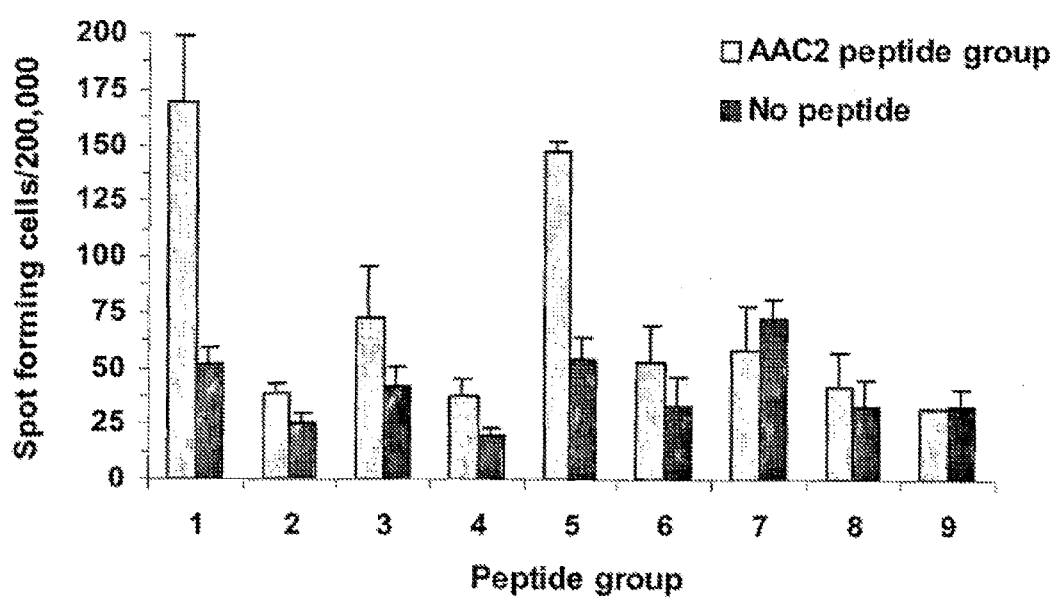
FIG. 6. T lymphocytes from C57BL/6 mice exhibit effector cell activity and secrete IFN-γ in response to peptides of human AAC2-2 following DNA vaccination with the pEF6-hAAC2-2 expression plasmid. These peptides can exhibit cross-reactivity on B6 MHC class I. The peptides in group 1 and group 5 induce strong reactivity by C57BL/6 T cells.

Inhibition of melanoma solid tumor growth in C57BL/6 mice immunized with pEF6-hAAC2-2 correlates with an immune response against the protein (FIG. 6). Immunization of C57BL/6 mice was performed as described above. Spleen cells from immunized mice were re-stimulated with the same peptide pools used in experiments with HLA-A2-Kb transgenic mice (Table III). A significant number of peptides cross-react on C57BL/6 class I MHC (Kb and Db molecules). Two pools of peptides in particular (group 1 and group 5) were found to elicit strong effector cell activity in the IFN-γ ELISPOT assays (FIG. 6). All of the peptides in these groups are also identical to the corresponding sequence in the murine BAZF protein. These results strongly suggest that immunization with the human AAC2-2 activates an immune response against its murine orthologue BAZF in mice and can inhibit tumor angiogenesis as a result.

Example 5

BFA4 Tumor Antigen

The BFA4 sequence was found to be the "trichorhinophalangeal syndrome 1" (TRPS-1) gene (Genebank ID #6684533; Momeniet et al, *Nature Genetics*, 24(1), 71-74, 2000), a known transcription factor with no function attributed previously in any form of cancer. The BFA4 cDNA sequence is shown in FIG. 7 (SEQ ID NO.: 28) and the deduced amino acid sequence is shown in FIG. 8 (SEQ ID NO.: 29).

A. BFA4 Peptides and Polyclonal Antisera

For monitoring purposes, rabbit anti-BFA4 polyclonal antibodies were generated. Six peptides (22-mers) were designed and synthesized to elicit antibody response to BFA4, as shown below:

| CLP 2589 | MVRKKNPPLRNVASEGEGQILE | BFA4 (1-22) |
| CLP 2590 | SPKATEETGQAQSGQANCQGLS | BFA4 (157-178) |
| CLP 2591 | VAKPSEKNSNKSIPALQSSDSG | BFA4 (371-392) |
| CLP 2592 | NHLQGSDGQQSVKESKEHSCTK | BFA4 (649-670) |
| CLP 2593 | NGEQIIRRRTRKRLNPEALQAE | BFA4 (940-961) |
| CLP 2594 | ANGASKEKTKAPPNVKNEGPLNV | BFA4 (1178-1199) |

Rabbits were immunized with the peptides, serum was isolated, and the following antibody titers were observed:

| Rabbit # | Peptide | Titer (Bleed 2) | Titer (Final Bleed) |
| --- | --- | --- | --- |
| 1, 2 | CLP2589 | 800000, 1600000 | 2560000, 2560000 |
| 3, 4 | CLP2590 | 12800, 6400 | 40000, 40000 |
| 5, 6 | CLP2591 | 400000, 400000 | 320000, 320000 |
| 7, 8 | CLP2592 | 25600, 12800 | 80000, 40000 |
| 9, 10 | CLP2593 | 3200000, 51200 | 2560000, 160000 |
| 11, 12 | CLP2594 | 409600, 409600 | 320000, 320000 |

These peptides were also modified by coupling with KLH peptides to enhance immune responses as shown below:

| BFA4 (1-22) | KLH-MVRKKNPPLRNVASEGEGQILE | (CLP-2589) |
| BFA4 (157-178) | KLH-SPKATEETGQAQSGQANCQGLS | (CLP-2590) |
| BFA4 (371-392) | KLH-VAKPSEKNSNKSIPALQSSDSG | (CLP-2591) |
| BFA4 (649-670) | KLH-NHLQGSDGQQSVKESKEHSCTK | (CLP-2592) |
| BFA4 (940-961) | KLH-NGEQIIRRRTRKRLNPEALQAE | (CLP-2593) |
| BFA4 (1178-1200) | KLH-ANGASKEKTKAPPNVKNEGPLNV | (CLP-2594) |

The pcDNA3.2BFA4 (3.6 mg) was also used for DNA immunization to generate polyclonal sera in chickens.

B. Cloning of BFA4

Complete cDNA sequence for BFA4 is ~10 kb and gene is expressed in BT474 ductal carcinoma cells. Primers 7717 (forward primer) and 7723 (reverse primer) were designed to amplify full-length BFA4 gene by amplification of 4 kb, 7 kb or 10 kb products by RT-PCR.

```
Primer 7717:
BFA4-BamH1/F1 (5' end forward) with Kozak:
5' CGGGATCCACCATGGTCCGGAAAAAGAACCCC 3'
(BamHI for DNA3.1, MP76)

Primer 7723: BFA4-BamHI/R1 (3' end reverse 4kb):
5' CGGGATCCCTCTTTAGGTTTTCCATTTTTTTCCAC 3'
(BamHI for DNA3.1, MP76)
```

Ten mg of total RNA isolated and frozen in different batches from BT-474 cells using Trizol as indicated by the manufacturer (Gibco BRL) was used in RT-PCR to amplify the BFA4 gene. RT-PCR conditions were optimized using Taq Platinum High Fidelity enzyme, OPC (Oligo Purification Cartridge; Applied Biosystems) purified primers and purified total RNA/polyA mRNA (BT 474 cells). Optimization resulted in a 4.0 kb fragment as a single band.

To re-amplify the BFA4 sequence, mRNA was treated with DNase per manufacturers' instructions (Gibco BRL). The 4 kb DNA was reamplified using PCR using primers 7717 and 7723 primers (10 pmole/microliter) and Taq Platinum High Fidelity polymerase (GIBCO BRL) enzyme. Thermocycler conditions for both sets of reactions were as under: 94° C. (2 min), followed by 30 cycles of 94° C. (30 sec), 52° C. (30 sec), 67° C. (4 min) and 67° C. (5 min) and finally 40° C. for 10 min. Three BFA4 clones were identified after pCR2.1/TOPO-TA cloning.

Several mutations were identified during analysis of the BFA4 sequence. To correct these sequences, the BamHI/XhoI fragment (5') of the BFA4 gene from clone JB-3552-1-2 (pCR2.1/TOPO/BFA4) was exchanged with the XhoI/BamHI fragment (3') of the BFA4 gene from clone JB-3552-1-4 (pCR2.1/TOPO/BFA4). This recombined fragment was then ligated into pMCS5 BamHI/CAP. Clone JB-3624-1-5 was generated and found to contain the correct sequence.

Nucleotide 344 of the isolated BFA4 clone was different from the reported sequence (C in BFA4, T in TRPS-1). The change resulted in a phe to ser amino acid change. To change this sequence to the reported sequence, the EcoRI/BglII fragment (5') of the BFA4 gene from clone JB-3552-1-2 (pCR2.1/TOPO/BFA4) was subcloned into pUC8:2 to generate clone JB-3631-2. This clone was used as a template for Quickchange (Stratagene) mutagenesis to change amino acid 115 of the BFA4 protein from a serine to a phenylalanine as in the TRPS1 protein. The selected clone was JB-3648-2-3. Mutagenesis was also repeated with pMCS5 BFA4 (BT474) as a template for Quickchange (Stratagene) mutagenesis to change amino acid 115 of the BFA4 protein from a serine to a phenylalanine as in the TRPS1 protein. Several clones were found to be correct by DNA sequencing and one of the clones (JB-3685-1-18) was used for further subcloning.

JB-3685-1-18 was then used to subclone the BFA4 coding sequence into the BamHI sites of four different expression vectors: 1) the poxyiral (NYVAC) vector pSD554VC (COPAK/H6; JB-3707-1-7); 2) pcDNA3.1/Zeo (+) (JB-3707-3-2); 3) pCAMycHis (JB-3707-5-1); and, 4) Semiliki Forest virus alphaviral replicon vector pMP76 (JB-3735-1-23). The BFA4 coding sequence within JB-3707-1-7, JB-3707-5-1, and JB-3735-1-23 was confirmed by DNA sequencing.

A stop codon was introduced near the end of the cloned sequence in the pcDNA3.1/Zeo/BFA4 construct (JB-3707-3-2). A unique EcoR1 site was opened and filled in to introduce a stop codon in-frame with BFA4 coding sequence. Several putative clones were identified by the loss of EcoR1 site, however three clones (JB-3756-1-2; JB-3756-3-1; and JB-3756-4-1) were sequenced. All three were found to be correct in the area of the fill-in. Clone JB-3756-3-1 identified as having the correct sequence and orientation.

Myc and myc/his tags (Evans et al, 1985) were introduced using oligonucleotides, which were annealed and ligated into the pcDNA3.1/Zeo/BFA4 construct (JB-3707-3-2) at the EcoRI/EcoRV sites. Several clones were obtained for these constructs. Three clones having the correct sequences and orientations were obtained: 1) PcDNA3.1/Zeo/BFA4/myc-tag (JB-3773-1-2); 2) PcDNA3.1/Zeo/BFA4/mychis-tag (JB-3773-2-1); and, 3) PcDNA3.1/Zeo/BFA4/mychis-tag (JB-3773-2-2).

C. Expression of BFA4

1. Expression from Poxyiral Vectors

The pSD554VC (COPAK/H6; JB-3707-1-7) vector was used to generate NYVAC-BFA4 virus. In vitro recombination was performed with plasmid COPAK/H6/BFA4 and NYVAC in RK13/CEF cells. NYVAC-BFA4 (vP2033-NYVAC-RK13) was generated and amplified to P3 level after completion of three enrichments with final stock concentrations of $1.12 \times 10^9$/ml (10 ml). Vero cells were infected with NYVAC-BFA4 at an M.O.I. of 0.5 pfu/cell. Lysates and media were harvested 24 h post-infection to confirm expression of BFA4 protein. One-twentieth of the concentrated media and 1/40 of the lysate were loaded onto a western blot and incubated with rabbit antisera against the BFA4 peptides CLP 2589, 2591, 2598 and 2594 (see above for peptide sequences and preparation of anti-BFA4 antisera). An approximate 120 kD band was detected in both the lysate and the concentrated media of NYVAC-BFA4-infected Vero cells which was not evident in either Vero control cells ("mock-infected"), Vero cells infected with the parental NYVAC virus, or concentrated media.

2. Expression from pcDNA3.1-Based Vectors

Transient transfection studies were performed to verify expression of BFA4 from the pcDNA-based vectors and to analyze quality of polyclonal sera raised against BFA4 peptides. The following constructs were used to study expression of BFA4 gene: pcDNA 3.1 zeo$^R$/BFA4, pMP76/BFA4, pcDNA 3.1 zeo$^R$/BFA4/Myc tag and pcDNA 3.1 zeo$^R$/BFA4/MycHis tag. BFA4 expression plasmids (5 µg and 10 µg) were co-transfected with pGL3 Luciferase (1 µg) (Promega) with the Gene porter reagent (Gene Therapy Systems) as the transfection reagent. At 48 h post-transfection, whole cell extract was prepared by scraping cells in cell lysis reagent (200 µl) and 1 cycle of freeze-thaw (−20° C. freeze, 37° C. thaw). Transfection efficiency was quantitated by analyzing expression of the luciferase reporter gene by measuring Relative Luciferase Units (RLU) in duplicate. Similar RLU values were obtained in the samples co-transfected with luciferase construct in the presence and absence of BFA4 expression vectors. There was no significant difference observed in toxicity or RLU values with differential amount (5 µg and 10 µg) of BFA4 expression vectors. Preliminary western blot analysis using alkaline phosphatase system with the CHOK1 cell extracts (pcDNA3.1/zeo/BFA4/MycHisTag) and an anti-BFA4 polyclonal antisera, revealed a band at approximately 120 kDa band in extracts of BFA4 vector-transfected cells.

A stable transfection study was initiated to obtain stable clones of BFA4 expressing COS A2 cells. These cells are useful for in vitro stimulation assays pcDNA 3.1 zeo$^R$/BFA4 (2.5 µg and 20 µg), and pcDNA 3.1 zeo$^R$/BFA4/MycHis tag (2.5 µg) were used to study expression of BFA4). pGL3 Luciferase (2.5 µg) was used as a control vector to monitor transfection efficiency. The Gene porter reagent was used to facilitate transfection of DNA vectors. After 48 h post-transfection, whole cell extract were prepared by scraping cells in the cell lysis reagent (200 µl) and 1 cycle of freeze-thaw at −20° C./37° C. for first experiment. Transfected cells obtained from the second experiment were trypsinized, frozen stock established and cells were plated in increasing concentrations of Zeocin (0, 250, 500, 750 and 1000 µg/ml). Non-transfected CosA2cells survived at 60-80% confluency for three weeks at 100 µg/ml (Zeocin) and 10% confluency at 250 µg/ml (Zeocin). However, after three weeks, at higher drug concentration (500-1000 µg/ml), live cells were not observed in the plates containing non-transfected cells and high Zeocin concentration (500-1000 µg/ml).

Several Zeocin-resistant clones growing in differential drug concentrations (Zeocin-250, 500, 750 and 1000 µg/ml) were picked from 10 cm plates after three weeks. These clones were further expanded in a 3.5 cm plate(s) in the presence of Zeocin at 500, 750 and 1000 µg/ml. Frozen lots of these clones were prepared and several clones from each pool (pcDNA 3.1 zeo$^R$/BFA4, and pcDNA 3.1 zeo$^R$/BFA4/MycHis tag) were expanded to T75 cm$^2$ flasks in the presence of Zeocin at 1 mg/ml. Five clones from each pool (pcDNA 3.1 zeo$^R$/BFA4, and pcDNA 3.1 zeo$^R$/BFA4/MycHis tag) were expanded to T75 cm$^2$ flasks in the presence of Zeocin at 1 mg/ml. Cells are maintained under Zeocin drug (1 mg/ml) selection. Six clones were used in BFA4 peptide-pulsed target experiment, and two clones were found to express BFA4 at a moderate level by immunological assays. The non-adherent cell lines K562A2 and EL4A2 were also transfected with these vectors to generate stable cell lines.

3. Prokaryotic Expression Vector

The BamHI-Xho-1 fragment (1.5 Kbp) fragment encoding N-terminal 54 kDa BFDA4 from pcDNA3.1/BFA4 was cloned into pGEX4T1-6His (Veritas) plasmid. This vector contains the tac promoter followed by the N-terminal glutathione S-transferase (GST~26 kDa) and a hexahistidine tag to C terminus of the GST fusion protein.

The BFA4-N54 expression plasmid was transformed into BL21 cells and grown at 25° C. in antibiotic selection medium (2L culture) to an OD (600 nm) and thereafter induced with 1 mM IPTG. GST-BFA4-N54 was found to be soluble protein. Clarified extract of the soluble fraction was adsorbed batchwise to glutathione-Sepharose 4B and eluted with 10 mM reduced glutathione. Fractions were analyzed after estimation of protein concentration and TCA precipitation. Specific polypeptide of Mr=85 kDa in the eluate was confirmed by SDS-PAGE. The recombinant protein was purified by gluathione-Sepharose was absorbed on a NiNTA column for further purification. The bound protein was eluted with 0.25M imidazole. The protein was dialyzed versus TBS containing 40% Glycerol, resulting in 4.5 mg GST-BFA4-N54-6 His (N terminus BFA4 protein) protein. Expression of BFA4 was confirmed using the rabbit anti-BFA4 polyclonal antibody by western blot.

D. Anti-BFA4 Immune Responses

1. BFA4 Peptides

In addition to genetic immunization vectors for BFA4, immunological reagents for BFA4 have been generated. A library of 100 nonamer peptides spanning the BFA4 gene product was synthesized. The peptides were chosen based on their potential ability to bind to HLA-A*0201. Table V lists 100 nonamer peptide epitopes for HLA-A*0201 from the BFA4 protein tested (see below):

| PEPTIDE DESIGNATION | SEQUENCE | POSITION IN PROTEIN |
|---|---|---|
| CLP-2421 | MVRKKNPPL | BFA4 (1-9)I$^-$ |
| CLP-2422 | KKNPPLRNV | BFA4 (4-12)I$^-$ |
| CLP-2423 | VASEGEGQI | BFA4 (12-20)I$^-$ |
| CLP-2424 | QILEPIGTE | BFA4 (19-27)I$^-$ |
| CLP-2425 | RNMLAFSFP | BFA4 (108-116)I$^-$ |
| CLP-2426 | NMLAFSFPA | BFA4 (109-117)I$^-$ |
| CLP-2427 | MLAFSFPAA | BFA4 (110-118)I$^-$ |
| CLP-2428 | FSFPAAGGV | BFA4 (113-121)I$^-$ |
| CLP-2429 | AAGGVCEPL | BFA4 (117-125)I$^-$ |
| CLP-2430 | SGQANCQGL | BFA4 (170-178)I$^-$ |
| CLP-2431 | ANCQGLSPV | BFA4 (172-180)I$^-$ |
| CLP-2432 | GLSPVSVAS | BFA4 (176-184)I$^-$ |
| CLP-2433 | SVASKNPQV | BFA4 (181-189)I$^-$ |
| CLP-2434 | RLNKSKTDL | BFA4 (196-204)I$^-$ |
| CLP-2435 | NDNPDPAPL | BFA4 (207-215)I$^-$ |
| CLP-2436 | DPAPLSPEL | BFA4 (211-219)I$^-$ |
| CLP-2437 | ELQDFKCNI | BFA4 (218-216)I$^-$ |
| CLP-2438 | GLHNRTRQD | BFA4 (249-257)I$^-$ |
| CLP-2439 | ELDSKILAL | BFA4 (259-267)I$^-$ |
| CLP-2440 | KILALHNMV | BFA4 (263-271)I$^-$ |
| CLP-2441 | ALHNMVQFS | BFA4 (266-284)I$^-$ |
| CLP-2442 | VNRSVFSGV | BFA4 (282-290)I$^-$ |
| CLP-2443 | FSGVLQDIN | BFA4 (287-295)I$^-$ |
| CLP-2444 | DINSSRPVL | BFA4 (293-301)I$^-$ |
| CLP-2445 | VLLNGTYDV | BFA4 (300-308)I$^-$ |
| CLP-2446 | FCNFTYMGN | BFA4 (337-345)I$^-$ |
| CLP-2447 | YMGNSSTEL | BFA4 (342-350)I$^-$ |
| CLP-2448 | FLQTHPNKI | BFA4 (354-362)I$^-$ |
| CLP-2449 | KASLPSSEV | BFA4 (363-371)I$^-$ |
| CLP-2450 | DLGKWQDKI | BFA4 (393-401)I$^-$ |
| CLP-2451 | VKAGDDTPV | BFA4 (403-411)I$^-$ |
| CLP-2452 | FSCESSSSL | BFA4 (441-449)I$^-$ |
| CLP-2453 | KLLEHYGKQ | BFA4 (450-458)I$^-$ |
| CLP-2454 | GLNPELNDK | BFA4 (466-474)I$^-$ |
| CLP-2455 | GSVINQNDL | BFA4 (478-486)I$^-$ |
| CLP-2456 | SVINQNDLA | BFA4 (479-487)I$^-$ |
| CLP-2457 | FCDFRYSKS | BFA4 (527-535)I$^-$ |
| CLP-2458 | SHGPDVIVV | BFA4 (535-543)I$^-$ |
| CLP-2459 | PLLRHYQQL | BFA4 (545-553)I$^-$ |
| CLP-2460 | GLCSPEKHL | BFA4 (570-578)I$^-$ |
| CLP-2461 | HLGEITYPF | BFA4 (577-585)I$^-$ |
| CLP-2462 | LGEITYPFA | BFA4 (578-586)I$^-$ |
| CLP-2463 | HCALLLLHL | BFA4 (594-602)I$^-$ |
| CLP-2464 | ALLLLHLSP | BFA4 (596-604)I$^-$ |

-continued

| PEPTIDE DESIGNATION | SEQUENCE | POSITION IN PROTEIN |
|---|---|---|
| CLP-2465 | LLLLHLSPG | BFA4 (597-605)I⁻ |
| CLP-2466 | LLLHLSPGA | BFA4 (598-606)I⁻ |
| CLP-2467 | LLHLSPGAA | BFA4 (599-607)I⁻ |
| CLP-2468 | FTTPDVDVL | BFA4 (621-629)I⁻ |
| CLP-2469 | TTPDVDVLL | BFA4 (622-630)I⁻ |
| CLP-2470 | VLLFHYESV | BFA4 (628-636)I⁻ |
| CLP-2471 | FITQVEEEI | BFA4 (673-681)I⁻ |
| CLP-2472 | FTAADTQSL | BFA4 (699-707)I⁻ |
| CLP-2473 | SLLEHFNTV | BFA4 (706-714)I⁻ |
| CLP-2474 | STIKEEPKI | BFA4 (734-742)I⁻ |
| CLP-2475 | KIDFRVYNL | BFA4 (741-749)I⁻ |
| CLP-2476 | NLLTPDSKM | BFA4 (748-756)I⁻ |
| CLP-2479 | VTWRGADIL | BFA4 (792-800)I⁻ |
| CLP-2480 | ILRGSPSYT | BFA4 (799-807)I⁻ |
| CLP-2481 | YTQASLGLL | BFA4 (806-814)I⁻ |
| CLP-2482 | ASLGLLTPV | BFA4 (809-817)I⁻ |
| CLP-2483 | GLLTPVSGT | BFA4 (812-820)I⁻ |
| CLP-2484 | GTQEQTKTL | BFA4 (819-827)I⁻ |
| CLP-2485 | KTLRDSPNV | BFA4 (825-833)I⁻ |
| CLP-2486 | HLARPIYGL | BFA4 (837-845)I⁻ |
| CLP-2487 | PIYGLAVET | BFA4 (841-849)I⁻ |
| CLP-2488 | LAVETKGFL | BFA4 (845-853)I⁻ |
| CLP-2489 | FLQGAPAGG | BFA4 (852-860)I⁻ |
| CLP-2490 | AGGEKSGAL | BFA4 (858-866)I⁻ |
| CLP-2491 | GALPQQYPA | BFA4 (864-872)I⁻ |
| CLP-2492 | ALPQQYPAS | BFA4 (865-873)I⁻ |
| CLP-2493 | FCANCLTTK | BFA4 (895-903)I⁻ |
| CLP-2494 | ANGGYVCNA | BFA4 (911-919)I⁻ |
| CLP-2495 | NACGLYQKL | BFA4 (918-926)I⁻ |
| CLP-2496 | GLYQKLHST | BFA4 (921-929)I⁻ |
| CLP-2497 | KLHSTPRPL | BFA4 (925-933)I⁻ |
| CLP-2498 | STPRPLNII | BFA4 (928-936)I⁻ |
| CLP-2499 | RLNPEALQA | BFA4 (952-960)I⁻ |
| CLP-2500 | VLVSQTLDI | BFA4 (1020-1028)I⁻ |
| CLP-2501 | DIHKRMQPL | BFA4 (1027-1035)I⁻ |
| CLP-2502 | RMQPLHIQI | BFA4 (1031-1039)I⁻ |
| CLP-2503 | YPLFGLPFV | BFA4 (1092-1100)I⁻ |
| CLP-2504 | GLPFVHNDF | BFA4 (1096-1104)I⁻ |
| CLP-2505 | FVHNDFQSE | BFA4 (1099-1107)I⁻ |

-continued

| PEPTIDE DESIGNATION | SEQUENCE | POSITION IN PROTEIN |
|---|---|---|
| CLP-2506 | SVPGNPHYL | BFA4 (1120-1128)I⁻ |
| CLP-2507 | GNPHYLSHV | BFA4 (1123-1131)I⁻ |
| CLP-2508 | HYLSHVPGL | BFA4 (1126-1134)I⁻ |
| CLP-2509 | YVPYPTFNL | BFA4 (1141-1149)I⁻ |
| CLP-2510 | FNLPPHFSA | BFA4 (1147-1155)I⁻ |
| CLP-2511 | NLPPHFSAV | BFA4 (1148-1156)I⁻ |
| CLP-2512 | SAVGSDNDI | BFA4 (1154-1162)I⁻ |
| CLP-2513 | KNEGPLNVV | BFA4 (1192-1200)I⁻ |
| CLP-2514 | TKCVHCGIV | BFA4 (1215-1223)I⁻ |
| CLP-2515 | CVHCGIVFL | BFA4 (1217-1225)I⁻ |
| CLP-2516 | CGIVFLDEV | BFA4 (1220-1228)I⁻ |
| CLP-2517 | FLDEVMYAL | BFA4 (1224-1232)I⁻ |
| CLP-2518 | VMYALHMSC | BFA4 (1228-1236)I⁻ |
| CLP-2519 | FQCSICQHL | BFA4 (1243-1251)I⁻ |
| CLP-2520 | GLHRNNAQV | BFA4 (1265-1273)I⁻ |

The peptide library was pooled into separate groups containing 7-10 different peptides for immunological testing as shown in Table VI (see below). In addition to a peptide library spanning BFA4, a recombinant protein spanning the N-terminal 300 amino acids (positions 1-300) has been synthesized and purified from *E. coli*.

| PEPTIDE GROUP | PEPTIDE NUMBER | SEQUENCE |
|---|---|---|
| 1 | CLP-2421 | MVRKKNPPL |
|   | CLP-2422 | KKNPPLRNV |
|   | CLP-2423 | VASEGEGQI |
|   | CLP-2424 | QILEPIGTE |
|   | CLP-2425 | RNMLAFSFP |
|   | CLP-2426 | NMLAFSFPA |
|   | CLP-2427 | MLAFSFPAA |
|   | CLP-2428 | FSFPAAGGV |
|   | CLP-2429 | AAGGVCEPL |
|   | CLP-2430 | SGQANCQGL |
| 2 | CLP-2431 | ANCQGLSPV |
|   | CLP-2432 | GLSPVSVAS |
|   | CLP-2433 | SVASKNPQV |
|   | CLP-2434 | RLNKSKTDL |
|   | CLP-2435 | NDNPDPAPL |
|   | CLP-2436 | DPAPLSPEL |
|   | CLP-2437 | ELQDFKCNI |
|   | CLP-2438 | GLHNRTRQD |
|   | CLP-2439 | ELDSKILAL |
|   | CLP-2440 | KILALHNMV |
| 3 | CLP-2441 | ALHNMVQFS |
|   | CLP-2442 | VNRSVFSGV |
|   | CLP-2443 | FSGVLQDIN |
|   | CLP-2444 | DINSSRPVL |
|   | CLP-2445 | VLLNGTYDV |
|   | CLP-2446 | FCNFTYMGN |
|   | CLP-2447 | YMGNSSTEL |
|   | CLP-2448 | FLQTHPNKI |
|   | CLP-2449 | KASLPSSEV |
|   | CLP-2450 | DLGKWQDKI |

| PEPTIDE GROUP | PEPTIDE NUMBER | SEQUENCE |
|---|---|---|
| 4 | CLP-2451 | VKAGDDTPV |
|  | CLP-2452 | FSCESSSSL |
|  | CLP-2453 | KLLEHYGKQ |
|  | CLP-2454 | GLNPELNDK |
|  | CLP-2455 | GSVINQNDL |
|  | CLP-2456 | SVINQNDLA |
|  | CLP-2457 | FCDFRYSKS |
|  | CLP-2458 | SHGPDVIVV |
|  | CLP-2459 | PLLRHYQQL |
|  | CLP-2460 | GLCSPEKHL |
| 5 | CLP-2461 | HLGEITYPF |
|  | CLP-2462 | LGEITYPFA |
|  | CLP-2463 | HCALLLLHL |
|  | CLP-2464 | ALLLLHLSP |
|  | CLP-2465 | LLLLHLSPG |
|  | CLP-2466 | LLLHLSPGA |
|  | CLP-2467 | LLHLSPGAA |
|  | CLP-2468 | FTTPDVDVL |
|  | CLP-2469 | TTPDVDVLL |
|  | CLP-2470 | VLLFHYESV |
| 6 | CLP-2471 | FITQVEEEI |
|  | CLP-2472 | FTAADTQSL |
|  | CLP-2473 | SLLEHFNTV |
|  | CLP-2474 | STIKEEPKI |
|  | CLP-2475 | KIDFRVYNL |
|  | CLP-2476 | NLLTPDSKM |
|  | CLP-2477 | KMGEPVSES |
|  | CLP-2478 | GLKEKVWTE |
|  | CLP-2479 | VTWRGADIL |
|  | CLP-2480 | ILRGSPSYT |
| 7 | CLP-2481 | YTQASLGLL |
|  | CLP-2482 | ASLGLLTPV |
|  | CLP-2483 | GLLTPVSGT |
|  | CLP-2484 | GTQEQTKTL |
|  | CLP-2485 | KTLRDSPNV |
|  | CLP-2486 | HLARPIYGL |
|  | CLP-2487 | PIYGLAVET |
|  | CLP-2488 | LAVETKGFL |
|  | CLP-2489 | FLQGAPAGG |
|  | CLP-2490 | AGGEKSGAL |
| 8 | CLP-2491 | GALPQQYPA |
|  | CLP-2492 | ALPQQYPAS |
|  | CLP-2493 | FCANCLTTK |
|  | CLP-2494 | ANGGYVCNA |
|  | CLP-2495 | NACGLYQKL |
|  | CLP-2496 | GLYQKLHST |
|  | CLP-2497 | KLHSTPRPL |
|  | CLP-2498 | STPRPLNII |
|  | CLP-2499 | RLNPEALQA |
|  | CLP-2500 | VLVSQTLDI |
| 9 | CLP-2501 | DIHKRMQPL |
|  | CLP-2502 | RMQPLHIQI |
|  | CLP-2503 | YPLFGLPFV |
|  | CLP-2504 | GLPFVHNDF |
|  | CLP-2505 | FVHNDFQSE |
|  | CLP-2506 | SVPGNPHYL |
|  | CLP-2507 | GNPHYLSHV |
|  | CLP-2508 | HYLSHVPGL |
|  | CLP-2509 | YVPYPTFNL |
|  | CLP-2510 | FNLPPHFSA |
| 10 | CLP-2511 | NLPPHFSAV |
|  | CLP-2512 | SAVGSDNDI |
|  | CLP-2513 | KNEGPLNVV |
|  | CLP-2514 | TKCVHCGIV |
|  | CLP-2515 | CVHCGIVFL |
|  | CLP-2516 | CGIVFLDEV |
|  | CLP-2517 | FLDEVMYAL |
|  | CLP-2518 | VMYALHMSC |
|  | CLP-2519 | FQCSICQHL |
|  | CLP-2520 | GLHRNNAQV |

2. Immune Reactivity of BFA4 Peptides and Generation of Human Effector T Cells:

The BFA4 peptides were grouped into different pools of 7-10 peptides for immunological testing. Dissolved peptide pools were pulsed onto autologous HLA-A*0201 dendritic cells and used to activate autologous T-cell-enriched PBMC preparations. Activated T cells from each peptide-pool-stimulated culture were re-stimulated another 3 to 5 times using CD40L-activated autologous B-cells. IFN-γ ELISPOT analysis and assays for CTL killing of peptide-pulsed target cells was performed to demonstrate the immunogenicity of these epitopes from BFA4.

Human T cells demonstrated effector cell activity against a number of pools of peptides from the BFA4 protein, as shown by their ability to secrete IFN-γ in ELISPOT assays. These experiments were repeated after different rounds of APC stimulation resulting in the same reactive peptide groups. Peptide groups 1, 2, 4, 5, 6, 7, 8, 9, and 10 were found to be immunoreactive in these assays. Subsequently, these reactive peptide groups were de-convoluted in additional IFN-γ ELISPOT assays in which single peptides from each group were tested separately. The individual peptides from BFA4 peptide groups 1, 5 6, 7, 8, 9, and 10 in ELISPOT assays. This analysis revealed a number of individual strongly reactive peptides from the BFA4 protein recognized by human T cells. It was also observed that many of these single peptides also induced CTL activity killing peptide-loaded human T2 lymphoma cell targets. These peptides are listed in Table VII:

TABLE VII

List of highly immunoreactive peptides from BFA4

| Strong IFN-γ Killing | | Strong CTL Killing | |
|---|---|---|---|
| CLP 2425 | RNMLAFSFP | CLP 2425 | RNMLAFSFP |
| CLP 2426 | NMLAFSFPA | CLP 2426 | NMLAFSFPA |
| CLP 2427 | MLAFSFPAA | CLP 2427 | MLAFSFPAA |
| CLP 2461 | HLGEITYPF | | |
| CLP 2468 | FTTPDVDVL | CLP 2468 | FTTPDVDVL |
| CLP 2470 | VLLFHYESV | CLP 2470 | VLLFHYYESV |
| CLP 2474 | KIDFRVYNL | | |
| CLP 2482 | ASLGLLTPV | CLP 2482 | ASLGLLTPV |
| CLP 2486 | HLARPIYGL | CLP 2486 | HLARPIYGL |
| CLP 2495 | NACGLYQKL | CLP 2495 | NACGLYQKL |
| CLP 2497 | KLHSTPRPL | | |
| CLP 2499 | RLNPEALQA | CLP 2499 | RLNPEALQA |
| CLP 2503 | YPLFGLPFV | | |
| CLP 2509 | YVPYPTFNL | CLP 2509 | YVPYPTFNL |
| CLP 2511 | NLPPHFSAV | | |

TABLE VII-continued

List of highly immunoreactive peptides from BFA4

| Strong IFN-γ Killing | | Strong CTL Killing | |
|---|---|---|---|
| CLP 2518 | VMYALHMSC | | |
| CLP 2520 | GLHRNNAQV | CLP 2520 | GLHRNNAQV |

D. Immune Responses Against BFA4 after Immunization In Vivo:

The pcDNA3.1/Zeo-BFA4 plasmid was used to immunize transgenic mice expressing a hybrid HLA-A*0201 α1α2 domain fused to a murine Kb α3 domain in C57BL/6 mice (A2-Kb mice). IFN-γ ELISPOT analysis using the groups of pooled peptides after DNA immunization and removal of activated spleen cells revealed a number of reactive BFA4 peptide groups. Some of these groups (especially group 7 and 8) also reacted strongly in human T-cell cultures suggesting that overlapping groups of peptides are recognized by human T cells and are naturally processed and presented on HLA-A2 after vaccination.

Vaccination experiments were also performed with the NYVAC-BFA4 and the MP76-18-BFA4 vectors in A2-Kb mice. Mice were immunized subcutaneously with 10-20 μg of MP-76-18-BFA4 and 1-2×10⁷ pfu vP2033 (NYVAC-BFA4) and boosted 28 days later with the same amounts of each vector. Re-stimulation of spleen cells from the immunized mice with the pools of BFA4 peptides revealed induction of IFN-γ production in response to BFA4 peptide groups 2, 3, 4, 5, 7, 9, and 10 in ELISPOT assays. Thus, the BFA4 gene encoded in a CMV promoter driven eukaryotic plasmid, NYVAC, or a Semliki replicase-based DNA plasmid, were all capable of inducing T-cell responses against the BFA4 protein in vivo.

Example 6

BCY1 Tumor Antigen

The BCY1 gene was detected as a partial open reading frame (ORF) homologous to a nematode gene called "posterior-expressed maternal gene-3" (PEM-3) playing a role in posterior to anterior patterning in Caenorhabtidis elegans embryos. No previous involvement of this gene in cancer has been documented.

A. BCY1 and Amino Acid DNA Sequences

A partial DNA sequence was originally determined for BCY1. Primers, 9616SXC and 9617SXC, are derived from the BCY I partial DNA sequence and are designed to clone BCY I by RT-PCR from Calu 6 total RNA. The primers are designed such that the PCR product has BamHI sites at both ends and an ATG start codon and a Kozak sequence at the 5' end, as shown below:

```
9616SXC: 5' CAGTACGGATCCACCATGGCCGAGCTGCGCCTGA
         AGGGC 3'

9617SXC: 5' CCACGAGGATCCTTAGGAGAATATTCGGATGGCTT
         GCG 3'
```

The 1.2 Kb expected amplicon was obtained using ThermoScript RT-PCR System (Invitrogen) under optimized conditions. The PCR products from three separate RT-PCR's were digested with BamHI and respectively inserted in pcDNA3.1/Zeo(+). The resulting clones were MC50A6, MC50A8 and MC50A19 from the first RT-PCR; MC54.21 from the second RT-PCR and MC55.29; and, MC55.32 from the third RT-PCR. The following primers were utilized in sequencing the clones:

```
9620MC: 5' TAATACGACTCACTATAGGG 3'

9621MC: 5' TAGAAGGCACAGTCGAGG 3'

9618MC: 5' GAAAACGACTTCCTGGCGGGGAG 3'

9619MC: 5' GCTCACCCAGGCGTGGGGCCTC 3'
```

DNA sequencing of all six clones indicated a consensus sequence (SEQ ID NO.: 30), as shown in FIGS. 9A and 9B, having the following differences from the original partial BCY1 sequence: a C to G substitution at position 1031 resulting in an amino acid change of Ala to Gly; a GC deletion at position 1032-1034 resulting in a Thr deletion; and, an A to G substitution at position 1177 resulting in an amino acid change of Thr to Ala. Clones MC50A8 and MC55.29 are identical to the consensus sequence. The amino acid sequence of BCY1 is shown in FIG. 9B and (SEQ ID NO.: 31).

B. Immunological Reagents for BCY1 Breast Cancer Antigen:

A library of 100 nonamer peptides spanning the BCY1 gene product was synthesized. The peptides were chosen based on their potential ability to bind to HLA-A*0201. Table VIII lists 100 nonamer peptide epitopes for HLA-A*0201 from the BCY1 protein tested (see below):

TABLE VIII

| Peptide Designation | Sequence | Position in Protein |
|---|---|---|
| *CLP-2599 | VPVPTSEHV | 2 |
| *CLP-2602 | PTSEHVAEI | 5 |
| *CLP-2609 | EIVGRQCKI | 12 |
| *CLP-2616 | KIKALRAKT | 19 |
| *CLP-2618 | KALRAKTNT | 21 |
| *CLP-2619 | ALRAKTNTY | 22 |
| *CLP-2620 | LRAKTNTYI | 23 |
| *CLP-2624 | TNTYIKTPV | 27 |
| *CLP-2627 | YIKTPVRGE | 30 |
| *CLP-2630 | TPVRGEEPV | 33 |
| *CLP-2633 | RGEEPVFMV | 36 |
| *CLP-2640 | MVTGRREDV | 43 |
| CLP-2641 | VTGRREDVA | 44 |
| *CLP-2643 | GRREDVATA | 46 |
| CLP-2647 | DVATARREI | 50 |
| CLP-2648 | VATARREII | 51 |
| *CLP-2650 | TARREIISA | 53 |
| *CLP-2651 | ARREIISAA | 54 |
| *CLP-2655 | IISAAEHFS | 58 |
| *CLP-2656 | ISAAEHFSM | 59 |

TABLE VIII-continued

| Peptide Designation | Sequence | Position in Protein |
|---|---|---|
| CLP-2657 | SAAEHFSMI | 60 |
| *CLP-2659 | AEHFSMIRA | 62 |
| *CLP-2663 | SMIRASRNK | 66 |
| CLP-2666 | RASRNKSGA | 69 |
| *CLP-2670 | NKSGAAFGV | 73 |
| *CLP-2673 | GAAFGVAPA | 76 |
| *CLP-2674 | AAFGVAPAL | 77 |
| *CLP-2677 | GVAPALPGQ | 80 |
| *CLP-2678 | VAPALPGQV | 81 |
| *CLP-2680 | PALPGQVTI | 83 |
| *CLP-2681 | ALPGQVTIR | 84 |
| *CLP-2682 | LPGQVTIRV | 85 |
| CLP-2684 | GQVTIRVRV | 87 |
| *CLP-2689 | RVRVPYRVV | 92 |
| *CLP-2691 | RVPYRVVGL | 94 |
| *CLP-2692 | VPYRVVGLV | 95 |
| *CLP-2695 | RVVGLVVGP | 98 |
| *CLP-2698 | GLVVGPKGA | 101 |
| *CLP-2699 | LVVGPKGAT | 102 |
| *CLP-2700 | VVGPKGATI | 103 |
| *CLP-2710 | RIQQQTNTY | 113 |
| *CLP-2711 | IQQQTNTYI | 114 |
| *CLP-2712 | QQQTNTYII | 115 |
| *CLP-2713 | QQTNTYIIT | 116 |
| *CLP-2718 | YIITPSRDR | 121 |
| CLP-2721 | TPSRDRDPV | 124 |
| CLP-2724 | RDRDPVFEI | 127 |
| CLP-2731 | EITGAPGNV | 134 |
| CLP-2734 | GAPGNVERA | 137 |
| CLP-2738 | NVERAREEI | 141 |
| CLP-2744 | EEIETHIAV | 147 |
| CLP-2746 | IETHIAVRT | 149 |
| CLP-2749 | HIAVRTGKI | 152 |
| CLP-2750 | IAVRTGKIL | 153 |
| CLP-2756 | KILEYNNEN | 159 |
| CLP-2760 | YNNENDFLA | 163 |
| CLP-2762 | NENDFLAGS | 165 |
| CLP-2766 | FLAGSPDAA | 169 |
| CLP-2767 | LAGSPDAAI | 170 |
| CLP-2774 | AIDSRYSDA | 177 |
| CLP-2777 | SRYSDAWRV | 180 |
| CLP-2785 | VHQPGCKPL | 188 |
| CLP-2793 | LSTFRQNSL | 196 |
| CLP-2801 | LGCIGECGV | 204 |
| CLP-2807 | CGVDSGFEA | 210 |
| CLP-2812 | GFEAPRLDV | 215 |
| CLP-2817 | RLDVYYGVA | 220 |
| CLP-2819 | DVYYGVAET | 222 |
| CLP-2823 | GVAETSPPL | 226 |
| CLP-2825 | AETSPPLWA | 228 |
| CLP-2830 | PLWAGQENA | 233 |
| CLP-2833 | AGQENATPT | 236 |
| CLP-2835 | QENATPTSV | 238 |
| CLP-2843 | VLFSSASSS | 246 |
| CLP-2857 | KARAGPPGA | 260 |
| CLP-2869 | PATSAGPEL | 272 |
| CLP-2870 | ATSAGPELA | 273 |
| CLP-2872 | SAGPELAGL | 275 |
| CLP-2879 | GLPRRPPGE | 282 |
| CLP-2887 | EPLQGFSKL | 290 |
| CLP-2892 | FSKLGGGGL | 295 |
| CLP-2894 | KLGGGGLRS | 297 |
| CLP-2899 | GLRSPGGGR | 302 |
| CLP-2909 | CMVCFESEV | 312 |
| CLP-2910 | MVCFESEVT | 313 |
| CLP-2911 | VCFESEVTA | 314 |
| CLP-2913 | FESEVTAAL | 316 |
| CLP-2916 | EVTAALVPC | 319 |
| CLP-2917 | VTAALVPCG | 320 |
| CLP-2920 | ALVPCGHNL | 323 |
| CLP-2921 | LVPCGHNLF | 324 |
| CLP-2922 | VPCGHNLFC | 325 |
| CLP-2927 | NLFCMECAV | 330 |
| CLP-2929 | FCMECAVRI | 332 |
| CLP-2933 | CAVRICERT | 336 |
| CLP-2936 | RICERTDPE | 339 |
| CLP-2940 | RTDPECPVC | 343 |
| CLP-2945 | CPVCHITAT | 348 |

TABLE VIII-continued

| Peptide Designation | Sequence | Position in Protein |
|---|---|---|
| CLP-2947 | VCHITATQA | 350 |
| CLP-2950 | ITATQAIRI | 353 |

Table IX shows the groups of peptides used for immunological testing:

| Peptide Group | Peptide Number | Peptide Sequence |
|---|---|---|
| 1 | CLP 2887 | EPLQGFSKL |
|   | CLP 2916 | EVTAALVPC |
|   | CLP 2945 | CPVCHITAT |
|   | CLP 2673 | KIKALRAKT |
|   | CLP 2699 | IISAAEHFS |
|   | CLP 2616 | RASRNKSGA |
|   | CLP 2655 | GAAFGVAPA |
|   | CLP 2731 | LVVGPKGAT |
|   | CLP 2734 | EITGAPGNV |
|   | CLP 2666 | GAPGNVERA |
| 2 | CLP 2724 | ALRAKTNTY |
|   | CLP 2689 | VATARREII |
|   | CLP 2648 | PALPGQVTI |
|   | CLP 2680 | ALPGQVTIR |
|   | CLP 2619 | RVRVPYRVV |
|   | CLP 2681 | RDRDPVFEI |
|   | CLP 2689 | RVRVPYRVV |
|   | CLP 2947 | HIAVRTGKI |
|   | CLP 2762 | NENDFLAGS |
|   | CLP 2933 | CAVRICERT |
|   | CLP 2749 | VCHITATQA |
| 3 | CLP 2647 | GRREDVATA |
|   | CLP 2677 | DVATARREI |
|   | CLP 2643 | TARREIISA |
|   | CLP 2785 | GVAPALPGQ |
|   | CLP 2917 | RVVGLVVGP |
|   | CLP 2695 | VHQPGCKPL |
|   | CLP 2650 | PATSAGPEL |
|   | CLP 2869 | VTAALVPCG |
| 4 | CLP 2812 | VPVPTSEHV |
|   | CLP 2892 | ARREIISAA |
|   | CLP 2738 | RIQQQTNTY |
|   | CLP 2651 | NVERAREEI |
|   | CLP 2870 | GFEAPRLDV |
|   | CLP 2899 | ATSAGPELA |
|   | CLP 2710 | FSKLGGGGL |
|   | CLP 2599 | GLRSPGGGR |
| 5 | CLP 2609 | PTSEHVAEI |
|   | CLP 2602 | EIVGRQCKI |
|   | CLP 2641 | LRAKTNTYI |
|   | CLP 2620 | VTGRREDVA |
|   | CLP 2940 | SMIRASRNK |
|   | CLP 2921 | CMVCFESEV |
|   | CLP 2936 | LVPCGHNLF |
|   | CLP 2663 | NLFCMECAV |
|   | CLP 2927 | RICERTDPE |
|   | CLP 2909 | RTDPECPVC |
| 6 | CLP 2766 | MVTGRREDV |
|   | CLP 2711 | GLVVGPKGA |
|   | CLP 2913 | IQQQTNTYI |
|   | CLP 2823 | FLAGSPDAA |
|   | CLP 2640 | GVAETSPPL |
|   | CLP 2698 | FESEVTAAL |
|   | CLP 2929 | FCMECAVRI |
| 7 | CLP 2760 | KALRAKTNT |
|   | CLP 2633 | RGEEPVFMV |
|   | CLP 2700 | SAAEHFSMI |
|   | CLP 2835 | AAFGVAPAL |
|   | CLP 2618 | VVGPKGATI |
|   | CLP 2657 | YNNENDFLA |
|   | CLP 2674 | LGCIGECGV |
|   | CLP 2911 | QENATPTSV |
|   | CLP 2801 | VCFESEVTA |
| 8 | CLP 2807 | TNTYIKTPV |
|   | CLP 2872 | NKSGAAFGV |
|   | CLP 2670 | QQTNTYIIT |
|   | CLP 2756 | KILEYNNEN |
|   | CLP 2825 | CGVDSGFEA |
|   | CLP 2843 | AETSPPLWA |
|   | CLP 2713 | PLWAGQENA |
|   | CLP 2624 | VLFSSASSS |
|   | CLP 2830 | SAGPELAGL |
| 9 | CLP 2712 | ISAAEHFSM |
|   | CLP 2744 | QQQTNTYII |
|   | CLP 2774 | EEIETHIAV |
|   | CLP 2819 | IETHIAVRT |
|   | CLP 2656 | LAGSPDAAI |
|   | CLP 2922 | AIDSRYSDA |
|   | CLP 2746 | DVYYGVAET |
|   | CLP 2767 | VPCGHNLFC |
|   | CLP 2950 | ITATQAIRI |
| 10 | CLP 2793 | TPVRGEEPV |
|   | CLP 2777 | AEHFSMIRA |
|   | CLP 2910 | VAPALPGQV |
|   | CLP 2721 | TPSRDRDPV |
|   | CLP 2630 | IAVRTGKIL |
|   | CLP 2659 | SRYSDAWRV |
|   | CLP 2678 | LSTFRQNSL |
|   | CLP 2750 | RLDVYYGVA |
|   | CLP 2833 | AGQENATPT |
|   | CLP 2817 | MVCFESEVT |

C. Immune reactivity of BCY1 peptides and generation of human effector T cells

The library of 100 peptides from BCY1 was separated into 10 groups of 7-10 peptides for immunological testing. Dissolved peptide pools were pulsed onto autologous HLA-A*0201 dendritic cells and used to activate autologous T-cell-enriched PBMC preparations. Activated T cells from each peptide-pool-stimulated culture were re-stimulated another 3 to 5 times using CD40L-activated autologous B-cells. IFN-γ ELISPOT analysis and assays for CTL killing of peptide-pulsed target cells was performed to demonstrate the immunogenicity of these epitopes from BCY1.

Figure 10:
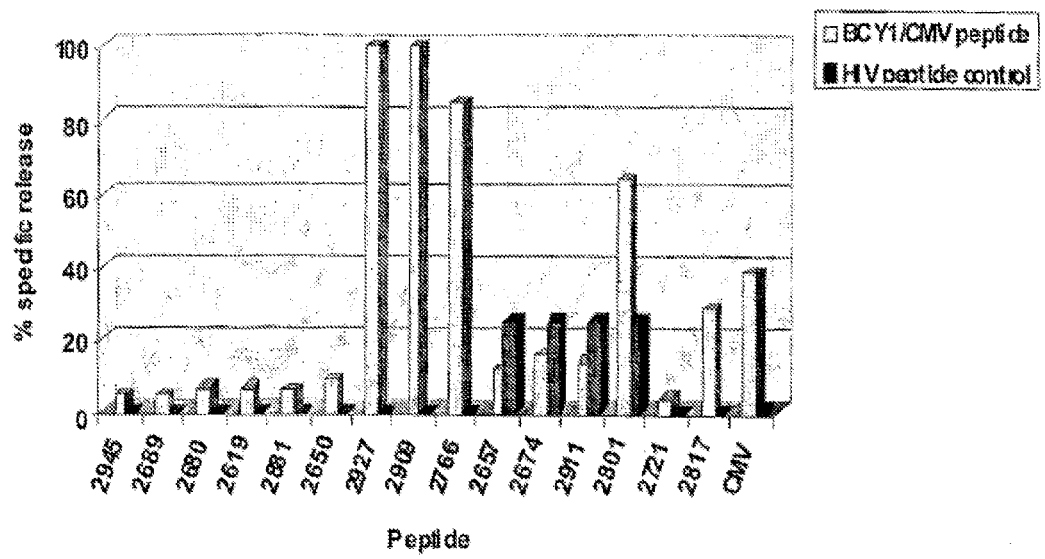
FIG. 10. Immune response against specific BCY1 peptides.

Human T cells demonstrated effector cell activity against a number of pools of peptides from the BCY1 protein, as shown by their ability to secrete IFN-γ in ELISPOT assays. These experiments were repeated after different rounds of APC stimulation resulting in the same reactive peptide groups. Peptide groups 1, 2, 3, 4, 5, 6, and 7 were found to be immunoreactive in these assays. Subsequently, these reactive peptide groups were de-convoluted in additional IFN-γ ELISPOT assays in which single peptides from each group were tested separately. This analysis revealed a number of individual strongly reactive peptides from the BCY1 protein recognized by human T cells (FIG. 10). Many of these single peptides also induced CTL activity killing peptide-loaded human T2 lymphoma cell targets. Table IX lists these peptides.

Example 7

BFA5/NYBR-1 Breast Cancer Antigen

A. Identification of BFA5

Microarray profiling analysis indicated that BFA5 was expressed at low to high levels in 41 out of 54 breast tumor biopsy samples (76%) and at high levels in 31 out of 54 breast tumors (57%), as compared to a panel of 52 normal, non-tumor tissues. In situ hybridization (ISH) was performed using a series of BFA5 DNA probes and confirmed the microarray with at least 61% of the tumors showing fairly strong signals. Further bioinformatics assessment confirmed the results of these gene expression analysis results.

Sequence analysis of the BFA5 nucleotide sequence revealed a high degree of similarity to two unidentified human genes: KIAA1074 (GenBank Accession No. XM_159732); and, KIAA0565 (GenBank Accession No. AB011137) isolated from a number of fetal and adult brain cDNA clones (Kikuno, et al. The complete sequences of 100 new cDNA clones, from brain which code for large proteins in vitro. *DNA Res.* 6: 197-205). These genes were found to contain putative Zn finger regions and a nuclear localization sequence. BFA5 was suggested by others to be a potential breast cancer antigen (Jager, et al. 2001. Identification of a tissue-specific putative transcription factor in breast tissue by serological screening of a breast cancer library. *Cancer Res.* 61: 2055-2061 and WO 01/47959). In each of these publications, the nucleotide sequence BFA5 was designated NYBR-1 ("New York Breast Cancer-1"; GenBank Accession Nos. AF269087 (nucleotide) and AAK27325 (amino acid). For the purposes of this application, the sequence is referred to as BFA-5, the terms BFA-5 and NYBR-I are interchangeable.

As shown previously by Jager, et al. and described in WO 01/47959, supra, BFA5 is specifically expressed in mammary gland, being expressed in 12/19 breast tumors analyzed. The structure of the BFA5/NYBR-1 gene has revealed that it encodes a 150-160 kD nuclear transcription factor with a bZIP site (DNA-binding domain followed by a leucine zipper motif). The gene also contains 5 tandem ankyrin repeats implying a role in protein-protein interactions. These ankyrin repeats may play a role in homo-dimerization of the protein. The BFA5 cDNA sequence is shown in FIG. 11 and SEQ ID NO.: 32. The BFA5 amino acid sequence is shown in FIG. 12 and SEQ ID NO.: 33.

B. Immunoreactivity of BFA5

1. Activation of Human T Cells and IFN-γ Secretion in ELISPOT.

A library of 100 peptides from the BFA5/NYBR-1 coding sequence that are predicted to be medium to high binders to HLA-A*0201 were designed using Rammensee and Parker algorithms. The library was sub-divided into 10 pools of ten peptides (see Table XI), and each pool was used to activate 10 different T cell cultures after pulsing peptides on to mature autologous dendritic cells. Two experiments were performed with the library of BFA5/NYBR-1 peptides demonstrating immunoreactivity in HLA-A*0201 human T cells, as described below.

TABLE X

| Peptide Group | CLP number | Sequence |
|---|---|---|
| | 2983 | LMDMQTFKA |
| | 2984 | KVSIPTKAL |
| | 2985 | SIPTKALEL |
| BFA5 | 2986 | LELKNEQTL |
| Group 1 | 2987 | TVSQKDVCL |
| | 2988 | SVPNKALEL |
| | 2989 | QEIVSQKDV |
| | 2990 | KINGKLEES |
| | 2991 | SLVEKIPCE |
| | 2992 | SLCETVSQK |

TABLE X-continued

| Peptide Group | CLP number | Sequence |
|---|---|---|
| | 2993 | BIDKINGKL |
| | 2994 | MLLQQNVDV |
| BFA5 | 2995 | NWWLQQQLV |
| Group 2 | 2996 | FLVDRKQQL |
| | 2997 | YLLHENQML |
| | 2998 | SLFESSAKI |
| | 2999 | KITIDIHFL |
| | 3000 | QLQSKNMWL |
| | 3001 | SLDQKLFQL |
| | 3002 | FLLIKNANA |
| | 3003 | KILDTVHSC |
| | 3004 | SLSKILDTV |
| | 3005 | ILIDSGADI |
| BFA5 | 3006 | KVMEINREV |
| Group 3 | 3007 | KLLSHGAM |
| | 3009 | AVYSEILSV |
| | 3010 | KMNVDVSST |
| | 3011 | ILSVVAKLL |
| | 3012 | VLIAENTML |
| | 3013 | KLSKNHQNT |
| | 3014 | SLTPLLLSI |
| BFA5 | 3015 | SQYSGQLKV |
| Group 4 | 3016 | KELEVKQQL |
| | 3017 | QIMEYIRKL |
| | 3018 | AMLKLEIAT |
| | 3019 | VLHCPLSEA |
| | 3020 | GLLKATDGM |
| | 3021 | GLLKANDGM |
| | 3022 | QQLEQALRI |
| | 3023 | CMLKKEIAM |
| | 3024 | EQMKKKFCV |
| BFA5 | 3025 | IQDIELKSV |
| Group 5 | 3026 | SVPNKAFEL |
| | 3027 | SIYQKVMEI |
| | 3028 | NLNYAGDAL |
| | 3029 | AVQDHDQIV |
| | 3030 | LIAENTMLT |
| | 3031 | FELKNEQTL |
| | 3033 | FESSAKIQV |
| | 3034 | GVTAEHYAV |
| BFA5 | 3035 | RVTSNKTKV |
| Group 6 | 3036 | TVSQKDVCV |
| | 3037 | KSQIEPAFH |
| | 3038 | KVLIAENIM |
| | 3039 | MLKLEIATL |
| | 3040 | EILSVVAKL |
| | 3041 | MLKKEIAML |
| | 3042 | LLKEKNEEI |
| | 3043 | ALRICDIEL |
| | 3044 | KIREELGRI |
| BFA5 | 3045 | TLKLKEESL |
| Group 7 | 3046 | ILNEKIREE |
| | 3047 | VLKKKLSEA |
| | 3048 | GTSDKIQDL |
| | 3049 | GADINLVDV |
| | 3050 | ELCSVRLTL |
| | 3051 | SVESNLNQV |
| | 3052 | SLKINLNYA |
| | 3053 | KTPDEAASL |
| | 3054 | ATDGMKVSI |
| BFA5 | 3055 | LSHGAVIEV |
| Group 8 | 3056 | EIAMLKLEI |
| | 3057 | AELQMTLKL |
| | 3058 | VFAADICGV |
| | 3060 | PAIEMQNSV |
| | 3061 | EIFNYNNHL |
| | 3062 | ILKEKNAEL |
| | 3063 | QLVHAHKKA |
| | 3065 | NQIDAQKRT |

TABLE X-continued

BFA5 Peptide Pools

| Peptide Group | CLP number | Sequence |
|---|---|---|
| BFA5 Group 9 | 3066 | NLVDVYGNM |
| | 3067 | KCTALMLAV |
| | 3068 | KIQCLEKAT |
| | 3069 | KIAWEKKET |
| | 3070 | IAWEKKEDT |
| | 3071 | VGMLLQQNV |
| | 3072 | VKTGCVARV |
| | 3074 | ALHYAVYSE |
| | 3075 | QMKKKFCVL |
| BFA5 Group 10 | 3076 | ALQQHQEAC |
| | 3077 | SEQTVEFLL |
| | 3078 | AVIENHNKA |
| | 3079 | AVTDGFHHI |
| | 3080 | AQLQRKMNV |
| | 3081 | SLVEGTSDK |

Figure 13A:
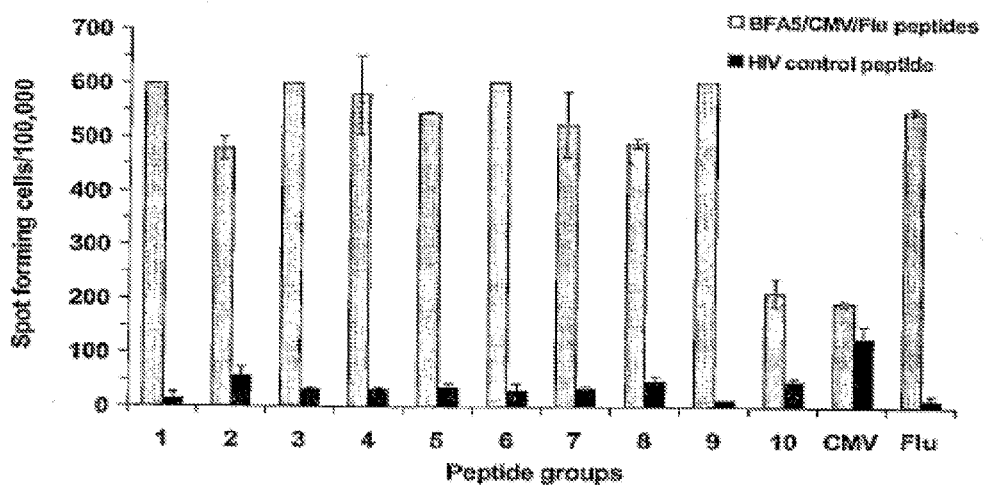
FIGS. 13A, B and C. Immune response against BFA5-derived peptides.

ELISPOT analysis was performed on human T-cell cultures activated through four rounds of stimulation with each pool of BFA5 peptides. In FIG. 13A, the numbers under the X-axis indicate the number of each peptide pool (1-10). Reactivity against a CMV pp65 peptide, and a Flu matrix peptide were used as positive controls for T-cell activation in the experiments. Each experiment was performed with PBMC and dendritic cells from a single HLA-A*0201+ donor designated as "AP10". The results show that, although BFA4 is markedly reactive with high ELISPOT counts per 100,000 cells in the assay, BFA5 is even more reactive with 9/10 pools demonstrating ELISPOT reactivity. Similar results were obtained for both BFA4 and BFA5/NYBR-1 with a different HLA-A*0201. The bars reach a maximum at 600 spots because beyond that the ELISPOT reader does not give accurate counts. Cultures having a reading of 600 spots have more than this number of spots.

Figure 13B:
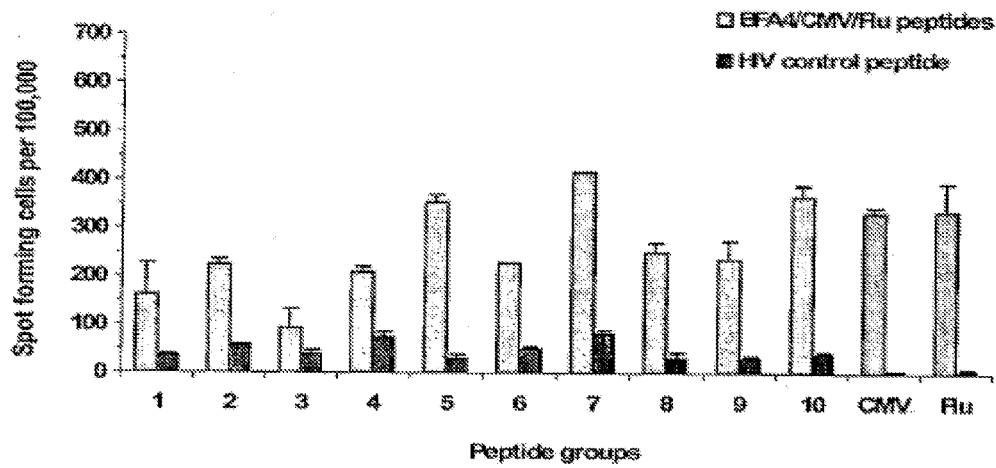

A large number of the BFA5 peptide pools of are reactive as shown by the high levels of IFN-γ production (FIG. 13A). Each reactive peptide pool was then separated into individual peptides and analyzed for immunogenicity using ELISPOT analysis to isolate single reactive BFA5 peptides. As shown in FIG. 13B, BFA5 is highly immunogenic with several reactive single peptides than that of BFA4. Similar results were obtained in two independent PBMC culture experiments.

Figure 13C:
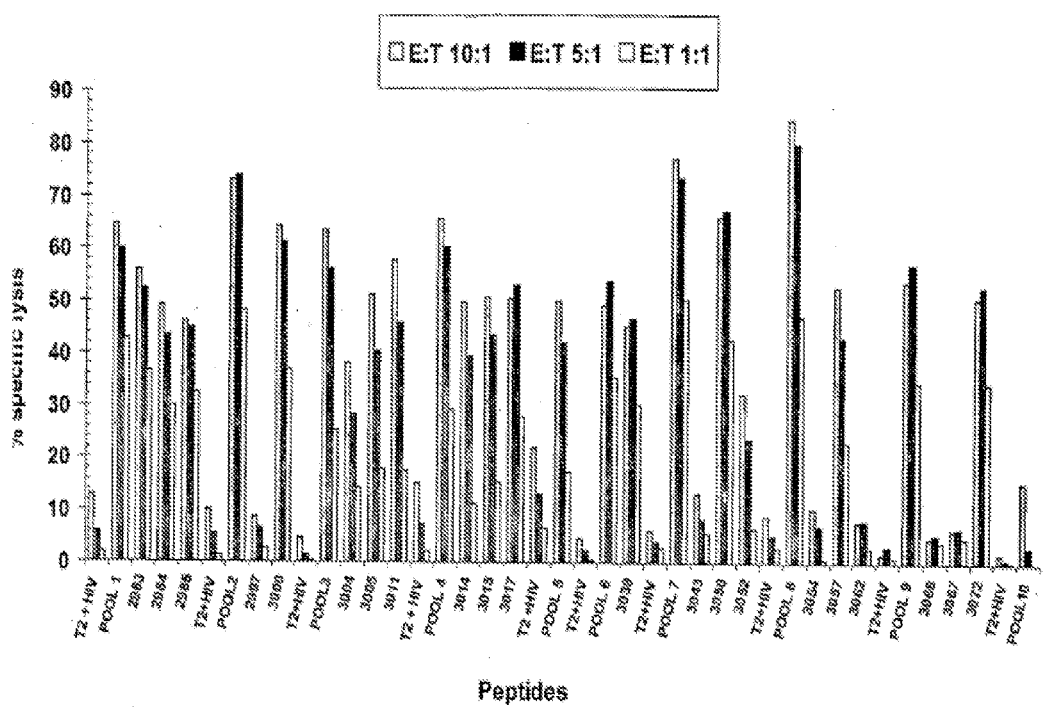

In addition to ELISPOT analysis, human T cells activated by BFA5 peptides were assayed to determine their ability to function as CTL. The cells were activated using peptide-pulsed dendritic cells followed by CD40 ligand-activated B cells (5 rounds of stimulation). The experiment shown was performed with isolated PBMC from HLA-A*0201+ donor AP31. Isolated T cells were tested in $^{51}$Cr-release assays using peptide-loaded T2 cells. The % specific lysis at a 10:1, 5:1, and 1:1 T-cell to target ratio is shown for T2 cells pulsed with either pools of BFA5/NYBR-1 peptides or with individual peptides. The graph shows CTL activity induced against targets loaded with a c non-specific HLA-A*0201-binding HIV peptide (control) followed by the CTL activity against the peptide pool (Pool 1 etc.) and then the activity induced by individual peptides from the respective pool to the right. A high level of cytotoxicity was observed for some peptides at a 1:1 E:T ratio. CTL activity (percent specific lysis) induced by the control HIV peptide was generally <10%. Similar results were obtained with another PBMC donor expressing HLA-A*0201 (AP10). FIG. 13C shows that a large number of BFA5 peptides trigger T cell-mediated cytotoxicity of BFA5 peptide-loaded target cells. Table XI lists those peptides having immunogenic properties. Five peptides (LMDMQTFKA, ILIDSGADI, ILSVVAKLL, SQYSGQLKV, and ELCSVRLTL) were found to induce both IFN-γ secretion and CTL activity in T cells from both donors.

TABLE XI

Immunoreactive peptides from BFA5

| BFA5 peptides eliciting high IFN-γ release (>200 spots/ 100,000 cells) | | BFA5 peptides inducing CTL lysis of pulsed cells | |
|---|---|---|---|
| Donor AP10 | Donor AP31 | Donor AP10 | Donor AP31 |
| LMDMQTFKA | LMDMQTFKA | LMDMQTFKA | LMDMQTFKA |
| KVSIPTKAL | | | KVSIPTKAL |
| SIPTKALEL | | | SIPTKALEL |
| TVSQKDVCL | | | |
| SVPNKALEL | | | |
| YLLHENCML | YLLHENCML | YLLHENCML | |
| QLQSKNMWL | QLQSKNMWL | | QLQSKNMWL |
| SLSKILDTV | SLSKILDTV | | SLSKILDTV |
| ILIDSGADI | ILIDSGADI | ILIDSGADI | ILIDSGADI |
| KVMEINREV | | | |
| AVYSEILSV | | | |
| ILSVVAKLL | ILSVVAKLL | ILSVVAKLL | ILSVVAKLL |
| SLTPLLLSI | SLTPLLLSI | | SLTPLLLSI |
| SQYSGQLKV | SQYSGQLKV | SQYSGQLKV | SQYSGQLKV |
| QIMEYIRKL | QIMEYIRKL | | QIMEYIRKL |
| SVPNKAFEL | | | |
| NLNYAGDAL | NLNYAGDAL | | |
| | GVTAEHYAV | | |
| | KSQEPAFHI | | |
| MLKLEIATL | MLKLEIATL | | MLKLEIATL |
| | MLKKEIAML | | |
| ALRIQDIEL | | | |
| | VLKKKLSEA | | |
| ELCSVRLTL | ELCSVRLTL | ELCSVRLTL | ELCSVRLTL |
| SLKINLNYA | SLKINLNYA | | SLKINLNYA |
| ATCGMKVSI | | ATCGMKVSI | |
| AELQMTLKL | | AELQMTLKL | AELQMTLKL |
| | VFAADICGV | | |
| ILKEKNAEL | ILKEKNAEL | | |
| NLVDVYGNM | | NLVDVYGNM | |
| KCTALMLAV | | | |

C. Immunological Reagents

Polyclonal antisera were generated against the following series of 22- to 23-mer peptides of BFA5:

| | |
|---|---|
| BFA5(1-23) | KLH-MTKRKKTINLNIQDAQKRTALHW (CLP-2977) |
| BFA5(312-334) | KLH-TSEKFTWPAKGRPRKIAWEKKED (CLP-2978) |
| BFA5(612-634) | KLH-DEILPSESKQKDYEENSWDTESL (CLP-2979) |
| BFA5(972-994) | KLH-RLTLNQEEEKRRNADILNEKIRE (CLP-2980) |
| BFA5(1117-1139) | KLH-AENTMLTSKLKEKQDKEILEAEI (CLP-2981) |
| BFA5(1319-1341) | KLH-NYNNHLKNRIYQYEKEKAETENS (CLP-2982) |

Prebleed samples from rabbits were processed and stored at −20° C. Rabbits were immunized as follows: 1) the peptides were administered as an emulsion with Freund's Complete Adjuvant (FCA); and, 2) two weeks later, the peptides were coupled with Keyhole-Limpet Hemocyanin (KLH)- coupled and administered as an emulsion with Freund's Incomplete Adjuvant FIA. The following results were observed:

TABLE XII

| Peptide/protein | IgG titer × 10⁵ (after first Immunization Rb1/Rb2) | IgG titer × 10⁵ (after second Immunization Rb1/Rb2) |
| --- | --- | --- |
| CLP 2977 | 25/6 | 256/64 |
| CLP 2978 | 25/25 | 64/256 |
| CLP 2979 | 12/25 | 256/512 |
| CLP 2980 | 25/12 | 1024/128 |
| CLP 2981 | 8/4 | 256/64 |
| CLP 2982 | 2/2 | 64/32 |

Prebleed sample results exhibited IgG titers <100 for all samples.

To assess the quality of the polyclonal antisera, western blots were performed using sera against BFA5. Sera were separately screened against cell extracts obtained from the BT474, MDMB453, MCF-7, Calu-6, and CosA2 cells. The approximate expected MW, of BFA5 protein is 153 kDa. A 220 kD band was observed in the BT474 extract with CLP2980 antibody but not in the MDMB453 cell extracts however a ~130 kD band was present in the MDMB453 extract. Both bands were found to be consistent with the polyclonal antibosera tested in this analysis. Neither of these bands is present in the negative control. Thus, it can be concluded that the polyclonal antisera are to specific for BFA5.

Example 8

BCZ4 Tumor Antigen

A. BCZ4 Sequence

The BCZ4 sequence was detected as an over-expressed sequence in breast cancer samples.

The nucleotide sequence and deduced amino acid sequence of BCZ4 are shown in FIG. 14, SEQ ID NO. 34 (BCZ4 cDNA), and SEQ ID NO. 35 (BCZ4 amino acid sequence).

B. Immunological Reagents for BCZ4 Breast Cancer Antigen:

A library of 100 nonamer peptides spanning the BCZ4 gene product was synthesized. The peptides were chosen based on their potential ability to bind to HLA-A*0201. Table XIII lists 100 nonamer peptide epitopes for HLA-A*0201 from the BCZ4 protein tested (see below):

TABLE XIII

BCZ4 Peptide Pools

| Peptide Group | CLP number | Sequence |
| --- | --- | --- |
| | 3220 | LDLETLTDI |
| | 3221 | DILQHQIRA |
| | 3222 | ILQHQIRAV |
| BCZ4 | 3223 | AVPFENLNI |
| Group 1 | 3224 | NLNIHCGDA |
| | 3225 | AMDLGLEAI |
| | 3226 | GLEAIFDQV |
| | 3227 | LEAIFDQVV |
| | 3228 | WCLQVNHLL |
| | 3229 | QVNHLLYWA |
| | 3230 | VNHLLYWAL |
| | 3231 | HLLYWALTT |
| BCZ4 | 3232 | LLYWALTTI |
| Group 2 | 3233 | ALTTIGFET |
| | 3234 | LTTIGFETT |

TABLE XIII-continued

BCZ4 Peptide Pools

| Peptide Group | CLP number | Sequence |
| --- | --- | --- |
| | 3235 | TTIGFETTM |
| | 3236 | TIGFETTML |
| | 3237 | TMLGGYVYS |
| | 3238 | MLGGYVYST |
| | 3239 | YSTGMIHLL |
| | 3240 | STGMIHLLL |
| | 3241 | GMIHLLLQV |
| | 3242 | MIHLLLQVT |
| BCZ4 | 3243 | LLLQVTIDG |
| Group 3 | 3244 | VTIDGRNYI |
| | 3245 | TIDGRNYIV |
| | 3246 | YIVDAGFGR |
| | 3247 | RSYQMWQPL |
| | 3248 | YQMWQPLEL |
| | 3249 | QMWQPLELI |
| | 3250 | ISGKDQPQV |
| | 3251 | KDQPQVPCV |
| BCZ4 | 3252 | PQVPCVFRL |
| Group 4 | 3253 | QVPCVFRLT |
| | 3254 | RLTEENGFW |
| | 3255 | TEENGFWYL |
| | 3256 | NGFWYLDQI |
| | 3257 | DQIRREQYI |
| | 3258 | YIPNEEFLH |
| | 3259 | YSFTLKPRT |
| | 3260 | RTIEDFESM |
| | 3261 | YLQTSPSSV |
| BCZ4 | 3262 | QTSPSSVFT |
| Group 5 | 3263 | SVFTSKSFC |
| | 3264 | FTSKSFCSL |
| | 3265 | CSLQTPDGV |
| | 3266 | LQTPDGVHC |
| | 3267 | QTPDGVHCL |
| | 3268 | TPDGVHCLV |
| | 3269 | GVHCLVGFT |
| | 3270 | CLVGFTLTH |
| | 3271 | TLTHRRFNY |
| BCZ4 | 3272 | FNYKDNTDL |
| Group 6 | 3273 | NTDLIEFKT |
| | 3274 | TDLIEFKTL |
| | 3275 | LSEEEIEKV |
| | 3276 | KVLKNIFNI |
| | 3277 | LKNIFNISL |
| | 3278 | NISLQRKLV |
| | 3279 | KHGDRFFTI |
| | 3280 | DIEAYLERI |
| | 3281 | YLERIGYKK |
| BCZ4 | 3282 | RNKLDLETL |
| Group 7 | 3283 | NKLDLETLT |
| | 3284 | KLDLETLTD |
| | 3285 | DLETLTDIL |
| | 3286 | TLTDILQHQ |
| | 3287 | LTDILQHQI |
| | 3288 | QIRAVPFEN |
| | 3289 | IRAVPFENL |
| | 3290 | IHCGDAMDL |
| | 3291 | HCGDAMDLG |
| BCZ4 | 3292 | DLGLEAIFD |
| Group 8 | 3293 | AIFDQVVRR |
| | 3294 | GWCLQVNHL |
| | 3295 | LQVNHLLYW |
| | 3296 | GGYVYSTPA |
| | 3297 | YVYSTPAKK |
| | 3298 | STPAKKYST |
| | 3299 | IHLLLQVTI |
| | 3300 | HLLLQVTID |
| | 3301 | LLQVTIDGR |

TABLE XIII-continued

BCZ4 Peptide Pools

| Peptide Group | CLP number | Sequence |
|---|---|---|
| BCZ4 Group 9 | 3302 | YLDQIRREQ |
| | 3303 | QYIPNEEFL |
| | 3304 | FLHSDLLED |
| | 3305 | DLLEDSKYR |
| | 3306 | YRKIYSFTL |
| | 3307 | KIYSFTLKP |
| | 3308 | TLKPRTIED |
| | 3309 | VHCLVGFTL |
| | | |
| | 3310 | LTHRRFNYK |
| | 3311 | DLIEFKTLS |
| BCZ4 Group 10 | 3312 | LIEFKTLSE |
| | 3313 | FKTLSEEEI |
| | 3314 | TLSEEEIEK |
| | 3315 | EIEKVLKNI |
| | 3316 | FNISLQRKL |
| | 3317 | SLQRKLVPK |
| | 3318 | KLVPKHGDR |
| | 3319 | PKHGDRFFT |

C. Immune Reactivity of BCZ4 Peptides and Generation of Human Effector T Cells

Figure 15A:
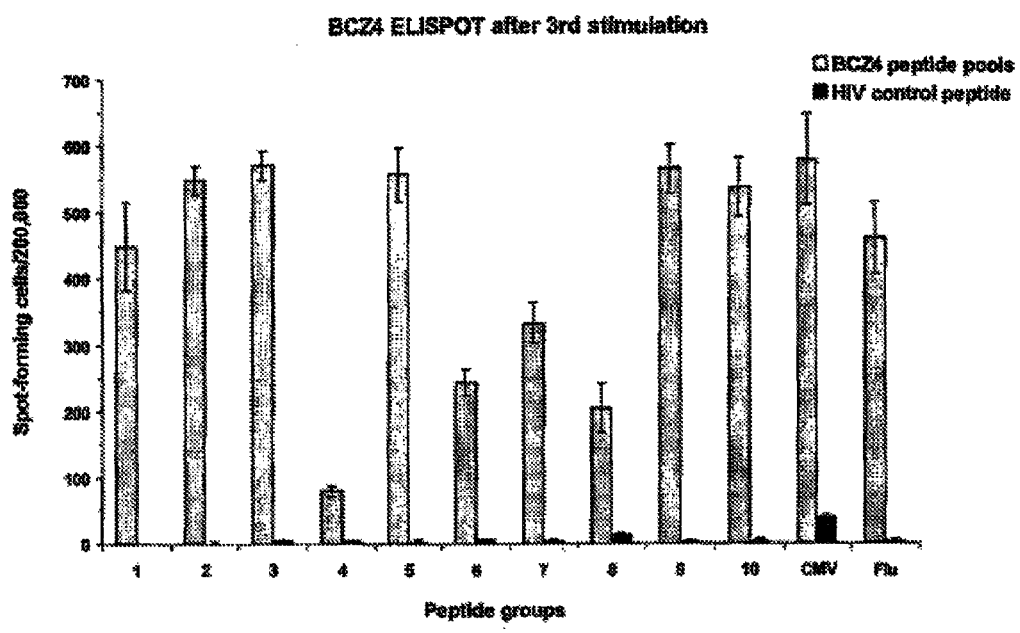
FIG. 15. Immune response against BCZ4-derived peptides (A: BCZ4 ELISPOT; B: BCZ4 Peptide Deconvolution; C: CTL response).

Human PBMC from an HLA-A2.1 positive donor designated AP10 were activated with autologous dendritic cells pulsed with different pools of 9-mer peptides from the BCZ4 antigen (see Table XIII for list). The activated T cells were re-stimulated after 12 days with activated autologous CD40-ligand-activated B cells pulsed with the same respective peptide pools for another 8 to 10 days. This secondary activation was repeated more time for a total of 3 stimulations. The activated T cells were isolated after the 3$^{rd}$ stimulation and subjected to ELISPOT analysis for human IFN-γ production against their respective BCZ4 peptide pools as shown (FIG. 15A). In FIG. 15A, the blue bars show reactivity against the BCZ4 peptide pools and the red bars are for an HLA-A2.1-binding HIV peptide as a negative control. Positive control HLA-A2.1-binding recall antigen peptides for CMV and flu were as used as positive control in the experiment. Standard deviations are indicated. The experiment was repeated on activated T cells after an additional round of peptide stimulation with the similar results.

Figure 15B:
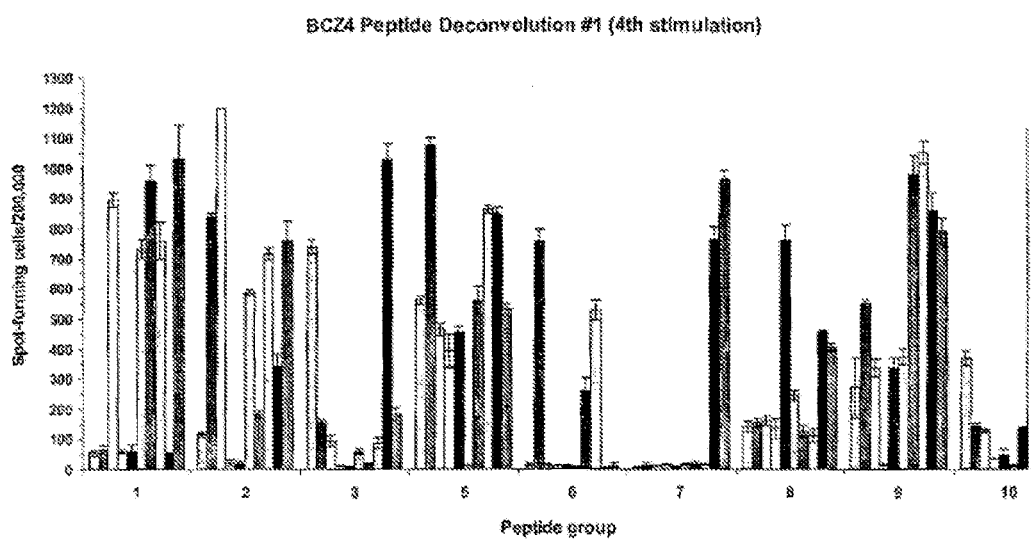

The peptide pools were deconvoluted using IFN-γ ELISPOT assays (FIG. 15B). Human T cells from donor AP10 were stimulated with the different pools of BCZ4 peptides shown in Table XIII. Stimulation was performed as described earlier for the other antigens described. After 4 and 5 rounds of stimulation, T cells were harvested and subjected to ELISPOT analysis for IFN-γ production with each individual peptide in each pool. The bars shown represent individual peptide reactivity for each specific pool. Table XIII identifies each of the reactive peptides. This experiment was repeated with similar results following another round of stimulation of AP10 donor T cells.

In addition to ELISPOT analysis, human T cells activated by BCZ4 peptides were assayed to determine their ability to function as CTL. The cells were activated using peptide-pulsed dendritic cells followed by CD40 ligand-activated B cells (5 rounds of stimulation). The experiment shown was performed with isolated PBMC from HLA-A*0201$^+$ donor AP31. Isolated T cells were tested in $^{51}$Cr-release assays using peptide-loaded T2 cells. The % specific lysis at a 10:1 T-cell to target ratio is shown for T2 cells pulsed with individual BCZ4 peptides. A high level of cytotoxicity was observed for some peptides (FIG. 15C). CTL activity (percent specific lysis) induced by the control HIV peptide was generally <10%. Similar results were obtained with another PBMC donor expressing HLA-A*0201 (AP10). Table XIV lists the reactivity of the individual peptides:

TABLE XIV

| | Peptides eliciting strong IFN-γ ELISPOT activity | Peptides eliciting CTL activity (peptide pulsed targets) | SEQ ID |
|---|---|---|---|
| CLP 3222 | ILQHQIRAV | ILQHQIRAV | 391 |
| CLP 3225 | AMDLGLEAI | | 394 |
| CLP 3226 | GLEAIFDQV | GLEAIFDQV | 395 |
| CLP 3227 | LEAIFDQVV | | 396 |
| CLP 3229 | QVNHLLYWA | | 398 |
| CLP 3231 | HLLYWALTT | | 400 |
| CLP 3232 | LLYWALTTI | LLYWALTTI | 401 |
| CLP 3235 | TTIGFETTM | | 404 |
| CLP 3237 | TMLGGYVYS | | 406 |
| CLP 3239 | YSTGMIHLL | | 408 |
| CLP 3240 | STGMIHLLL | | 409 |
| CLP 3248 | YQMWQPLEL | YQMWQPLEL | 417 |
| CLP 3260 | RTIEDFESM | | 429 |
| CLP 3261 | YLQTSPSSV | YLQTSPSSV | 430 |
| CLP 3266 | LQTPDGVHC | | 435 |
| CLP 3267 | QTPDGVHCL | | 436 |
| CLP 3268 | TPDGVHCLV | | 437 |
| CLP 3269 | GVHCLVGFT | | 438 |
| CLP 3271 | TLTHRRFNY | | 440 |
| CLP 3277 | LKNIFNISL | | 446 |
| CLP 3288 | QIRAVPFEN | | 457 |
| CLP 3289 | IRAVPFENL | | 458 |
| CLP 3294 | GWCLQVNHL | | 463 |
| CLP 3298 | STPAKKYST | | 467 |
| CLP 3299 | IHLLLQVTI | IHLLLQVTI | 468 |
| CLP 3301 | LLQVTIDGR | | 470 |
| CLP 3306 | YRKIYSFTL | | 475 |
| CLP 3307 | KYSFTLKP | | 476 |
| CLP 3308 | TLKPRTIED | | 477 |
| CLP 3309 | VHCLVGFTL | | 478 |
| CLP 3317 | SLQRKLVPK | | 486 |
| CLP 3319 | PKHGDRFFT | | 488 |

D. BCZ4 Expression Vectors

BCZ4 was PCR amplified using plasmid called pSporty/BCZ4 as the template using Platinum Taq (Invitrogen). Amplification conditions were as follows: 1) 94° C. 2 minutes; 2) 35 cycles of 94° C., 30 seconds, 53° C. 30 seconds, 67° C. 2.5 minutes; and, 3) 67° C. 7 minutes. PCR primers were designed to include EcoRI restriction sites and directly flank the ORF (i.e., no extraneous sequence). Primer sequences were as follows: AS032F (forward primer) 5' GGAATTCAACATGGACATTGAAG-CATATCTTGAAAGAATTG 3' (SEQ ID NO.:591), AS034R (reverse primer) 5' GGAATTCCTGGTGAGCTGGATGA-CAAATAGAC AAGATTG 3' (SEQ ID NO.: 592). A Kozak sequence was also included in the forward primer. pcDNA3.1/Zeo(+) was cut with EcoRI and treated with CIP to prevent self-ligation. The BCZ4 amplicon was then ligated into EcoRI digested pcDNA3/Zeo(+). Sequencing produced one clone (AS-579-5) which matched the expected BCZ4 sequence. BCZ4 protein was then expressed from this expression vector using standard techniques.

Example 9

BFY3 Tumor Antigen

A. BFY3 Sequence

The BFY3 sequence was detected as an over-expressed sequence in breast cancer samples. RT-PCR amplification of BFY3 w/EcoRI ends from HTB131 total RNA with AS007F (forward primer) 5' GGAATTCACC ATGCTTTGGAAATTGACGGAT 3' (SEQ ID NO.: 593) and AS010R (reverse primer) 5' GGAATTCC TCACTTTCTGTGCT TCTC CTCTTTGTCA 3' (SEQ ID NO.: 594) was performed. PCR product was digested with EcoR1 and cloned into EcoRI digested and CIP treated pcDNA3.1/Zeo(+) vector by ligation. Several positive clones were identified by restriction digestion and sequence results of AS-391-2 match expected BFY3 sequence. The nucleotide sequence and deduced amino acid sequence of BFY3 are shown in FIG. 16, SEQ ID NO. 36 (BFY3 cDNA), and SEQ ID NO. 37 (BFY3 amino acid sequence).

B. Immunological Reagents for BFY3 Breast Cancer Antigen

A library of 100 nonamer peptides spanning the BFY3 gene product was synthesized. The peptides were chosen based on their potential ability to bind to HLA-A*0201. Table XV lists 100 nonamer peptide epitopes for HLA-A*0201 from the BFY3 protein tested (see below):

TABLE XV

BFY3 Peptide Pools Used to Activate Human T Cells

| Peptide Group | CLP number | Sequence |
|---|---|---|
| BFY3 Group 1 | 3320 | MLWKLTDNI |
| | 3321 | KLTDNIKYE |
| | 3322 | GTSNGTARL |
| | 3323 | NGTARLPQL |
| | 3324 | ARLPQLGTV |
| | 3325 | GTVGQSPYT |
| | 3326 | SPYTSAPPL |
| | 3327 | FQPPYFPPP |
| | 3328 | YFPPPYQPI |
| | 3329 | QSQDPYSHV |
| BFY3 Group 2 | 3330 | SHVNDPYSL |
| | 3331 | SLNPLHAQP |
| | 3332 | RQSQESGLL |
| | 3333 | GLLHTHRGL |
| | 3334 | GLPHQLSGL |
| | 3335 | GLDPRRDYR |
| | 3336 | DLLHGPHAL |
| | 3337 | LLHGPHALS |
| | 3338 | ALSSGLGDL |
| | 3339 | SSGLGDLSI |
| BFY3 Group 3 | 3340 | GLGDLSIHS |
| | 3341 | LGDLSIHSL |
| | 3342 | SIHSLPHAI |
| | 3343 | SLPHAIEEV |
| | 3344 | HAIEEVPHV |
| | 3345 | GINIPDQTV |
| | 3346 | QTVIKKGPV |
| | 3347 | VIKKGPVSL |
| | 3348 | SLSKSNSNA |
| | 3349 | SNSNAVSAI |
| BFY3 Group 4 | 3350 | AIPINKDNL |
| | 3351 | NLFGGVVNP |
| | 3352 | FGGVVNPNE |
| | 3353 | GGVVNPNEV |
| | 3355 | NPNEVFCSV |
| | 3356 | CSVPGRLSL |
| | 3357 | SVPGRLSLL |
| | 3358 | SLLSSTSKY |
| | 3359 | LLSSTSKYK |
| BFY3 Group 5 | 3360 | LSSTSKYKV |
| | 3361 | STSKYKVTV |
| | 3362 | KYKVTVAEV |
| | 3363 | YKVTVAEVQ |
| | 3364 | TVAEVQRRL |
| | 3365 | RLSPPECLN |
| | 3366 | LNASLLGGV |
| | 3367 | NASLLGGVL |
| | 3368 | SLLGGVLRR |
| | 3369 | LLGGVLRRA |

TABLE XV-continued

BFY3 Peptide Pools Used to Activate Human T Cells

| Peptide Group | CLP number | Sequence |
|---|---|---|
| BFY3 Group 6 | 3370 | VLRRAKSKN |
| | 3371 | SLREKLDKI |
| | 3372 | KLDKIGLNL |
| | 3373 | KIGLNLPAG |
| | 3374 | GLNLPAGRR |
| | 3375 | NLPAGRRKA |
| | 3376 | AGRRKAANV |
| | 3377 | RKAANVTLL |
| | 3378 | KAANVTLLT |
| | 3379 | ANVTLLTSL |
| BFY3 Group 7 | 3380 | NVTLLTSLV |
| | 3381 | TLLTSLVEG |
| | 3382 | LLTSLVEGE |
| | 3383 | TSLVEGEAV |
| | 3384 | SLVEGEAVH |
| | 3385 | LVEGEAVHL |
| | 3386 | VEGEAVHLA |
| | 3387 | HLARDFGYV |
| | 3388 | YVCETEFPA |
| | 3389 | CETEFPAKA |
| BFY3 Group 8 | 3390 | AKAVAEFLN |
| | 3391 | AVAEFLNRQ |
| | 3392 | FLNRQHSDP |
| | 3393 | QVTRKNMLL |
| | 3394 | NMLLATKQI |
| | 3395 | MLLATKQIC |
| | 3396 | LLATKQICK |
| | 3397 | QICKEFTDL |
| | 3398 | ICKEFTDLL |
| | 3399 | LLAQDRSPL |
| BFY3 Group 9 | 3400 | ILEPGIQSC |
| | 3401 | LEPGIQSCL |
| | 3402 | QSCLTHFNL |
| | 3403 | SCLTHFNLI |
| | 3404 | NLISHGFGS |
| | 3405 | LISHGFGSP |
| | 3406 | ISHGFGSPA |
| | 3407 | SHGFGSPAV |
| | 3408 | FGSPAVCAA |
| | 3409 | GSPAVCAAV |
| BFY3 Group 10 | 3410 | AVCAAVTAL |
| | 3411 | AVTALQNYL |
| | 3412 | VTALQNYLT |
| | 3413 | ALQNYLTEA |
| | 3414 | LQNYLTEAL |
| | 3415 | YLTEALKAM |
| | 3416 | LKAMDKMYL |
| | 3417 | AMDKMYLSN |
| | 3418 | KMYLSNNPN |
| | 3419 | YLSNNPNSH |

Figure 17A:
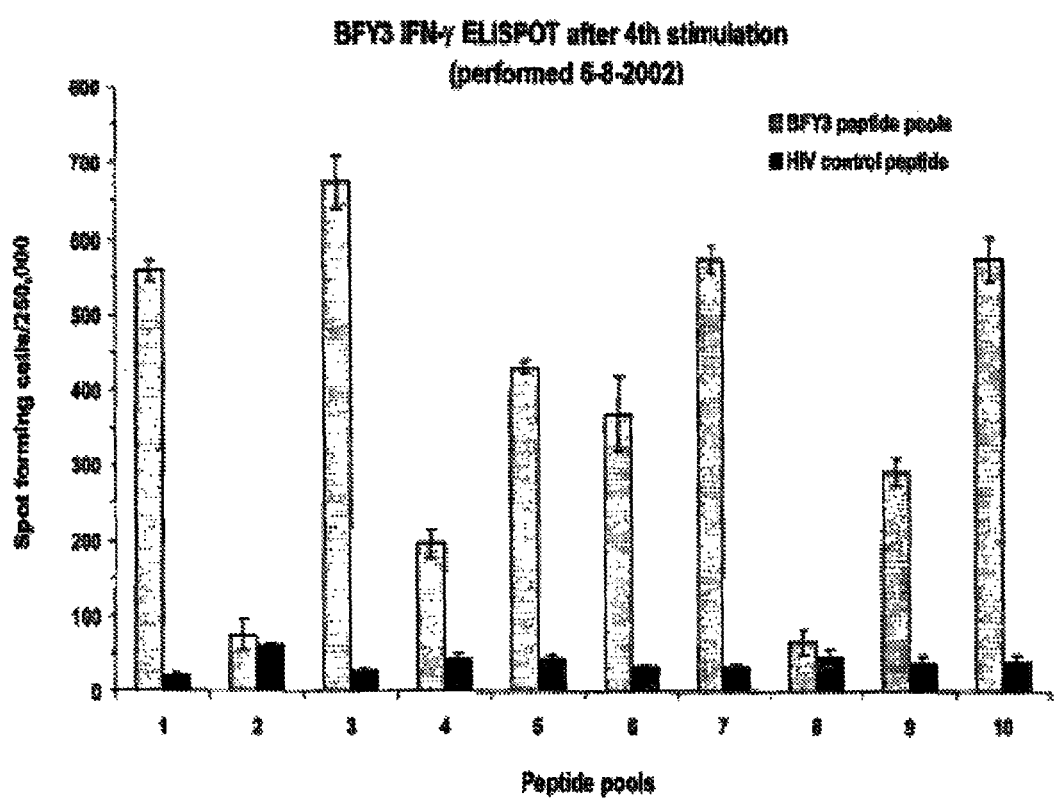
FIGS. 17A-E. Immune response against BFY3-derived peptides.

Human PBMC from an HLA-A2.1 positive donor designated AP31 were activated with autologous dendritic cells pulsed with different pools of 9-mer peptides from the BFY3 antigen (see Table I for list). The activated T cells were re-stimulated after 12 days with activated autologous CD40-ligand-activated B cells pulsed with the same respective peptide pools for another 8 to 10 days. This secondary activation was repeated 2 more time for a total of 4 stimulations. The activated T cells were isolated after the 4$^{th}$ stimulation and subjected to ELISPOT analysis for human IFN-γ production against their respective BFY3 peptide pools as shown. The blue bars show reactivity against the BFY3 peptide pools and the red bars are for an HLA-A2.1-binding HIV peptide as a negative control. Standard deviations are indicated. The experiment was repeated 2 times on activated T cells from different rounds of peptide stimulation with the similar results (FIG. 17A).

Figure 17B:
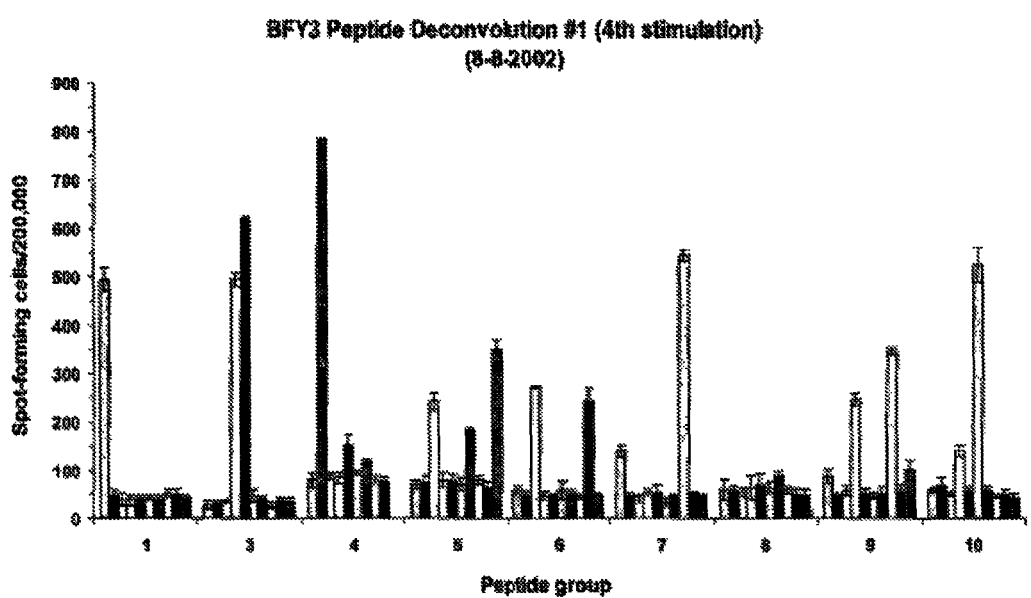

The BFY3 peptide pools were deconvoluted and studied in IFN-γ ELISPOT assays. Human T cells from donor AP10 were stimulated with the different pools of BFY3 peptides shown in Table XV. Stimulation was performed as described earlier for the other antigens described. After 4 rounds of stimulation, the T cells from each culture were harvested and subjected to ELISPOT analysis for IFN-γ production with each individual peptide in each pool. FIG. 17B illustrates individual peptide reactivity for each specific pool.

Figure 17C:
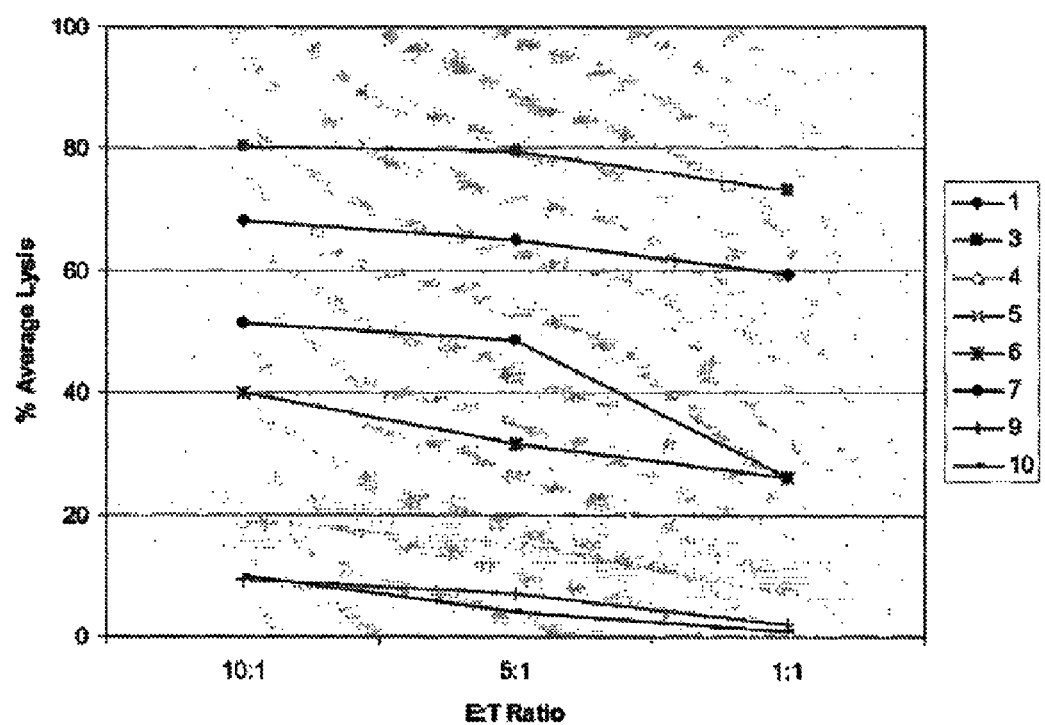
Figure 17D:
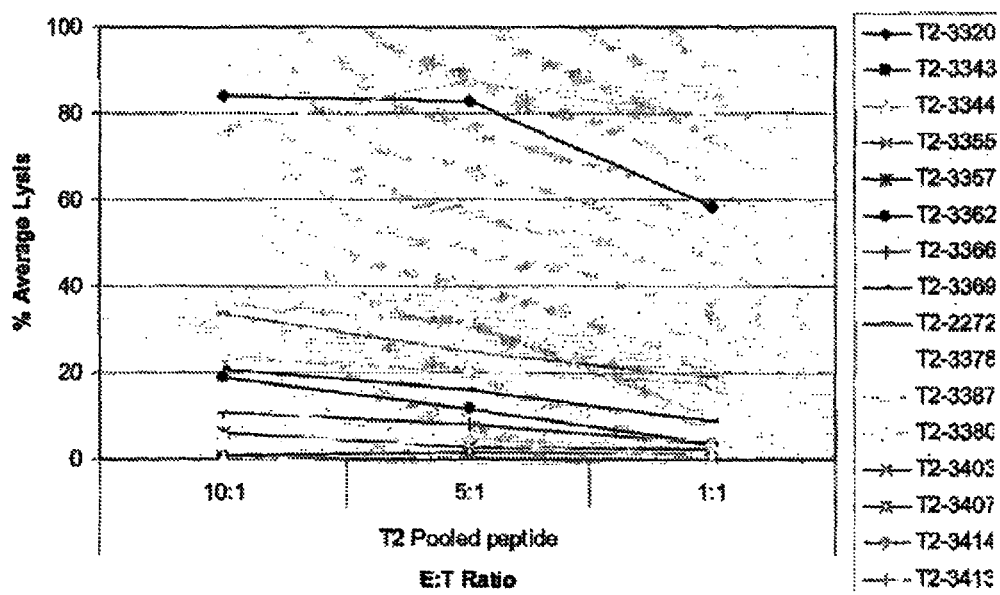
Figure 17E:
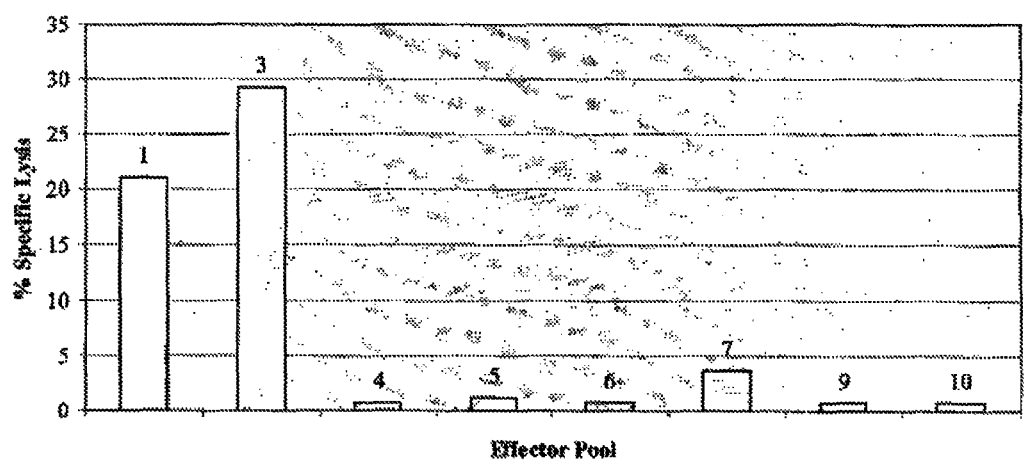

In addition to ELISPOT analysis, human T cells activated by BFY3 peptides were assayed for reactivity. Ten pools of peptides consisting often peptides per pool used to generate CTL. These 10 groups of effectors used to kill targets pulsed with corresponding peptide pools. Peptides from pools 1, 3, 5, 6, and 7 found to be recognized, indicating that peptides in those pools are capable of generating CTL (FIG. 17C). From these ten pools, peptides 3344, 3320, 3378, 2272, and 3387 were strongly recognized by CTL (FIG. 17D). "Moderately recognized" peptides include 3369, 3355, and 336218D (FIG. 17D). CosA2 cells transfected with BFY3 were killed by CTL generated from pools 1 and 3 indicating that processed and presented epitopes from these pools are immunologically relevant (FIG. 17E). The peptides responsible for this cytotoxicity are 3320 and 3344. Table XVI summarizes the properties of the BFY3 peptides.

TABLE XVI

Summary of Immunoreactive BFY3 Nonamer Peptides

|  | Peptides eliciting strong IFN-γ ELISPOT activity | Peptides eliciting CTL activity (peptide pulsed targets) | SEQ ID |
|---|---|---|---|
| CLP 3320 | MLWKLTDNI | MLWKLTDNI | 489 |
| CLP 3343 | SLPHAIEEV |  | 512 |
| CLP 3344 | HAIEEVPHV | HAIEEVPHV | 513 |
| CLP 3351 | NLFGGVVNP |  | 520 |
| CLP 3362 | KYKVTVAEV | KYKVTVAEV | 530 |
| CLP 3366 | LNASLLGGV |  | 534 |
| CLP 3369 | LLGGVLRRA | LLGGVLRRA | 537 |
| CLP 3372 | KLDKIGLNL | KLDKIGLNL | 540 |
| CLP 3378 | KAANVTLLT | KAANVTLLT | 546 |
| CLP 3380 | NVTLLTSLV |  | 548 |
| CLP 3387 | HLARDFGYV | HLARDFGYV | 555 |
| CLP 3403 | SCLTHFNLI |  | 571 |
| CLP 3407 | SHGFGSPAV |  | 575 |
| CLP 3415 | YLTEALKAM |  | 583 |

C. BFY3 Expression Vectors

To construct a BFY3 expression vector, RT-PCT amplification of BFY3 w/EcoRI ends from HTB131 total RNA with AS007F (forward primer) 5' GGAATTCACCATGCTTTG-GAAATTGACGGAT 3' (SEQ ID NO.: 595) and AS010R (reverse primer) 5' GGAATTCCTCACTTTCTGTGCT-TCTCCTCTTTGTCA 3' (SEQ ID NO.: 596) was performed. PCR was performed using standard techniques. The amplified product was digested with EcoRI and cloned into CIP treated pcDNA3.1/Zeo(+) vector by ligation using standard techniques. Several positive clones were identified by restriction digestion and sequenced. Sequencing indicated that the sequence of clone AS-391-2 matched the expected BFY3 sequence. BFY3 protein was then expressed from the BFY3 expression vector using standard techniques.

Example 10

Expression Vectors Encoding Multiple Tumor Antigens

In certain instances, it may be desirable to construct expression vectors encoding multiple tumor antigens. It has been determined that certain combinations of antigens, when combined into a single expression vector, encompasses the expression profiles of many patients in a single vector. For instance, one study of breast cancer samples from different patients indicated that the combination of BFA4 and BFA5 covered expression profiles of 74% of the samples; the combination of BCY1 and BFA5 covered 65% of the samples; the combination of BCZ4 and BFA5 covered 69% of the samples; the combination of BFY3 and BFA5 covered 67% of the samples; the combination of BCY1, BFA4 and BFA5 covered 78% of the samples; the combination of BCZ4, BFA4 and BFA5 covered 81% of the samples; and, the combination of BFY3, BFA4, and BFA5 covered 74% of the samples. Accordingly, a multi-antigen expression construct may be built such that the most common expression profiles among breast cancer patients may be addressed using a single vector. Such a multiantigen expression vector is constructed using standard cloning techniques positioning nucleic acids encoding each of the tumor antigen sequences in proximity to a promoter or other transcriptional regulatory sequence. The expression vector may be engineered such that each nucleotide sequence encoding a tumor antigen is operably linked to a specific promoter, or the tumor antigens may collectively be operably linked to a single promoter and expressed as a single expression unit. Where a single expression unit is constructed, nucleotide, sequences useful in separating the tumor antigen sequences following expression may be inserted between the tumor antigen sequences. Sequences useful for include IRES sequences, nucleotide sequences encoding amino acid sequences corresponding to protease cleavage sites, and the like. Suitable vectors for constructing such multiantigen expression vectors include, for example, poxviruses such as vaccinia, avipox, ALVAC and NYVAC.

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An expression vector comprising a nucleic acid sequence encoding SEQ ID NO.: 35 and SEQ ID NO.: 31.

2. The expression vector of claim 1 wherein the nucleic acid sequence encoding SEQ ID NO.: 35 is SEQ ID NO.: 34.

3. The expression vector of claim 1 further comprising a nucleic acid sequence encoding an amino acid sequence selected from the group consisting of SEQ ID NO.: 29, SEQ ID NO.: 33, and SEQ ID NO.: 37.

4. The expression vector of claim 3 wherein the nucleic acid encoding SEQ ID NO.: 29 is SEQ ID NO.: 28, the nucleic acid encoding SEQ ID NO.: 31 is SEQ ID NO.: 30, the nucleic acid encoding SEQ ID NO.: 33 is SEQ ID NO.: 32, and the nucleic acid molecule encoding SEQ ID NO.: 37 is SEQ ID NO.: 36.

5. The expression vector of claim 1 further comprising at least one nucleic acid sequence encoding human B7.1.

6. The expression vector of claim 1 wherein the vector is a plasmid or a viral vector.

7. The expression vector of claim 6 wherein the viral vector is selected from the group consisting of poxvirus, adenovirus, retrovirus, herpesvirus, and adeno-associated virus.

8. The expression vector of claim 7 wherein the poxvirus is vaccinia or NYVAC.

9. The expression vector of claim 7 wherein the poxvirus is an avipox virus.

10. The expression vector of claim 9 wherein the avipox virus is selected from the group consisting of canarypox, ALVAC, and ALVAC(2).

11. A composition comprising an expression vector of claim 1 in a pharmaceutically acceptable carrier.

12. A composition comprising an expression vector of claim 2 in a pharmaceutically acceptable carrier.

13. A composition comprising an expression vector of claim 3 in a pharmaceutically acceptable carrier.

14. A composition comprising an expression vector of claim 4 in a pharmaceutically acceptable carrier.

15. A composition comprising an expression vector of claim 5 in a pharmaceutically acceptable carrier.

16. A composition comprising an expression vector of claim 6 in a pharmaceutically acceptable carrier.

17. A composition comprising an expression vector of claim 7 in a pharmaceutically acceptable carrier.

18. A composition comprising an expression vector of claim 8 in a pharmaceutically acceptable carrier.

19. A composition comprising an expression vector of claim 9 in a pharmaceutically acceptable carrier.

20. A composition comprising an expression vector of claim 10 in a pharmaceutically acceptable carrier.

21. The expression vector of claim 1 wherein the nucleic acid sequence encoding SEQ ID NO.: 31 is SEQ ID NO.: 30.

* * * * *

SEQUENCE LISTING

<160> NUMBER OF SEQ ID NOS: 597

<210> SEQ ID NO 1
<211> LENGTH: 3562
<212> TYPE: DNA
<213> ORGANISM: Homo sapiens
<220> FEATURE:
<221> NAME/KEY: misc_feature
<222> LOCATION: (1663)..(1663)
<223> OTHER INFORMATION: n is A, T, G, or C -continued

```
<400> SEQUENCE: 1
agcaggaccg gggcctgtgt cgctatgggt tcccccgccg ccccggaggg agcgctgggc      60
tacgtccgcg agttcactcg ccactcctcc gacgtgctgg gcaacctcaa cgagctgcgc     120
ctgcgcggga tcctcactga cgtcacgctg ctggttggcg ggcaacccct cagagcacac     180
aaggcagttc tcatcgcctg cagtggcttc ttctattcaa ttttccgggg ccgtgcggga     240
gtcggggtgg acgtgctctc tctgcccggg ggtcccgaag cgagaggctt cgcccctcta     300
ttggacttca tgtacacttc gcgcctgcgc ctctctccag ccactgcacc agcagtccta     360
gcggccgcca cctatttgca gatggagcac gtggtccagg catgccaccg cttcatccag     420
gccagctatg aacctctggg catctccctg cgcccctgg aagcagaacc cccaacaccc      480
ccaacggccc ctccaccagg tagtcccagg cgctccgaag acacccaga cccacctact      540 gaatctcgaa gctgcagtca aggcccccc agtccagcca gccctgaccc caaggcctgc      600
aactggaaaa agtacaagta catcgtgcta aactctcagg cctcccaagc agggagcctg     660
gtcggggaga gaagttctgg tcaaccttgc ccccaagcca ggctccccag tggagacgag     720
gcctccagca gcagcagcag cagcagcagc agcagcagtg aagaaggacc cattcctggt     780
ccccagagca ggctctctcc aactgctgcc actgtgcagt tcaaatgtgg ggctccagcc     840 agtacccct acctcctcac atcccaggct caagacacct ctggatcacc ctctgaacgg      900
gctcgtccac taccgggagt gaattttca gctgccagaa ctgtgaggct gtggcagggt      960
gctcatcggg ggctggactc cttggttcct ggggacgaag acaaaccta taagtgtcag     1020 ctgtgccggt cttcgttccg ctacaagggc aaccttgcca gtcaccgtac agtgcacaca    1080
ggggaaaagc cttaccactg ctcaatctgc ggagcccgtt ttaacggcc agcaaacctg     1140 aaaacgcaca gccgcatcca ttcgggagag aagccgtata agtgtgagac gtgcggctcg    1200
cgctttgtac aggtggcaca tctgcgggcg cacgtgctga tccacaccgg ggagaagccc    1260
tacccttgcc ctacctgcgg aacccgcttc cgccacctgc agaccctcaa gagccacgtt    1320
cgcatccaca ccggagagaa gccttaccac tgcgacccct gtggcctgca tttccggcac    1380
aagagtcaac tgcggctgca tctgcgccag aaacacggag ctgctaccaa caccaaagtg    1440
cactaccaca ttctcggggg gcccctagctg agcgcaggcc caggccccac ttgcttcctg    1500
cgggtgggaa agctgcaggc ccaggccttg cttccctatc aggcttgggc ataggggtgt    1560
gccaggccac tttggtatca gaaattgcca ccctcttaat ttctcactgg ggagagcagg    1620
ggtggcagat cctggctaga tctgcctctg ttttgctggt canaccctct tccccacaag    1680
ccagattgtt tctgaggaga gagctagcta ggggctggga aagggagag attggagtcc     1740 tggtctccct aagggaatag ccctccacct gtggccccca ttgcattcag tttatctgta    1800
aaatataatt tattgaggcc tttgggtggc accgggcct tcattcgatt gcatttccca     1860
ctcccctctt ccacaagtgt gattaaaagt gaccagaaac acagaaggtg agatcacagc    1920
tctgctggca gagattacta gcccttggct ctccgttttg gcttgggtat tttatattat    1980
ttctgtcata acttttatct ttagaattgt tctttctcct gtttgtttgc ttgttagttt    2040
gtttaaaatg gaaaagggg ttctctgtgt tctgcccctg taattctagg tctggaacct     2100
ttatttgttc tagggcagct ctgggaacat gcgggattgt ggaattgggt caggaaccct    2160
ctctggtatt ctggatgttg taggttctct agcagtctag aaatggatac agacatttct    2220 ctgttccttca agggtgatag gaaccattat gttgagccca aatgaagt aataataaat      2280 gcctcctgga ggctgtgggt gtggggggatt ctgtatctgg attccgtatc actccaactg    2340
```

-continued

```
gaggctgtgg gtgtggggga ttctgtatct ggattccgta tcactccaag tggaggctgg    2400
caggtttttc tgcaagatgg tccagaatct aaaatgtccc attaatctgg tcacttgggt    2460
ttggctctgc tgtatccatc tatagtggta gagacccacc agggctcaag tggagtccat    2520
catcctccca cggggggcctg ttcttagtac tgagttgatc gctccatggg ggagagatca    2580
gacattcctt atcagagatg atgtgacctt tctgactct gcccagtctc tatgaatgtt     2640
atggcctagg gaagaatcat gaaactcttt agcttgatta gatggtaaac agtgttaacc    2700
catcctttac tacagaggca tatgggtttg aatgttacct ggggttctct ctattgagtt    2760
gagccccttc ttcctttagt gggttttgga catcttctgg caagtgtcca gatgccagaa    2820
ccttcttttc ctctagaagg gatggtgctt ggtaacctta ccttttaaaa gctgggtctg    2880
tgacctggtc ttcccatccc tgcattcctg tctggaacca gtgaatgcat agaaccttc     2940 cataggaaaa gaaaggggc tgagttccat tctgggtttg ctgtagtttg gttgggatta     3000
ttgttggcat tacagatgta aaagattgac tagcccatag gccaaaggcc tgttctagtt    3060
gaccaagttt caagtaggat taagaggttg gttgaggggt gcagtttctg gtgtaggcca    3120
ggtaggtaga aagtgaggaa cagggttgcc tcttggctgg gtggagtctc tgaaatgtta    3180
gaagaagcgc tgaagccttg attgatagtt ctgcccccttg ttgccctggg cttatctga    3240 ttatgggacg agggtagaaa gtaagaagca cttttgaatt tgtggggtag aacttcaaca    3300
ataagtcagt tctagtggct gtcgcctggg gactagtgag aaagctactc ttctccctct    3360
tccctctttc tccccatggc cccactgcag aattaaagaa ggaagaaggg aaggcggagg    3420
agtctataag aaggaatcat gatttctatt tagcagattg gatgggcagg tggagaatgc    3480
ctgggggtag aaatgttaga tcttgcaaca tcagatcctt ggaataaaga agcctctctg    3540
cgcaaaaaaa aaaaaaaaaa aa                                             3562
```

<210> SEQ ID NO 2
<211> LENGTH: 480
<212> TYPE: PRT
<213> ORGANISM: Homo sapiens

<400> SEQUENCE: 2

```
Met Gly Ser Pro Ala Ala Pro Glu Gly Ala Leu Gly Tyr Val Arg Glu
1               5                   10                  15

Phe Thr Arg His Ser Ser Asp Val Leu Gly Asn Leu Asn Glu Leu Arg
            20                  25                  30

Leu Arg Gly Ile Leu Thr Asp Thr Leu Leu Val Gly Gly Gln Pro
        35                  40                  45

Leu Arg Ala His Lys Ala Val Leu Ile Ala Cys Ser Gly Phe Phe Tyr
    50                  55                  60

Ser Ile Phe Arg Gly Arg Ala Gly Val Gly Val Asp Val Leu Ser Leu
65                  70                  75                  80

Pro Gly Gly Pro Glu Ala Arg Gly Phe Ala Pro Leu Leu Asp Phe Met
                85                  90                  95

Tyr Thr Ser Arg Leu Arg Leu Ser Pro Ala Thr Ala Pro Ala Val Leu
            100                 105                 110

Ala Ala Ala Thr Tyr Leu Gln Met Glu His Val Val Gln Ala Cys His
        115                 120                 125

Arg Phe Ile Gln Ala Ser Tyr Glu Pro Leu Gly Ile Ser Leu Arg Pro
    130                 135                 140

Leu Glu Ala Glu Pro Pro Thr Pro Pro Thr Ala Pro Pro Pro Gly Ser
145                 150                 155                 160
```

```
Pro Arg Arg Ser Glu Gly His Pro Asp Pro Thr Glu Ser Arg Ser
            165                 170                 175
Cys Ser Gln Gly Pro Ser Pro Ala Ser Pro Asp Pro Lys Ala Cys
            180                 185                 190
Asn Trp Lys Lys Tyr Lys Tyr Ile Val Leu Asn Ser Gln Ala Ser Gln
            195                 200                 205
Ala Gly Ser Leu Val Gly Glu Arg Ser Ser Gly Gln Pro Cys Pro Gln
            210                 215                 220
Ala Arg Leu Pro Ser Gly Asp Glu Ala Ser Ser Ser Ser Ser
225                 230                 235                 240
Ser Ser Ser Ser Ser Glu Gly Pro Ile Pro Gly Pro Gln Ser Arg
            245                 250                 255
Leu Ser Pro Thr Ala Ala Thr Val Gln Phe Lys Cys Gly Ala Pro Ala
            260                 265                 270
Ser Thr Pro Tyr Leu Leu Thr Ser Gln Ala Gln Asp Thr Ser Gly Ser
            275                 280                 285
Pro Ser Glu Arg Ala Arg Pro Leu Pro Gly Val Asn Phe Ser Ala Ala
            290                 295                 300
Arg Thr Val Arg Leu Trp Gln Gly Ala His Arg Gly Leu Asp Ser Leu
305                 310                 315                 320
Val Pro Gly Asp Glu Asp Lys Pro Tyr Lys Cys Gln Leu Cys Arg Ser
            325                 330                 335
Ser Phe Arg Tyr Lys Gly Asn Leu Ala Ser His Arg Thr Val His Thr
            340                 345                 350
Gly Glu Lys Pro Tyr His Cys Ser Ile Cys Gly Ala Arg Phe Asn Arg
            355                 360                 365
Pro Ala Asn Leu Lys Thr His Ser Arg Ile His Ser Gly Glu Lys Pro
            370                 375                 380
Tyr Lys Cys Glu Thr Cys Gly Ser Arg Phe Val Gln Val Ala His Leu
385                 390                 395                 400
Arg Ala His Val Leu Ile His Thr Gly Glu Lys Pro Tyr Pro Cys Pro
            405                 410                 415
Thr Cys Gly Thr Arg Phe Arg His Leu Gln Thr Leu Lys Ser His Val
            420                 425                 430
Arg Ile His Thr Gly Glu Lys Pro Tyr His Cys Asp Pro Cys Gly Leu
            435                 440                 445
His Phe Arg His Lys Ser Gln Leu Arg Leu His Leu Arg Gln Lys His
            450                 455                 460
Gly Ala Ala Thr Asn Thr Lys Val His Tyr His Ile Leu Gly Gly Pro
465                 470                 475                 480

<210> SEQ ID NO 3
<211> LENGTH: 3676
<212> TYPE: DNA
<213> ORGANISM: Homo sapiens

<400> SEQUENCE: 3
tctgcgtgtg ccggggctag gggctggaag tcctggctct agttgcacct cggaaggaaa      60
aggcaaacag aggagggaag gcgtcttagg actgcctgga tccagagcac tttcctcggc     120
ctctacaggc ctgtgtcgct atgggttccc ccgccgcccc ggagggagcg ctgggctacg     180
tccgcgagtt cactcgccac tcctccgacg tgctgggcaa cctcaacgag ctgcgcctgc     240
gcgggatcct cactgacgtc acgctgctgg ttggcgggca accctcagaa gcacacaagg     300
cagttctcat cgcctgcagt ggcttcttct attcaatttt ccggggccgt gcgggagtcg     360
```

| | |
|---|---|
| gggtggacgt gctctctctg cccgggggtc ccgaagcgag aggcttcgcc cctctattgg | 420 |
| acttcatgta cacttcgcgc ctgcgcctct ctccagccac tgcaccagca gtcctagcgg | 480 |
| ccgccaccta tttgcagatg gagcacgtgg tccaggcatg ccaccgcttc atccaggcca | 540 |
| gctatgaacc tctgggcatc tccctgcgcc ccctggaagc agaaccccca acacccccaa | 600 |
| cggcccctcc accaggtagt cccaggcgct ccgaaggaca cccagaccca cctactgaat | 660 |
| ctcgaagctg cagtcaaggc cccccagtc cagccagccc tgaccccaag gcctgcaact | 720 |
| ggaaaaagta caagtacatc gtgctaaact ctcaggcctc ccaagcaggg agcctggtcg | 780 |
| gggagagaag ttctggtcaa ccttgccccc aagccaggct ccccagtgga gacgaggcct | 840 |
| ccagcagcag cagcagcagc agcagcagca gtgaagaagg acccattcct ggtccccaga | 900 |
| gcaggctctc tccaactgct gccactgtgc agttcaaatg tggggctcca gccagtaccc | 960 |
| cctacctcct cacatcccag gctcaagaca cctctggatc accctctgaa cgggctcgtc | 1020 |
| cactaccggg aagtgaattt ttcagctgcc agaactgtga ggctgtggca gggtgctcat | 1080 |
| cggggctgga ctccttggtt ctggggacg aagacaaacc ctataagtgt cagctgtgcc | 1140 |
| ggtcttcgtt ccgctacaag ggcaaccttg ccagtcatcg tacagtgcac acaggggaaa | 1200 |
| agccttacca ctgctcaatc tgcggagccc gttttaaccg ccagcaaac ctgaaaacgc | 1260 |
| acagccgcat ccattcggga gagaagccgt ataagtgtga cgtgcggc tcgcgctttg | 1320 |
| tacaggtggc acatctgcgg gcgcacgtgc tgatccacac cggggagaag ccctacccett | 1380 |
| gccctacctg cggaacccgc ttccgccacc tgcagaccct caagagccac gttcgcatcc | 1440 |
| acaccggaga gaagccttac cactgcgacc cctgtggcct gcatttccgg cacaagagtc | 1500 |
| aactgcggct gcatctgcgc cagaaacacg gagctgctac caacaccaaa gtgcactacc | 1560 |
| acattctcgg ggggccctag ctgagcgcag gcccaggccc cacttgcttc ctgcgggtgg | 1620 |
| gaaagctgca ggcccaggcc ttgcttccct atcaggcttg gcataggggt gtgccaggc | 1680 |
| cactttggta tcagaaattg ccaccctctt aatttctcac tggggagagc aggggtggca | 1740 |
| gatcctggct agatctgcct ctgttttgct ggtcaaaacc tcttccccac aagccagatt | 1800 |
| gtttctgagg agagagctag ctaggggctg ggaaagggga gagattggag tcctggtctc | 1860 |
| cctaagggaa tagccctcca cctgtggccc ccattgcatt cagtttatct gtaaatataa | 1920 |
| tttattgagg cctttgggtg gcaccgggc cttcattcga ttgcatttcc cactcccctc | 1980 |
| ttccacaagt gtgattaaaa gtgaccagaa acacagaagg tgagatcaca gctctgctgg | 2040 |
| cagagattac tagcccttgg ctctctcgtt tggcttgggt attttatatt atttctgtca | 2100 |
| taactttat ctttagaatt gttctttctc ctgtttgttt gcttgttagt ttgtttaaaa | 2160 |
| tggaaaaagg ggttctctgt gttctgcccc tgtaattcta ggtctggaac ctttatttgt | 2220 |
| tctagggcag ctctgggaac atgcgggatt gtggaattgg gtcaggaacc ctctctggta | 2280 |
| ttctggatgt tgtaggttct ctagcagtct agaaatggat acagacattt ctctgttctt | 2340 |
| caagggtgat aggaaccatt atgttgagcc caaaatggaa gtaataataa atgcctcctg | 2400 |
| gaggctgtgg gtgtggggga ttctgtatct ggattccgta tcactccaac tggaggctgt | 2460 |
| gggtgtgggg gattctgtat ctggattccg tatcactcca agtggaggct ggcaggtttt | 2520 |
| tctgcaagat ggtccagaat ctaaaatgtc ccattaatct ggtcacttgg gtttggctct | 2580 |
| gctgtatcca tctatagtgg tagagaccca ccagggctca agtggagtcc atcatcctcc | 2640 |
| cacgggggcc tgttcttagc actgagttga tcgctccatg ggggagagat cagacattcc | 2700 |
| ttatcagaga tgatgtgacc ttttctgact ctgcccagtc tctatgaatg ttatggccta | 2760 |

```
gggaagaatc atgaaactct ttagcttgat tagatggtaa acagtgttaa cccatccttt   2820
actacagagg catatgggtt tgaatgttac ctggggttct ctctattgag ttgagcccct   2880
tcttccttta gtgggttttg gacatcttct ggcaagtgtc cagatgccag aaccttcttt   2940
tcctctagaa gggatggtgc ttggtaacct tacctttaa aagctgggtc tgtgacctgg    3000
tcttcccatc cctgcattcc tgtctggaac cagtgaatgc attagaacct tccataggaa   3060
aagaaaaggg gctgagttcc attctgggtt tgctgtagtt tggttgggat tattgttggc   3120
attacagatg taaaagattg actagcccat aggccaaagg cctgttctag ttgaccaagt   3180
ttcaagtagg attaagaggt tggttgaggg gtgcagtttc tggtgtaggc caggtaggta   3240
gaaagtgagg aacagggttg cctcttggct gggtggagtc tctgaaatgt tagaagaagc   3300
gctgaagcct tgattgatag ttctgcccct tgttgccctg ggcttatct gattatggga    3360 cgagggtaga agtaagaag cacttttgaa tttgtggggt agaacttcaa caataagtca     3420
gttctagtgg ctgtcgcctg ggactagtg agaaagctac tcttctccct cttccctctt    3480
tctccccatg gccccactgc agaattaaag aaggaagaag ggaaggcgga ggagtctata   3540
agaaggaatc atgatttcta tttagcagat tggatgggca ggtggagaat gcctgggggt   3600
agaaatgtta gatcttgcaa catcagatcc ttggaataaa gaagcctctc tgygcwraaa   3660
aaaaaaaaaa aaaaaa                                                    3676

<210> SEQ ID NO 4
<211> LENGTH: 1440
<212> TYPE: DNA
<213> ORGANISM: Homo sapiens

<400> SEQUENCE: 4
atgggttccc ccgccgcccc ggagggagcg ctgggctacg tccgcgagtt cactcgccac     60
tcctccgacg tgctgggcaa cctcaacgag ctgcgcctgc gcgggatcct cactgacgtc    120
acgctgctgg ttgcgggca accccctcaga gcacacaagg cagttctcat cgcctgcagt    180
ggcttcttct attcaatttt ccggggccgt gcgggagtcg gggtggacgt gctctctctg    240
cccgggggtc ccgaagcgag aggcttcgcc cctctattgg acttcatgta cacttcgcgc    300
ctgcgcctct ctccagccac tgcaccagca gtcctagcgg ccgccaccta tttgcagatg    360
gagcacgtgg tccaggcatg ccaccgcttc atccaggcca gctatgaacc tctgggcatc    420
tccctgcgcc cctggaagc agaaccccca acacccccaa cggcccctcc accaggtagt    480
cccaggcgct ccgaaggaca cccagaccca cctactgaat ctcgaagctg cagtcaaggc   540
ccccccagtc cagccagccc tgaccccaag gcctgcaact ggaaaaagta caagtacatc    600 gtgctaaaact ctcaggcctc ccaagcaggg agcctggtcg gggagagaag ttctggtcaa   660
ccttgccccc aagccaggct ccccagtgga gacgaggcct ccagcagcag cagcagcagc    720
agcagcagca gtgaagaagg accattcct ggtccccaga gcaggctctc tccaactgct    780
gccactgtgc agttcaaatg tggggctcca gccagtaccc cctacctcct cacatcccag   840
gctcaagaca cctctggatc accctctgaa cgggctcgtc cactaccggg aagtgaattt    900
ttcagctgcc agaactgtga ggctgtggca gggtgctcat cggggctgga ctccttggtt    960
cctggggacg aagacaaacc ctataagtgt cagctgtgcc ggtcttcgtt ccgctacaag   1020
ggcaaccttg ccagtcatcg tacagtgcac acaggggaaa agccttacca ctgctcaatc   1080
tgcggagccc gttttaaccg gccagcaaac ctgaaaacgc acagccgcat ccattcggga   1140
gagaagccgt ataagtgtga gacgtgcggc tcgcgctttg tacaggtggc acatctgcgg   1200
```

```
gcgcacgtgc tgatccacac cggggagaag ccctacccct tgccctacctg cggaacccgc    1260 ttccgccacc tgcagaccct caagagccac gttcgcatcc acaccggaga gaagccttac    1320
cactgcgacc cctgtggcct gcatttccgg cacaagagtc aactgcggct gcatctgcgc    1380
cagaaacacg gagctgctac caacaccaaa gtgcactacc acattctcgg ggggccctag    1440
```

<210> SEQ ID NO 5
<211> LENGTH: 479
<212> TYPE: PRT
<213> ORGANISM: Homo sapiens

<400> SEQUENCE: 5

```
Met Gly Ser Pro Ala Ala Pro Glu Gly Ala Leu Gly Tyr Val Arg Glu
1               5                   10                  15

Phe Thr Arg His Ser Ser Asp Val Leu Gly Asn Leu Asn Glu Leu Arg
            20                  25                  30

Leu Arg Gly Ile Leu Thr Asp Val Thr Leu Leu Val Gly Gly Gln Pro
        35                  40                  45

Leu Arg Ala His Lys Ala Val Leu Ile Ala Cys Ser Gly Phe Phe Tyr
    50                  55                  60

Ser Ile Phe Arg Gly Arg Ala Gly Val Gly Val Asp Val Leu Ser Leu
65                  70                  75                  80

Pro Gly Gly Pro Glu Ala Arg Gly Phe Ala Pro Leu Leu Asp Phe Met
                85                  90                  95

Tyr Thr Ser Arg Leu Arg Leu Ser Pro Ala Thr Ala Pro Ala Val Leu
            100                 105                 110

Ala Ala Ala Thr Tyr Leu Gln Met Glu His Val Val Gln Ala Cys His
        115                 120                 125

Arg Phe Ile Gln Ala Ser Tyr Glu Pro Leu Gly Ile Ser Leu Arg Pro
    130                 135                 140

Leu Glu Ala Glu Pro Pro Thr Pro Pro Thr Ala Pro Pro Pro Gly Ser
145                 150                 155                 160

Pro Arg Arg Ser Glu Gly His Pro Asp Pro Pro Thr Glu Ser Arg Ser
                165                 170                 175

Cys Ser Gln Gly Pro Pro Ser Pro Ala Ser Pro Asp Pro Lys Ala Cys
            180                 185                 190

Asn Trp Lys Lys Tyr Lys Tyr Ile Val Leu Asn Ser Gln Ala Ser Gln
        195                 200                 205

Ala Gly Ser Leu Val Gly Glu Arg Ser Ser Gly Gln Pro Cys Pro Gln
    210                 215                 220

Ala Arg Leu Pro Ser Gly Asp Glu Ala Ser Ser Ser Ser Ser Ser Ser
225                 230                 235                 240

Ser Ser Ser Ser Glu Glu Gly Pro Ile Pro Gly Pro Gln Ser Arg Leu
                245                 250                 255

Ser Pro Thr Ala Ala Thr Val Gln Phe Lys Cys Gly Pro Ala Ser
            260                 265                 270

Thr Pro Tyr Leu Leu Thr Ser Gln Ala Gln Asp Thr Ser Gly Ser Pro
        275                 280                 285

Ser Glu Arg Ala Arg Pro Leu Pro Gly Ser Glu Phe Phe Ser Cys Gln
    290                 295                 300

Asn Cys Glu Ala Val Ala Gly Cys Ser Ser Gly Leu Asp Ser Leu Val
305                 310                 315                 320

Pro Gly Asp Glu Asp Lys Pro Tyr Lys Cys Gln Leu Cys Arg Ser Ser
                325                 330                 335
```

```
Phe Arg Tyr Lys Gly Asn Leu Ala Ser His Arg Thr Val His Thr Gly
                340                 345                 350
Glu Lys Pro Tyr His Cys Ser Ile Cys Gly Ala Arg Phe Asn Arg Pro
            355                 360                 365
Ala Asn Leu Lys Thr His Ser Arg Ile His Ser Gly Glu Lys Pro Tyr
        370                 375                 380
Lys Cys Glu Thr Cys Gly Ser Arg Phe Val Gln Val Ala His Leu Arg
385                 390                 395                 400
Ala His Val Leu Ile His Thr Gly Glu Lys Pro Tyr Pro Cys Pro Thr
                405                 410                 415
Cys Gly Thr Arg Phe Arg His Leu Gln Thr Leu Lys Ser His Val Arg
            420                 425                 430
Ile His Thr Gly Glu Lys Pro Tyr His Cys Asp Pro Cys Gly Leu His
        435                 440                 445
Phe Arg His Lys Ser Gln Leu Arg Leu His Leu Arg Gln Lys His Gly
    450                 455                 460
Ala Ala Thr Asn Thr Lys Val His Tyr His Ile Leu Gly Gly Pro
465                 470                 475
```

<210> SEQ ID NO 6
<211> LENGTH: 27
<212> TYPE: DNA
<213> ORGANISM: Homo sapiens
<400> SEQUENCE: 6
caccatgggt tccccgccg ccccgga                                      27

<210> SEQ ID NO 7
<211> LENGTH: 33
<212> TYPE: DNA
<213> ORGANISM: Homo sapiens
<400> SEQUENCE: 7
ctagggcccc ccgagaatgt ggtagtgcac ttt                              33

<210> SEQ ID NO 8
<211> LENGTH: 65
<212> TYPE: DNA
<213> ORGANISM: Homo sapiens
<400> SEQUENCE: 8
atacccggaa ctccctaagc cttctattag ctccaataat agtaagcctg tcgaagacaa  60
agatg                                                             65

<210> SEQ ID NO 9
<211> LENGTH: 70
<212> TYPE: DNA
<213> ORGANISM: Homo sapiens
<400> SEQUENCE: 9
gcctgtgtcc cctagactcc aactcagcaa cggaaataga actctgaccc tgtttaacgt  60
gaccaggaac                                                        70

<210> SEQ ID NO 10
<211> LENGTH: 70
<212> TYPE: DNA
<213> ORGANISM: Homo sapiens
<400> SEQUENCE: 10
acgtgcttta cggacccgat gctcctacaa tcagccctct aaacacaagc tatagatcag  60

```
gggaaaatct                                                             70

<210> SEQ ID NO 11
<211> LENGTH: 70
<212> TYPE: DNA
<213> ORGANISM: Homo sapiens

<400> SEQUENCE: 11
acgttaaaca gggtcagagt tctatttccg ttgctgagtt ggagtctagg ggacacaggc      60
agggactggt                                                             70

<210> SEQ ID NO 12
<211> LENGTH: 70
<212> TYPE: DNA
<213> ORGANISM: Homo sapiens

<400> SEQUENCE: 12
ctgatctata gcttgtgttt agagggctga ttgtaggagc atcgggtccg taaagcacgt      60
tgagaatcac                                                             70

<210> SEQ ID NO 13
<211> LENGTH: 63
<212> TYPE: DNA
<213> ORGANISM: Homo sapiens

<400> SEQUENCE: 13
gatccactat tgttcacggt aatattggga atgaacagtt cctgggtgga ctgttggaaa      60
gtg                                                                    63

<210> SEQ ID NO 14
<211> LENGTH: 70
<212> TYPE: DNA
<213> ORGANISM: Homo sapiens

<400> SEQUENCE: 14
gacacagcaa gctacaaatg cgaaacccaa aatccagtca gcgccaggag gtctgattca      60
gtgattctca                                                             70

<210> SEQ ID NO 15
<211> LENGTH: 70
<212> TYPE: DNA
<213> ORGANISM: Homo sapiens

<400> SEQUENCE: 15
tgaatcagac ctcctggcgc tgactggatt ttgggtttcg catttgtagc ttgctgtgtc      60
gttcctggtc                                                             70

<210> SEQ ID NO 16
<211> LENGTH: 79
<212> TYPE: DNA
<213> ORGANISM: Homo sapiens

<400> SEQUENCE: 16
gatcctacac gtgccaagct cacaatagcg acaccggact caaccgcaca accgtgacga      60
cgattaccgt gtatgccga                                                   79

<210> SEQ ID NO 17
<211> LENGTH: 70
<212> TYPE: DNA
<213> ORGANISM: Homo sapiens
```

```
<400> SEQUENCE: 17
catcctcaac tgggttagaa ttgttactag ttatgaatgg ttttggtggc tcggcataca      60
cggtaatcgt                                                            70

<210> SEQ ID NO 18
<211> LENGTH: 80
<212> TYPE: DNA
<213> ORGANISM: Homo sapiens

<400> SEQUENCE: 18
ttctaaccca gttgaggatg aggacgcagt tgcattaact tgtgagccag agattcaaaa      60
taccacttat ttatggtggg                                                 80

<210> SEQ ID NO 19
<211> LENGTH: 80
<212> TYPE: DNA
<213> ORGANISM: Homo sapiens

<400> SEQUENCE: 19
gtctaatgat aaccgcacat tgacactcct gtccgttact cgcaatgatg taggacctta      60
tgagtgtggc attcagaatg                                                 80

<210> SEQ ID NO 20
<211> LENGTH: 80
<212> TYPE: DNA
<213> ORGANISM: Homo sapiens

<400> SEQUENCE: 20
tttgtatggc ccagacgacc caactatatc tccatcatac acctactacc gtcccggcgt      60
gaacttgagc ctttcttgcc                                                 80

<210> SEQ ID NO 21
<211> LENGTH: 80
<212> TYPE: DNA
<213> ORGANISM: Homo sapiens

<400> SEQUENCE: 21
tgatggaaac attcagcagc atactcaaga gttatttata agcaacataa ctgagaagaa      60
cagcggactc tatacttgcc                                                 80

<210> SEQ ID NO 22
<211> LENGTH: 80
<212> TYPE: DNA
<213> ORGANISM: Homo sapiens

<400> SEQUENCE: 22
taaaacaata actgtttccg cggagctgcc caagccctcc atctccagca acaactccaa      60
acccgtggag gacaaggatg                                                 80

<210> SEQ ID NO 23
<211> LENGTH: 80
<212> TYPE: DNA
<213> ORGANISM: Homo sapiens

<400> SEQUENCE: 23
atgtgcggtt atcattagac aactgcaagc gtgggctaac cggcaaactt tggttattga      60
cccaccataa ataagtggta                                                 80
```

```
<210> SEQ ID NO 24
<211> LENGTH: 80
<212> TYPE: DNA
<213> ORGANISM: Homo sapiens

<400> SEQUENCE: 24
ggtcgtctgg gccatacaaa acattaagga taacagggtc ggagtgatca acggataatt      60
cattctgaat gccacactca                                                  80

<210> SEQ ID NO 25
<211> LENGTH: 80
<212> TYPE: DNA
<213> ORGANISM: Homo sapiens

<400> SEQUENCE: 25
gctgctgaat gtttccatca atcagccagg agtactgtgc aggggggttg gatgctgcat      60
ggcaagaaag gctcaagttc                                                  80

<210> SEQ ID NO 26
<211> LENGTH: 80
<212> TYPE: DNA
<213> ORGANISM: Homo sapiens

<400> SEQUENCE: 26
cggaaacagt tattgtttta actgtagtcc tgctgtgacc actggctgag ttattggcct      60
ggcaagtata gagtccgctg                                                  80

<210> SEQ ID NO 27
<211> LENGTH: 47
<212> TYPE: DNA
<213> ORGANISM: Homo sapiens

<400> SEQUENCE: 27
cctcaggttc acaggtgaag gccacagcat ccttgtcctc cacgggt                    47

<210> SEQ ID NO 28
<211> LENGTH: 3846
<212> TYPE: DNA
<213> ORGANISM: Homo sapiens

<400> SEQUENCE: 28
atggtccgga aaagaaccc ccctctgaga acgttgcaa gtgaaggcga gggccagatc        60
ctggagccta taggtacaga aagcaaggta tctggaaaga caaagaatt ctctgcagat      120 cagatgtcag aaaatacgga tcagagtgat gctgcagaac taaatcataa ggaggaacat    180
agcttgcatg ttcaagatcc atcttctagc agtaagaagg acttgaaaag cgcagttctg    240
agtgagaagg ctggcttcaa ttatgaaagc cccagtaagg aggaaacttt ccctcctttt    300
ccgcatgatg aggtgacaga cagaaatatg ttggctttct catttccagc tgctggggga    360
gtctgtgagc ccttgaagtc tccgcaaaga gcagaggcag atgaccctca agatatggcc    420
tgcaccccct caggggactc actgagacat aaggaagatc agaagatgtc accaaaggct    480
acagaggaaa cagggcaagc acagagtggt caagccaatt gtcaaggttt gagcccagtt    540
tcagtggcct caaaaaaccc acaagtgcct tcagatgggg gtgtaagact gaataaatcc    600
aaaactgact tactggtgaa tgacaaccca gacccgcac ctctgtctcc agagcttcag    660
gactttaaat gcaatatctg tggatatggt tactacggca acgacccac agatctgatt    720 aagcacttcc gaaagtatca cttaggactg cataaccgca ccaggcaaga tgctgagctg    780
gacagcaaaa tcttggccct tcataacatg gtgcagttca gccattccaa agacttccag    840
```

```
aaggtcaacc gttctgtgtt ttctggtgtg ctgcaggaca tcaattcttc aaggcctgtt    900
ttactaaatg ggacctatga tgtgcaggtg acttcaggtg gaacattcat tggcattgga    960
cggaaaacac cagattgcca agggaacacc aagtatttcc gctgtaaatt ctgcaatttc   1020
acttatatgg gcaactcatc caccgaatta gaacaacatt ttcttcagac tcacccaaac   1080
aaaataaaag cttctctccc ctcctctgag gttgcaaaac cttcagagaa aaactctaac   1140
aagtccatcc ctgcacttca atccagtgat tctggagact tgggaaaatg gcaggacaag   1200
ataacagtca aagcaggaga tgacactcct gttgggtact cagtgcccat aaagcccctc   1260
gattcctcta gacaaaatgg tacagaggcc accagttact actggtgtaa attttgtagt   1320
ttcagctgtg agtcatctag ctcacttaaa ctgctagaac attatggcaa gcagcacgga   1380
gcagtgcagt caggcggcct taatccagag ttaaatgata agcttttccag gggctctgtc   1440 attaatcaga atgatctagc caaaagttca aaggagagaca caatgaccaa gacagacaag   1500
```

-continued

```
tcaccaccag gcagccctat tgaaaagtac cagtacccac ttttggact tcccttgta      3300 cataatgact tccagagtga agctgattgg ctgcggttct ggagtaaata taagctctcc     3360
gttcctggga atccgcacta cttgagtcac gtgcctggcc taccaaatcc ttgccaaaac    3420
tatgtgcctt atcccacctt caatctgcct cctcattttt cagctgttgg atcagacaat    3480
gacattcctc tagatttggc gatcaagcat tccagacctg gccaactgc aaacggtgcc     3540 tccaaggaga aaacgaaggc accaccaaat gtaaaaaatg aaggtcccctt gaatgtagta   3600 aaaacagaga aagttgatag aagtactcaa gatgaacttt caacaaaatg tgtgcactgt    3660
ggcattgtct ttctggatga agtgatgtat gctttgcata tgagttgcca tggtgacagt    3720
ggacctttcc agtgcagcat atgccagcat ctttgcacgg acaaatatga cttcacaaca    3780
catatccaga ggggcctgca taggaacaat gcacaagtgg aaaaaaatgg aaaacctaaa    3840
gagtaa                                                                3846
```

```
<210> SEQ ID NO 29
<211> LENGTH: 1281
<212> TYPE: PRT
<213> ORGANISM: Homo sapiens

<400> SEQUENCE: 29
```

| Met | Val | Arg | Lys | Lys | Asn | Pro | Pro | Leu | Arg | Asn | Val | Ala | Ser | Glu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Gly | Gln | Ile | Leu | Glu | Pro | Ile | Gly | Thr | Glu | Ser | Lys | Val | Ser | Gly |
|     |     |     | 20  |     |     |     |     | 25  |     |     |     |     | 30  |     |     |

| Lys | Asn | Lys | Glu | Phe | Ser | Ala | Asp | Gln | Met | Ser | Glu | Asn | Thr | Asp | Gln |
|     |     | 35  |     |     |     |     | 40  |     |     |     |     | 45  |     |     |     |

| Ser | Asp | Ala | Ala | Glu | Leu | Asn | His | Lys | Glu | Glu | His | Ser | Leu | His | Val |
|     | 50  |     |     |     |     | 55  |     |     |     |     | 60  |     |     |     |     |

| Gln | Asp | Pro | Ser | Ser | Ser | Lys | Lys | Asp | Leu | Lys | Ser | Ala | Val | Leu |
| 65  |     |     |     |     | 70  |     |     |     |     | 75  |     |     |     | 80  |

| Ser | Glu | Lys | Ala | Gly | Phe | Asn | Tyr | Glu | Ser | Pro | Ser | Lys | Gly | Gly | Asn |
|     |     |     |     | 85  |     |     |     |     | 90  |     |     |     |     | 95  |     |

| Phe | Pro | Ser | Phe | Pro | His | Asp | Glu | Val | Thr | Asp | Arg | Asn | Met | Leu | Ala |
|     |     |     | 100 |     |     |     |     | 105 |     |     |     |     | 110 |     |     |

| Phe | Ser | Phe | Pro | Ala | Ala | Gly | Gly | Val | Cys | Glu | Pro | Leu | Lys | Ser | Pro |
|     |     | 115 |     |     |     |     | 120 |     |     |     |     | 125 |     |     |     |

| Gln | Arg | Ala | Glu | Ala | Asp | Asp | Pro | Gln | Asp | Met | Ala | Cys | Thr | Pro | Ser |
|     | 130 |     |     |     |     | 135 |     |     |     |     | 140 |     |     |     |     |

| Gly | Asp | Ser | Leu | Glu | Thr | Lys | Glu | Asp | Gln | Lys | Met | Ser | Pro | Lys | Ala |
| 145 |     |     |     |     | 150 |     |     |     |     | 155 |     |     |     |     | 160 |

| Thr | Glu | Glu | Thr | Gly | Gln | Ala | Gln | Ser | Gly | Gln | Ala | Asn | Cys | Gln | Gly |
|     |     |     |     | 165 |     |     |     |     | 170 |     |     |     |     | 175 |     |

| Leu | Ser | Pro | Val | Ser | Val | Ala | Ser | Lys | Asn | Pro | Gln | Val | Pro | Ser | Asp |
|     |     |     | 180 |     |     |     |     | 185 |     |     |     |     | 190 |     |     |

| Gly | Gly | Val | Arg | Leu | Asn | Lys | Ser | Lys | Thr | Asp | Leu | Leu | Val | Asn | Asp |
|     |     |     | 195 |     |     |     |     | 200 |     |     |     |     | 205 |     |     |

| Asn | Pro | Asp | Pro | Ala | Pro | Leu | Ser | Pro | Glu | Leu | Gln | Asp | Phe | Lys | Cys |
|     | 210 |     |     |     |     | 215 |     |     |     |     | 220 |     |     |     |     |

| Asn | Ile | Cys | Gly | Tyr | Gly | Tyr | Tyr | Gly | Asn | Asp | Pro | Thr | Asp | Leu | Ile |
| 225 |     |     |     |     | 230 |     |     |     |     | 235 |     |     |     |     | 240 |

| Lys | His | Phe | Arg | Lys | Tyr | His | Leu | Gly | Leu | His | Asn | Arg | Thr | Arg | Gln |
|     |     |     |     | 245 |     |     |     |     | 250 |     |     |     |     | 255 |     |

| Asp | Ala | Glu | Leu | Asp | Ser | Lys | Ile | Leu | Ala | Leu | His | Asn | Met | Val | Gln |

```
                260                 265                 270
Phe Ser His Ser Lys Asp Phe Gln Lys Val Asn Arg Ser Val Phe Ser
            275                 280                 285
Gly Val Leu Gln Asp Ile Asn Ser Ser Arg Pro Val Leu Leu Asn Gly
            290                 295                 300
Thr Tyr Asp Val Gln Val Thr Ser Gly Gly Thr Phe Ile Gly Ile Gly
305                 310                 315                 320
Arg Lys Thr Pro Asp Cys Gln Gly Asn Thr Lys Tyr Phe Arg Cys Lys
                325                 330                 335
Phe Cys Asn Phe Thr Tyr Met Gly Asn Ser Ser Thr Glu Leu Glu Gln
            340                 345                 350
His Phe Leu Gln Thr His Pro Asn Lys Ile Lys Ala Ser Leu Pro Ser
            355                 360                 365
Ser Glu Val Ala Lys Pro Ser Glu Lys Asn Ser Asn Lys Ser Ile Pro
            370                 375                 380
Ala Leu Gln Ser Ser Asp Ser Gly Asp Leu Gly Lys Trp Gln Asp Lys
385                 390                 395                 400
Ile Thr Val Lys Ala Gly Asp Asp Thr Pro Val Gly Tyr Ser Val Pro
                405                 410                 415
Ile Lys Pro Leu Asp Ser Ser Arg Gln Asn Gly Thr Glu Ala Thr Ser
            420                 425                 430
Tyr Tyr Trp Cys Lys Phe Cys Ser Phe Ser Cys Glu Ser Ser Ser Ser
            435                 440                 445
Leu Lys Leu Leu Glu His Tyr Gly Lys Gln His Gly Ala Val Gln Ser
450                 455                 460
Gly Gly Leu Asn Pro Glu Leu Asn Asp Lys Leu Ser Arg Gly Ser Val
465                 470                 475                 480
Ile Asn Gln Asn Asp Leu Ala Lys Ser Ser Glu Gly Glu Thr Met Thr
                485                 490                 495
Lys Thr Asp Lys Ser Ser Ser Gly Ala Lys Lys Lys Asp Phe Ser Ser
            500                 505                 510
Lys Gly Ala Glu Asp Asn Met Val Thr Ser Tyr Asn Cys Gln Phe Cys
            515                 520                 525
Asp Phe Arg Tyr Ser Lys Ser His Gly Pro Asp Val Ile Val Val Gly
            530                 535                 540
Pro Leu Leu Arg His Tyr Gln Gln Leu His Asn Ile His Lys Cys Thr
545                 550                 555                 560
Ile Lys His Cys Pro Phe Cys Pro Arg Gly Leu Cys Ser Pro Glu Lys
                565                 570                 575
His Leu Gly Glu Ile Thr Tyr Pro Phe Ala Cys Arg Lys Ser Asn Cys
            580                 585                 590
Ser His Cys Ala Leu Leu Leu His Leu Ser Pro Gly Ala Ala Gly
            595                 600                 605
Ser Ser Arg Val Lys His Gln Cys His Gln Cys Ser Phe Thr Thr Pro
            610                 615                 620
Asp Val Asp Val Leu Leu Phe His Tyr Glu Ser Val His Glu Ser Gln
625                 630                 635                 640
Ala Ser Asp Val Lys Gln Glu Ala Asn His Leu Gln Gly Ser Asp Gly
                645                 650                 655
Gln Gln Ser Val Lys Glu Ser Lys Glu His Ser Cys Thr Lys Cys Asp
            660                 665                 670
Phe Ile Thr Gln Val Glu Glu Glu Ile Ser Arg His Tyr Arg Arg Ala
            675                 680                 685
```

-continued

His Ser Cys Tyr Lys Cys Arg Gln Cys Ser Phe Thr Ala Ala Asp Thr
690                 695                 700

Gln Ser Leu Leu Glu His Phe Asn Thr Val His Cys Gln Glu Gln Asp
705                 710                 715                 720

Ile Thr Thr Ala Asn Gly Glu Asp Gly His Ala Ile Ser Thr Ile
            725                 730                 735

Lys Glu Glu Pro Lys Ile Asp Phe Arg Val Tyr Asn Leu Leu Thr Pro
            740                 745                 750

Asp Ser Lys Met Gly Glu Pro Val Ser Glu Ser Val Val Lys Arg Glu
            755                 760                 765

Lys Leu Glu Glu Lys Asp Gly Leu Lys Gly Lys Val Trp Thr Glu Ser
770                 775                 780

Ser Ser Asp Asp Leu Arg Asn Val Thr Trp Arg Gly Ala Asp Ile Leu
785                 790                 795                 800

Arg Gly Ser Pro Ser Tyr Thr Gln Ala Ser Leu Gly Leu Leu Thr Pro
            805                 810                 815

Val Ser Gly Thr Gln Glu Gln Thr Lys Thr Leu Arg Asp Ser Pro Asn
            820                 825                 830

Val Glu Ala Ala His Leu Ala Arg Pro Ile Tyr Gly Leu Ala Val Glu
            835                 840                 845

Thr Lys Gly Phe Leu Gln Gly Ala Pro Ala Gly Glu Lys Ser Gly
850                 855                 860

Ala Leu Pro Gln Gln Tyr Pro Ala Ser Gly Glu Asn Lys Ser Lys Asp
865                 870                 875                 880

Glu Ser Gln Ser Leu Leu Arg Arg Arg Gly Ser Gly Val Phe Cys
            885                 890                 895

Ala Asn Cys Leu Thr Thr Lys Thr Ser Leu Trp Arg Lys Asn Ala Asn
            900                 905                 910

Gly Gly Tyr Val Cys Asn Ala Cys Gly Leu Tyr Gln Lys Leu His Ser
            915                 920                 925

Thr Pro Arg Pro Leu Asn Ile Ile Lys Gln Asn Asn Gly Glu Gln Ile
930                 935                 940

Ile Arg Arg Arg Thr Arg Lys Arg Leu Asn Pro Glu Ala Leu Gln Ala
945                 950                 955                 960

Glu Gln Leu Asn Lys Gln Gln Arg Gly Ser Asn Glu Glu Gln Val Asn
            965                 970                 975

Gly Ser Pro Leu Glu Arg Arg Ser Glu Asp His Leu Thr Glu Ser His
            980                 985                 990

Gln Arg Glu Ile Pro Leu Pro Ser Leu Ser Lys Tyr Glu Ala Gln Gly
            995                 1000                1005

Ser Leu Thr Lys Ser His Ser Ala Gln Gln Pro Val Leu Val Ser
    1010                1015                1020

Gln Thr Leu Asp Ile His Lys Arg Met Gln Pro Leu His Ile Gln
    1025                1030                1035

Ile Lys Ser Pro Gln Glu Ser Thr Gly Asp Pro Gly Asn Ser Ser
    1040                1045                1050

Ser Val Ser Glu Gly Lys Gly Ser Ser Glu Arg Gly Ser Pro Ile
    1055                1060                1065

Glu Lys Tyr Met Arg Pro Ala Lys His Pro Asn Tyr Ser Pro Pro
    1070                1075                1080

Gly Ser Pro Ile Glu Lys Tyr Gln Tyr Pro Leu Phe Gly Leu Pro
    1085                1090                1095

Phe Val His Asn Asp Phe Gln Ser Glu Ala Asp Trp Leu Arg Phe
    1100                1105                1110

| | | | | | | | | | | |
|---|---|---|---|---|---|---|---|---|---|---|
| Trp | Ser | Lys | Tyr | Lys | Leu | Ser | Val | Pro | Gly | Asn | Pro | His | Tyr | Leu |
| | 1115 | | | | 1120 | | | | | 1125 | | | | |

Trp Ser Lys Tyr Lys Leu Ser Val Pro Gly Asn Pro His Tyr Leu
    1115                    1120                    1125

Ser His Val Pro Gly Leu Pro Asn Pro Cys Gln Asn Tyr Val Pro
    1130                    1135                    1140

Tyr Pro Thr Phe Asn Leu Pro Pro His Phe Ser Ala Val Gly Ser
    1145                    1150                    1155

Asp Asn Asp Ile Pro Leu Asp Leu Ala Ile Lys His Ser Arg Pro
    1160                    1165                    1170

Gly Pro Thr Ala Asn Gly Ala Ser Lys Glu Lys Thr Lys Ala Pro
    1175                    1180                    1185

Pro Asn Val Lys Asn Glu Gly Pro Leu Asn Val Val Lys Thr Glu
    1190                    1195                    1200

Lys Val Asp Arg Ser Thr Gln Asp Glu Leu Ser Thr Lys Cys Val
    1205                    1210                    1215

His Cys Gly Ile Val Phe Leu Asp Glu Val Met Tyr Ala Leu His
    1220                    1225                    1230

Met Ser Cys His Gly Asp Ser Gly Pro Phe Gln Cys Ser Ile Cys
    1235                    1240                    1245

Gln His Leu Cys Thr Asp Lys Tyr Asp Phe Thr Thr His Ile Gln
    1250                    1255                    1260

Arg Gly Leu His Arg Asn Asn Ala Gln Val Glu Lys Asn Gly Lys
    1265                    1270                    1275

Pro Lys Glu
    1280

<210> SEQ ID NO 30
<211> LENGTH: 1203
<212> TYPE: DNA
<213> ORGANISM: Homo sapiens

<400> SEQUENCE: 30

```
atggccgagc tgcgcctgaa gggcagcagc aacaccacgg agtgtgttcc cgtgcccacc        60
tccgagcacg tggccgagat cgtgggcagg caaggctgca agattaaggc cttgagggcc       120
aagaccaaca cctacatcaa gacaccggtg aggggcgagg aaccagtgtt catggtgaca       180
gggcgacggg aggacgtggc cacagcccgg cgggaaatca tctcagcagc ggagcacttc       240
tccatgatcc gtgcctcccg caacaagtca ggcgccgcct ttggtgtggc tcctgctctg       300
cccggccagg tgaccatccg tgtgcgggtg ccctaccgcg tggtgggct ggtggtgggc        360
cccaaagggg caaccatcaa gcgcatccag cagcaaacca acacatacat tatcacacca       420
agccgtgacc gcgaccccgt gttcgagatc acgggtgccc caggcaacgt ggagcgtgcg       480
cgcgaggaga tcgagacgca catcgcggtg cgcactggca agatcctcga gtacaacaat       540
gaaaacgact tcctggcggg gagccccgac gcagcaatcg atagccgcta ctccgacgcc       600
tggcgggtgc accagcccgg ctgcaagccc ctctccacct tccggcagaa cagcctgggc       660
tgcatcggcg agtgcggagt ggactctggc tttgaggccc cacgcctggg tgagcagggc       720
ggggactttg gctacggcgg gtacctctt ccgggctatg gcgtgggcaa gcaggatgtg        780
tactacggcg tggccgagac tagcccccg ctgtgggcgg gccaggagaa cgccacgccc         840
acctccgtgc tcttctcctc tgcctcctcc tcctcctcct cttccgccaa ggcccgcgct       900
gggcccccgg gcgcacaccg ctcccctgcc acttccgcgg acccgagct ggccggactc         960
ccgaggcgcc ccccgggaga gccgctccag ggcttctcta aacttggtgg gggcggcctc      1020
cggagccccg gcggcgggcg ggattgcatg gtctgctttg agagcgaagt gactgccgcc      1080
```

```
cttgtgccct gcggacacaa cctgttctgc atggagtgtg cagtacgcat ctgcgagagg    1140
acggacccag agtgtcccgt ctgccacatc acagccgcgc aagccatccg aatattctcc    1200
taa                                                                  1203
```

<210> SEQ ID NO 31
<211> LENGTH: 400
<212> TYPE: PRT
<213> ORGANISM: Homo sapiens

<400> SEQUENCE: 31

```
Met Ala Glu Leu Arg Leu Lys Gly Ser Ser Asn Thr Thr Glu Cys Val
1               5                   10                  15

Pro Val Pro Thr Ser Glu His Val Ala Glu Ile Val Gly Arg Gln Gly
            20                  25                  30

Cys Lys Ile Lys Ala Leu Arg Ala Lys Thr Asn Thr Tyr Ile Lys Thr
        35                  40                  45

Pro Val Arg Gly Glu Glu Pro Val Phe Met Val Thr Gly Arg Arg Glu
    50                  55                  60

Asp Val Ala Thr Ala Arg Arg Glu Ile Ile Ser Ala Ala Glu His Phe
65                  70                  75                  80

Ser Met Ile Arg Ala Ser Arg Asn Lys Ser Gly Ala Ala Phe Gly Val
                85                  90                  95

Ala Pro Ala Leu Pro Gly Gln Val Thr Ile Arg Val Arg Val Pro Tyr
            100                 105                 110

Arg Val Val Gly Leu Val Val Gly Pro Lys Gly Ala Thr Ile Lys Arg
        115                 120                 125

Ile Gln Gln Gln Thr Asn Thr Tyr Ile Ile Thr Pro Ser Arg Asp Arg
    130                 135                 140

Asp Pro Val Phe Glu Ile Thr Gly Ala Pro Gly Asn Val Glu Arg Ala
145                 150                 155                 160

Arg Glu Glu Ile Glu Thr His Ile Ala Val Arg Thr Gly Lys Ile Leu
                165                 170                 175

Glu Tyr Asn Asn Glu Asn Asp Phe Leu Ala Gly Ser Pro Asp Ala Ala
            180                 185                 190

Ile Asp Ser Arg Tyr Ser Asp Ala Trp Arg Val His Gln Pro Gly Cys
        195                 200                 205

Lys Pro Leu Ser Thr Phe Arg Gln Asn Ser Leu Gly Cys Ile Gly Glu
    210                 215                 220

Cys Gly Val Asp Ser Gly Phe Glu Ala Pro Arg Leu Gly Glu Gln Gly
225                 230                 235                 240

Gly Asp Phe Gly Tyr Gly Gly Tyr Leu Phe Pro Gly Tyr Gly Val Gly
                245                 250                 255

Lys Gln Asp Val Tyr Tyr Gly Val Ala Glu Thr Ser Pro Pro Leu Trp
            260                 265                 270

Ala Gly Gln Glu Asn Ala Thr Pro Thr Ser Val Leu Phe Ser Ser Ala
        275                 280                 285

Ser Ser Ser Ser Ser Ser Ala Lys Ala Arg Ala Gly Pro Pro Gly Gly
    290                 295                 300

Ala His Arg Ser Pro Ala Thr Ser Ala Gly Pro Glu Leu Ala Gly Leu
305                 310                 315                 320

Pro Arg Arg Pro Pro Gly Glu Pro Leu Gln Gly Phe Ser Lys Leu Gly
                325                 330                 335

Gly Gly Gly Leu Arg Ser Pro Gly Gly Gly Arg Asp Cys Met Val Cys
            340                 345                 350
```

```
Phe Glu Ser Glu Val Thr Ala Ala Leu Val Pro Cys Gly His Asn Leu
        355                 360                 365
Phe Cys Met Glu Cys Ala Val Arg Ile Cys Glu Arg Thr Asp Pro Glu
        370                 375                 380
Cys Pro Val Cys His Ile Thr Ala Ala Gln Ala Ile Arg Ile Phe Ser
385                 390                 395                 400
```

<210> SEQ ID NO 32
<211> LENGTH: 4026
<212> TYPE: DNA
<213> ORGANISM: Homo sapiens

<400> SEQUENCE: 32

| | | | | | |
|---|---|---|---|---|---|
| atgacaaaga | ggaagaagac | catcaacctt | aatatacaag | acgcccagaa | gaggactgct | 60 |
| ctacactggg | cctgtgtcaa | tggccatgag | aagtagtaa | catttctggt | agacagaaag | 120 |
| tgccagcttg | acgtccttga | tggcgaacac | aggacacctc | tgatgaaggc | tctacaatgc | 180 |
| catcaggagg | cttgtgcaaa | tattctgata | gattctggtg | ccgatataaa | tctcgtagat | 240 |
| gtgtatggca | acatggctct | ccattatgct | gtttatagtg | agattttgtc | agtggtggca | 300 |
| aaactgctgt | cccatggtgc | agtcatcgaa | gtgcacaaca | aggctagcct | cacaccactt | 360 |
| ttactatcca | taacgaaaag | aagtgagcaa | attgtggaat | ttttgctgat | aaaaaatgca | 420 |
| aatgcgaatg | cagttaataa | gtataaatgc | acagccctca | tgcttgctgt | atgtcatgga | 480 |
| tcatcagaga | tagttggcat | gcttcttcag | caaaatgttg | acgtctttgc | tgcagatata | 540 |
| tgtggagtaa | ctgcagaaca | ttatgctgtt | acttgtggat | tcatcacat | tcatgaacaa | 600 |
| attatggaat | atatacgaaa | attatctaaa | aatcatcaaa | ataccaatcc | agaaggaaca | 660 |
| tctgcaggaa | cacctgatga | ggctgcaccc | ttggcggaaa | gaacacctga | cacagctgaa | 720 |
| agcttggtgg | aaaaaacacc | tgatgaggct | gcacccttgg | tggaaagaac | acctgacacg | 780 |
| gctgaaagct | tggtggaaaa | aacacctgat | gaggctgcat | ccttggtgga | gggaacatct | 840 |
| gacaaaattc | aatgtttgga | gaaagcgaca | tctggaaagt | tcgaacagtc | agcagaagaa | 900 |
| acacctaggg | aaattacgag | tcctgcaaaa | gaaacatctg | agaaatttac | gtggccagca | 960 |
| aaaggaagac | ctaggaagat | cgcatgggag | aaaaagaag | acacacctag | ggaaattatg | 1020 |
| agtcccgcaa | agaaacatc | tgagaaattt | acgtgggcag | caaaaggaag | acctaggaag | 1080 |
| atcgcatggg | agaaaaaaga | acacctgta | aagactggat | gcgtggcaag | agtaacatct | 1140 |
| aataaaacta | agttttgga | aaaggaaga | tctaagatga | ttgcatgtcc | tacaaaagaa | 1200 |
| tcatctacaa | aagcaagtgc | caatgatcag | aggttcccat | cagaatccaa | acaagaggaa | 1260 |
| gatgaagaat | attcttgtga | ttctcggagt | ctctttgaga | gttctgcaaa | gattcaagtg | 1320 |
| tgtatacctg | agtctatata | tcaaaaagta | atggagataa | atagagaagt | agaagagcct | 1380 |
| cctaagaagc | catctgcctt | caagcctgcc | attgaaatgc | aaaactctgt | tccaaataaa | 1440 |
| gcctttgaat | tgaagaatga | acaaacattg | agagcagatc | cgatgttccc | accagaatcc | 1500 |
| aaacaaaagg | actatgaaga | aaattcttgg | gattctgaga | gtctctgtga | gactgtttca | 1560 |
| cagaaggatg | tgtgtttacc | caaggctaca | catcaaaaag | aaatagataa | aataaatgga | 1620 |
| aaattagaag | agtctcctaa | taagatggt | cttctgaagg | ctacctgcgg | aatgaaagtt | 1680 |
| tctattccaa | ctaaagcctt | agaattgaag | gacatgcaaa | ctttcaaagc | ggagcctccg | 1740 |
| gggaagccat | ctgccttcga | gcctgccact | gaaatgcaaa | agtctgtccc | aaataaagcc | 1800 |
| ttggaattga | aaaatgaaca | acatggaga | gcagatgaga | tactcccatc | agaatccaaa | 1860 |

```
caaaaggact atgaagaaaa ttcttgggat actgagagtc tctgtgagac tgtttcacag    1920
aaggatgtgt gtttacccaa ggctgcgcat caaaaagaaa tagataaaat aaatggaaaa    1980
ttagaagggt ctcctgttaa agatggtctt ctgaaggcta actgcggaat gaaagtttct    2040
attccaacta aagccttaga attgatggac atgcaaactt tcaaagcaga gcctcccgag    2100
aagccatctg ccttcgagcc tgccattgaa atgcaaaagt ctgttccaaa taaagccttg    2160
gaattgaaga atgaacaaac attgagagca gatgagatac tcccatcaga atccaaacaa    2220
aaggactatg aagaaagttc ttgggattct gagagtctct gtgagactgt tcacagaag     2280 gatgtgtgtt tacccaaggc tacacatcaa aaagaaatag ataaataaa tggaaaatta    2340 gaagagtctc ctgataatga tggttttctg aaggctccct gcagaatgaa agtttctatt    2400
ccaactaaag ccttagaatt gatggacatg caaactttca aagcagagcc tcccgagaag    2460
ccatctgcct tcgagcctgc cattgaaatg caaaagtctg ttccaaataa agccttggaa    2520
ttgaagaatg aacaaacatt gagagcagat cagatgttcc cttcagaatc aaaacaaaag    2580
aaggttgaag aaaattcttg ggattctgag agtctccgtg agactgtttc acagaaggat    2640
gtgtgtgtac ccaaggctac acatcaaaaa gaaatggata aataagtgg aaaattagaa     2700 gattcaacta gcctatcaaa aatcttggat acagttcatt cttgtgaaag agcaagggaa    2760
cttcaaaaag atcactgtga acaacgtaca ggaaaaatgg aacaaatgaa aaagaagttt    2820
tgtgtactga aaaagaaact gtcagaagca aagaaataa atcacagtt agagaaccaa     2880 aaagttaaat gggaacaaga gctctgcagt gtgagattga ctttaaacca agaagaagag    2940
aagagaagaa atgccgatat attaaatgaa aaaattaggg aagaattagg aagaatcgaa    3000
gagcagcata ggaaagagtt agaagtgaaa caacaacttg aacaggctct cagaatacaa    3060
gatatagaat tgaagagtgt agaaagtaat ttgaatcagg tttctcacac tcatgaaaat    3120
gaaaattatc tcttacatga aaattgcatg ttgaaaaagg aaattgccat gctaaaactg    3180
gaaatagcca cactgaaaca ccaataccag gaaaaggaaa ataaatactt tgaggacatt    3240 aagatttttaa aagaaaagaa tgctgaactt cagatgaccc taaaactgaa agaggaatca    3300
ttaactaaaa gggcatctca atatagtggg cagcttaaag ttctgatagc tgagaacaca    3360
atgctcactt ctaaattgaa ggaaaaacaa gacaaagaaa tactagaggc agaaattgaa    3420
tcacaccatc ctagactggc ttctgctgta caagaccatg atcaaattgt gacatcaaga    3480
aaaagtcaag aacctgcttt ccacattgca ggagatgctt gtttgcaaag aaaaatgaat    3540
gttgatgtga gtagtacgat atataacaat gaggtgctcc atcaaccact ttctgaagct    3600
caaaggaaat ccaaaagcct aaaaattaat ctcaattatg caggagatgc tctaagagaa    3660
aatacattgg tttcagaaca tgcacaaaga gaccaacgtg aaacacagtg tcaaatgaag    3720
gaagctgaac acatgtatca aaacgaacaa gataatgtga acaaacacac tgaacagcag    3780
gagtctctag atcagaaatt attcaactca caaagcaaaa atatgtggct tcaacagcaa    3840
ttagttcatg cacataagaa agctgacaac aaaagcaaga taacaattga tattcatttt    3900
cttgagagga aaatgcaaca tcatctccta aaagagaaaa atgaggagat atttaattac    3960
aataaccatt taaaaaaccg tatatatcaa tatgaaaaag agaaagcaga aacagaaaac    4020
tcatga                                                               4026
```

<210> SEQ ID NO 33
<211> LENGTH: 1341
<212> TYPE: PRT
<213> ORGANISM: Homo sapiens

```
<400> SEQUENCE: 33

Met Thr Lys Arg Lys Lys Thr Ile Asn Leu Asn Ile Gln Asp Ala Gln
1               5                   10                  15

Lys Arg Thr Ala Leu His Trp Ala Cys Val Asn Gly His Glu Glu Val
            20                  25                  30

Val Thr Phe Leu Val Asp Arg Lys Cys Gln Leu Asp Val Leu Asp Gly
        35                  40                  45

Glu His Arg Thr Pro Leu Met Lys Ala Leu Gln Cys His Gln Glu Ala
    50                  55                  60

Cys Ala Asn Ile Leu Ile Asp Ser Gly Ala Asp Ile Asn Leu Val Asp
65                  70                  75                  80

Val Tyr Gly Asn Met Ala Leu His Tyr Ala Val Tyr Ser Glu Ile Leu
                85                  90                  95

Ser Val Val Ala Lys Leu Leu Ser His Gly Ala Val Ile Glu Val His
            100                 105                 110

Asn Lys Ala Ser Leu Thr Pro Leu Leu Leu Ser Ile Thr Lys Arg Ser
        115                 120                 125

Glu Gln Ile Val Glu Phe Leu Leu Ile Lys Asn Ala Asn Ala Asn Ala
130                 135                 140

Val Asn Lys Tyr Lys Cys Thr Ala Leu Met Leu Ala Val Cys His Gly
145                 150                 155                 160

Ser Ser Glu Ile Val Gly Met Leu Leu Gln Gln Asn Val Asp Val Phe
                165                 170                 175

Ala Ala Asp Ile Cys Gly Val Thr Ala Glu His Tyr Ala Val Thr Cys
            180                 185                 190

Gly Phe His His Ile His Glu Gln Ile Met Glu Tyr Ile Arg Lys Leu
        195                 200                 205

Ser Lys Asn His Gln Asn Thr Asn Pro Glu Gly Thr Ser Ala Gly Thr
    210                 215                 220

Pro Asp Glu Ala Ala Pro Leu Ala Glu Arg Thr Pro Asp Thr Ala Glu
225                 230                 235                 240

Ser Leu Val Glu Lys Thr Pro Asp Glu Ala Pro Leu Val Glu Arg
                245                 250                 255

Thr Pro Asp Thr Ala Glu Ser Leu Val Glu Lys Thr Pro Asp Glu Ala
            260                 265                 270

Ala Ser Leu Val Glu Gly Thr Ser Asp Lys Ile Gln Cys Leu Glu Lys
        275                 280                 285

Ala Thr Ser Gly Lys Phe Glu Gln Ser Ala Glu Glu Thr Pro Arg Glu
    290                 295                 300

Ile Thr Ser Pro Ala Lys Glu Thr Ser Glu Lys Phe Thr Trp Pro Ala
305                 310                 315                 320

Lys Gly Arg Pro Arg Lys Ile Ala Trp Glu Lys Lys Glu Asp Thr Pro
                325                 330                 335

Arg Glu Ile Met Ser Pro Ala Lys Glu Thr Ser Glu Lys Phe Thr Trp
            340                 345                 350

Ala Ala Lys Gly Arg Pro Arg Lys Ile Ala Trp Glu Lys Lys Glu Thr
        355                 360                 365

Pro Val Lys Thr Gly Cys Val Ala Arg Val Thr Ser Asn Lys Thr Lys
    370                 375                 380

Val Leu Glu Lys Gly Arg Ser Lys Met Ile Ala Cys Pro Thr Lys Glu
385                 390                 395                 400

Ser Ser Thr Lys Ala Ser Ala Asn Asp Gln Arg Phe Pro Ser Glu Ser
                405                 410                 415
```

-continued

```
Lys Gln Glu Glu Asp Glu Tyr Ser Cys Asp Ser Arg Ser Leu Phe
            420                 425                 430

Glu Ser Ser Ala Lys Ile Gln Val Cys Ile Pro Glu Ser Ile Tyr Gln
            435                 440                 445

Lys Val Met Glu Ile Asn Arg Glu Val Glu Pro Pro Lys Lys Pro
    450                 455                 460

Ser Ala Phe Lys Pro Ala Ile Glu Met Gln Asn Ser Val Pro Asn Lys
465                 470                 475                 480

Ala Phe Glu Leu Lys Asn Glu Gln Thr Leu Arg Ala Asp Pro Met Phe
                485                 490                 495

Pro Pro Glu Ser Lys Gln Lys Asp Tyr Glu Glu Asn Ser Trp Asp Ser
            500                 505                 510

Glu Ser Leu Cys Glu Thr Val Ser Gln Lys Asp Val Cys Leu Pro Lys
            515                 520                 525

Ala Thr His Gln Lys Glu Ile Asp Lys Ile Asn Gly Lys Leu Glu Glu
            530                 535                 540

Ser Pro Asn Lys Asp Gly Leu Leu Lys Ala Thr Cys Gly Met Lys Val
545                 550                 555                 560

Ser Ile Pro Thr Lys Ala Leu Glu Leu Lys Asp Met Gln Thr Phe Lys
                565                 570                 575

Ala Glu Pro Pro Gly Lys Pro Ser Ala Phe Glu Pro Ala Thr Glu Met
            580                 585                 590

Gln Lys Ser Val Pro Asn Lys Ala Leu Glu Leu Lys Asn Glu Gln Thr
            595                 600                 605

Trp Arg Ala Asp Glu Ile Leu Pro Ser Glu Ser Lys Gln Lys Asp Tyr
    610                 615                 620

Glu Glu Asn Ser Trp Asp Thr Glu Ser Leu Cys Glu Thr Val Ser Gln
625                 630                 635                 640

Lys Asp Val Cys Leu Pro Lys Ala Ala His Gln Lys Glu Ile Asp Lys
                645                 650                 655

Ile Asn Gly Lys Leu Glu Gly Ser Pro Val Lys Asp Gly Leu Leu Lys
            660                 665                 670

Ala Asn Cys Gly Met Lys Val Ser Ile Pro Thr Lys Ala Leu Glu Leu
            675                 680                 685

Met Asp Met Gln Thr Phe Lys Ala Glu Pro Pro Glu Lys Pro Ser Ala
    690                 695                 700

Phe Glu Pro Ala Ile Glu Met Gln Lys Ser Val Pro Asn Lys Ala Leu
705                 710                 715                 720

Glu Leu Lys Asn Glu Gln Thr Leu Arg Ala Asp Glu Ile Leu Pro Ser
                725                 730                 735

Glu Ser Lys Gln Lys Asp Tyr Glu Glu Ser Ser Trp Asp Ser Glu Ser
            740                 745                 750

Leu Cys Glu Thr Val Ser Gln Lys Asp Val Cys Leu Pro Lys Ala Thr
    755                 760                 765

His Gln Lys Glu Ile Asp Lys Ile Asn Gly Lys Leu Glu Glu Ser Pro
    770                 775                 780

Asp Asn Asp Gly Phe Leu Lys Ala Pro Cys Arg Met Lys Val Ser Ile
785                 790                 795                 800

Pro Thr Lys Ala Leu Glu Leu Met Asp Met Gln Thr Phe Lys Ala Glu
                805                 810                 815

Pro Pro Glu Lys Pro Ser Ala Phe Glu Pro Ala Ile Glu Met Gln Lys
            820                 825                 830

Ser Val Pro Asn Lys Ala Leu Glu Leu Lys Asn Glu Gln Thr Leu Arg
            835                 840                 845
```

```
Ala Asp Gln Met Phe Pro Ser Glu Ser Lys Gln Lys Val Glu Glu
    850                 855                 860

Asn Ser Trp Asp Ser Glu Ser Leu Arg Glu Thr Val Ser Gln Lys Asp
865                 870                 875                 880

Val Cys Val Pro Lys Ala Thr His Gln Lys Glu Met Asp Lys Ile Ser
                885                 890                 895

Gly Lys Leu Glu Asp Ser Thr Ser Leu Ser Lys Ile Leu Asp Thr Val
                900                 905                 910

His Ser Cys Glu Arg Ala Arg Glu Leu Gln Lys Asp His Cys Glu Gln
            915                 920                 925

Arg Thr Gly Lys Met Glu Gln Met Lys Lys Lys Phe Cys Val Leu Lys
    930                 935                 940

Lys Lys Leu Ser Glu Ala Lys Glu Ile Lys Ser Gln Leu Glu Asn Gln
945                 950                 955                 960

Lys Val Lys Trp Glu Gln Glu Leu Cys Ser Val Arg Leu Thr Leu Asn
                965                 970                 975

Gln Glu Glu Glu Lys Arg Arg Asn Ala Asp Ile Leu Asn Gly Lys Ile
                980                 985                 990

Arg Glu Glu Leu Gly Arg Ile Glu  Glu Gln His Arg Lys  Glu Leu Glu
    995                 1000                1005

Val Lys  Gln Gln Leu Glu Gln  Ala Leu Arg Ile Gln  Asp Ile Glu
    1010                1015                1020

Leu Lys  Ser Val Glu Ser Asn  Leu Asn Gln Val Ser  His Thr His
    1025                1030                1035

Glu Asn  Glu Asn Tyr Leu Leu  His Glu Asn Cys Met  Leu Lys Lys
    1040                1045                1050

Glu Ile  Ala Met Leu Lys Leu  Glu Ile Ala Thr Leu  Lys His Gln
    1055                1060                1065

Tyr Gln  Glu Lys Glu Asn Lys  Tyr Phe Glu Asp Ile  Lys Ile Leu
    1070                1075                1080

Lys Glu  Lys Asn Ala Glu Leu  Gln Met Thr Leu Lys  Leu Lys Glu
    1085                1090                1095

Glu Ser  Leu Thr Lys Arg Ala  Ser Gln Tyr Ser Gly  Gln Leu Lys
    1100                1105                1110

Val Leu  Ile Ala Glu Asn Thr  Met Leu Thr Ser Lys  Leu Lys Glu
    1115                1120                1125

Lys Gln  Asp Lys Glu Ile Leu  Glu Ala Glu Ile Glu  Ser His His
    1130                1135                1140

Pro Arg  Leu Ala Ser Ala Val  Gln Asp His Asp Gln  Ile Val Thr
    1145                1150                1155

Ser Arg  Lys Ser Gln Glu Pro  Ala Phe His Ile Ala  Gly Asp Ala
    1160                1165                1170

Cys Leu  Gln Arg Lys Met Asn  Val Asp Val Ser Ser  Thr Ile Tyr
    1175                1180                1185

Asn Asn  Glu Val Leu His Gln  Pro Leu Ser Glu Ala  Gln Arg Lys
    1190                1195                1200

Ser Lys  Ser Leu Lys Ile Asn  Leu Asn Tyr Ala Gly  Asp Ala Leu
    1205                1210                1215

Arg Glu  Asn Thr Leu Val Ser  Glu His Ala Gln Arg  Asp Gln Arg
    1220                1225                1230

Glu Thr  Gln Cys Gln Met Lys  Glu Ala Glu His Met  Tyr Gln Asn
    1235                1240                1245

Glu Gln  Asp Asn Val Asn Lys  His Thr Glu Gln Gln  Glu Ser Leu
```

```
                     1250                1255                1260
Asp Gln Lys Leu Phe Gln Leu Ser Lys Asn Met Trp Leu Gln
            1265                1270                1275
Gln Gln Leu Val His Ala His Lys Lys Ala Asp Asn Lys Ser Lys
        1280                1285                1290
Ile Thr Ile Asp Ile His Phe Leu Glu Arg Lys Met Gln His His
    1295                1300                1305
Leu Leu Lys Glu Lys Asn Glu Ile Phe Asn Tyr Asn Asn His
        1310                1315                1320
Leu Lys Asn Arg Ile Tyr Gln Tyr Glu Lys Glu Lys Ala Glu Thr
        1325                1330                1335
Glu Asn Ser
    1340

<210> SEQ ID NO 34
<211> LENGTH: 873
<212> TYPE: DNA
<213> ORGANISM: Homo sapiens

<400> SEQUENCE: 34
atggacattg aagcatatct tgaaagaatt ggctataaga agtctaggaa caaattggac       60
ttggaaacat taactgacat tcttcaacac cagatccgag ctgttccctt tgagaacctt      120
aacatccatt gtggggatgc catggactta ggcttagagg ccattttga tcaagttgtg       180 agaagaaatc ggggtggatg gtgtctccag gtcaatcatc ttctgtactg ggctctgacc      240
actattggtt ttgagaccac gatgttggga gggtatgttt acagcactcc agccaaaaaa      300
tacagcactg gcatgattca ccttctcctg caggtgacca ttgatggcag gaactacatt      360
gtcgatgctg ggtttggacg ctcataccag atgtggcagc tctggagtt aatttctggg       420 aaggatcagc tcaggtgcc ttgtgtcttc cgtttgacgg aagagaatgg attctggtat       480
ctagaccaaa tcagaaggga acagtacatt ccaaatgaag aatttcttca ttctgatctc      540
ctagaagaca gcaaataccg aaaaatctac tcctttactc ttaagcctcg aacaattgaa      600
gattttgagt ctatgaatac atacctgcag acatctccat catctgtgtt tactagtaaa      660
tcattttgtt ccttgcagac cccagatggg gttcactgtt tggtgggctt caccctcacc      720
cataggagat tcaattataa ggacaataca gatctaatag agttcaagac tctgagtgag      780
gaagaaatag aaaaagtgct gaaaaatata tttaatattt ccttgcagag aaagcttgtg      840
cccaaacatg gtgatagatt ttttactatt tag                                   873

<210> SEQ ID NO 35
<211> LENGTH: 290
<212> TYPE: PRT
<213> ORGANISM: Homo sapiens

<400> SEQUENCE: 35

Met Asp Ile Glu Ala Tyr Leu Glu Arg Ile Gly Tyr Lys Lys Ser Arg
1               5                   10                  15
Asn Lys Leu Asp Leu Glu Thr Leu Thr Asp Ile Leu Gln His Gln Ile
            20                  25                  30
Arg Ala Val Pro Phe Glu Asn Leu Asn Ile His Cys Gly Asp Ala Met
        35                  40                  45
Asp Leu Gly Leu Glu Ala Ile Phe Asp Gln Val Val Arg Arg Asn Arg
    50                  55                  60
Gly Gly Trp Cys Leu Gln Val Asn His Leu Leu Tyr Trp Ala Leu Thr
65                  70                  75                  80
```

```
Thr Ile Gly Phe Glu Thr Thr Met Leu Gly Gly Tyr Val Tyr Ser Thr
                85                  90                  95
Pro Ala Lys Lys Tyr Ser Thr Gly Met Ile His Leu Leu Gln Val
            100                 105                 110
Thr Ile Asp Gly Arg Asn Tyr Ile Val Asp Ala Gly Phe Gly Arg Ser
        115                 120                 125
Tyr Gln Met Trp Gln Pro Leu Glu Leu Ile Ser Gly Lys Asp Gln Pro
    130                 135                 140
Gln Val Pro Cys Val Phe Arg Leu Thr Glu Glu Asn Gly Phe Trp Tyr
145                 150                 155                 160
Leu Asp Gln Ile Arg Arg Glu Gln Tyr Ile Pro Asn Glu Glu Phe Leu
                165                 170                 175
His Ser Asp Leu Leu Glu Asp Ser Lys Tyr Arg Lys Ile Tyr Ser Phe
            180                 185                 190
Thr Leu Lys Pro Arg Thr Ile Glu Asp Phe Glu Ser Met Asn Thr Tyr
        195                 200                 205
Leu Gln Thr Ser Pro Ser Ser Val Phe Thr Ser Lys Ser Phe Cys Ser
    210                 215                 220
Leu Gln Thr Pro Asp Gly Val His Cys Leu Val Gly Phe Thr Leu Thr
225                 230                 235                 240
His Arg Arg Phe Asn Tyr Lys Asp Asn Thr Asp Leu Ile Glu Phe Lys
                245                 250                 255
Thr Leu Ser Glu Glu Glu Ile Glu Lys Val Leu Lys Asn Ile Phe Asn
            260                 265                 270
Ile Ser Leu Gln Arg Lys Leu Val Pro Lys His Gly Asp Arg Phe Phe
        275                 280                 285
Thr Ile
    290

<210> SEQ ID NO 36
<211> LENGTH: 1314
<212> TYPE: DNA
<213> ORGANISM: Homo sapiens

<400> SEQUENCE: 36
atgctttgga aattgacgga taatatcaag tacgaggact gcgaggaccg tcacgacggc     60
accagcaacg ggacggcacg gttgccccag ctgggcactg taggtcaatc tccctacacg    120
agcgccccgc cgctgtccca caccccaat gccgacttcc agcccccata cttcccccca    180
ccctaccagc ctatctaccc ccagtcgcaa gatccttact ccacgtcaa cgaccctac     240 agcctgaacc cctgcacgc ccagccgcag ccgcagcacc caggctggcc cggccagagg    300
cagagccagg agtctgggct cctgcacacg caccggggc tgcctcacca gctgtcgggc    360
ctggatcctc gcagggacta caggcggcac gaggacctcc tgcacggccc acacgcgctc    420
agctcaggac tcggagacct ctcgatccac tccttacctc acgccatcga ggaggtcccg    480
catgtagaag acccgggtat taacatccca gatcaaactg taattaagaa aggccccgtg    540
tccctgtcca agtccaacag caatgccgtc tccgccatcc ctattaacaa ggacaacctc    600
ttcggcggcg tggtgaaccc caacgaagtc ttctgttcag ttccgggtcg cctctcgctc    660
ctcagctcca cctcgaagta caaggtcacg gtggcggaag tgcagcggcg gctctcacca    720
cccgagtgtc tcaacgcgtc gctgctgggc ggagtgctcc ggagggcgaa gtctaaaaat    780
ggaggaagat ctttaagaga aaaactggac aaaataggt aaatctgcc tgcagggaga    840 cgtaaagctg ccaacgttac cctgctcaca tcactagtag agggagaagc tgtccaccta    900
```

```
gccagggact tgggtacgt gtgcgaaacc gaatttcctg ccaaagcagt agctgaattt      960
ctcaaccgac aacattccga tcccaatgag caagtgacaa gaaaaaacat gctcctggct    1020
acaaaacaga tatgcaaaga gttcaccgac ctgctggctc aggaccgatc tcccctgggg    1080
aactcacggc ccaaccccat cctggagccc ggcatccaga gctgcttgac ccacttcaac    1140
ctcatctccc acggcttcgg cagccccgcg gtgtgtgccg cggtcacggc cctgcagaac    1200
tatctcaccg aggccctcaa ggccatggac aaaatgtacc tcagcaacaa ccccaacagc    1260
cacacggaca caacgccaa aagcagtgac aaagaggaga agcacagaaa gtga           1314
```

<210> SEQ ID NO 37
<211> LENGTH: 437
<212> TYPE: PRT
<213> ORGANISM: Homo sapiens

<400> SEQUENCE: 37

```
Met Leu Trp Lys Leu Thr Asp Asn Ile Lys Tyr Glu Asp Cys Glu Asp
1               5                   10                  15

Arg His Asp Gly Thr Ser Asn Gly Thr Ala Arg Leu Pro Gln Leu Gly
                20                  25                  30

Thr Val Gly Gln Ser Pro Tyr Thr Ser Ala Pro Pro Leu Ser His Thr
            35                  40                  45

Pro Asn Ala Asp Phe Gln Pro Tyr Phe Pro Pro Tyr Gln Pro
    50                  55                  60

Ile Tyr Pro Gln Ser Gln Asp Pro Tyr Ser His Val Asn Asp Pro Tyr
65                  70                  75                  80

Ser Leu Asn Pro Leu His Ala Gln Pro Gln Pro Gln His Pro Gly Trp
                85                  90                  95

Pro Gly Gln Arg Gln Ser Gln Glu Ser Gly Leu Leu His Thr His Arg
            100                 105                 110

Gly Leu Pro His Gln Leu Ser Gly Leu Asp Pro Arg Arg Asp Tyr Arg
        115                 120                 125

Arg His Glu Asp Leu Leu His Gly Pro His Ala Leu Ser Ser Gly Leu
    130                 135                 140

Gly Asp Leu Ser Ile His Ser Leu Pro His Ala Ile Glu Glu Val Pro
145                 150                 155                 160

His Val Glu Asp Pro Gly Ile Asn Ile Pro Asp Gln Thr Val Ile Lys
                165                 170                 175

Lys Gly Pro Val Ser Leu Ser Lys Ser Asn Ser Asn Ala Val Ser Ala
            180                 185                 190

Ile Pro Ile Asn Lys Asp Asn Leu Phe Gly Gly Val Val Asn Pro Asn
        195                 200                 205

Glu Val Phe Cys Ser Val Pro Gly Arg Leu Ser Leu Leu Ser Ser Thr
    210                 215                 220

Ser Lys Tyr Lys Val Thr Val Ala Glu Val Gln Arg Arg Leu Ser Pro
225                 230                 235                 240

Pro Glu Cys Leu Asn Ala Ser Leu Leu Gly Gly Val Leu Arg Arg Ala
                245                 250                 255

Lys Ser Lys Asn Gly Gly Arg Ser Leu Arg Glu Lys Leu Asp Lys Ile
            260                 265                 270

Gly Leu Asn Leu Pro Ala Gly Arg Arg Lys Ala Ala Asn Val Thr Leu
        275                 280                 285

Leu Thr Ser Leu Val Glu Gly Glu Ala Val His Leu Ala Arg Asp Phe
    290                 295                 300
```

```
Gly Tyr Val Cys Glu Thr Glu Phe Pro Ala Lys Ala Val Ala Glu Phe
305                 310                 315                 320

Leu Asn Arg Gln His Ser Asp Pro Asn Glu Gln Val Thr Arg Lys Asn
            325                 330                 335

Met Leu Leu Ala Thr Lys Gln Ile Cys Lys Glu Phe Thr Asp Leu Leu
        340                 345                 350

Ala Gln Asp Arg Ser Pro Leu Gly Asn Ser Arg Pro Asn Pro Ile Leu
    355                 360                 365

Glu Pro Gly Ile Gln Ser Cys Leu Thr His Phe Asn Leu Ile Ser His
370                 375                 380

Gly Phe Gly Ser Pro Ala Val Cys Ala Ala Val Thr Ala Leu Gln Asn
385                 390                 395                 400

Tyr Leu Thr Glu Ala Leu Lys Ala Met Asp Lys Met Tyr Leu Ser Asn
                405                 410                 415

Asn Pro Asn Ser His Thr Asp Asn Asn Ala Lys Ser Ser Asp Lys Glu
            420                 425                 430

Glu Lys His Arg Lys
        435

<210> SEQ ID NO 38
<211> LENGTH: 41
<212> TYPE: DNA
<213> ORGANISM: Homo sapiens

<400> SEQUENCE: 38
ggaattcaac atggacattg aagcatatct tgaaagaatt g                 41

<210> SEQ ID NO 39
<211> LENGTH: 39
<212> TYPE: DNA
<213> ORGANISM: Homo sapiens

<400> SEQUENCE: 39
ggaattcctg gtgagctgga tgacaaatag acaagattg                    39

<210> SEQ ID NO 40
<211> LENGTH: 31
<212> TYPE: DNA
<213> ORGANISM: Homo sapiens

<400> SEQUENCE: 40
ggaattcacc atgctttgga aattgacgga t                            31

<210> SEQ ID NO 41
<211> LENGTH: 36
<212> TYPE: DNA
<213> ORGANISM: Homo sapiens

<400> SEQUENCE: 41
ggaattcctc actttctgtg cttctcctct ttgtca                       36

<210> SEQ ID NO 42
<211> LENGTH: 17
<212> TYPE: PRT
<213> ORGANISM: Homo sapiens

<400> SEQUENCE: 42

Ser Ser Arg Arg His His Cys Arg Ser Lys Ala Lys Arg Ser Arg His
1               5                   10                  15

His
```

```
<210> SEQ ID NO 43
<211> LENGTH: 17
<212> TYPE: PRT
<213> ORGANISM: Homo sapiens

<400> SEQUENCE: 43

Ser Glu Phe Phe Ser Cys Gln Asn Cys Glu Ala Val Ala Gly Cys Ser
1               5                   10                  15

Ser

<210> SEQ ID NO 44
<211> LENGTH: 9
<212> TYPE: PRT
<213> ORGANISM: Homo sapiens

<400> SEQUENCE: 44

Arg Leu Ser Pro Thr Ala Ala Thr Val
1               5

<210> SEQ ID NO 45
<211> LENGTH: 9
<212> TYPE: PRT
<213> ORGANISM: Homo sapiens

<400> SEQUENCE: 45

Ser Ile Phe Arg Phe Arg Ala Gly Val
1               5

<210> SEQ ID NO 46
<211> LENGTH: 9
<212> TYPE: PRT
<213> ORGANISM: Homo sapiens

<400> SEQUENCE: 46

Asp Val Leu Gly Asn Leu Asn Glu Leu
1               5

<210> SEQ ID NO 47
<211> LENGTH: 9
<212> TYPE: PRT
<213> ORGANISM: Homo sapiens

<400> SEQUENCE: 47

Gly Val Gly Val Asp Val Leu Ser Leu
1               5

<210> SEQ ID NO 48
<211> LENGTH: 9
<212> TYPE: PRT
<213> ORGANISM: Homo sapiens

<400> SEQUENCE: 48

Leu Leu Thr Ser Gln Ala Gln Asp Thr
1               5

<210> SEQ ID NO 49
<211> LENGTH: 9
<212> TYPE: PRT
<213> ORGANISM: Homo sapiens

<400> SEQUENCE: 49

Val Leu Asn Ser Gln Ala Ser Gln Ala
1               5
```

```
<210> SEQ ID NO 50
<211> LENGTH: 9
<212> TYPE: PRT
<213> ORGANISM: Homo sapiens

<400> SEQUENCE: 50

Val Gln Phe Lys Cys Gly Ala Pro Ala
1               5

<210> SEQ ID NO 51
<211> LENGTH: 9
<212> TYPE: PRT
<213> ORGANISM: Homo sapiens

<400> SEQUENCE: 51

Gly Gln Pro Cys Pro Gln Ala Arg Leu
1               5

<210> SEQ ID NO 52
<211> LENGTH: 9
<212> TYPE: PRT
<213> ORGANISM: Homo sapiens

<400> SEQUENCE: 52

Gly Ala His Arg Gly Leu Asp Ser Leu
1               5

<210> SEQ ID NO 53
<211> LENGTH: 9
<212> TYPE: PRT
<213> ORGANISM: Homo sapiens

<400> SEQUENCE: 53

Gly Ala Pro Ala Ser Thr Pro Tyr Leu
1               5

<210> SEQ ID NO 54
<211> LENGTH: 9
<212> TYPE: PRT
<213> ORGANISM: Homo sapiens

<400> SEQUENCE: 54

Val Val Gln Ala Cys His Arg Phe Ile
1               5

<210> SEQ ID NO 55
<211> LENGTH: 9
<212> TYPE: PRT
<213> ORGANISM: Homo sapiens

<400> SEQUENCE: 55

Pro Leu Gly Ile Ser Leu Arg Pro Leu
1               5

<210> SEQ ID NO 56
<211> LENGTH: 9
<212> TYPE: PRT
<213> ORGANISM: Homo sapiens

<400> SEQUENCE: 56

Pro Leu Arg Ala His Lys Ala Val Leu
1               5

<210> SEQ ID NO 57
<211> LENGTH: 9
<212> TYPE: PRT
```

<213> ORGANISM: Homo sapiens

<400> SEQUENCE: 57

Phe Val Gln Val Ala His Leu Arg Ala
1               5

<210> SEQ ID NO 58
<211> LENGTH: 9
<212> TYPE: PRT
<213> ORGANISM: Homo sapiens

<400> SEQUENCE: 58

Ala Pro Leu Leu Asp Phe Met Tyr Thr
1               5

<210> SEQ ID NO 59
<211> LENGTH: 9
<212> TYPE: PRT
<213> ORGANISM: Homo sapiens

<400> SEQUENCE: 59

Arg Ala Gly Val Gly Val Asp Val Leu
1               5

<210> SEQ ID NO 60
<211> LENGTH: 9
<212> TYPE: PRT
<213> ORGANISM: Homo sapiens

<400> SEQUENCE: 60

Cys Glu Thr Cys Gly Ser Arg Phe Val
1               5

<210> SEQ ID NO 61
<211> LENGTH: 9
<212> TYPE: PRT
<213> ORGANISM: Homo sapiens

<400> SEQUENCE: 61

Ala Thr Ala Pro Ala Val Leu Ala Ala
1               5

<210> SEQ ID NO 62
<211> LENGTH: 9
<212> TYPE: PRT
<213> ORGANISM: Homo sapiens

<400> SEQUENCE: 62

Ser Arg Phe Val Gln Val Ala His Leu
1               5

<210> SEQ ID NO 63
<211> LENGTH: 9
<212> TYPE: PRT
<213> ORGANISM: Homo sapiens

<400> SEQUENCE: 63

Cys Asn Trp Lys Lys Tyr Lys Tyr Ile
1               5

<210> SEQ ID NO 64
<211> LENGTH: 9
<212> TYPE: PRT
<213> ORGANISM: Homo sapiens

<400> SEQUENCE: 64

```
Ser Pro Ala Ala Pro Glu Gly Ala Leu
1               5
```

<210> SEQ ID NO 65
<211> LENGTH: 9
<212> TYPE: PRT
<213> ORGANISM: Homo sapiens

<400> SEQUENCE: 65

```
Ala Leu Gly Tyr Val Arg Glu Phe Thr
1               5
```

<210> SEQ ID NO 66
<211> LENGTH: 9
<212> TYPE: PRT
<213> ORGANISM: Homo sapiens

<400> SEQUENCE: 66

```
Arg Leu Arg Gly Ile Leu Thr Asp Val
1               5
```

<210> SEQ ID NO 67
<211> LENGTH: 9
<212> TYPE: PRT
<213> ORGANISM: Homo sapiens

<400> SEQUENCE: 67

```
Gly Ile Leu Thr Asp Val Thr Leu Leu
1               5
```

<210> SEQ ID NO 68
<211> LENGTH: 9
<212> TYPE: PRT
<213> ORGANISM: Homo sapiens

<400> SEQUENCE: 68

```
Ile Leu Thr Asp Val Thr Leu Leu Val
1               5
```

<210> SEQ ID NO 69
<211> LENGTH: 9
<212> TYPE: PRT
<213> ORGANISM: Homo sapiens

<400> SEQUENCE: 69

```
Thr Leu Leu Val Gly Gly Gln Pro Leu
1               5
```

<210> SEQ ID NO 70
<211> LENGTH: 9
<212> TYPE: PRT
<213> ORGANISM: Homo sapiens

<400> SEQUENCE: 70

```
Phe Met Tyr Thr Ser Arg Leu Arg Leu
1               5
```

<210> SEQ ID NO 71
<211> LENGTH: 9
<212> TYPE: PRT
<213> ORGANISM: Homo sapiens

<400> SEQUENCE: 71

```
Arg Leu Ser Pro Ala Thr Ala Pro Ala
1               5
```

<210> SEQ ID NO 72
<211> LENGTH: 9
<212> TYPE: PRT
<213> ORGANISM: Homo sapiens

<400> SEQUENCE: 72

Ala Val Leu Ala Ala Ala Thr Tyr Leu
1               5

<210> SEQ ID NO 73
<211> LENGTH: 9
<212> TYPE: PRT
<213> ORGANISM: Homo sapiens

<400> SEQUENCE: 73

Ala Thr Tyr Leu Gln Met Glu His Val
1               5

<210> SEQ ID NO 74
<211> LENGTH: 9
<212> TYPE: PRT
<213> ORGANISM: Homo sapiens

<400> SEQUENCE: 74

Leu Gln Met Glu His Val Val Gln Ala
1               5

<210> SEQ ID NO 75
<211> LENGTH: 9
<212> TYPE: PRT
<213> ORGANISM: Homo sapiens

<400> SEQUENCE: 75

Gln Val Ala His Leu Arg Ala His Val
1               5

<210> SEQ ID NO 76
<211> LENGTH: 9
<212> TYPE: PRT
<213> ORGANISM: Homo sapiens

<400> SEQUENCE: 76

His Leu Gln Thr Leu Lys Ser His Val
1               5

<210> SEQ ID NO 77
<211> LENGTH: 9
<212> TYPE: PRT
<213> ORGANISM: Homo sapiens

<400> SEQUENCE: 77

Val Val Gln Ala Cys His Arg Phe Ile
1               5

<210> SEQ ID NO 78
<211> LENGTH: 22
<212> TYPE: PRT
<213> ORGANISM: Homo sapiens

<400> SEQUENCE: 78

Met Val Arg Lys Lys Asn Pro Pro Leu Arg Asn Val Ala Ser Glu Gly
1               5                   10                  15

Glu Gly Gln Ile Leu Glu
            20

<210> SEQ ID NO 79
<211> LENGTH: 22
<212> TYPE: PRT
<213> ORGANISM: Homo sapiens

<400> SEQUENCE: 79

Ser Pro Lys Ala Thr Glu Glu Thr Gly Gln Ala Gln Ser Gly Gln Ala
1               5                   10                  15

Asn Cys Gln Gly Leu Ser
            20

<210> SEQ ID NO 80
<211> LENGTH: 22
<212> TYPE: PRT
<213> ORGANISM: Homo sapiens

<400> SEQUENCE: 80

Val Ala Lys Pro Ser Glu Lys Asn Ser Asn Lys Ser Ile Pro Ala Leu
1               5                   10                  15

Gln Ser Ser Asp Ser Gly
            20

<210> SEQ ID NO 81
<211> LENGTH: 22
<212> TYPE: PRT
<213> ORGANISM: Homo sapiens

<400> SEQUENCE: 81

Asn His Leu Gln Gly Ser Asp Gly Gln Gln Ser Val Lys Glu Ser Lys
1               5                   10                  15

Glu His Ser Cys Thr Lys
            20

<210> SEQ ID NO 82
<211> LENGTH: 22
<212> TYPE: PRT
<213> ORGANISM: Homo sapiens

<400> SEQUENCE: 82

Asn Gly Glu Gln Ile Ile Arg Arg Arg Thr Arg Lys Arg Leu Asn Pro
1               5                   10                  15

Glu Ala Leu Gln Ala Glu
            20

<210> SEQ ID NO 83
<211> LENGTH: 23
<212> TYPE: PRT
<213> ORGANISM: Homo sapiens

<400> SEQUENCE: 83

Ala Asn Gly Ala Ser Lys Glu Lys Thr Lys Ala Pro Pro Asn Val Lys
1               5                   10                  15

Asn Glu Gly Pro Leu Asn Val
            20

<210> SEQ ID NO 84
<211> LENGTH: 31
<212> TYPE: DNA
<213> ORGANISM: Homo sapiens

<400> SEQUENCE: 84
cggatccacc atggtccgga aaaagaaccc c                           31

<210> SEQ ID NO 85
<211> LENGTH: 35
<212> TYPE: DNA
<213> ORGANISM: Homo sapiens

<400> SEQUENCE: 85
cgggatccct ctttaggttt tccatttttt tccac					35

<210> SEQ ID NO 86
<211> LENGTH: 9
<212> TYPE: PRT
<213> ORGANISM: Homo sapiens

<400> SEQUENCE: 86

Ser Thr Ile Lys Glu Glu Pro Lys Ile
1               5

<210> SEQ ID NO 87
<211> LENGTH: 9
<212> TYPE: PRT
<213> ORGANISM: Homo sapiens

<400> SEQUENCE: 87

Lys Ile Asp Phe Arg Val Tyr Asn Leu
1               5

<210> SEQ ID NO 88
<211> LENGTH: 9
<212> TYPE: PRT
<213> ORGANISM: Homo sapiens

<400> SEQUENCE: 88

Asn Leu Leu Thr Pro Asp Ser Lys Met
1               5

<210> SEQ ID NO 89
<211> LENGTH: 9
<212> TYPE: PRT
<213> ORGANISM: Homo sapiens

<400> SEQUENCE: 89

Val Thr Trp Arg Gly Ala Asp Ile Leu
1               5

<210> SEQ ID NO 90
<211> LENGTH: 9
<212> TYPE: PRT
<213> ORGANISM: Homo sapiens

<400> SEQUENCE: 90

Ile Leu Arg Gly Ser Pro Ser Tyr Thr
1               5

<210> SEQ ID NO 91
<211> LENGTH: 9
<212> TYPE: PRT
<213> ORGANISM: Homo sapiens

<400> SEQUENCE: 91

Tyr Thr Gln Ala Ser Leu Gly Leu Leu
1               5

<210> SEQ ID NO 92
<211> LENGTH: 9

```
<212> TYPE: PRT
<213> ORGANISM: Homo sapiens

<400> SEQUENCE: 92

Ala Ser Leu Gly Leu Leu Thr Pro Val
1               5

<210> SEQ ID NO 93
<211> LENGTH: 9
<212> TYPE: PRT
<213> ORGANISM: Homo sapiens

<400> SEQUENCE: 93

Gly Leu Leu Thr Pro Val Ser Gly Thr
1               5

<210> SEQ ID NO 94
<211> LENGTH: 9
<212> TYPE: PRT
<213> ORGANISM: Homo sapiens

<400> SEQUENCE: 94

Gly Thr Gln Glu Gln Thr Lys Thr Leu
1               5

<210> SEQ ID NO 95
<211> LENGTH: 9
<212> TYPE: PRT
<213> ORGANISM: Homo sapiens

<400> SEQUENCE: 95

Lys Thr Leu Arg Asp Ser Pro Asn Val
1               5

<210> SEQ ID NO 96
<211> LENGTH: 9
<212> TYPE: PRT
<213> ORGANISM: Homo sapiens

<400> SEQUENCE: 96

His Leu Ala Arg Pro Ile Tyr Gly Leu
1               5

<210> SEQ ID NO 97
<211> LENGTH: 9
<212> TYPE: PRT
<213> ORGANISM: Homo sapiens

<400> SEQUENCE: 97

Pro Ile Tyr Gly Leu Ala Val Glu Thr
1               5

<210> SEQ ID NO 98
<211> LENGTH: 9
<212> TYPE: PRT
<213> ORGANISM: Homo sapiens

<400> SEQUENCE: 98

Leu Ala Val Glu Thr Lys Gly Phe Leu
1               5

<210> SEQ ID NO 99
<211> LENGTH: 9
<212> TYPE: PRT
<213> ORGANISM: Homo sapiens
```

```
<400> SEQUENCE: 99

Phe Leu Gln Gly Ala Pro Ala Gly Gly
1               5

<210> SEQ ID NO 100
<211> LENGTH: 9
<212> TYPE: PRT
<213> ORGANISM: Homo sapiens

<400> SEQUENCE: 100

Ala Gly Gly Glu Lys Ser Gly Ala Leu
1               5

<210> SEQ ID NO 101
<211> LENGTH: 9
<212> TYPE: PRT
<213> ORGANISM: Homo sapiens

<400> SEQUENCE: 101

Gly Ala Leu Pro Gln Gln Tyr Pro Ala
1               5

<210> SEQ ID NO 102
<211> LENGTH: 9
<212> TYPE: PRT
<213> ORGANISM: Homo sapiens

<400> SEQUENCE: 102

Ala Leu Pro Gln Gln Tyr Pro Ala Ser
1               5

<210> SEQ ID NO 103
<211> LENGTH: 9
<212> TYPE: PRT
<213> ORGANISM: Homo sapiens

<400> SEQUENCE: 103

Phe Cys Ala Asn Cys Leu Thr Thr Lys
1               5

<210> SEQ ID NO 104
<211> LENGTH: 9
<212> TYPE: PRT
<213> ORGANISM: Homo sapiens

<400> SEQUENCE: 104

Ala Asn Gly Gly Tyr Val Cys Asn Ala
1               5

<210> SEQ ID NO 105
<211> LENGTH: 9
<212> TYPE: PRT
<213> ORGANISM: Homo sapiens

<400> SEQUENCE: 105

Asn Ala Cys Gly Leu Tyr Gln Lys Leu
1               5

<210> SEQ ID NO 106
<211> LENGTH: 9
<212> TYPE: PRT
<213> ORGANISM: Homo sapiens

<400> SEQUENCE: 106

Gly Leu Tyr Gln Lys Leu His Ser Thr
```

<210> SEQ ID NO 107
<211> LENGTH: 9
<212> TYPE: PRT
<213> ORGANISM: Homo sapiens

<400> SEQUENCE: 107

Lys Leu His Ser Thr Pro Arg Pro Leu
1               5

<210> SEQ ID NO 108
<211> LENGTH: 9
<212> TYPE: PRT
<213> ORGANISM: Homo sapiens

<400> SEQUENCE: 108

Ser Thr Pro Arg Pro Leu Asn Ile Ile
1               5

<210> SEQ ID NO 109
<211> LENGTH: 9
<212> TYPE: PRT
<213> ORGANISM: Homo sapiens

<400> SEQUENCE: 109

Arg Leu Asn Pro Glu Ala Leu Gln Ala
1               5

<210> SEQ ID NO 110
<211> LENGTH: 9
<212> TYPE: PRT
<213> ORGANISM: Homo sapiens

<400> SEQUENCE: 110

Val Leu Val Ser Gln Thr Leu Asp Ile
1               5

<210> SEQ ID NO 111
<211> LENGTH: 9
<212> TYPE: PRT
<213> ORGANISM: Homo sapiens

<400> SEQUENCE: 111

Asp Ile His Lys Arg Met Gln Pro Leu
1               5

<210> SEQ ID NO 112
<211> LENGTH: 9
<212> TYPE: PRT
<213> ORGANISM: Homo sapiens

<400> SEQUENCE: 112

Arg Met Gln Pro Leu His Ile Gln Ile
1               5

<210> SEQ ID NO 113
<211> LENGTH: 9
<212> TYPE: PRT
<213> ORGANISM: Homo sapiens

<400> SEQUENCE: 113

Tyr Pro Leu Phe Gly Leu Pro Phe Val
1               5

```
<210> SEQ ID NO 114
<211> LENGTH: 9
<212> TYPE: PRT
<213> ORGANISM: Homo sapiens

<400> SEQUENCE: 114

Gly Pro Leu Phe Val His Asn Asp Phe
1               5

<210> SEQ ID NO 115
<211> LENGTH: 9
<212> TYPE: PRT
<213> ORGANISM: Homo sapiens

<400> SEQUENCE: 115

Phe Val His Asn Asp Phe Gln Ser Glu
1               5

<210> SEQ ID NO 116
<211> LENGTH: 9
<212> TYPE: PRT
<213> ORGANISM: Homo sapiens

<400> SEQUENCE: 116

Ser Val Pro Gly Asn Pro His Tyr Leu
1               5

<210> SEQ ID NO 117
<211> LENGTH: 9
<212> TYPE: PRT
<213> ORGANISM: Homo sapiens

<400> SEQUENCE: 117

Gly Asn Pro His Tyr Leu Ser His Val
1               5

<210> SEQ ID NO 118
<211> LENGTH: 9
<212> TYPE: PRT
<213> ORGANISM: Homo sapiens

<400> SEQUENCE: 118

His Tyr Leu Ser His Val Pro Gly Leu
1               5

<210> SEQ ID NO 119
<211> LENGTH: 9
<212> TYPE: PRT
<213> ORGANISM: Homo sapiens

<400> SEQUENCE: 119

Tyr Val Pro Tyr Pro Thr Phe Asn Leu
1               5

<210> SEQ ID NO 120
<211> LENGTH: 9
<212> TYPE: PRT
<213> ORGANISM: Homo sapiens

<400> SEQUENCE: 120

Phe Asn Leu Pro Pro His Phe Ser Ala
1               5

<210> SEQ ID NO 121
<211> LENGTH: 9
<212> TYPE: PRT
```

<213> ORGANISM: Homo sapiens

<400> SEQUENCE: 121

Asn Leu Pro Pro His Phe Ser Ala Val
1               5

<210> SEQ ID NO 122
<211> LENGTH: 9
<212> TYPE: PRT
<213> ORGANISM: Homo sapiens

<400> SEQUENCE: 122

Ser Ala Val Gly Ser Asp Asn Asp Ile
1               5

<210> SEQ ID NO 123
<211> LENGTH: 9
<212> TYPE: PRT
<213> ORGANISM: Homo sapiens

<400> SEQUENCE: 123

Lys Asn Glu Gly Pro Leu Asn Val Val
1               5

<210> SEQ ID NO 124
<211> LENGTH: 9
<212> TYPE: PRT
<213> ORGANISM: Homo sapiens

<400> SEQUENCE: 124

Thr Lys Cys Val His Cys Gly Ile Val
1               5

<210> SEQ ID NO 125
<211> LENGTH: 9
<212> TYPE: PRT
<213> ORGANISM: Homo sapiens

<400> SEQUENCE: 125

Cys Val His Cys Gly Ile Val Phe Leu
1               5

<210> SEQ ID NO 126
<211> LENGTH: 9
<212> TYPE: PRT
<213> ORGANISM: Homo sapiens

<400> SEQUENCE: 126

Cys Gly Ile Val Phe Leu Asp Glu Val
1               5

<210> SEQ ID NO 127
<211> LENGTH: 9
<212> TYPE: PRT
<213> ORGANISM: Homo sapiens

<400> SEQUENCE: 127

Phe Leu Asp Glu Val Met Tyr Ala Leu
1               5

<210> SEQ ID NO 128
<211> LENGTH: 9
<212> TYPE: PRT
<213> ORGANISM: Homo sapiens

<400> SEQUENCE: 128

```
Val Met Tyr Ala Leu His Met Ser Cys
1               5

<210> SEQ ID NO 129
<211> LENGTH: 9
<212> TYPE: PRT
<213> ORGANISM: Homo sapiens

<400> SEQUENCE: 129

Phe Gln Cys Ser Ile Cys Gln His Leu
1               5

<210> SEQ ID NO 130
<211> LENGTH: 9
<212> TYPE: PRT
<213> ORGANISM: Homo sapiens

<400> SEQUENCE: 130

Gly Leu His Arg Asn Asn Ala Gln Val
1               5

<210> SEQ ID NO 131
<211> LENGTH: 9
<212> TYPE: PRT
<213> ORGANISM: Homo sapiens

<400> SEQUENCE: 131

Met Val Arg Lys Lys Asn Pro Pro Leu
1               5

<210> SEQ ID NO 132
<211> LENGTH: 9
<212> TYPE: PRT
<213> ORGANISM: Homo sapiens

<400> SEQUENCE: 132

Lys Lys Asn Pro Pro Leu Arg Asn Val
1               5

<210> SEQ ID NO 133
<211> LENGTH: 9
<212> TYPE: PRT
<213> ORGANISM: Homo sapiens

<400> SEQUENCE: 133

Val Ala Ser Glu Gly Glu Gly Gln Ile
1               5

<210> SEQ ID NO 134
<211> LENGTH: 9
<212> TYPE: PRT
<213> ORGANISM: Homo sapiens

<400> SEQUENCE: 134

Gln Ile Leu Glu Pro Ile Gly Thr Glu
1               5

<210> SEQ ID NO 135
<211> LENGTH: 9
<212> TYPE: PRT
<213> ORGANISM: Homo sapiens

<400> SEQUENCE: 135

Arg Asn Met Leu Ala Phe Ser Phe Pro
1               5
```

```
<210> SEQ ID NO 136
<211> LENGTH: 9
<212> TYPE: PRT
<213> ORGANISM: Homo sapiens

<400> SEQUENCE: 136

Asn Met Leu Ala Phe Ser Phe Pro Ala
1               5

<210> SEQ ID NO 137
<211> LENGTH: 9
<212> TYPE: PRT
<213> ORGANISM: Homo sapiens

<400> SEQUENCE: 137

Met Leu Ala Phe Ser Phe Pro Ala Ala
1               5

<210> SEQ ID NO 138
<211> LENGTH: 9
<212> TYPE: PRT
<213> ORGANISM: Homo sapiens

<400> SEQUENCE: 138

Phe Ser Phe Pro Ala Ala Gly Gly Val
1               5

<210> SEQ ID NO 139
<211> LENGTH: 9
<212> TYPE: PRT
<213> ORGANISM: Homo sapiens

<400> SEQUENCE: 139

Ala Ala Gly Gly Val Cys Glu Pro Leu
1               5

<210> SEQ ID NO 140
<211> LENGTH: 9
<212> TYPE: PRT
<213> ORGANISM: Homo sapiens

<400> SEQUENCE: 140

Ser Gly Gln Ala Asn Cys Gln Gly Leu
1               5

<210> SEQ ID NO 141
<211> LENGTH: 9
<212> TYPE: PRT
<213> ORGANISM: Homo sapiens

<400> SEQUENCE: 141

Gly Leu Ser Pro Val Ser Val Ala Ser
1               5

<210> SEQ ID NO 142
<211> LENGTH: 9
<212> TYPE: PRT
<213> ORGANISM: Homo sapiens

<400> SEQUENCE: 142

Gly Leu Ser Pro Val Ser Val Ala Ser
1               5

<210> SEQ ID NO 143
```

```
<211> LENGTH: 9
<212> TYPE: PRT
<213> ORGANISM: Homo sapiens

<400> SEQUENCE: 143

Ser Val Ala Ser Lys Asn Pro Gln Val
1               5

<210> SEQ ID NO 144
<211> LENGTH: 9
<212> TYPE: PRT
<213> ORGANISM: Homo sapiens

<400> SEQUENCE: 144

Arg Leu Asn Lys Ser Lys Thr Asp Leu
1               5

<210> SEQ ID NO 145
<211> LENGTH: 9
<212> TYPE: PRT
<213> ORGANISM: Homo sapiens

<400> SEQUENCE: 145

Asn Asp Asn Pro Asp Pro Ala Pro Leu
1               5

<210> SEQ ID NO 146
<211> LENGTH: 9
<212> TYPE: PRT
<213> ORGANISM: Homo sapiens

<400> SEQUENCE: 146

Asp Pro Ala Pro Leu Ser Pro Glu Leu
1               5

<210> SEQ ID NO 147
<211> LENGTH: 9
<212> TYPE: PRT
<213> ORGANISM: Homo sapiens

<400> SEQUENCE: 147

Glu Leu Gln Asp Phe Lys Cys Asn Ile
1               5

<210> SEQ ID NO 148
<211> LENGTH: 9
<212> TYPE: PRT
<213> ORGANISM: Homo sapiens

<400> SEQUENCE: 148

Gly Leu His Asn Arg Thr Arg Gln Asp
1               5

<210> SEQ ID NO 149
<211> LENGTH: 9
<212> TYPE: PRT
<213> ORGANISM: Homo sapiens

<400> SEQUENCE: 149

Glu Leu Asp Ser Lys Ile Leu Ala Leu
1               5

<210> SEQ ID NO 150
<211> LENGTH: 9
<212> TYPE: PRT
<213> ORGANISM: Homo sapiens
```

-continued

```
<400> SEQUENCE: 150

Lys Ile Leu Ala Leu His Asn Met Val
1               5

<210> SEQ ID NO 151
<211> LENGTH: 9
<212> TYPE: PRT
<213> ORGANISM: Homo sapiens

<400> SEQUENCE: 151

Ala Leu His Asn Met Val Gln Phe Ser
1               5

<210> SEQ ID NO 152
<211> LENGTH: 9
<212> TYPE: PRT
<213> ORGANISM: Homo sapiens

<400> SEQUENCE: 152

Val Asn Arg Ser Val Phe Ser Gly Val
1               5

<210> SEQ ID NO 153
<211> LENGTH: 9
<212> TYPE: PRT
<213> ORGANISM: Homo sapiens

<400> SEQUENCE: 153

Phe Ser Gly Val Leu Gln Asp Ile Asn
1               5

<210> SEQ ID NO 154
<211> LENGTH: 9
<212> TYPE: PRT
<213> ORGANISM: Homo sapiens

<400> SEQUENCE: 154

Asp Ile Asn Ser Ser Arg Pro Val Leu
1               5

<210> SEQ ID NO 155
<211> LENGTH: 9
<212> TYPE: PRT
<213> ORGANISM: Homo sapiens

<400> SEQUENCE: 155

Val Leu Leu Asn Gly Thr Tyr Asp Val
1               5

<210> SEQ ID NO 156
<211> LENGTH: 9
<212> TYPE: PRT
<213> ORGANISM: Homo sapiens

<400> SEQUENCE: 156

Phe Cys Asn Phe Thr Tyr Met Gly Asn
1               5

<210> SEQ ID NO 157
<211> LENGTH: 9
<212> TYPE: PRT
<213> ORGANISM: Homo sapiens

<400> SEQUENCE: 157
```

```
Tyr Met Gly Asn Ser Ser Thr Glu Leu
1               5
```

<210> SEQ ID NO 158
<211> LENGTH: 9
<212> TYPE: PRT
<213> ORGANISM: Homo sapiens

<400> SEQUENCE: 158

```
Phe Leu Gln Thr His Pro Asn Lys Ile
1               5
```

<210> SEQ ID NO 159
<211> LENGTH: 9
<212> TYPE: PRT
<213> ORGANISM: Homo sapiens

<400> SEQUENCE: 159

```
Lys Ala Ser Leu Pro Ser Ser Glu Val
1               5
```

<210> SEQ ID NO 160
<211> LENGTH: 9
<212> TYPE: PRT
<213> ORGANISM: Homo sapiens

<400> SEQUENCE: 160

```
Asp Leu Gly Lys Trp Gln Asp Lys Ile
1               5
```

<210> SEQ ID NO 161
<211> LENGTH: 9
<212> TYPE: PRT
<213> ORGANISM: Homo sapiens

<400> SEQUENCE: 161

```
Val Lys Ala Gly Asp Asp Thr Pro Val
1               5
```

<210> SEQ ID NO 162
<211> LENGTH: 9
<212> TYPE: PRT
<213> ORGANISM: Homo sapiens

<400> SEQUENCE: 162

```
Phe Ser Cys Glu Ser Ser Ser Ser Leu
1               5
```

<210> SEQ ID NO 163
<211> LENGTH: 10
<212> TYPE: PRT
<213> ORGANISM: Homo sapiens

<400> SEQUENCE: 163

```
Lys Leu Leu Leu Glu His Tyr Gly Lys Gln
1               5                   10
```

<210> SEQ ID NO 164
<211> LENGTH: 9
<212> TYPE: PRT
<213> ORGANISM: Homo sapiens

<400> SEQUENCE: 164

```
Gly Leu Asn Pro Glu Leu Asn Asp Lys
1               5
```

```
<210> SEQ ID NO 165
<211> LENGTH: 9
<212> TYPE: PRT
<213> ORGANISM: Homo sapiens

<400> SEQUENCE: 165

Gly Ser Val Ile Asn Gln Asn Asp Leu
1               5

<210> SEQ ID NO 166
<211> LENGTH: 9
<212> TYPE: PRT
<213> ORGANISM: Homo sapiens

<400> SEQUENCE: 166

Ser Val Ile Asn Gln Asn Asp Leu Ala
1               5

<210> SEQ ID NO 167
<211> LENGTH: 9
<212> TYPE: PRT
<213> ORGANISM: Homo sapiens

<400> SEQUENCE: 167

Phe Cys Asp Phe Arg Tyr Ser Lys Ser
1               5

<210> SEQ ID NO 168
<211> LENGTH: 9
<212> TYPE: PRT
<213> ORGANISM: Homo sapiens

<400> SEQUENCE: 168

Pro Leu Leu Arg His Tyr Gln Gln Leu
1               5

<210> SEQ ID NO 169
<211> LENGTH: 9
<212> TYPE: PRT
<213> ORGANISM: Homo sapiens

<400> SEQUENCE: 169

Gly Leu Cys Ser Pro Glu Lys His Leu
1               5

<210> SEQ ID NO 170
<211> LENGTH: 9
<212> TYPE: PRT
<213> ORGANISM: Homo sapiens

<400> SEQUENCE: 170

His Leu Gly Glu Ile Thr Tyr Pro Phe
1               5

<210> SEQ ID NO 171
<211> LENGTH: 9
<212> TYPE: PRT
<213> ORGANISM: Homo sapiens

<400> SEQUENCE: 171

Leu Gly Glu Ile Thr Tyr Pro Phe Ala
1               5

<210> SEQ ID NO 172
<211> LENGTH: 9
```

<212> TYPE: PRT
<213> ORGANISM: Homo sapiens

<400> SEQUENCE: 172

His Cys Ala Leu Leu Leu His Leu
1               5

<210> SEQ ID NO 173
<211> LENGTH: 9
<212> TYPE: PRT
<213> ORGANISM: Homo sapiens

<400> SEQUENCE: 173

Ala Leu Leu Leu Leu His Leu Ser Pro
1               5

<210> SEQ ID NO 174
<211> LENGTH: 9
<212> TYPE: PRT
<213> ORGANISM: Homo sapiens

<400> SEQUENCE: 174

Leu Leu Leu Leu His Leu Ser Pro Gly
1               5

<210> SEQ ID NO 175
<211> LENGTH: 9
<212> TYPE: PRT
<213> ORGANISM: Homo sapiens

<400> SEQUENCE: 175

Leu Leu Leu His Leu Ser Pro Gly Ala
1               5

<210> SEQ ID NO 176
<211> LENGTH: 9
<212> TYPE: PRT
<213> ORGANISM: Homo sapiens

<400> SEQUENCE: 176

Leu Leu His Leu Ser Pro Gly Ala Ala
1               5

<210> SEQ ID NO 177
<211> LENGTH: 9
<212> TYPE: PRT
<213> ORGANISM: Homo sapiens

<400> SEQUENCE: 177

Phe Thr Thr Pro Asp Val Asp Val Leu
1               5

<210> SEQ ID NO 178
<211> LENGTH: 9
<212> TYPE: PRT
<213> ORGANISM: Homo sapiens

<400> SEQUENCE: 178

Thr Thr Pro Asp Val Asp Val Leu Leu
1               5

<210> SEQ ID NO 179
<211> LENGTH: 9
<212> TYPE: PRT
<213> ORGANISM: Homo sapiens -continued

```
<400> SEQUENCE: 179

Val Leu Leu Phe His Tyr Glu Ser Val
1               5

<210> SEQ ID NO 180
<211> LENGTH: 9
<212> TYPE: PRT
<213> ORGANISM: Homo sapiens

<400> SEQUENCE: 180

Phe Ile Thr Gln Val Glu Glu Glu Ile
1               5

<210> SEQ ID NO 181
<211> LENGTH: 9
<212> TYPE: PRT
<213> ORGANISM: Homo sapiens

<400> SEQUENCE: 181

Phe Thr Ala Ala Asp Thr Gln Ser Leu
1               5

<210> SEQ ID NO 182
<211> LENGTH: 9
<212> TYPE: PRT
<213> ORGANISM: Homo sapiens

<400> SEQUENCE: 182

Ser Leu Leu Glu His Phe Asn Thr Val
1               5

<210> SEQ ID NO 183
<211> LENGTH: 39
<212> TYPE: DNA
<213> ORGANISM: Homo sapiens

<400> SEQUENCE: 183
cagtacggat ccaccatggc cgagctgcgc ctgaagggc                          39

<210> SEQ ID NO 184
<211> LENGTH: 38
<212> TYPE: DNA
<213> ORGANISM: Homo sapiens

<400> SEQUENCE: 184
ccacgaggat ccttaggaga atattcggat ggcttgcg                           38

<210> SEQ ID NO 185
<211> LENGTH: 20
<212> TYPE: DNA
<213> ORGANISM: Homo sapiens

<400> SEQUENCE: 185
taatacgact cactataggg                                               20

<210> SEQ ID NO 186
<211> LENGTH: 18
<212> TYPE: DNA
<213> ORGANISM: Homo sapiens

<400> SEQUENCE: 186
tagaaggcac agtcgagg                                                 18

<210> SEQ ID NO 187
```

-continued

```
<210> SEQ ID NO 187
<211> LENGTH: 23
<212> TYPE: DNA
<213> ORGANISM: Homo sapiens

<400> SEQUENCE: 187
gaaaacgact tcctggcggg gag                                              23

<210> SEQ ID NO 188
<211> LENGTH: 22
<212> TYPE: DNA
<213> ORGANISM: Homo sapiens

<400> SEQUENCE: 188
gctcacccag gcgtggggcc tc                                               22

<210> SEQ ID NO 189
<211> LENGTH: 9
<212> TYPE: PRT
<213> ORGANISM: Homo sapiens

<400> SEQUENCE: 189

Val Pro Val Pro Thr Ser Glu His Val
1               5

<210> SEQ ID NO 190
<211> LENGTH: 9
<212> TYPE: PRT
<213> ORGANISM: Homo sapiens

<400> SEQUENCE: 190

Pro Thr Ser Glu His Val Ala Glu Ile
1               5

<210> SEQ ID NO 191
<211> LENGTH: 9
<212> TYPE: PRT
<213> ORGANISM: Homo sapiens

<400> SEQUENCE: 191

Glu Ile Val Gly Arg Gln Cys Lys Ile
1               5

<210> SEQ ID NO 192
<211> LENGTH: 9
<212> TYPE: PRT
<213> ORGANISM: Homo sapiens

<400> SEQUENCE: 192

Lys Ile Lys Ala Leu Arg Ala Lys Thr
1               5

<210> SEQ ID NO 193
<211> LENGTH: 9
<212> TYPE: PRT
<213> ORGANISM: Homo sapiens

<400> SEQUENCE: 193

Lys Ala Leu Arg Ala Lys Thr Asn Thr
1               5

<210> SEQ ID NO 194
<211> LENGTH: 9
<212> TYPE: PRT
<213> ORGANISM: Homo sapiens

<400> SEQUENCE: 194
```

Ala Leu Arg Ala Lys Thr Asn Thr Tyr
1               5

<210> SEQ ID NO 195
<211> LENGTH: 9
<212> TYPE: PRT
<213> ORGANISM: Homo sapiens

<400> SEQUENCE: 195

Leu Arg Ala Lys Thr Asn Thr Tyr Ile
1               5

<210> SEQ ID NO 196
<211> LENGTH: 9
<212> TYPE: PRT
<213> ORGANISM: Homo sapiens

<400> SEQUENCE: 196

Thr Asn Thr Tyr Ile Lys Thr Pro Val
1               5

<210> SEQ ID NO 197
<211> LENGTH: 9
<212> TYPE: PRT
<213> ORGANISM: Homo sapiens

<400> SEQUENCE: 197

Tyr Ile Lys Thr Pro Val Arg Gly Glu
1               5

<210> SEQ ID NO 198
<211> LENGTH: 9
<212> TYPE: PRT
<213> ORGANISM: Homo sapiens

<400> SEQUENCE: 198

Thr Pro Val Arg Gly Glu Glu Pro Val
1               5

<210> SEQ ID NO 199
<211> LENGTH: 9
<212> TYPE: PRT
<213> ORGANISM: Homo sapiens

<400> SEQUENCE: 199

Arg Gly Glu Glu Pro Val Phe Met Val
1               5

<210> SEQ ID NO 200
<211> LENGTH: 9
<212> TYPE: PRT
<213> ORGANISM: Homo sapiens

<400> SEQUENCE: 200

Met Val Thr Gly Arg Arg Glu Asp Val
1               5

<210> SEQ ID NO 201
<211> LENGTH: 9
<212> TYPE: PRT
<213> ORGANISM: Homo sapiens

<400> SEQUENCE: 201

Val Thr Gly Arg Arg Glu Asp Val Ala
1               5

<210> SEQ ID NO 202
<211> LENGTH: 9
<212> TYPE: PRT
<213> ORGANISM: Homo sapiens

<400> SEQUENCE: 202

Gly Arg Arg Glu Asp Val Ala Thr Ala
1               5

<210> SEQ ID NO 203
<211> LENGTH: 9
<212> TYPE: PRT
<213> ORGANISM: Homo sapiens

<400> SEQUENCE: 203

Asp Val Ala Thr Ala Arg Arg Glu Ile
1               5

<210> SEQ ID NO 204
<211> LENGTH: 9
<212> TYPE: PRT
<213> ORGANISM: Homo sapiens

<400> SEQUENCE: 204

Val Ala Thr Ala Arg Arg Glu Ile Ile
1               5

<210> SEQ ID NO 205
<211> LENGTH: 9
<212> TYPE: PRT
<213> ORGANISM: Homo sapiens

<400> SEQUENCE: 205

Thr Ala Arg Arg Glu Ile Ile Ser Ala
1               5

<210> SEQ ID NO 206
<211> LENGTH: 9
<212> TYPE: PRT
<213> ORGANISM: Homo sapiens

<400> SEQUENCE: 206

Ala Arg Arg Glu Ile Ile Ser Ala Ala
1               5

<210> SEQ ID NO 207
<211> LENGTH: 9
<212> TYPE: PRT
<213> ORGANISM: Homo sapiens

<400> SEQUENCE: 207

Ile Ile Ser Ala Ala Glu His Phe Ser
1               5

<210> SEQ ID NO 208
<211> LENGTH: 9
<212> TYPE: PRT
<213> ORGANISM: Homo sapiens

<400> SEQUENCE: 208

Ile Ser Ala Ala Glu His Phe Ser Met
1               5

<210> SEQ ID NO 209

```
<211> LENGTH: 9
<212> TYPE: PRT
<213> ORGANISM: Homo sapiens

<400> SEQUENCE: 209

Ser Ala Ala Glu His Phe Ser Met Ile
1               5

<210> SEQ ID NO 210
<211> LENGTH: 9
<212> TYPE: PRT
<213> ORGANISM: Homo sapiens

<400> SEQUENCE: 210

Ala Glu His Phe Ser Met Ile Arg Ala
1               5

<210> SEQ ID NO 211
<211> LENGTH: 9
<212> TYPE: PRT
<213> ORGANISM: Homo sapiens

<400> SEQUENCE: 211

Ser Met Ile Arg Ala Ser Arg Asn Lys
1               5

<210> SEQ ID NO 212
<211> LENGTH: 9
<212> TYPE: PRT
<213> ORGANISM: Homo sapiens

<400> SEQUENCE: 212

Arg Ala Ser Arg Asn Lys Ser Gly Ala
1               5

<210> SEQ ID NO 213
<211> LENGTH: 9
<212> TYPE: PRT
<213> ORGANISM: Homo sapiens

<400> SEQUENCE: 213

Asn Lys Ser Gly Ala Ala Phe Gly Val
1               5

<210> SEQ ID NO 214
<211> LENGTH: 9
<212> TYPE: PRT
<213> ORGANISM: Homo sapiens

<400> SEQUENCE: 214

Gly Ala Ala Phe Gly Val Ala Pro Ala
1               5

<210> SEQ ID NO 215
<211> LENGTH: 9
<212> TYPE: PRT
<213> ORGANISM: Homo sapiens

<400> SEQUENCE: 215

Ala Ala Phe Gly Val Ala Pro Ala Leu
1               5

<210> SEQ ID NO 216
<211> LENGTH: 9
<212> TYPE: PRT
<213> ORGANISM: Homo sapiens
```

<400> SEQUENCE: 216

Gly Val Ala Pro Ala Leu Pro Gly Gln
1               5

<210> SEQ ID NO 217
<211> LENGTH: 9
<212> TYPE: PRT
<213> ORGANISM: Homo sapiens

<400> SEQUENCE: 217

Val Ala Pro Ala Leu Pro Gly Gln Val
1               5

<210> SEQ ID NO 218
<211> LENGTH: 9
<212> TYPE: PRT
<213> ORGANISM: Homo sapiens

<400> SEQUENCE: 218

Pro Ala Leu Pro Gly Gln Val Thr Ile
1               5

<210> SEQ ID NO 219
<211> LENGTH: 9
<212> TYPE: PRT
<213> ORGANISM: Homo sapiens

<400> SEQUENCE: 219

Ala Leu Pro Gly Gln Val Thr Ile Arg
1               5

<210> SEQ ID NO 220
<211> LENGTH: 9
<212> TYPE: PRT
<213> ORGANISM: Homo sapiens

<400> SEQUENCE: 220

Leu Pro Gly Gln Val Thr Ile Arg Val
1               5

<210> SEQ ID NO 221
<211> LENGTH: 9
<212> TYPE: PRT
<213> ORGANISM: Homo sapiens

<400> SEQUENCE: 221

Gly Gln Val Thr Ile Arg Val Arg Val
1               5

<210> SEQ ID NO 222
<211> LENGTH: 9
<212> TYPE: PRT
<213> ORGANISM: Homo sapiens

<400> SEQUENCE: 222

Arg Val Arg Val Pro Tyr Arg Val Val
1               5

<210> SEQ ID NO 223
<211> LENGTH: 9
<212> TYPE: PRT
<213> ORGANISM: Homo sapiens

<400> SEQUENCE: 223

```
Arg Val Pro Tyr Arg Val Val Gly Leu
1               5

<210> SEQ ID NO 224
<211> LENGTH: 9
<212> TYPE: PRT
<213> ORGANISM: Homo sapiens

<400> SEQUENCE: 224

Val Pro Tyr Arg Val Val Gly Leu Val
1               5

<210> SEQ ID NO 225
<211> LENGTH: 9
<212> TYPE: PRT
<213> ORGANISM: Homo sapiens

<400> SEQUENCE: 225

Arg Val Val Gly Leu Val Val Gly Pro
1               5

<210> SEQ ID NO 226
<211> LENGTH: 9
<212> TYPE: PRT
<213> ORGANISM: Homo sapiens

<400> SEQUENCE: 226

Gly Leu Val Val Gly Pro Lys Gly Ala
1               5

<210> SEQ ID NO 227
<211> LENGTH: 9
<212> TYPE: PRT
<213> ORGANISM: Homo sapiens

<400> SEQUENCE: 227

Leu Val Val Gly Pro Lys Gly Ala Thr
1               5

<210> SEQ ID NO 228
<211> LENGTH: 9
<212> TYPE: PRT
<213> ORGANISM: Homo sapiens

<400> SEQUENCE: 228

Val Val Gly Pro Lys Gly Ala Thr Ile
1               5

<210> SEQ ID NO 229
<211> LENGTH: 9
<212> TYPE: PRT
<213> ORGANISM: Homo sapiens

<400> SEQUENCE: 229

Arg Ile Gln Gln Gln Thr Asn Thr Tyr
1               5

<210> SEQ ID NO 230
<211> LENGTH: 9
<212> TYPE: PRT
<213> ORGANISM: Homo sapiens

<400> SEQUENCE: 230

Ile Gln Gln Gln Thr Asn Thr Tyr Ile
1               5
```

```
<210> SEQ ID NO 231
<211> LENGTH: 9
<212> TYPE: PRT
<213> ORGANISM: Homo sapiens

<400> SEQUENCE: 231

Gln Gln Gln Thr Asn Thr Tyr Ile Ile
1               5

<210> SEQ ID NO 232
<211> LENGTH: 9
<212> TYPE: PRT
<213> ORGANISM: Homo sapiens

<400> SEQUENCE: 232

Gln Gln Thr Asn Thr Tyr Ile Ile Thr
1               5

<210> SEQ ID NO 233
<211> LENGTH: 9
<212> TYPE: PRT
<213> ORGANISM: Homo sapiens

<400> SEQUENCE: 233

Tyr Ile Ile Thr Pro Ser Arg Asp Arg
1               5

<210> SEQ ID NO 234
<211> LENGTH: 9
<212> TYPE: PRT
<213> ORGANISM: Homo sapiens

<400> SEQUENCE: 234

Thr Pro Ser Arg Asp Arg Asp Pro Val
1               5

<210> SEQ ID NO 235
<211> LENGTH: 9
<212> TYPE: PRT
<213> ORGANISM: Homo sapiens

<400> SEQUENCE: 235

Arg Asp Arg Asp Pro Val Phe Glu Ile
1               5

<210> SEQ ID NO 236
<211> LENGTH: 9
<212> TYPE: PRT
<213> ORGANISM: Homo sapiens

<400> SEQUENCE: 236

Glu Ile Thr Gly Ala Pro Gly Asn Val
1               5

<210> SEQ ID NO 237
<211> LENGTH: 9
<212> TYPE: PRT
<213> ORGANISM: Homo sapiens

<400> SEQUENCE: 237

Gly Ala Pro Gly Asn Val Glu Arg Ala
1               5

<210> SEQ ID NO 238
<211> LENGTH: 9
```

```
<212> TYPE: PRT
<213> ORGANISM: Homo sapiens

<400> SEQUENCE: 238

Asn Val Glu Arg Ala Arg Glu Glu Ile
1               5

<210> SEQ ID NO 239
<211> LENGTH: 9
<212> TYPE: PRT
<213> ORGANISM: Homo sapiens

<400> SEQUENCE: 239

Glu Glu Ile Glu Thr His Ile Ala Val
1               5

<210> SEQ ID NO 240
<211> LENGTH: 9
<212> TYPE: PRT
<213> ORGANISM: Homo sapiens

<400> SEQUENCE: 240

Ile Glu Thr His Ile Ala Val Arg Thr
1               5

<210> SEQ ID NO 241
<211> LENGTH: 9
<212> TYPE: PRT
<213> ORGANISM: Homo sapiens

<400> SEQUENCE: 241

His Ile Ala Val Arg Thr Gly Lys Ile
1               5

<210> SEQ ID NO 242
<211> LENGTH: 9
<212> TYPE: PRT
<213> ORGANISM: Homo sapiens

<400> SEQUENCE: 242

Ile Ala Val Arg Thr Gly Lys Ile Leu
1               5

<210> SEQ ID NO 243
<211> LENGTH: 9
<212> TYPE: PRT
<213> ORGANISM: Homo sapiens

<400> SEQUENCE: 243

Lys Ile Leu Glu Tyr Asn Asn Glu Asn
1               5

<210> SEQ ID NO 244
<211> LENGTH: 9
<212> TYPE: PRT
<213> ORGANISM: Homo sapiens

<400> SEQUENCE: 244

Tyr Asn Asn Glu Asn Asp Phe Leu Ala
1               5

<210> SEQ ID NO 245
<211> LENGTH: 9
<212> TYPE: PRT
<213> ORGANISM: Homo sapiens
```

```
<400> SEQUENCE: 245

Asn Glu Asn Asp Phe Leu Ala Gly Ser
1               5

<210> SEQ ID NO 246
<211> LENGTH: 9
<212> TYPE: PRT
<213> ORGANISM: Homo sapiens

<400> SEQUENCE: 246

Phe Leu Ala Gly Ser Pro Asp Ala Ala
1               5

<210> SEQ ID NO 247
<211> LENGTH: 9
<212> TYPE: PRT
<213> ORGANISM: Homo sapiens

<400> SEQUENCE: 247

Leu Ala Gly Ser Pro Asp Ala Ala Ile
1               5

<210> SEQ ID NO 248
<211> LENGTH: 9
<212> TYPE: PRT
<213> ORGANISM: Homo sapiens

<400> SEQUENCE: 248

Ala Ile Asp Ser Arg Tyr Ser Asp Ala
1               5

<210> SEQ ID NO 249
<211> LENGTH: 9
<212> TYPE: PRT
<213> ORGANISM: Homo sapiens

<400> SEQUENCE: 249

Ser Arg Tyr Ser Asp Ala Trp Arg Val
1               5

<210> SEQ ID NO 250
<211> LENGTH: 9
<212> TYPE: PRT
<213> ORGANISM: Homo sapiens

<400> SEQUENCE: 250

Val His Gln Pro Gly Cys Lys Pro Leu
1               5

<210> SEQ ID NO 251
<211> LENGTH: 9
<212> TYPE: PRT
<213> ORGANISM: Homo sapiens

<400> SEQUENCE: 251

Leu Ser Thr Phe Arg Gln Asn Ser Leu
1               5

<210> SEQ ID NO 252
<211> LENGTH: 9
<212> TYPE: PRT
<213> ORGANISM: Homo sapiens

<400> SEQUENCE: 252

Leu Gly Cys Ile Gly Glu Cys Gly Val
```

1               5

<210> SEQ ID NO 253
<211> LENGTH: 9
<212> TYPE: PRT
<213> ORGANISM: Homo sapiens

<400> SEQUENCE: 253

Cys Gly Val Asp Ser Gly Phe Glu Ala
1               5

<210> SEQ ID NO 254
<211> LENGTH: 9
<212> TYPE: PRT
<213> ORGANISM: Homo sapiens

<400> SEQUENCE: 254

Gly Phe Glu Ala Pro Arg Leu Asp Val
1               5

<210> SEQ ID NO 255
<211> LENGTH: 9
<212> TYPE: PRT
<213> ORGANISM: Homo sapiens

<400> SEQUENCE: 255

Arg Leu Asp Val Tyr Tyr Gly Val Ala
1               5

<210> SEQ ID NO 256
<211> LENGTH: 9
<212> TYPE: PRT
<213> ORGANISM: Homo sapiens

<400> SEQUENCE: 256

Asp Val Tyr Tyr Gly Val Ala Glu Thr
1               5

<210> SEQ ID NO 257
<211> LENGTH: 9
<212> TYPE: PRT
<213> ORGANISM: Homo sapiens

<400> SEQUENCE: 257

Gly Val Ala Glu Thr Ser Pro Pro Leu
1               5

<210> SEQ ID NO 258
<211> LENGTH: 9
<212> TYPE: PRT
<213> ORGANISM: Homo sapiens

<400> SEQUENCE: 258

Ala Glu Thr Ser Pro Pro Leu Trp Ala
1               5

<210> SEQ ID NO 259
<211> LENGTH: 9
<212> TYPE: PRT
<213> ORGANISM: Homo sapiens

<400> SEQUENCE: 259

Pro Leu Trp Ala Gly Gln Glu Asn Ala
1               5

```
<210> SEQ ID NO 260
<211> LENGTH: 9
<212> TYPE: PRT
<213> ORGANISM: Homo sapiens

<400> SEQUENCE: 260

Gln Gly Gln Glu Asn Ala Thr Pro Thr
1               5

<210> SEQ ID NO 261
<211> LENGTH: 9
<212> TYPE: PRT
<213> ORGANISM: Homo sapiens

<400> SEQUENCE: 261

Gln Glu Asn Ala Thr Pro Thr Ser Val
1               5

<210> SEQ ID NO 262
<211> LENGTH: 9
<212> TYPE: PRT
<213> ORGANISM: Homo sapiens

<400> SEQUENCE: 262

Val Leu Phe Ser Ser Ala Ser Ser Ser
1               5

<210> SEQ ID NO 263
<211> LENGTH: 9
<212> TYPE: PRT
<213> ORGANISM: Homo sapiens

<400> SEQUENCE: 263

Lys Ala Arg Ala Gly Pro Pro Gly Ala
1               5

<210> SEQ ID NO 264
<211> LENGTH: 9
<212> TYPE: PRT
<213> ORGANISM: Homo sapiens

<400> SEQUENCE: 264

Pro Ala Thr Ser Ala Gly Pro Glu Leu
1               5

<210> SEQ ID NO 265
<211> LENGTH: 9
<212> TYPE: PRT
<213> ORGANISM: Homo sapiens

<400> SEQUENCE: 265

Ala Thr Ser Ala Gly Pro Glu Leu Ala
1               5

<210> SEQ ID NO 266
<211> LENGTH: 9
<212> TYPE: PRT
<213> ORGANISM: Homo sapiens

<400> SEQUENCE: 266

Ser Ala Gly Pro Glu Leu Ala Gly Leu
1               5

<210> SEQ ID NO 267
<211> LENGTH: 9
<212> TYPE: PRT
```

<213> ORGANISM: Homo sapiens

<400> SEQUENCE: 267

Gly Leu Pro Arg Arg Pro Gly Glu
1               5

<210> SEQ ID NO 268
<211> LENGTH: 9
<212> TYPE: PRT
<213> ORGANISM: Homo sapiens

<400> SEQUENCE: 268

Glu Pro Leu Gln Phe Gly Ser Lys Leu
1               5

<210> SEQ ID NO 269
<211> LENGTH: 9
<212> TYPE: PRT
<213> ORGANISM: Homo sapiens

<400> SEQUENCE: 269

Phe Ser Lys Leu Gly Gly Gly Gly Leu
1               5

<210> SEQ ID NO 270
<211> LENGTH: 9
<212> TYPE: PRT
<213> ORGANISM: Homo sapiens

<400> SEQUENCE: 270

Lys Leu Gly Gly Gly Gly Leu Arg Ser
1               5

<210> SEQ ID NO 271
<211> LENGTH: 9
<212> TYPE: PRT
<213> ORGANISM: Homo sapiens

<400> SEQUENCE: 271

Gly Leu Arg Ser Pro Gly Gly Gly Arg
1               5

<210> SEQ ID NO 272
<211> LENGTH: 9
<212> TYPE: PRT
<213> ORGANISM: Homo sapiens

<400> SEQUENCE: 272

Cys Met Val Cys Phe Glu Ser Glu Val
1               5

<210> SEQ ID NO 273
<211> LENGTH: 9
<212> TYPE: PRT
<213> ORGANISM: Homo sapiens

<400> SEQUENCE: 273

Met Val Cys Phe Glu Ser Glu Val Thr
1               5

<210> SEQ ID NO 274
<211> LENGTH: 9
<212> TYPE: PRT
<213> ORGANISM: Homo sapiens

<400> SEQUENCE: 274

Val Cys Phe Glu Ser Glu Val Thr Ala
1               5

<210> SEQ ID NO 275
<211> LENGTH: 9
<212> TYPE: PRT
<213> ORGANISM: Homo sapiens

<400> SEQUENCE: 275

Phe Glu Ser Glu Val Thr Ala Ala Leu
1               5

<210> SEQ ID NO 276
<211> LENGTH: 9
<212> TYPE: PRT
<213> ORGANISM: Homo sapiens

<400> SEQUENCE: 276

Glu Val Thr Ala Ala Leu Val Pro Cys
1               5

<210> SEQ ID NO 277
<211> LENGTH: 9
<212> TYPE: PRT
<213> ORGANISM: Homo sapiens

<400> SEQUENCE: 277

Val Thr Ala Ala Leu Val Pro Cys Gly
1               5

<210> SEQ ID NO 278
<211> LENGTH: 9
<212> TYPE: PRT
<213> ORGANISM: Homo sapiens

<400> SEQUENCE: 278

Ala Leu Val Pro Cys Gly His Asn Leu
1               5

<210> SEQ ID NO 279
<211> LENGTH: 9
<212> TYPE: PRT
<213> ORGANISM: Homo sapiens

<400> SEQUENCE: 279

Leu Val Pro Cys Gly His Asn Leu Phe
1               5

<210> SEQ ID NO 280
<211> LENGTH: 9
<212> TYPE: PRT
<213> ORGANISM: Homo sapiens

<400> SEQUENCE: 280

Val Pro Cys Gly His Asn Leu Phe Cys
1               5

<210> SEQ ID NO 281
<211> LENGTH: 9
<212> TYPE: PRT
<213> ORGANISM: Homo sapiens

<400> SEQUENCE: 281

Asn Leu Phe Cys Met Glu Cys Ala Val
1               5

-continued

<210> SEQ ID NO 282
<211> LENGTH: 9
<212> TYPE: PRT
<213> ORGANISM: Homo sapiens

<400> SEQUENCE: 282

Phe Cys Met Glu Cys Ala Val Arg Ile
1               5

<210> SEQ ID NO 283
<211> LENGTH: 9
<212> TYPE: PRT
<213> ORGANISM: Homo sapiens

<400> SEQUENCE: 283

Cys Ala Val Arg Ile Cys Glu Arg Thr
1               5

<210> SEQ ID NO 284
<211> LENGTH: 9
<212> TYPE: PRT
<213> ORGANISM: Homo sapiens

<400> SEQUENCE: 284

Arg Ile Cys Glu Arg Thr Asp Pro Glu
1               5

<210> SEQ ID NO 285
<211> LENGTH: 9
<212> TYPE: PRT
<213> ORGANISM: Homo sapiens

<400> SEQUENCE: 285

Arg Thr Asp Pro Glu Cys Pro Val Cys
1               5

<210> SEQ ID NO 286
<211> LENGTH: 9
<212> TYPE: PRT
<213> ORGANISM: Homo sapiens

<400> SEQUENCE: 286

Cys Pro Val Cys His Ile Thr Ala Thr
1               5

<210> SEQ ID NO 287
<211> LENGTH: 9
<212> TYPE: PRT
<213> ORGANISM: Homo sapiens

<400> SEQUENCE: 287

Val Cys His Ile Thr Ala Thr Gln Ala
1               5

<210> SEQ ID NO 288
<211> LENGTH: 9
<212> TYPE: PRT
<213> ORGANISM: Homo sapiens

<400> SEQUENCE: 288

Ile Thr Ala Thr Gln Ala Ile Arg Ile
1               5

<210> SEQ ID NO 289

```
<211> LENGTH: 9
<212> TYPE: PRT
<213> ORGANISM: Homo sapiens

<400> SEQUENCE: 289

Leu Met Asp Met Gln Thr Phe Lys Ala
1               5

<210> SEQ ID NO 290
<211> LENGTH: 9
<212> TYPE: PRT
<213> ORGANISM: Homo sapiens

<400> SEQUENCE: 290

Lys Val Ser Ile Pro Thr Lys Ala Leu
1               5

<210> SEQ ID NO 291
<211> LENGTH: 9
<212> TYPE: PRT
<213> ORGANISM: Homo sapiens

<400> SEQUENCE: 291

Ser Ile Pro Thr Lys Ala Leu Glu Leu
1               5

<210> SEQ ID NO 292
<211> LENGTH: 9
<212> TYPE: PRT
<213> ORGANISM: Homo sapiens

<400> SEQUENCE: 292

Leu Glu Leu Lys Asn Glu Gln Thr Leu
1               5

<210> SEQ ID NO 293
<211> LENGTH: 9
<212> TYPE: PRT
<213> ORGANISM: Homo sapiens

<400> SEQUENCE: 293

Thr Val Ser Gln Lys Asp Val Cys Leu
1               5

<210> SEQ ID NO 294
<211> LENGTH: 9
<212> TYPE: PRT
<213> ORGANISM: Homo sapiens

<400> SEQUENCE: 294

Ser Val Pro Asn Lys Ala Leu Glu Leu
1               5

<210> SEQ ID NO 295
<211> LENGTH: 9
<212> TYPE: PRT
<213> ORGANISM: Homo sapiens

<400> SEQUENCE: 295

Cys Glu Thr Val Ser Gln Lys Asp Val
1               5

<210> SEQ ID NO 296
<211> LENGTH: 9
<212> TYPE: PRT
<213> ORGANISM: Homo sapiens
```

```
<400> SEQUENCE: 296

Lys Ile Asn Gly Lys Leu Glu Glu Ser
1               5

<210> SEQ ID NO 297
<211> LENGTH: 9
<212> TYPE: PRT
<213> ORGANISM: Homo sapiens

<400> SEQUENCE: 297

Ser Leu Val Glu Lys Thr Pro Asp Glu
1               5

<210> SEQ ID NO 298
<211> LENGTH: 9
<212> TYPE: PRT
<213> ORGANISM: Homo sapiens

<400> SEQUENCE: 298

Ser Leu Cys Glu Thr Val Ser Gln Lys
1               5

<210> SEQ ID NO 299
<211> LENGTH: 9
<212> TYPE: PRT
<213> ORGANISM: Homo sapiens

<400> SEQUENCE: 299

Glu Ile Asp Lys Ile Asn Gly Lys Leu
1               5

<210> SEQ ID NO 300
<211> LENGTH: 9
<212> TYPE: PRT
<213> ORGANISM: Homo sapiens

<400> SEQUENCE: 300

Met Leu Leu Gln Gln Asn Val Asp Val
1               5

<210> SEQ ID NO 301
<211> LENGTH: 9
<212> TYPE: PRT
<213> ORGANISM: Homo sapiens

<400> SEQUENCE: 301

Asn Met Trp Leu Gln Gln Gln Leu Val
1               5

<210> SEQ ID NO 302
<211> LENGTH: 9
<212> TYPE: PRT
<213> ORGANISM: Homo sapiens

<400> SEQUENCE: 302

Phe Leu Val Asp Arg Lys Cys Gln Leu
1               5

<210> SEQ ID NO 303
<211> LENGTH: 9
<212> TYPE: PRT
<213> ORGANISM: Homo sapiens

<400> SEQUENCE: 303
```

```
Tyr Leu Leu His Glu Asn Cys Met Leu
1               5

<210> SEQ ID NO 304
<211> LENGTH: 9
<212> TYPE: PRT
<213> ORGANISM: Homo sapiens

<400> SEQUENCE: 304

Ser Leu Phe Glu Ser Ser Ala Lys Ile
1               5

<210> SEQ ID NO 305
<211> LENGTH: 9
<212> TYPE: PRT
<213> ORGANISM: Homo sapiens

<400> SEQUENCE: 305

Lys Ile Thr Ile Asp Ile His Phe Leu
1               5

<210> SEQ ID NO 306
<211> LENGTH: 9
<212> TYPE: PRT
<213> ORGANISM: Homo sapiens

<400> SEQUENCE: 306

Gln Leu Gln Ser Lys Asn Met Trp Leu
1               5

<210> SEQ ID NO 307
<211> LENGTH: 9
<212> TYPE: PRT
<213> ORGANISM: Homo sapiens

<400> SEQUENCE: 307

Ser Leu Asp Gln Lys Leu Phe Gln Leu
1               5

<210> SEQ ID NO 308
<211> LENGTH: 9
<212> TYPE: PRT
<213> ORGANISM: Homo sapiens

<400> SEQUENCE: 308

Phe Leu Leu Ile Lys Asn Ala Asn Ala
1               5

<210> SEQ ID NO 309
<211> LENGTH: 9
<212> TYPE: PRT
<213> ORGANISM: Homo sapiens

<400> SEQUENCE: 309

Lys Ile Leu Asp Thr Val His Ser Cys
1               5

<210> SEQ ID NO 310
<211> LENGTH: 9
<212> TYPE: PRT
<213> ORGANISM: Homo sapiens

<400> SEQUENCE: 310

Ser Leu Ser Lys Ile Leu Asp Thr Val
1               5
```

```
<210> SEQ ID NO 311
<211> LENGTH: 9
<212> TYPE: PRT
<213> ORGANISM: Homo sapiens

<400> SEQUENCE: 311

Ile Leu Ile Asp Ser Gly Ala Asp Ile
1               5

<210> SEQ ID NO 312
<211> LENGTH: 9
<212> TYPE: PRT
<213> ORGANISM: Homo sapiens

<400> SEQUENCE: 312

Lys Val Met Glu Ile Asn Arg Glu Val
1               5

<210> SEQ ID NO 313
<211> LENGTH: 9
<212> TYPE: PRT
<213> ORGANISM: Homo sapiens

<400> SEQUENCE: 313

Lys Leu Leu Ser His Gly Ala Val Ile
1               5

<210> SEQ ID NO 314
<211> LENGTH: 9
<212> TYPE: PRT
<213> ORGANISM: Homo sapiens

<400> SEQUENCE: 314

Ala Val Tyr Ser Glu Ile Leu Ser Val
1               5

<210> SEQ ID NO 315
<211> LENGTH: 9
<212> TYPE: PRT
<213> ORGANISM: Homo sapiens

<400> SEQUENCE: 315

Lys Met Asn Val Asp Val Ser Ser Thr
1               5

<210> SEQ ID NO 316
<211> LENGTH: 9
<212> TYPE: PRT
<213> ORGANISM: Homo sapiens

<400> SEQUENCE: 316

Ile Leu Ser Val Val Ala Lys Leu Leu
1               5

<210> SEQ ID NO 317
<211> LENGTH: 9
<212> TYPE: PRT
<213> ORGANISM: Homo sapiens

<400> SEQUENCE: 317

Val Leu Ile Ala Glu Asn Thr Met Leu
1               5

<210> SEQ ID NO 318
<211> LENGTH: 9
```

```
<212> TYPE: PRT
<213> ORGANISM: Homo sapiens

<400> SEQUENCE: 318

Lys Leu Ser Lys Asn His Gln Asn Thr
1               5

<210> SEQ ID NO 319
<211> LENGTH: 9
<212> TYPE: PRT
<213> ORGANISM: Homo sapiens

<400> SEQUENCE: 319

Ser Leu Thr Pro Leu Leu Leu Ser Ile
1               5

<210> SEQ ID NO 320
<211> LENGTH: 9
<212> TYPE: PRT
<213> ORGANISM: Homo sapiens

<400> SEQUENCE: 320

Ser Gln Tyr Ser Gly Gln Leu Lys Val
1               5

<210> SEQ ID NO 321
<211> LENGTH: 9
<212> TYPE: PRT
<213> ORGANISM: Homo sapiens

<400> SEQUENCE: 321

Lys Glu Leu Glu Val Lys Gln Gln Leu
1               5

<210> SEQ ID NO 322
<211> LENGTH: 9
<212> TYPE: PRT
<213> ORGANISM: Homo sapiens

<400> SEQUENCE: 322

Gln Ile Met Glu Tyr Ile Arg Lys Leu
1               5

<210> SEQ ID NO 323
<211> LENGTH: 9
<212> TYPE: PRT
<213> ORGANISM: Homo sapiens

<400> SEQUENCE: 323

Ala Met Leu Lys Leu Glu Ile Ala Thr
1               5

<210> SEQ ID NO 324
<211> LENGTH: 9
<212> TYPE: PRT
<213> ORGANISM: Homo sapiens

<400> SEQUENCE: 324

Val Leu His Gln Pro Leu Ser Glu Ala
1               5

<210> SEQ ID NO 325
<211> LENGTH: 9
<212> TYPE: PRT
<213> ORGANISM: Homo sapiens
```

```
<400> SEQUENCE: 325

Gly Leu Leu Lys Ala Thr Cys Gly Met
1               5

<210> SEQ ID NO 326
<211> LENGTH: 9
<212> TYPE: PRT
<213> ORGANISM: Homo sapiens

<400> SEQUENCE: 326

Gly Leu Leu Lys Ala Asn Cys Gly Met
1               5

<210> SEQ ID NO 327
<211> LENGTH: 9
<212> TYPE: PRT
<213> ORGANISM: Homo sapiens

<400> SEQUENCE: 327

Gln Gln Leu Glu Gln Ala Leu Arg Ile
1               5

<210> SEQ ID NO 328
<211> LENGTH: 9
<212> TYPE: PRT
<213> ORGANISM: Homo sapiens

<400> SEQUENCE: 328

Cys Met Leu Lys Lys Glu Ile Ala Met
1               5

<210> SEQ ID NO 329
<211> LENGTH: 9
<212> TYPE: PRT
<213> ORGANISM: Homo sapiens

<400> SEQUENCE: 329

Glu Gln Met Lys Lys Lys Phe Cys Val
1               5

<210> SEQ ID NO 330
<211> LENGTH: 9
<212> TYPE: PRT
<213> ORGANISM: Homo sapiens

<400> SEQUENCE: 330

Ile Gln Lys Ile Glu Leu Lys Ser Val
1               5

<210> SEQ ID NO 331
<211> LENGTH: 9
<212> TYPE: PRT
<213> ORGANISM: Homo sapiens

<400> SEQUENCE: 331

Ser Val Pro Asn Lys Ala Phe Glu Leu
1               5

<210> SEQ ID NO 332
<211> LENGTH: 9
<212> TYPE: PRT
<213> ORGANISM: Homo sapiens

<400> SEQUENCE: 332

Ser Ile Tyr Gln Lys Val Met Glu Ile
```

```
<210> SEQ ID NO 333
<211> LENGTH: 9
<212> TYPE: PRT
<213> ORGANISM: Homo sapiens

<400> SEQUENCE: 333

Asn Leu Asn Tyr Gln Gly Asp Ala Leu
1               5

<210> SEQ ID NO 334
<211> LENGTH: 9
<212> TYPE: PRT
<213> ORGANISM: Homo sapiens

<400> SEQUENCE: 334

Ala Val Gln Asp His Asp Gln Ile Val
1               5

<210> SEQ ID NO 335
<211> LENGTH: 9
<212> TYPE: PRT
<213> ORGANISM: Homo sapiens

<400> SEQUENCE: 335

Leu Ile Ala Glu Asn Thr Met Leu Thr
1               5

<210> SEQ ID NO 336
<211> LENGTH: 9
<212> TYPE: PRT
<213> ORGANISM: Homo sapiens

<400> SEQUENCE: 336

Phe Glu Leu Lys Asn Glu Gln Thr Leu
1               5

<210> SEQ ID NO 337
<211> LENGTH: 9
<212> TYPE: PRT
<213> ORGANISM: Homo sapiens

<400> SEQUENCE: 337

Phe Glu Ser Ser Ala Lys Ile Gln Val
1               5

<210> SEQ ID NO 338
<211> LENGTH: 9
<212> TYPE: PRT
<213> ORGANISM: Homo sapiens

<400> SEQUENCE: 338

Gly Val Thr Ala Glu His Tyr Ala Val
1               5

<210> SEQ ID NO 339
<211> LENGTH: 9
<212> TYPE: PRT
<213> ORGANISM: Homo sapiens

<400> SEQUENCE: 339

Arg Val Thr Ser Asn Lys Thr Lys Val
1               5
```

```
<210> SEQ ID NO 340
<211> LENGTH: 9
<212> TYPE: PRT
<213> ORGANISM: Homo sapiens

<400> SEQUENCE: 340

Thr Val Ser Gln Lys Asp Val Cys Val
1               5

<210> SEQ ID NO 341
<211> LENGTH: 9
<212> TYPE: PRT
<213> ORGANISM: Homo sapiens

<400> SEQUENCE: 341

Lys Ser Gln Glu Pro Ala Phe His Ile
1               5

<210> SEQ ID NO 342
<211> LENGTH: 9
<212> TYPE: PRT
<213> ORGANISM: Homo sapiens

<400> SEQUENCE: 342

Lys Asn Leu Ile Ala Glu Asn Thr Met
1               5

<210> SEQ ID NO 343
<211> LENGTH: 9
<212> TYPE: PRT
<213> ORGANISM: Homo sapiens

<400> SEQUENCE: 343

Met Leu Lys Leu Glu Ile Ala Thr Leu
1               5

<210> SEQ ID NO 344
<211> LENGTH: 9
<212> TYPE: PRT
<213> ORGANISM: Homo sapiens

<400> SEQUENCE: 344

Glu Ile Leu Ser Val Val Ala Lys Leu
1               5

<210> SEQ ID NO 345
<211> LENGTH: 9
<212> TYPE: PRT
<213> ORGANISM: Homo sapiens

<400> SEQUENCE: 345

Met Leu Lys Lys Glu Ile Ala Met Leu
1               5

<210> SEQ ID NO 346
<211> LENGTH: 9
<212> TYPE: PRT
<213> ORGANISM: Homo sapiens

<400> SEQUENCE: 346

Leu Leu Lys Glu Lys Asn Glu Glu Ile
1               5

<210> SEQ ID NO 347
<211> LENGTH: 9
<212> TYPE: PRT
```

<213> ORGANISM: Homo sapiens

<400> SEQUENCE: 347

Ala Leu Arg Ile Gln Asp Ile Glu Leu
1               5

<210> SEQ ID NO 348
<211> LENGTH: 9
<212> TYPE: PRT
<213> ORGANISM: Homo sapiens

<400> SEQUENCE: 348

Lys Ile Arg Glu Glu Leu Gly Arg Ile
1               5

<210> SEQ ID NO 349
<211> LENGTH: 9
<212> TYPE: PRT
<213> ORGANISM: Homo sapiens

<400> SEQUENCE: 349

Thr Leu Lys Leu Lys Glu Glu Ser Leu
1               5

<210> SEQ ID NO 350
<211> LENGTH: 9
<212> TYPE: PRT
<213> ORGANISM: Homo sapiens

<400> SEQUENCE: 350

Ile Leu Asn Glu Lys Ile Arg Glu Glu
1               5

<210> SEQ ID NO 351
<211> LENGTH: 9
<212> TYPE: PRT
<213> ORGANISM: Homo sapiens

<400> SEQUENCE: 351

Val Leu Lys Lys Lys Leu Ser Glu Ala
1               5

<210> SEQ ID NO 352
<211> LENGTH: 9
<212> TYPE: PRT
<213> ORGANISM: Homo sapiens

<400> SEQUENCE: 352

Gly Thr Ser Asp Lys Ile Gln Cys Leu
1               5

<210> SEQ ID NO 353
<211> LENGTH: 9
<212> TYPE: PRT
<213> ORGANISM: Homo sapiens

<400> SEQUENCE: 353

Gly Ala Asp Ile Asn Leu Val Asp Val
1               5

<210> SEQ ID NO 354
<211> LENGTH: 9
<212> TYPE: PRT
<213> ORGANISM: Homo sapiens

<400> SEQUENCE: 354

-continued

Glu Leu Cys Ser Val Arg Leu Thr Leu
1               5

<210> SEQ ID NO 355
<211> LENGTH: 9
<212> TYPE: PRT
<213> ORGANISM: Homo sapiens

<400> SEQUENCE: 355

Ser Val Glu Ser Asn Leu Asn Gln Val
1               5

<210> SEQ ID NO 356
<211> LENGTH: 9
<212> TYPE: PRT
<213> ORGANISM: Homo sapiens

<400> SEQUENCE: 356

Ser Leu Lys Ile Asn Leu Asn Tyr Ala
1               5

<210> SEQ ID NO 357
<211> LENGTH: 9
<212> TYPE: PRT
<213> ORGANISM: Homo sapiens

<400> SEQUENCE: 357

Lys Thr Pro Asp Glu Ala Ala Ser Leu
1               5

<210> SEQ ID NO 358
<211> LENGTH: 9
<212> TYPE: PRT
<213> ORGANISM: Homo sapiens

<400> SEQUENCE: 358

Ala Thr Cys Gly Met Lys Val Ser Ile
1               5

<210> SEQ ID NO 359
<211> LENGTH: 9
<212> TYPE: PRT
<213> ORGANISM: Homo sapiens

<400> SEQUENCE: 359

Leu Ser His Gly Ala Val Ile Glu Val
1               5

<210> SEQ ID NO 360
<211> LENGTH: 9
<212> TYPE: PRT
<213> ORGANISM: Homo sapiens

<400> SEQUENCE: 360

Glu Ile Ala Met Leu Lys Leu Glu Ile
1               5

<210> SEQ ID NO 361
<211> LENGTH: 9
<212> TYPE: PRT
<213> ORGANISM: Homo sapiens

<400> SEQUENCE: 361

Ala Glu Leu Gln Met Thr Leu Lys Leu
1               5

```
<210> SEQ ID NO 362
<211> LENGTH: 9
<212> TYPE: PRT
<213> ORGANISM: Homo sapiens

<400> SEQUENCE: 362

Val Phe Ala Ala Asp Ile Cys Gly Val
1               5

<210> SEQ ID NO 363
<211> LENGTH: 9
<212> TYPE: PRT
<213> ORGANISM: Homo sapiens

<400> SEQUENCE: 363

Pro Ala Ile Glu Met Gln Asn Ser Val
1               5

<210> SEQ ID NO 364
<211> LENGTH: 9
<212> TYPE: PRT
<213> ORGANISM: Homo sapiens

<400> SEQUENCE: 364

Glu Ile Phe Asn Tyr Asn Asn His Leu
1               5

<210> SEQ ID NO 365
<211> LENGTH: 9
<212> TYPE: PRT
<213> ORGANISM: Homo sapiens

<400> SEQUENCE: 365

Ile Leu Lys Glu Lys Asn Ala Glu Leu
1               5

<210> SEQ ID NO 366
<211> LENGTH: 9
<212> TYPE: PRT
<213> ORGANISM: Homo sapiens

<400> SEQUENCE: 366

Gln Leu Val His Ala His Lys Lys Ala
1               5

<210> SEQ ID NO 367
<211> LENGTH: 9
<212> TYPE: PRT
<213> ORGANISM: Homo sapiens

<400> SEQUENCE: 367

Asn Ile Gln Asp Ala Gln Lys Arg Thr
1               5

<210> SEQ ID NO 368
<211> LENGTH: 9
<212> TYPE: PRT
<213> ORGANISM: Homo sapiens

<400> SEQUENCE: 368

Asn Leu Val Asp Val Tyr Gly Asn Met
1               5

<210> SEQ ID NO 369
```

```
<211> LENGTH: 9
<212> TYPE: PRT
<213> ORGANISM: Homo sapiens

<400> SEQUENCE: 369

Lys Cys Thr Ala Leu Met Leu Ala Val
1               5

<210> SEQ ID NO 370
<211> LENGTH: 9
<212> TYPE: PRT
<213> ORGANISM: Homo sapiens

<400> SEQUENCE: 370

Lys Ile Gln Cys Leu Glu Lys Ala Thr
1               5

<210> SEQ ID NO 371
<211> LENGTH: 9
<212> TYPE: PRT
<213> ORGANISM: Homo sapiens

<400> SEQUENCE: 371

Lys Ile Ala Trp Glu Lys Lys Glu Thr
1               5

<210> SEQ ID NO 372
<211> LENGTH: 9
<212> TYPE: PRT
<213> ORGANISM: Homo sapiens

<400> SEQUENCE: 372

Ile Ala Trp Glu Lys Lys Glu Asp Thr
1               5

<210> SEQ ID NO 373
<211> LENGTH: 9
<212> TYPE: PRT
<213> ORGANISM: Homo sapiens

<400> SEQUENCE: 373

Val Gly Met Leu Leu Gln Gln Asn Val
1               5

<210> SEQ ID NO 374
<211> LENGTH: 9
<212> TYPE: PRT
<213> ORGANISM: Homo sapiens

<400> SEQUENCE: 374

Val Lys Thr Gly Cys Val Ala Arg Val
1               5

<210> SEQ ID NO 375
<211> LENGTH: 9
<212> TYPE: PRT
<213> ORGANISM: Homo sapiens

<400> SEQUENCE: 375

Ala Leu His Tyr Ala Val Tyr Ser Glu
1               5

<210> SEQ ID NO 376
<211> LENGTH: 9
<212> TYPE: PRT
<213> ORGANISM: Homo sapiens
```

```
<400> SEQUENCE: 376

Gln Met Lys Lys Lys Phe Cys Val Leu
1               5

<210> SEQ ID NO 377
<211> LENGTH: 9
<212> TYPE: PRT
<213> ORGANISM: Homo sapiens

<400> SEQUENCE: 377

Ala Leu Gln Cys His Gln Glu Ala Cys
1               5

<210> SEQ ID NO 378
<211> LENGTH: 9
<212> TYPE: PRT
<213> ORGANISM: Homo sapiens

<400> SEQUENCE: 378

Ser Glu Gln Ile Val Glu Phe Leu Leu
1               5

<210> SEQ ID NO 379
<211> LENGTH: 9
<212> TYPE: PRT
<213> ORGANISM: Homo sapiens

<400> SEQUENCE: 379

Ala Val Ile Glu Val His Asn Lys Ala
1               5

<210> SEQ ID NO 380
<211> LENGTH: 9
<212> TYPE: PRT
<213> ORGANISM: Homo sapiens

<400> SEQUENCE: 380

Ala Val Thr Cys Gly Phe His His Ile
1               5

<210> SEQ ID NO 381
<211> LENGTH: 9
<212> TYPE: PRT
<213> ORGANISM: Homo sapiens

<400> SEQUENCE: 381

Ala Cys Leu Gln Arg Lys Met Asn Val
1               5

<210> SEQ ID NO 382
<211> LENGTH: 9
<212> TYPE: PRT
<213> ORGANISM: Homo sapiens

<400> SEQUENCE: 382

Ser Leu Val Glu Gly Thr Ser Asp Lys
1               5

<210> SEQ ID NO 383
<211> LENGTH: 23
<212> TYPE: PRT
<213> ORGANISM: Homo sapiens

<400> SEQUENCE: 383
```

Met Thr Lys Arg Lys Lys Thr Ile Asn Leu Asn Ile Gln Asp Ala Gln
1               5                   10                  15

Lys Arg Thr Ala Leu His Trp
            20

<210> SEQ ID NO 384
<211> LENGTH: 23
<212> TYPE: PRT
<213> ORGANISM: Homo sapiens

<400> SEQUENCE: 384

Thr Ser Glu Lys Phe Thr Trp Pro Ala Lys Gly Arg Pro Arg Lys Ile
1               5                   10                  15

Ala Trp Glu Lys Lys Glu Asp
            20

<210> SEQ ID NO 385
<211> LENGTH: 23
<212> TYPE: PRT
<213> ORGANISM: Homo sapiens

<400> SEQUENCE: 385

Asp Glu Ile Leu Pro Ser Glu Ser Lys Gln Lys Asp Tyr Glu Glu Asn
1               5                   10                  15

Ser Trp Asp Thr Glu Ser Leu
            20

<210> SEQ ID NO 386
<211> LENGTH: 23
<212> TYPE: PRT
<213> ORGANISM: Homo sapiens

<400> SEQUENCE: 386

Arg Leu Thr Leu Asn Gln Glu Glu Lys Arg Arg Asn Ala Asp Ile
1               5                   10                  15

Leu Asn Glu Lys Ile Arg Glu
            20

<210> SEQ ID NO 387
<211> LENGTH: 23
<212> TYPE: PRT
<213> ORGANISM: Homo sapiens

<400> SEQUENCE: 387

Ala Glu Asn Thr Met Leu Thr Ser Lys Leu Lys Glu Lys Gln Asp Lys
1               5                   10                  15

Glu Ile Leu Glu Ala Glu Ile
            20

<210> SEQ ID NO 388
<211> LENGTH: 23
<212> TYPE: PRT
<213> ORGANISM: Homo sapiens

<400> SEQUENCE: 388

Asn Tyr Asn Asn His Leu Lys Asn Arg Ile Tyr Gln Tyr Glu Lys Glu
1               5                   10                  15

Lys Ala Glu Thr Glu Asn Ser
            20

<210> SEQ ID NO 389
<211> LENGTH: 9
<212> TYPE: PRT

<213> ORGANISM: Homo sapiens

<400> SEQUENCE: 389

Leu Asp Leu Glu Thr Leu Thr Asp Ile
1               5

<210> SEQ ID NO 390
<211> LENGTH: 9
<212> TYPE: PRT
<213> ORGANISM: Homo sapiens

<400> SEQUENCE: 390

Asp Ile Leu Gln His Gln Ile Arg Ala
1               5

<210> SEQ ID NO 391
<211> LENGTH: 9
<212> TYPE: PRT
<213> ORGANISM: Homo sapiens

<400> SEQUENCE: 391

Ile Leu Gln His Gln Ile Arg Ala Val
1               5

<210> SEQ ID NO 392
<211> LENGTH: 9
<212> TYPE: PRT
<213> ORGANISM: Homo sapiens

<400> SEQUENCE: 392

Ala Val Pro Phe Glu Asn Leu Asn Ile
1               5

<210> SEQ ID NO 393
<211> LENGTH: 9
<212> TYPE: PRT
<213> ORGANISM: Homo sapiens

<400> SEQUENCE: 393

Asn Leu Asn Ile His Cys Gly Asp Ala
1               5

<210> SEQ ID NO 394
<211> LENGTH: 9
<212> TYPE: PRT
<213> ORGANISM: Homo sapiens

<400> SEQUENCE: 394

Ala Met Asp Leu Gly Leu Glu Ala Ile
1               5

<210> SEQ ID NO 395
<211> LENGTH: 9
<212> TYPE: PRT
<213> ORGANISM: Homo sapiens

<400> SEQUENCE: 395

Gly Leu Glu Ala Ile Phe Asp Gln Val
1               5

<210> SEQ ID NO 396
<211> LENGTH: 9
<212> TYPE: PRT
<213> ORGANISM: Homo sapiens

<400> SEQUENCE: 396

Leu Glu Ala Ile Phe Asp Gln Val Val
1               5

<210> SEQ ID NO 397
<211> LENGTH: 9
<212> TYPE: PRT
<213> ORGANISM: Homo sapiens

<400> SEQUENCE: 397

Trp Cys Leu Gln Val Asn His Leu Leu
1               5

<210> SEQ ID NO 398
<211> LENGTH: 9
<212> TYPE: PRT
<213> ORGANISM: Homo sapiens

<400> SEQUENCE: 398

Gln Val Asn His Leu Leu Tyr Trp Ala
1               5

<210> SEQ ID NO 399
<211> LENGTH: 9
<212> TYPE: PRT
<213> ORGANISM: Homo sapiens

<400> SEQUENCE: 399

Val Asn His Leu Leu Tyr Trp Ala Leu
1               5

<210> SEQ ID NO 400
<211> LENGTH: 9
<212> TYPE: PRT
<213> ORGANISM: Homo sapiens

<400> SEQUENCE: 400

His Leu Leu Tyr Trp Ala Leu Thr Thr
1               5

<210> SEQ ID NO 401
<211> LENGTH: 9
<212> TYPE: PRT
<213> ORGANISM: Homo sapiens

<400> SEQUENCE: 401

Leu Leu Tyr Trp Ala Leu Thr Thr Ile
1               5

<210> SEQ ID NO 402
<211> LENGTH: 9
<212> TYPE: PRT
<213> ORGANISM: Homo sapiens

<400> SEQUENCE: 402

Ala Leu Thr Thr Ile Gly Phe Glu Thr
1               5

<210> SEQ ID NO 403
<211> LENGTH: 9
<212> TYPE: PRT
<213> ORGANISM: Homo sapiens

<400> SEQUENCE: 403

Leu Thr Thr Ile Gly Phe Glu Thr Thr
1               5

<210> SEQ ID NO 404
<211> LENGTH: 9
<212> TYPE: PRT
<213> ORGANISM: Homo sapiens

<400> SEQUENCE: 404

Thr Thr Ile Gly Phe Glu Thr Thr Met
1               5

<210> SEQ ID NO 405
<211> LENGTH: 9
<212> TYPE: PRT
<213> ORGANISM: Homo sapiens

<400> SEQUENCE: 405

Thr Ile Gly Phe Glu Thr Thr Met Leu
1               5

<210> SEQ ID NO 406
<211> LENGTH: 9
<212> TYPE: PRT
<213> ORGANISM: Homo sapiens

<400> SEQUENCE: 406

Thr Met Leu Gly Gly Tyr Val Tyr Ser
1               5

<210> SEQ ID NO 407
<211> LENGTH: 9
<212> TYPE: PRT
<213> ORGANISM: Homo sapiens

<400> SEQUENCE: 407

Met Leu Gly Gly Tyr Val Tyr Ser Thr
1               5

<210> SEQ ID NO 408
<211> LENGTH: 9
<212> TYPE: PRT
<213> ORGANISM: Homo sapiens

<400> SEQUENCE: 408

Tyr Ser Thr Gly Met Ile His Leu Leu
1               5

<210> SEQ ID NO 409
<211> LENGTH: 9
<212> TYPE: PRT
<213> ORGANISM: Homo sapiens

<400> SEQUENCE: 409

Ser Thr Gly Met Ile His Leu Leu Leu
1               5

<210> SEQ ID NO 410
<211> LENGTH: 9
<212> TYPE: PRT
<213> ORGANISM: Homo sapiens

<400> SEQUENCE: 410

Gly Met Ile His Leu Leu Leu Gln Val
1               5

<210> SEQ ID NO 411

```
<211> LENGTH: 9
<212> TYPE: PRT
<213> ORGANISM: Homo sapiens

<400> SEQUENCE: 411

Met Ile His Leu Leu Gln Val Thr
1               5

<210> SEQ ID NO 412
<211> LENGTH: 9
<212> TYPE: PRT
<213> ORGANISM: Homo sapiens

<400> SEQUENCE: 412

Leu Leu Leu Gln Val Thr Ile Asp Gly
1               5

<210> SEQ ID NO 413
<211> LENGTH: 9
<212> TYPE: PRT
<213> ORGANISM: Homo sapiens

<400> SEQUENCE: 413

Val Thr Ile Asp Gly Arg Asn Tyr Ile
1               5

<210> SEQ ID NO 414
<211> LENGTH: 9
<212> TYPE: PRT
<213> ORGANISM: Homo sapiens

<400> SEQUENCE: 414

Thr Ile Asp Gly Arg Asn Tyr Ile Val
1               5

<210> SEQ ID NO 415
<211> LENGTH: 9
<212> TYPE: PRT
<213> ORGANISM: Homo sapiens

<400> SEQUENCE: 415

Tyr Ile Val Asp Ala Gly Phe Gly Arg
1               5

<210> SEQ ID NO 416
<211> LENGTH: 9
<212> TYPE: PRT
<213> ORGANISM: Homo sapiens

<400> SEQUENCE: 416

Arg Ser Tyr Gln Met Trp Gln Pro Leu
1               5

<210> SEQ ID NO 417
<211> LENGTH: 9
<212> TYPE: PRT
<213> ORGANISM: Homo sapiens

<400> SEQUENCE: 417

Tyr Gln Met Trp Gln Pro Leu Glu Leu
1               5

<210> SEQ ID NO 418
<211> LENGTH: 9
<212> TYPE: PRT
<213> ORGANISM: Homo sapiens
```

```
<400> SEQUENCE: 418

Gln Met Trp Gln Pro Leu Glu Leu Ile
1               5

<210> SEQ ID NO 419
<211> LENGTH: 9
<212> TYPE: PRT
<213> ORGANISM: Homo sapiens

<400> SEQUENCE: 419

Ile Ser Gly Lys Asp Gln Pro Gln Val
1               5

<210> SEQ ID NO 420
<211> LENGTH: 9
<212> TYPE: PRT
<213> ORGANISM: Homo sapiens

<400> SEQUENCE: 420

Lys Asp Gln Pro Gln Val Pro Cys Val
1               5

<210> SEQ ID NO 421
<211> LENGTH: 9
<212> TYPE: PRT
<213> ORGANISM: Homo sapiens

<400> SEQUENCE: 421

Pro Gln Val Pro Cys Val Phe Arg Leu
1               5

<210> SEQ ID NO 422
<211> LENGTH: 9
<212> TYPE: PRT
<213> ORGANISM: Homo sapiens

<400> SEQUENCE: 422

Gln Val Pro Cys Val Phe Arg Leu Thr
1               5

<210> SEQ ID NO 423
<211> LENGTH: 9
<212> TYPE: PRT
<213> ORGANISM: Homo sapiens

<400> SEQUENCE: 423

Arg Leu Thr Glu Glu Asn Gly Phe Trp
1               5

<210> SEQ ID NO 424
<211> LENGTH: 9
<212> TYPE: PRT
<213> ORGANISM: Homo sapiens

<400> SEQUENCE: 424

Thr Glu Glu Asn Gly Phe Trp Tyr Leu
1               5

<210> SEQ ID NO 425
<211> LENGTH: 9
<212> TYPE: PRT
<213> ORGANISM: Homo sapiens

<400> SEQUENCE: 425
```

```
Asn Gly Phe Trp Tyr Leu Asp Gln Ile
1               5
```

<210> SEQ ID NO 426
<211> LENGTH: 9
<212> TYPE: PRT
<213> ORGANISM: Homo sapiens

<400> SEQUENCE: 426

```
Asp Gln Ile Arg Arg Glu Gln Tyr Ile
1               5
```

<210> SEQ ID NO 427
<211> LENGTH: 9
<212> TYPE: PRT
<213> ORGANISM: Homo sapiens

<400> SEQUENCE: 427

```
Tyr Ile Pro Asn Glu Glu Phe Leu His
1               5
```

<210> SEQ ID NO 428
<211> LENGTH: 9
<212> TYPE: PRT
<213> ORGANISM: Homo sapiens

<400> SEQUENCE: 428

```
Tyr Ser Phe Thr Leu Lys Pro Arg Thr
1               5
```

<210> SEQ ID NO 429
<211> LENGTH: 9
<212> TYPE: PRT
<213> ORGANISM: Homo sapiens

<400> SEQUENCE: 429

```
Arg Thr Ile Glu Asp Phe Glu Ser Met
1               5
```

<210> SEQ ID NO 430
<211> LENGTH: 9
<212> TYPE: PRT
<213> ORGANISM: Homo sapiens

<400> SEQUENCE: 430

```
Tyr Leu Gln Thr Ser Pro Ser Ser Val
1               5
```

<210> SEQ ID NO 431
<211> LENGTH: 9
<212> TYPE: PRT
<213> ORGANISM: Homo sapiens

<400> SEQUENCE: 431

```
Gln Thr Ser Pro Ser Ser Val Phe Thr
1               5
```

<210> SEQ ID NO 432
<211> LENGTH: 9
<212> TYPE: PRT
<213> ORGANISM: Homo sapiens

<400> SEQUENCE: 432

```
Ser Val Phe Thr Ser Lys Ser Phe Cys
1               5
```

<210> SEQ ID NO 433
<211> LENGTH: 9
<212> TYPE: PRT
<213> ORGANISM: Homo sapiens

<400> SEQUENCE: 433

Phe Thr Ser Lys Ser Phe Cys Ser Leu
1               5

<210> SEQ ID NO 434
<211> LENGTH: 9
<212> TYPE: PRT
<213> ORGANISM: Homo sapiens

<400> SEQUENCE: 434

Cys Ser Leu Gln Thr Pro Asp Gly Val
1               5

<210> SEQ ID NO 435
<211> LENGTH: 9
<212> TYPE: PRT
<213> ORGANISM: Homo sapiens

<400> SEQUENCE: 435

Leu Gln Thr Pro Asp Gly Val His Cys
1               5

<210> SEQ ID NO 436
<211> LENGTH: 9
<212> TYPE: PRT
<213> ORGANISM: Homo sapiens

<400> SEQUENCE: 436

Gln Thr Pro Asp Gly Val His Cys Leu
1               5

<210> SEQ ID NO 437
<211> LENGTH: 9
<212> TYPE: PRT
<213> ORGANISM: Homo sapiens

<400> SEQUENCE: 437

Thr Pro Asp Gly Val His Cys Leu Val
1               5

<210> SEQ ID NO 438
<211> LENGTH: 9
<212> TYPE: PRT
<213> ORGANISM: Homo sapiens

<400> SEQUENCE: 438

Gly Val His Cys Leu Val Gly Phe Thr
1               5

<210> SEQ ID NO 439
<211> LENGTH: 9
<212> TYPE: PRT
<213> ORGANISM: Homo sapiens

<400> SEQUENCE: 439

Cys Leu Val Gly Phe Thr Leu Thr His
1               5

<210> SEQ ID NO 440
<211> LENGTH: 9

```
<212> TYPE: PRT
<213> ORGANISM: Homo sapiens

<400> SEQUENCE: 440

Thr Leu Thr His Arg Arg Phe Asn Tyr
1               5

<210> SEQ ID NO 441
<211> LENGTH: 9
<212> TYPE: PRT
<213> ORGANISM: Homo sapiens

<400> SEQUENCE: 441

Phe Asn Tyr Lys Asp Asn Thr Asp Leu
1               5

<210> SEQ ID NO 442
<211> LENGTH: 9
<212> TYPE: PRT
<213> ORGANISM: Homo sapiens

<400> SEQUENCE: 442

Asn Thr Asp Leu Ile Glu Phe Lys Thr
1               5

<210> SEQ ID NO 443
<211> LENGTH: 9
<212> TYPE: PRT
<213> ORGANISM: Homo sapiens

<400> SEQUENCE: 443

Thr Lys Leu Ile Glu Phe Lys Thr Leu
1               5

<210> SEQ ID NO 444
<211> LENGTH: 9
<212> TYPE: PRT
<213> ORGANISM: Homo sapiens

<400> SEQUENCE: 444

Leu Ser Glu Glu Glu Ile Glu Lys Val
1               5

<210> SEQ ID NO 445
<211> LENGTH: 9
<212> TYPE: PRT
<213> ORGANISM: Homo sapiens

<400> SEQUENCE: 445

Lys Val Leu Lys Asn Ile Phe Asn Ile
1               5

<210> SEQ ID NO 446
<211> LENGTH: 9
<212> TYPE: PRT
<213> ORGANISM: Homo sapiens

<400> SEQUENCE: 446

Leu Lys Asn Ile Phe Asn Ile Ser Leu
1               5

<210> SEQ ID NO 447
<211> LENGTH: 9
<212> TYPE: PRT
<213> ORGANISM: Homo sapiens
```

```
<400> SEQUENCE: 447

Asn Ile Ser Leu Gln Arg Lys Leu Val
1               5

<210> SEQ ID NO 448
<211> LENGTH: 9
<212> TYPE: PRT
<213> ORGANISM: Homo sapiens

<400> SEQUENCE: 448

Lys His Gly Asp Arg Phe Phe Thr Ile
1               5

<210> SEQ ID NO 449
<211> LENGTH: 9
<212> TYPE: PRT
<213> ORGANISM: Homo sapiens

<400> SEQUENCE: 449

Asp Ile Glu Ala Tyr Leu Glu Arg Ile
1               5

<210> SEQ ID NO 450
<211> LENGTH: 9
<212> TYPE: PRT
<213> ORGANISM: Homo sapiens

<400> SEQUENCE: 450

Tyr Leu Glu Thr Ile Gly Tyr Lys Lys
1               5

<210> SEQ ID NO 451
<211> LENGTH: 9
<212> TYPE: PRT
<213> ORGANISM: Homo sapiens

<400> SEQUENCE: 451

Arg Asn Lys Leu Asp Leu Glu Thr Leu
1               5

<210> SEQ ID NO 452
<211> LENGTH: 9
<212> TYPE: PRT
<213> ORGANISM: Homo sapiens

<400> SEQUENCE: 452

Asn Lys Leu Asp Leu Glu Thr Leu Thr
1               5

<210> SEQ ID NO 453
<211> LENGTH: 9
<212> TYPE: PRT
<213> ORGANISM: Homo sapiens

<400> SEQUENCE: 453

Lys Leu Asp Leu Glu Thr Leu Thr Asp
1               5

<210> SEQ ID NO 454
<211> LENGTH: 9
<212> TYPE: PRT
<213> ORGANISM: Homo sapiens

<400> SEQUENCE: 454

Asp Leu Glu Thr Leu Thr Asp Ile Leu
```

```
<210> SEQ ID NO 455
<211> LENGTH: 9
<212> TYPE: PRT
<213> ORGANISM: Homo sapiens

<400> SEQUENCE: 455

Thr Leu Thr Asp Ile Leu Gln His Gln
1               5

<210> SEQ ID NO 456
<211> LENGTH: 9
<212> TYPE: PRT
<213> ORGANISM: Homo sapiens

<400> SEQUENCE: 456

Leu Thr Asp Ile Leu Gln His Gln Ile
1               5

<210> SEQ ID NO 457
<211> LENGTH: 9
<212> TYPE: PRT
<213> ORGANISM: Homo sapiens

<400> SEQUENCE: 457

Gln Ile Arg Ala Val Pro Phe Glu Asn
1               5

<210> SEQ ID NO 458
<211> LENGTH: 9
<212> TYPE: PRT
<213> ORGANISM: Homo sapiens

<400> SEQUENCE: 458

Ile Arg Ala Val Pro Phe Glu Asn Leu
1               5

<210> SEQ ID NO 459
<211> LENGTH: 9
<212> TYPE: PRT
<213> ORGANISM: Homo sapiens

<400> SEQUENCE: 459

Ile His Cys Gly Asp Ala Met Asp Leu
1               5

<210> SEQ ID NO 460
<211> LENGTH: 9
<212> TYPE: PRT
<213> ORGANISM: Homo sapiens

<400> SEQUENCE: 460

His Cys Gly Asp Ala Met Asp Leu Gly
1               5

<210> SEQ ID NO 461
<211> LENGTH: 9
<212> TYPE: PRT
<213> ORGANISM: Homo sapiens

<400> SEQUENCE: 461

Asp Leu Gly Leu Glu Ala Ile Phe Asp
1               5
```

<210> SEQ ID NO 462
<211> LENGTH: 9
<212> TYPE: PRT
<213> ORGANISM: Homo sapiens

<400> SEQUENCE: 462

Ala Ile Phe Asp Gln Val Val Arg Arg
1               5

<210> SEQ ID NO 463
<211> LENGTH: 9
<212> TYPE: PRT
<213> ORGANISM: Homo sapiens

<400> SEQUENCE: 463

Gly Trp Cys Leu Gln Val Asn His Leu
1               5

<210> SEQ ID NO 464
<211> LENGTH: 9
<212> TYPE: PRT
<213> ORGANISM: Homo sapiens

<400> SEQUENCE: 464

Leu Gln Val Asn His Leu Leu Tyr Trp
1               5

<210> SEQ ID NO 465
<211> LENGTH: 9
<212> TYPE: PRT
<213> ORGANISM: Homo sapiens

<400> SEQUENCE: 465

Gly Gly Tyr Val Tyr Ser Thr Pro Ala
1               5

<210> SEQ ID NO 466
<211> LENGTH: 9
<212> TYPE: PRT
<213> ORGANISM: Homo sapiens

<400> SEQUENCE: 466

Tyr Val Tyr Ser Thr Pro Ala Lys Lys
1               5

<210> SEQ ID NO 467
<211> LENGTH: 9
<212> TYPE: PRT
<213> ORGANISM: Homo sapiens

<400> SEQUENCE: 467

Ser Thr Pro Ala Lys Lys Tyr Ser Thr
1               5

<210> SEQ ID NO 468
<211> LENGTH: 9
<212> TYPE: PRT
<213> ORGANISM: Homo sapiens

<400> SEQUENCE: 468

Ile His Leu Leu Leu Gln Val Thr Ile
1               5

<210> SEQ ID NO 469
<211> LENGTH: 9
<212> TYPE: PRT

<213> ORGANISM: Homo sapiens

<400> SEQUENCE: 469

His Leu Leu Leu Gln Val Thr Ile Asp
1               5

<210> SEQ ID NO 470
<211> LENGTH: 9
<212> TYPE: PRT
<213> ORGANISM: Homo sapiens

<400> SEQUENCE: 470

Leu Leu Gln Val Thr Ile Asp Gly Arg
1               5

<210> SEQ ID NO 471
<211> LENGTH: 9
<212> TYPE: PRT
<213> ORGANISM: Homo sapiens

<400> SEQUENCE: 471

Tyr Leu Asp Gln Ile Arg Arg Glu Gln
1               5

<210> SEQ ID NO 472
<211> LENGTH: 9
<212> TYPE: PRT
<213> ORGANISM: Homo sapiens

<400> SEQUENCE: 472

Gln Tyr Ile Pro Asn Glu Glu Phe Leu
1               5

<210> SEQ ID NO 473
<211> LENGTH: 9
<212> TYPE: PRT
<213> ORGANISM: Homo sapiens

<400> SEQUENCE: 473

Phe Leu His Ser Asp Leu Leu Glu Asp
1               5

<210> SEQ ID NO 474
<211> LENGTH: 9
<212> TYPE: PRT
<213> ORGANISM: Homo sapiens

<400> SEQUENCE: 474

Asp Leu Leu Glu Asp Ser Lys Tyr Arg
1               5

<210> SEQ ID NO 475
<211> LENGTH: 9
<212> TYPE: PRT
<213> ORGANISM: Homo sapiens

<400> SEQUENCE: 475

Tyr Arg Lys Ile Tyr Ser Phe Thr Leu
1               5

<210> SEQ ID NO 476
<211> LENGTH: 9
<212> TYPE: PRT
<213> ORGANISM: Homo sapiens

<400> SEQUENCE: 476

```
Lys Ile Tyr Ser Phe Thr Leu Lys Pro
1               5
```

<210> SEQ ID NO 477
<211> LENGTH: 9
<212> TYPE: PRT
<213> ORGANISM: Homo sapiens

<400> SEQUENCE: 477

```
Thr Leu Lys Pro Arg Thr Ile Glu Asp
1               5
```

<210> SEQ ID NO 478
<211> LENGTH: 9
<212> TYPE: PRT
<213> ORGANISM: Homo sapiens

<400> SEQUENCE: 478

```
Val His Cys Leu Val Gly Phe Thr Leu
1               5
```

<210> SEQ ID NO 479
<211> LENGTH: 9
<212> TYPE: PRT
<213> ORGANISM: Homo sapiens

<400> SEQUENCE: 479

```
Leu Thr His Arg Arg Phe Asn Tyr Lys
1               5
```

<210> SEQ ID NO 480
<211> LENGTH: 9
<212> TYPE: PRT
<213> ORGANISM: Homo sapiens

<400> SEQUENCE: 480

```
Asp Leu Ile Glu Phe Lys Thr Leu Ser
1               5
```

<210> SEQ ID NO 481
<211> LENGTH: 9
<212> TYPE: PRT
<213> ORGANISM: Homo sapiens

<400> SEQUENCE: 481

```
Leu Ile Glu Phe Lys Thr Leu Ser Glu
1               5
```

<210> SEQ ID NO 482
<211> LENGTH: 9
<212> TYPE: PRT
<213> ORGANISM: Homo sapiens

<400> SEQUENCE: 482

```
Phe Lys Thr Leu Ser Glu Glu Glu Ile
1               5
```

<210> SEQ ID NO 483
<211> LENGTH: 9
<212> TYPE: PRT
<213> ORGANISM: Homo sapiens

<400> SEQUENCE: 483

```
Thr Leu Ser Glu Glu Glu Ile Glu Lys
1               5
```

```
<210> SEQ ID NO 484
<211> LENGTH: 9
<212> TYPE: PRT
<213> ORGANISM: Homo sapiens

<400> SEQUENCE: 484

Glu Ile Glu Lys Val Leu Lys Asn Ile
1               5

<210> SEQ ID NO 485
<211> LENGTH: 9
<212> TYPE: PRT
<213> ORGANISM: Homo sapiens

<400> SEQUENCE: 485

Phe Asn Ile Ser Leu Gln Arg Lys Leu
1               5

<210> SEQ ID NO 486
<211> LENGTH: 9
<212> TYPE: PRT
<213> ORGANISM: Homo sapiens

<400> SEQUENCE: 486

Ser Leu Gln Arg Lys Leu Val Pro Lys
1               5

<210> SEQ ID NO 487
<211> LENGTH: 9
<212> TYPE: PRT
<213> ORGANISM: Homo sapiens

<400> SEQUENCE: 487

Lys Leu Val Pro Lys His Gly Asp Arg
1               5

<210> SEQ ID NO 488
<211> LENGTH: 9
<212> TYPE: PRT
<213> ORGANISM: Homo sapiens

<400> SEQUENCE: 488

Pro Lys His Gly Asp Arg Phe Phe Thr
1               5

<210> SEQ ID NO 489
<211> LENGTH: 9
<212> TYPE: PRT
<213> ORGANISM: Homo sapiens

<400> SEQUENCE: 489

Met Leu Trp Lys Leu Thr Asp Asn Ile
1               5

<210> SEQ ID NO 490
<211> LENGTH: 9
<212> TYPE: PRT
<213> ORGANISM: Homo sapiens

<400> SEQUENCE: 490

Lys Leu Thr Asp Asn Ile Lys Tyr Glu
1               5

<210> SEQ ID NO 491
```

```
<211> LENGTH: 9
<212> TYPE: PRT
<213> ORGANISM: Homo sapiens

<400> SEQUENCE: 491

Gly Thr Ser Asn Gly Thr Ala Arg Leu
1               5

<210> SEQ ID NO 492
<211> LENGTH: 9
<212> TYPE: PRT
<213> ORGANISM: Homo sapiens

<400> SEQUENCE: 492

Asn Gly Thr Ala Arg Leu Pro Gln Leu
1               5

<210> SEQ ID NO 493
<211> LENGTH: 9
<212> TYPE: PRT
<213> ORGANISM: Homo sapiens

<400> SEQUENCE: 493

Ala Arg Leu Pro Gln Leu Gly Thr Val
1               5

<210> SEQ ID NO 494
<211> LENGTH: 9
<212> TYPE: PRT
<213> ORGANISM: Homo sapiens

<400> SEQUENCE: 494

Gly Thr Val Gly Gln Ser Pro Tyr Thr
1               5

<210> SEQ ID NO 495
<211> LENGTH: 9
<212> TYPE: PRT
<213> ORGANISM: Homo sapiens

<400> SEQUENCE: 495

Ser Pro Tyr Thr Ser Ala Pro Pro Leu
1               5

<210> SEQ ID NO 496
<211> LENGTH: 9
<212> TYPE: PRT
<213> ORGANISM: Homo sapiens

<400> SEQUENCE: 496

Phe Gln Pro Pro Tyr Phe Pro Pro Pro
1               5

<210> SEQ ID NO 497
<211> LENGTH: 9
<212> TYPE: PRT
<213> ORGANISM: Homo sapiens

<400> SEQUENCE: 497

Tyr Phe Pro Pro Pro Tyr Gln Pro Ile
1               5

<210> SEQ ID NO 498
<211> LENGTH: 9
<212> TYPE: PRT
<213> ORGANISM: Homo sapiens
```

```
<400> SEQUENCE: 498

Gln Ser Gln Asp Pro Tyr Ser His Val
1               5

<210> SEQ ID NO 499
<211> LENGTH: 9
<212> TYPE: PRT
<213> ORGANISM: Homo sapiens

<400> SEQUENCE: 499

Ser His Val Asn Asp Pro Tyr Ser Leu
1               5

<210> SEQ ID NO 500
<211> LENGTH: 9
<212> TYPE: PRT
<213> ORGANISM: Homo sapiens

<400> SEQUENCE: 500

Ser Leu Asn Pro Leu His Ala Gln Pro
1               5

<210> SEQ ID NO 501
<211> LENGTH: 9
<212> TYPE: PRT
<213> ORGANISM: Homo sapiens

<400> SEQUENCE: 501

Arg Gln Ser Gln Glu Ser Gly Leu Leu
1               5

<210> SEQ ID NO 502
<211> LENGTH: 9
<212> TYPE: PRT
<213> ORGANISM: Homo sapiens

<400> SEQUENCE: 502

Gly Leu Leu His Thr His Arg Gly Leu
1               5

<210> SEQ ID NO 503
<211> LENGTH: 9
<212> TYPE: PRT
<213> ORGANISM: Homo sapiens

<400> SEQUENCE: 503

Gly Leu Pro His Gln Leu Ser Gly Leu
1               5

<210> SEQ ID NO 504
<211> LENGTH: 9
<212> TYPE: PRT
<213> ORGANISM: Homo sapiens

<400> SEQUENCE: 504

Gly Leu Asp Pro Arg Arg Asp Tyr Arg
1               5

<210> SEQ ID NO 505
<211> LENGTH: 9
<212> TYPE: PRT
<213> ORGANISM: Homo sapiens

<400> SEQUENCE: 505
```

Asp Leu Leu His Gly Pro His Ala Leu
1               5

<210> SEQ ID NO 506
<211> LENGTH: 9
<212> TYPE: PRT
<213> ORGANISM: Homo sapiens

<400> SEQUENCE: 506

Leu Leu His Gly Pro His Ala Leu Ser
1               5

<210> SEQ ID NO 507
<211> LENGTH: 9
<212> TYPE: PRT
<213> ORGANISM: Homo sapiens

<400> SEQUENCE: 507

Ala Leu Ser Ser Gly Leu Gly Asp Leu
1               5

<210> SEQ ID NO 508
<211> LENGTH: 9
<212> TYPE: PRT
<213> ORGANISM: Homo sapiens

<400> SEQUENCE: 508

Ser Ser Gly Leu Gly Asp Leu Ser Ile
1               5

<210> SEQ ID NO 509
<211> LENGTH: 9
<212> TYPE: PRT
<213> ORGANISM: Homo sapiens

<400> SEQUENCE: 509

Gly Leu Gly Asp Leu Ser Ile His Ser
1               5

<210> SEQ ID NO 510
<211> LENGTH: 9
<212> TYPE: PRT
<213> ORGANISM: Homo sapiens

<400> SEQUENCE: 510

Leu Gly Asp Leu Ser Ile His Ser Leu
1               5

<210> SEQ ID NO 511
<211> LENGTH: 9
<212> TYPE: PRT
<213> ORGANISM: Homo sapiens

<400> SEQUENCE: 511

Ser Ile His Ser Leu Pro His Ala Ile
1               5

<210> SEQ ID NO 512
<211> LENGTH: 9
<212> TYPE: PRT
<213> ORGANISM: Homo sapiens

<400> SEQUENCE: 512

Ser Leu Pro His Ala Ile Glu Glu Val
1               5

```
<210> SEQ ID NO 513
<211> LENGTH: 9
<212> TYPE: PRT
<213> ORGANISM: Homo sapiens

<400> SEQUENCE: 513

His Ala Ile Glu Glu Val Pro His Val
1               5

<210> SEQ ID NO 514
<211> LENGTH: 9
<212> TYPE: PRT
<213> ORGANISM: Homo sapiens

<400> SEQUENCE: 514

Gly Ile Asn Ile Pro Asp Gln Thr Val
1               5

<210> SEQ ID NO 515
<211> LENGTH: 9
<212> TYPE: PRT
<213> ORGANISM: Homo sapiens

<400> SEQUENCE: 515

Gln Thr Val Ile Lys Lys Gly Pro Val
1               5

<210> SEQ ID NO 516
<211> LENGTH: 9
<212> TYPE: PRT
<213> ORGANISM: Homo sapiens

<400> SEQUENCE: 516

Val Ile Lys Lys Gly Pro Val Ser Leu
1               5

<210> SEQ ID NO 517
<211> LENGTH: 9
<212> TYPE: PRT
<213> ORGANISM: Homo sapiens

<400> SEQUENCE: 517

Ser Leu Ser Lys Ser Asn Ser Asn Ala
1               5

<210> SEQ ID NO 518
<211> LENGTH: 9
<212> TYPE: PRT
<213> ORGANISM: Homo sapiens

<400> SEQUENCE: 518

Ser Asn Ser Asn Ala Val Ser Ala Ile
1               5

<210> SEQ ID NO 519
<211> LENGTH: 9
<212> TYPE: PRT
<213> ORGANISM: Homo sapiens

<400> SEQUENCE: 519

Ala Ile Pro Ile Asn Lys Asp Asn Leu
1               5

<210> SEQ ID NO 520
<211> LENGTH: 9
```

```
<212> TYPE: PRT
<213> ORGANISM: Homo sapiens

<400> SEQUENCE: 520

Asn Leu Phe Gly Gly Val Val Asn Pro
1               5

<210> SEQ ID NO 521
<211> LENGTH: 9
<212> TYPE: PRT
<213> ORGANISM: Homo sapiens

<400> SEQUENCE: 521

Phe Gly Gly Val Val Asn Pro Asn Glu
1               5

<210> SEQ ID NO 522
<211> LENGTH: 9
<212> TYPE: PRT
<213> ORGANISM: Homo sapiens

<400> SEQUENCE: 522

Gly Gly Val Val Asn Pro Asn Glu Val
1               5

<210> SEQ ID NO 523
<211> LENGTH: 9
<212> TYPE: PRT
<213> ORGANISM: Homo sapiens

<400> SEQUENCE: 523

Asn Pro Asn Glu Val Phe Cys Ser Val
1               5

<210> SEQ ID NO 524
<211> LENGTH: 9
<212> TYPE: PRT
<213> ORGANISM: Homo sapiens

<400> SEQUENCE: 524

Cys Ser Val Pro Gly Arg Leu Ser Leu
1               5

<210> SEQ ID NO 525
<211> LENGTH: 9
<212> TYPE: PRT
<213> ORGANISM: Homo sapiens

<400> SEQUENCE: 525

Ser Val Pro Gly Arg Leu Ser Leu Leu
1               5

<210> SEQ ID NO 526
<211> LENGTH: 9
<212> TYPE: PRT
<213> ORGANISM: Homo sapiens

<400> SEQUENCE: 526

Ser Leu Leu Ser Ser Thr Ser Lys Tyr
1               5

<210> SEQ ID NO 527
<211> LENGTH: 9
<212> TYPE: PRT
<213> ORGANISM: Homo sapiens
```

```
<400> SEQUENCE: 527

Leu Leu Ser Ser Thr Ser Lys Tyr Lys
1               5

<210> SEQ ID NO 528
<211> LENGTH: 9
<212> TYPE: PRT
<213> ORGANISM: Homo sapiens

<400> SEQUENCE: 528

Leu Ser Ser Thr Ser Lys Tyr Lys Val
1               5

<210> SEQ ID NO 529
<211> LENGTH: 9
<212> TYPE: PRT
<213> ORGANISM: Homo sapiens

<400> SEQUENCE: 529

Ser Thr Ser Lys Tyr Lys Val Thr Val
1               5

<210> SEQ ID NO 530
<211> LENGTH: 9
<212> TYPE: PRT
<213> ORGANISM: Homo sapiens

<400> SEQUENCE: 530

Lys Tyr Lys Val Thr Val Ala Glu Val
1               5

<210> SEQ ID NO 531
<211> LENGTH: 9
<212> TYPE: PRT
<213> ORGANISM: Homo sapiens

<400> SEQUENCE: 531

Tyr Lys Val Thr Val Ala Glu Val Gln
1               5

<210> SEQ ID NO 532
<211> LENGTH: 9
<212> TYPE: PRT
<213> ORGANISM: Homo sapiens

<400> SEQUENCE: 532

Thr Val Ala Glu Val Gln Arg Arg Leu
1               5

<210> SEQ ID NO 533
<211> LENGTH: 9
<212> TYPE: PRT
<213> ORGANISM: Homo sapiens

<400> SEQUENCE: 533

Arg Leu Ser Pro Pro Glu Cys Leu Asn
1               5

<210> SEQ ID NO 534
<211> LENGTH: 9
<212> TYPE: PRT
<213> ORGANISM: Homo sapiens

<400> SEQUENCE: 534

Leu Asn Ala Ser Leu Leu Gly Gly Val
```

<210> SEQ ID NO 535
<211> LENGTH: 9
<212> TYPE: PRT
<213> ORGANISM: Homo sapiens

<400> SEQUENCE: 535

Asn Ala Ser Leu Leu Gly Gly Val Leu
1               5

<210> SEQ ID NO 536
<211> LENGTH: 9
<212> TYPE: PRT
<213> ORGANISM: Homo sapiens

<400> SEQUENCE: 536

Ser Leu Leu Gly Gly Val Leu Arg Arg
1               5

<210> SEQ ID NO 537
<211> LENGTH: 9
<212> TYPE: PRT
<213> ORGANISM: Homo sapiens

<400> SEQUENCE: 537

Leu Leu Gly Gly Val Leu Arg Arg Ala
1               5

<210> SEQ ID NO 538
<211> LENGTH: 9
<212> TYPE: PRT
<213> ORGANISM: Homo sapiens

<400> SEQUENCE: 538

Val Leu Arg Arg Ala Lys Ser Lys Asn
1               5

<210> SEQ ID NO 539
<211> LENGTH: 9
<212> TYPE: PRT
<213> ORGANISM: Homo sapiens

<400> SEQUENCE: 539

Ser Leu Arg Glu Lys Leu Asp Lys Ile
1               5

<210> SEQ ID NO 540
<211> LENGTH: 9
<212> TYPE: PRT
<213> ORGANISM: Homo sapiens

<400> SEQUENCE: 540

Lys Leu Asp Lys Ile Gly Leu Asn Leu
1               5

<210> SEQ ID NO 541
<211> LENGTH: 9
<212> TYPE: PRT
<213> ORGANISM: Homo sapiens

<400> SEQUENCE: 541

Lys Ile Gly Leu Asn Leu Pro Ala Gly
1               5

```
<210> SEQ ID NO 542
<211> LENGTH: 9
<212> TYPE: PRT
<213> ORGANISM: Homo sapiens

<400> SEQUENCE: 542

Gly Leu Asn Leu Pro Ala Gly Arg Arg
1               5

<210> SEQ ID NO 543
<211> LENGTH: 9
<212> TYPE: PRT
<213> ORGANISM: Homo sapiens

<400> SEQUENCE: 543

Asn Leu Pro Ala Gly Arg Arg Lys Ala
1               5

<210> SEQ ID NO 544
<211> LENGTH: 9
<212> TYPE: PRT
<213> ORGANISM: Homo sapiens

<400> SEQUENCE: 544

Ala Gly Arg Arg Lys Ala Ala Asn Val
1               5

<210> SEQ ID NO 545
<211> LENGTH: 9
<212> TYPE: PRT
<213> ORGANISM: Homo sapiens

<400> SEQUENCE: 545

Arg Lys Ala Ala Asn Val Thr Leu Leu
1               5

<210> SEQ ID NO 546
<211> LENGTH: 9
<212> TYPE: PRT
<213> ORGANISM: Homo sapiens

<400> SEQUENCE: 546

Lys Ala Ala Asn Val Thr Leu Leu Thr
1               5

<210> SEQ ID NO 547
<211> LENGTH: 9
<212> TYPE: PRT
<213> ORGANISM: Homo sapiens

<400> SEQUENCE: 547

Ala Asn Val Thr Leu Leu Thr Ser Leu
1               5

<210> SEQ ID NO 548
<211> LENGTH: 9
<212> TYPE: PRT
<213> ORGANISM: Homo sapiens

<400> SEQUENCE: 548

Asn Val Thr Leu Leu Thr Ser Leu Val
1               5

<210> SEQ ID NO 549
<211> LENGTH: 9
<212> TYPE: PRT
```

<213> ORGANISM: Homo sapiens

<400> SEQUENCE: 549

Thr Leu Leu Thr Ser Leu Val Glu Gly
1               5

<210> SEQ ID NO 550
<211> LENGTH: 9
<212> TYPE: PRT
<213> ORGANISM: Homo sapiens

<400> SEQUENCE: 550

Leu Leu Thr Ser Leu Val Glu Gly Glu
1               5

<210> SEQ ID NO 551
<211> LENGTH: 9
<212> TYPE: PRT
<213> ORGANISM: Homo sapiens

<400> SEQUENCE: 551

Thr Ser Leu Val Glu Gly Glu Ala Val
1               5

<210> SEQ ID NO 552
<211> LENGTH: 9
<212> TYPE: PRT
<213> ORGANISM: Homo sapiens

<400> SEQUENCE: 552

Ser Leu Val Glu Gly Glu Ala Val His
1               5

<210> SEQ ID NO 553
<211> LENGTH: 9
<212> TYPE: PRT
<213> ORGANISM: Homo sapiens

<400> SEQUENCE: 553

Leu Val Glu Gly Glu Ala Val His Leu
1               5

<210> SEQ ID NO 554
<211> LENGTH: 9
<212> TYPE: PRT
<213> ORGANISM: Homo sapiens

<400> SEQUENCE: 554

Val Glu Gly Glu Ala Val His Leu Ala
1               5

<210> SEQ ID NO 555
<211> LENGTH: 9
<212> TYPE: PRT
<213> ORGANISM: Homo sapiens

<400> SEQUENCE: 555

His Leu Ala Arg Asp Phe Gly Tyr Val
1               5

<210> SEQ ID NO 556
<211> LENGTH: 9
<212> TYPE: PRT
<213> ORGANISM: Homo sapiens

<400> SEQUENCE: 556

```
Tyr Val Cys Glu Thr Glu Phe Pro Ala
1               5
```

<210> SEQ ID NO 557
<211> LENGTH: 9
<212> TYPE: PRT
<213> ORGANISM: Homo sapiens

<400> SEQUENCE: 557

```
Cys Glu Thr Glu Phe Pro Ala Lys Ala
1               5
```

<210> SEQ ID NO 558
<211> LENGTH: 9
<212> TYPE: PRT
<213> ORGANISM: Homo sapiens

<400> SEQUENCE: 558

```
Ala Lys Ala Val Ala Glu Phe Leu Asn
1               5
```

<210> SEQ ID NO 559
<211> LENGTH: 9
<212> TYPE: PRT
<213> ORGANISM: Homo sapiens

<400> SEQUENCE: 559

```
Ala Val Ala Glu Phe Leu Asn Arg Gln
1               5
```

<210> SEQ ID NO 560
<211> LENGTH: 9
<212> TYPE: PRT
<213> ORGANISM: Homo sapiens

<400> SEQUENCE: 560

```
Phe Leu Asn Arg Gln His Ser Asp Pro
1               5
```

<210> SEQ ID NO 561
<211> LENGTH: 9
<212> TYPE: PRT
<213> ORGANISM: Homo sapiens

<400> SEQUENCE: 561

```
Gln Val Thr Arg Lys Asn Met Leu Leu
1               5
```

<210> SEQ ID NO 562
<211> LENGTH: 9
<212> TYPE: PRT
<213> ORGANISM: Homo sapiens

<400> SEQUENCE: 562

```
Asn Met Leu Leu Ala Thr Lys Gln Ile
1               5
```

<210> SEQ ID NO 563
<211> LENGTH: 9
<212> TYPE: PRT
<213> ORGANISM: Homo sapiens

<400> SEQUENCE: 563

```
Met Leu Leu Ala Thr Lys Gln Ile Cys
1               5
```

<210> SEQ ID NO 564
<211> LENGTH: 9
<212> TYPE: PRT
<213> ORGANISM: Homo sapiens

<400> SEQUENCE: 564

Leu Leu Ala Thr Lys Gln Ile Cys Lys
1               5

<210> SEQ ID NO 565
<211> LENGTH: 9
<212> TYPE: PRT
<213> ORGANISM: Homo sapiens

<400> SEQUENCE: 565

Gln Ile Cys Lys Glu Phe Thr Asp Leu
1               5

<210> SEQ ID NO 566
<211> LENGTH: 9
<212> TYPE: PRT
<213> ORGANISM: Homo sapiens

<400> SEQUENCE: 566

Ile Cys Lys Glu Phe Thr Asp Leu Leu
1               5

<210> SEQ ID NO 567
<211> LENGTH: 9
<212> TYPE: PRT
<213> ORGANISM: Homo sapiens

<400> SEQUENCE: 567

Leu Leu Ala Gln Asp Arg Ser Pro Leu
1               5

<210> SEQ ID NO 568
<211> LENGTH: 9
<212> TYPE: PRT
<213> ORGANISM: Homo sapiens

<400> SEQUENCE: 568

Ile Leu Glu Pro Gly Ile Gln Ser Cys
1               5

<210> SEQ ID NO 569
<211> LENGTH: 9
<212> TYPE: PRT
<213> ORGANISM: Homo sapiens

<400> SEQUENCE: 569

Leu Glu Pro Gly Ile Gln Ser Cys Leu
1               5

<210> SEQ ID NO 570
<211> LENGTH: 9
<212> TYPE: PRT
<213> ORGANISM: Homo sapiens

<400> SEQUENCE: 570

Gln Ser Cys Leu Thr His Phe Asn Leu
1               5

<210> SEQ ID NO 571

```
<211> LENGTH: 9
<212> TYPE: PRT
<213> ORGANISM: Homo sapiens

<400> SEQUENCE: 571

Ser Cys Leu Thr His Phe Asn Leu Ile
1               5

<210> SEQ ID NO 572
<211> LENGTH: 9
<212> TYPE: PRT
<213> ORGANISM: Homo sapiens

<400> SEQUENCE: 572

Asn Leu Ile Ser His Gly Phe Gly Ser
1               5

<210> SEQ ID NO 573
<211> LENGTH: 9
<212> TYPE: PRT
<213> ORGANISM: Homo sapiens

<400> SEQUENCE: 573

Leu Ile Ser His Gly Phe Gly Ser Pro
1               5

<210> SEQ ID NO 574
<211> LENGTH: 9
<212> TYPE: PRT
<213> ORGANISM: Homo sapiens

<400> SEQUENCE: 574

Ile Ser His Gly Phe Gly Ser Pro Ala
1               5

<210> SEQ ID NO 575
<211> LENGTH: 9
<212> TYPE: PRT
<213> ORGANISM: Homo sapiens

<400> SEQUENCE: 575

Ser His Gly Phe Gly Ser Pro Ala Val
1               5

<210> SEQ ID NO 576
<211> LENGTH: 9
<212> TYPE: PRT
<213> ORGANISM: Homo sapiens

<400> SEQUENCE: 576

Phe Gly Ser Pro Ala Val Cys Ala Ala
1               5

<210> SEQ ID NO 577
<211> LENGTH: 9
<212> TYPE: PRT
<213> ORGANISM: Homo sapiens

<400> SEQUENCE: 577

Gly Ser Pro Ala Val Cys Ala Ala Val
1               5

<210> SEQ ID NO 578
<211> LENGTH: 9
<212> TYPE: PRT
<213> ORGANISM: Homo sapiens
```

```
<400> SEQUENCE: 578

Ala Val Cys Ala Ala Val Thr Ala Leu
1               5

<210> SEQ ID NO 579
<211> LENGTH: 9
<212> TYPE: PRT
<213> ORGANISM: Homo sapiens

<400> SEQUENCE: 579

Ala Val Thr Ala Leu Gln Asn Tyr Leu
1               5

<210> SEQ ID NO 580
<211> LENGTH: 9
<212> TYPE: PRT
<213> ORGANISM: Homo sapiens

<400> SEQUENCE: 580

Val Thr Ala Leu Gln Asn Tyr Leu Thr
1               5

<210> SEQ ID NO 581
<211> LENGTH: 9
<212> TYPE: PRT
<213> ORGANISM: Homo sapiens

<400> SEQUENCE: 581

Ala Leu Gln Asn Tyr Leu Thr Glu Ala
1               5

<210> SEQ ID NO 582
<211> LENGTH: 9
<212> TYPE: PRT
<213> ORGANISM: Homo sapiens

<400> SEQUENCE: 582

Leu Gln Asn Tyr Leu Thr Glu Ala Leu
1               5

<210> SEQ ID NO 583
<211> LENGTH: 9
<212> TYPE: PRT
<213> ORGANISM: Homo sapiens

<400> SEQUENCE: 583

Tyr Leu Thr Glu Ala Leu Lys Ala Met
1               5

<210> SEQ ID NO 584
<211> LENGTH: 9
<212> TYPE: PRT
<213> ORGANISM: Homo sapiens

<400> SEQUENCE: 584

Leu Lys Ala Met Asp Lys Met Tyr Leu
1               5

<210> SEQ ID NO 585
<211> LENGTH: 9
<212> TYPE: PRT
<213> ORGANISM: Homo sapiens

<400> SEQUENCE: 585
```

Ala Met Asp Lys Met Tyr Leu Ser Asn
1               5

<210> SEQ ID NO 586
<211> LENGTH: 9
<212> TYPE: PRT
<213> ORGANISM: Homo sapiens

<400> SEQUENCE: 586

Lys Met Tyr Leu Ser Asn Asn Pro Asn
1               5

<210> SEQ ID NO 587
<211> LENGTH: 9
<212> TYPE: PRT
<213> ORGANISM: Homo sapiens

<400> SEQUENCE: 587

Tyr Leu Ser Asn Asn Pro Asn Ser His
1               5

<210> SEQ ID NO 588
<211> LENGTH: 9
<212> TYPE: PRT
<213> ORGANISM: Homo sapiens

<400> SEQUENCE: 588

Ala Asn Cys Gln Gly Leu Ser Pro Val
1               5

<210> SEQ ID NO 589
<211> LENGTH: 9
<212> TYPE: PRT
<213> ORGANISM: Homo sapiens

<400> SEQUENCE: 589

Lys Met Gly Glu Pro Val Ser Glu Ser
1               5

<210> SEQ ID NO 590
<211> LENGTH: 9
<212> TYPE: PRT
<213> ORGANISM: Homo sapiens

<400> SEQUENCE: 590

Gly Leu Lys Glu Lys Val Trp Thr Glu
1               5

<210> SEQ ID NO 591
<211> LENGTH: 41
<212> TYPE: DNA
<213> ORGANISM: Homo sapiens

<400> SEQUENCE: 591
ggaattcaac atggacattg aagcatatct tgaaagaatt g        41

<210> SEQ ID NO 592
<211> LENGTH: 39
<212> TYPE: DNA
<213> ORGANISM: Homo sapiens

<400> SEQUENCE: 592
ggaattcctg gtgagctgga tgacaaatag acaagattg           39

<210> SEQ ID NO 593

```
<211> LENGTH: 31
<212> TYPE: DNA
<213> ORGANISM: Homo sapiens

<400> SEQUENCE: 593
ggaattcacc atgctttgga aattgacgga t                                  31

<210> SEQ ID NO 594
<211> LENGTH: 36
<212> TYPE: DNA
<213> ORGANISM: Homo sapiens

<400> SEQUENCE: 594
ggaattcctc actttctgtg cttctcctct ttgtca                             36

<210> SEQ ID NO 595
<211> LENGTH: 31
<212> TYPE: DNA
<213> ORGANISM: Homo sapiens

<400> SEQUENCE: 595
ggaattcacc atgctttgga aattgacgga t                                  31

<210> SEQ ID NO 596
<211> LENGTH: 36
<212> TYPE: DNA
<213> ORGANISM: Homo sapiens

<400> SEQUENCE: 596
ggaattcctc actttctgtg cttctcctct ttgtca                             36

<210> SEQ ID NO 597
<211> LENGTH: 1443
<212> TYPE: DNA
<213> ORGANISM: Homo sapiens

<400> SEQUENCE: 597
atgggttccc ccgccgcccc ggagggagcg ctgggctacg tccgcgagtt cactcgccac     60
tcctccgacg tgctgggcaa cctcaacgag ctgcgcctgc gcgggatcct cactgacgtc    120
acgctgctgg ttggcgggca accccctcaga gcacacaagg cagttctcat cgcctgcagt   180
ggcttcttct attcaatttt ccggggccgt gcggagtcg gggtgacgt gctctctctg      240
cccgggggtc ccgaagcgag aggcttcgcc cctctattgg acttcatgta cacttcgcgc    300
ctgcgcctct ctccagccac tgcaccagca gtcctagcgg ccgccaccta tttgcagatg    360
gagcacgtgg tccaggcatg ccaccgcttc atccaggcca gctatgaacc tctgggcatc    420
tccctgcgcc cctggaagc agaaccccca acacccccaa cggcccctcc accaggtagt    480
cccaggcgct ccgaaggaca cccagaccca cctactgaat ctcgaagctg cagtcaaggc   540
ccccccagtc cagccagccc tgaccccaag gcctgcaact ggaaaaagta caagtacatc   600
gtgctaaact ctcaggcctc ccaagcaggg agcctggtcg gggagagaag ttctggtcaa   660
ccttgccccc aagccaggct ccccagtgga gacgaggcct ccagcagcag cagcagcagc   720
agcagcagca gcagtgaaga aggacccatt cctggtcccc agagcaggct ctctccaact   780
gctgccactg tgcagttcaa atgtgggggc ccagccagta ccccctacct cctcacatcc   840
caggctcaag acacctctgg atcaccctct gaacgggctc gtccactacc gggagtgaat   900
ttttcagctg ccagaactgt gaggctgtgg cagggtgctc atcggggggct ggactccttg   960
gttcctgggg acgaagacaa accctataag tgtcagctgt gccggtcttc gttccgctac  1020
```

-continued

```
aagggcaacc ttgccagtca tcgtacagtg cacacagggg aaaagcctta ccactgctca   1080
atctgcggag cccgttttaa ccggccagca aacctgaaaa cgcacagccg catccattcg   1140
ggagagaagc cgtataagtg tgagacgtgc ggctcgcgct ttgtacaggt ggcacatctg   1200
cgggcgcacg tgctgatcca caccggggag aagccctacc cttgccctac ctgcggaacc   1260
cgcttccgcc acctgcagac cctcaagagc cacgttcgca tccacaccgg agagaagcct   1320
taccactgcg acccctgtgg cctgcatttc cggcacaaga gtcaactgcg gctgcatctg   1380
cgccagaaac acggagctgc taccaacacc aaagtgcact accacattct cggggggccc   1440
tag                                                                 1443
```